(12) United States Patent
Dolle et al.

(10) Patent No.: US 7,034,051 B2
(45) Date of Patent: Apr. 25, 2006

(54) FUSED BICYCLIC CARBOXAMIDE DERIVATIVES AND METHODS OF THEIR USE

(75) Inventors: Roland E. Dolle, King of Prussia, PA (US); Guo-Hua Chu, Wilmington, DE (US)

(73) Assignee: Adolor Corporation, Exton, PA (US)

( * ) Notice: Subject to any disclaimer, the term of this patent is extended or adjusted under 35 U.S.C. 154(b) by 219 days.

(21) Appl. No.: 10/651,197

(22) Filed: Aug. 28, 2003

(65) Prior Publication Data

US 2005/0054630 A1 Mar. 10, 2005

(51) Int. Cl.
*A61K 31/40* (2006.01)
*C07D 405/00* (2006.01)

(52) U.S. Cl. ..................... 514/422; 548/525
(58) Field of Classification Search .............. 514/422; 548/525
See application file for complete search history.

(56) References Cited

U.S. PATENT DOCUMENTS

| | | | |
|---|---|---|---|
| 4,065,573 A | 12/1977 | Lednicer | 424/278 |
| 4,098,904 A | 7/1978 | Szmuszkovicz | 424/324 |
| 4,212,878 A | 7/1980 | Lednicer et al. | 424/274 |
| 4,359,476 A | 11/1982 | Kaplan et al. | 424/274 |
| 4,438,130 A | 3/1984 | Kaplan | 424/274 |
| 4,663,343 A | 5/1987 | Horwell et al. | 514/429 |
| 4,906,655 A | 3/1990 | Horwell et al. | 514/422 |
| 5,109,135 A | 4/1992 | D'Ambra et al. | 544/73 |
| 5,242,944 A | 9/1993 | Park et al. | 514/466 |
| 5,345,943 A | 9/1994 | Hargreaves et al. | 128/742 |
| 5,369,131 A | 11/1994 | Poli et al. | 514/772.4 |
| 5,434,292 A | 7/1995 | Saita et al. | 560/51 |
| 5,532,266 A | 7/1996 | Gottschlich et al. | 514/428 |
| 5,688,955 A | 11/1997 | Kruse et al. | 546/276.4 |
| 5,804,595 A | 9/1998 | Portoghese et al. | 514/428 |
| 6,057,357 A | 5/2000 | Horwell et al. | 514/422 |
| 6,177,438 B1 | 1/2001 | Nagase et al. | 514/280 |
| 6,713,502 B1 | 3/2004 | Dhanak et al. | 514/422 |
| 6,747,054 B1 | 6/2004 | Cameron et al. | 514/422 |
| 6,784,167 B1 | 8/2004 | Wood et al. | 514/63 |
| 6,784,197 B1 | 8/2004 | Differding et al. | 514/365 |

FOREIGN PATENT DOCUMENTS

| | | |
|---|---|---|
| EP | 0 254 545 A2 | 1/1988 |
| EP | 0 261 842 A1 | 3/1988 |
| WO | WO 91/08206 | 6/1991 |
| WO | WO 98/49141 | 11/1998 |
| WO | WO 99/32475 | 7/1999 |

OTHER PUBLICATIONS

Jain, K.K., "A guide to drug evaluation for chronic pain," *Emerging Drugs*, 2000, 5(2), 241-257.

Andreev, N., et al., "Opioids suppress spontaneous activity of polymodal nociceptors in rat paw skin induced by ultraviolet irradiation," *Neurosci.*, 1994, 58(4), 793-798.

Antonijevic, I., et al., "Perineurial defect and peripheral opioid analgesia in inflammation," *J. Neurosci.*, Jan. 1995, 15(1), 165-172.

Barber, A., et al., "Opioid agonists and antagonists: an evaluation of their peripheral actions in inflammation," *Med. Res. Rev.*, 1992, 12(5), 525-562.

Buschmann, H., et al., (Eds.), *Analgesics*, Wiley-VCH, Verlag GMbH & Co. KgaA, Weinheim, 2002.

Flynn, G., "Mechanism of percutaneous absorption from physicochemical evidence," *Percutaneous Absorption*, Bronaugh, R.L., et al. (Eds.), Marcel Dekker, Inc., 1985, Chapter 2, 17-42.

Greene, T.W., et al., *Protective Groups in Organic Synthesis*, 2nd Ed., Wiley & Sons, 1991.

Handwerker, H.O., et al., "Pain and Inflammation," *Proceedings of the VIth World Congress on Pain*, Bond, et al. (Eds.), Elsevier Science Publishers BV, 1991, Chapter 7, 59-70.

Hargreaves, K.M., et al., "The peripheral analgesic effects of opioids," *APS Journal*, 1993, 2(1), 51-59.

Hassan, A.H., et al., "Inflammation of the rat paw enhances axonal transport of opioid receptors in the sciatic nerve and increase their density in the inflamed tissue," *Neuroscience*, 1993, 55(1), 185-195.

Iyengar, S., et al., "*Kappa* opiate agonists modulate the hypothalamic-pituitary-adrenocortical axis in the rat," *J. Pharmacol. Exp. Ther.*, 1986, 238(2), 429-436.

Leander, J.D., et al., "Diuresis and suppression of vasopressin by *Kappa* opioids: comparison with *Mu* and *Delta* opioids and clonidine," *J. Pharmacol. Exp. Ther.*, 1985, 234(2), 463-469.

Lutz, R.A., et al., "Opioid receptors and their pharmacological profiles," *J. Recept. Res.*, 1992, 12(3), 267-286.

Mansour, A., et al., "Anatomical distribution of opioid receptors in mammalians: an overview," *Opioids I*, A. Herz (Ed.), Springer-Verlag, 1993, 79-105.

Manzanares, J., et al., "Kappa-opioid-receptor-mediated regulation to α-melanocyte-stimulating hormone secretion and tuberohypophysical dopaminergic neuronal activity," *Neuroendrocrinology*, 1990, 52, 200-205.

Millan, M.J., "κ-opioid receptors and analgesia," *Trends in Pharmacol. Sci.*, Feb. 1990, 11, 70-76.

Morley, J.E., et al., "Involvement of dynorphin and the kappa opioid receptor in feeding," *Peptides*, 1983, 4, 797-800.

(Continued)

Primary Examiner—Deborah C. Lambkin
(74) Attorney, Agent, or Firm—Woodstock Washburn LLP

(57) ABSTRACT

Fused bicyclic carboxamide derivatives are disclosed. Pharmaceutical compositions containing the compounds and methods for their use are also disclosed.

54 Claims, No Drawings

OTHER PUBLICATIONS

Neugebauer, V., et al., "N-methyl-D-aspartate (NMDA) and non-NMDA receptor antagonists block the hyperexcitability of dorsal horn neurons during development of acute arthritis in rat's knee joint," *J. Neurophysiology*, Oct. 1993, 70(4), 1365-1377.

Pershing, L.K., et al., "In vivo pharmacokinetics and pharmacodynamics of topical ketoconazole and miconazole in human stratum corneum," *Antimicrob. Agents Chemother.*, Jan. 1994, 38(1), 90-95.

Przewlocki, R., et al., "Gene expression and localization of opioid peptides in immune cells of inflamed tissue: functional role in antinociception," *Neuroscience*, 1992, 48(2), 491-500.

Ramabadran, K., et al., "A critical analysis of the experimental evaluation of nonciceptive reactions in animals," *Pharm. Res.*, 1986, 3(5), 263-270.

Randall, L.O., et al., "A method for measurement of analgesic activity on inflamed tissue," *Arch. Int. Pharmacodyn.*, 1957, CXI(4), 409-419.

Remington's Pharmaceutical Sciences, *Mack Publishing Co.*, Easton, PA, 1980.

Roy, S.D., et al., "Transdermal delivery of narcotic analgesics: pH, anatomical, and subject influences on cutaneous permeability of fentanyl and sufentanil," *Pharm. Res.*, 1990, 7(8), 842-847.

Sato, A., et al., "Changes in blood pressure and heart rate induced by movements of normal and inflamed knee joints," *Neurosci. Lett.*, 1984, 52, 55-60.

Schaible, H.-G., et al, "Effects of an experimental arthritis on the sensory properties of fine articular afferent units," *J. Neurophysiol.*, Nov. 1985, 54(5), 1109-1122.

Schaible, H.-G., et al., "Afferent and spinal mechanisms of joint pain," *Pain*, 1993, 55, 5-54.

Simon, E.J., "Opioid receptors and endogenous opioid peptides,"*Med. Res. Rev.*, 1991, 11(4), 357-374.

Stein, C., et al., "Peripheral opioid receptors mediating antinociception in inflammation. Evidence of involvement of *Mu, Delta* and *Kappa* receptors," *J. Pharmacol. and Exp. Ther.*, 1989, 248(3), 1269-1275.

Stein, C., et al., "Peripheral effect of fentanyl upon nociception in inflamed tissue of the rate," *Neurosci. Lett.*, 1988, 84, 225-228.

Taber, R.I., et al., "Agonist and antagonist interactions of opioids on acetic acid-induced abdominal stretching in mice," *J. Pharmacol. Exp. Ther.*, 1969, 169(1), 29-38.

Tjølsen, A., et al., "The formalin test: an evaluation of the method," *Pain*, 1992, 51, 5-17.

Wheeler-Aceto, H., et al., "Standardization of the rat paw formalin test for the evaluation of analgesics," *Psychopharmacology*, 1991, 104, Springer-Verlag, 35-44.

Williamson, J.W., et al., "Reflex increase in blood pressure induced by leg compression in man," *J. Physiol.*, 1994, 475.2, 351-357.

Wood, P.L., "Multiple opiate receptors: support for unique mu, delta and kappa sites," *Neuropharmacology*, 1982, 21, 487-497.

FUSED BICYCLIC CARBOXAMIDE DERIVATIVES AND METHODS OF THEIR USE

FIELD OF THE INVENTION

The invention relates to fused bicyclic carboxamides, pharmaceutical compositions containing these compounds, and methods for their pharmaceutical use. In certain embodiments, the carboxamide derivatives are agonists of the kappa opioid receptor and are useful, inter alia, for treating and/or preventing pain, pruritus, and gastrointestinal disorders.

BACKGROUND OF THE INVENTION

Opium and its derivatives are potent analgesics that also have other pharmacological effects, and exert their effects by interacting with high-affinity receptors. It has been shown by investigators that there are at least three major opioid receptor types in the central nervous system (hereinafter CNS) and in the periphery. These receptors, known as mu (μ), delta (δ) and kappa (κ), have distinct pharmacological profiles, anatomical distributions and functions. See, for example: Wood, P. L., *Neuropharmacology,* 21, 487–497, 1982; Simon, E. J., *Med. Res. Rev.,* 11, 357–374, 1991; Lutz et al., *J. Recept. Res.* 12, 267–286; and Mansour et al., *Opioid I,* ed. Herz, A. (Springer, Berlin) pp. 79–106, 1993. The δ receptors are abundant in the CNS and mediate analgesia, gastrointestinal motility and various hormonal functions. The μ receptors bind morphine-like drugs and mediate the opiate phenomena associated with morphine, including analgesia, opiate dependence, cardiovascular and respiratory functions, and several neuroendocrine effects. The κ receptors have a wide distribution in CNS and mediate a spectrum of functions including the modulation of drinking, water balance, food intake, tussis, gut motility, temperature control and various endocrine functions. They are also involved in analgesia. See, for example: Leander et al., *J. Pharmacol. Exp. Ther.* 234, 463–469, 1985; Morley et al., *Peptides* 4, 797–800, 1983; Manzanares et al., *Neuroendocrinology* 52, 200–205, 1990; and Iyengar et al., *J. Pharmacol. Exp. Ther,* 238, 429–436, 1986; U.S. Pat. No. 6,177, 438 B1.

Most clinically used opioid analgesics, such as morphine and codeine, act as μ receptor agonists. These opioids have well-known, undesirable and potentially dangerous dependence forming side effects. Compounds that are κ-receptor agonists act as analgesics through interaction with κ opioid receptors. The advantage of these agonists over the classical μ receptor agonists, such as morphine, lies in their ability to cause analgesia while being devoid of morphine-like behavioral effects and addiction liability.

A large number of classes of compounds which act as agonists at κ opioid receptors have been described in the art including the following illustrative classes of compounds:

U.S. Pat. No. 4,065,573 discloses 4-amino-4-phenylcyclohexane ketal compounds allegedly having analgesic activity.

U.S. Pat. No. 4,145,435 discloses N-(2-amino-cycloaliphatic)-phenylacetamide compounds allegedly having analgesic activity and narcotic antagonist activity.

U.S. Pat. No. 4,098,904 discloses N-(2-amino-cycloaliphatic)-benzoamides and naphthamides allegedly useful for relieving pain.

U.S. Pat. No. 4,212,878 discloses phenylacetamide derivatives allegedly having analgesic properties and reduced physical dependence liability properties, relative to morphine and methadone.

U.S. Pat. No. 4,359,476 discloses substituted cycloalkane-amides allegedly useful as analgesic and having low abuse liability.

U.S. Pat. No. 4,438,130 discloses 1-oxa-, aza- and thiaspirocyclic compounds allegedly having analgesic activity, low physical dependence and abuse liability properties and little dysphoric inducing properties.

U.S. Pat. No. 4,663,343 discloses substituted naphthalenyloxy-1,2-diaminocyclohexyl amides allegedly useful as analgesics.

U.S. Pat. No. 4,906,655 discloses 1,2-cyclohexylaminoaryl amides allegedly having high kappa-opioid affinity, selectivity and potency and allegedly useful as analgesics, diuretics, anti-inflammatory and psychotherapeutic agents.

U.S. Pat. No. 5,532,266 discloses arylacetamides allegedly having high kappa-opioid affinity useful as pharmaceutical agents for providing an analgesic effect and/or neuroprotective effect.

U.S. Pat. No. 5,688,955 discloses substituted piperidines, substituted naphthalenes, aryl-substituted amides, and cyclohexyl-substituted amides having kappa opioid agonist activity, compositions containing them and methods of using them as analgesics.

U.S. Pat. No. 5,804,595 discloses amino acid conjugates of substituted 2-phenyl-N-[1-(phenyl)-2-(1-heterocycloalkyl- or heterocycloaryl-)ethyl]acetamides allegedly useful for selectively agonizing kappa opioid receptors in mammalian tissue.

U.S. Pat. No. 6,057,357 discloses substituted benzofuran and thianaphthene acetamides having kappa opioid agonist activity, compositions containing them and methods of their use.

WO 99/32475 discloses sulfonamide substituted chroman derivatives having beta-3 adrenoreceptor agonist activity, compositions containing them and methods of their use.

WO 98/49141 discloses benzofuranyl and substituted phenyl carboxamides having kappa opioid agonist activity, compositions containing them and methods of their use.

EP-A-0,261,842 discloses N1 acylated-(1-(phenyl or benzyl))-1,2-ethylene diamines having kappa opioid agonist activity, compositions containing them and methods of their use.

EP-A-0,254,545 discloses N1 acylated-1,2-ethylene diamines having kappa opioid agonist activity, compositions containing them and methods of their use.

WO 91/08206 discloses N-acyl-substituted azacyclic compounds, process for their preparation, and methods of their use.

Although numerous compounds have been reported to be potent and selective κ opioid agonists, many of these compounds are potent inhibitors of a number of human cytochrome P450 enzymes, particularly CYP2D6, CYP2C9 and CYP3A4.

Cytochrome P450 enzymes are heme-containing membrane proteins localized in the smooth endoplasmic reticulum of numerous tissues, including, in particular, the liver. This family of enzymes catalyzes a wide variety of oxidative and reductive reactions and has activity towards a chemically diverse group of substrates. Oxidative biotransformations catalyzed by cytochrome P450 monooxygenases include aromatic and side chain hydroxylation, N-, O-, and S-dealkylation, N- and S-oxidation, N-hydroxylation, deamination, dehalogenation, and desulfuration. These enzymes are the major catalysts of drug biotransformation reactions and also serve an important detoxification role in the body. The cytochrome P450 enzymes catalyze oxidative reactions of toxins in the body by making them more water-soluble.

Inhibitors of cytochrome P450 enzymes can interfere with the body's ability to detoxify. For example, lethal clinical consequences can result from combining CYP3A4 inhibitors with drugs that are metabolized by this enzyme. As a further example, the use of an inhibitor of cytochrome P450 could render a normally safe and effective dose of a drug that is metabolized by cytochrome P450 toxic because the enzyme does not reduce the level of the drug in the patient to safe levels. In this way, the inhibition of cytochrome P450 enzymes could preclude clinical development of a given compound. For further discussion on drug interactions, see, for example, the Guidance for Industry: *In Vivo Drug Metabolism/Drug Interaction Studies—Study Design, Data Analysis, and Recommendations for Dosing and Labeling* prepared by the Food and Drug Administration (November 1999), the disclosure of which is incorporated herein by reference.

Thus, there is still an unfulfilled need for compounds with κ opioid receptor activity that may be used in methods to provide beneficial pharmaceutical characteristics while minimizing undesirable side effects generally associated with administering these exogenous opioids, particularly inhibition of cytochrome P450 enzymes. The present invention is directed to these, as well as other important ends.

SUMMARY OF THE INVENTION

The present invention is generally directed to carboxamide derivatives, pharmaceutical compositions containing these compounds, and methods for their pharmaceutical use. The present invention relates to compounds that, preferably:

(1) bind with high affinity to κ opioid receptors;

(2) display good opioid receptor selectivity of κ versus μ and κ versus δ; and (3) do not substantially inhibit cytochrome P450 enzymatic activity, in particular CYP2D6, CYP2C9 and CYP3A4.

In one embodiment, the invention is directed to compounds of formula I:

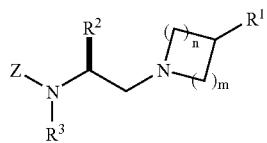

I wherein:
$R^1$ is H or OH;
$R^2$ is alkyl, aralkyl, or aryl;
$R^3$ is alkyl or aralkyl;
n and m are each independently the integer 1 or 2;

Z is:

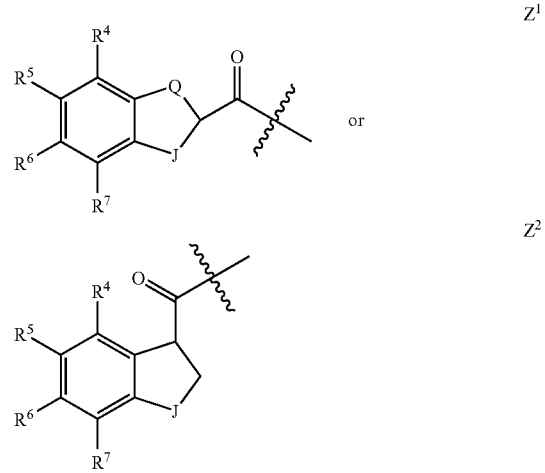

Q is —O—, —CH$_2$—, or —N(R$^8$)—;
J is —(CH$_2$)$_k$—, —O—(CH$_2$)$_{k-1}$—, —(CH=CH—CH$_2$)—, or —C(A)(B)CH$_2$—, provided that when Z is $Z_1$, k is the integer 1, and J is —O—(CH$_2$)$_{k-1}$—, then Q is —CH$_2$—;
k is the integer 1, 2, or 3;
A is H and B is alkyl or H, or when taken together, A and B are =O or =CH$_2$;
$R^4$, $R^5$, $R^6$, and $R^7$ are each independently H, alkyl, halo, aryl, heteroaryl, —OH, —OR$^9$, —SO$_2$NR$^{10}$R$^{11}$, —(CH$_2$)$_r$NR$^{12}$R$^{13}$, nitro, —CN, —CF$_3$, —CF$_2$CF$_3$, —OCF$_3$, —SR$^9$, —SO$_2$R$^9$, —(CH$_2$)$_r$C(=O)OR$^9$, —(CH$_2$)$_r$C(=O)NR$^{12}$R$^{12a}$, or —(CH$_2$)$_r$NHC(=O)NR$^{12}$R$^{12a}$, provided that at least two of $R^4$, $R^5$, $R^6$, and $R^7$ are other than —SO$_2$NR$^{10}$R$^{11}$, —(CH$_2$)$_r$NR$^{12}$R$^{13}$, —(CH$_2$)$_r$C(=O)NR$^{12}$R$^{12a}$, or —(CH$_2$)$_r$NHC(=O)NR$^{12}$R$^{12a}$;
$R^8$ is H, alkyl, —C(=O)R$^9$, or —S(=O)$_2$R$^9$;
$R^9$ is alkyl or aralkyl;
$R^{10}$ and $R^{11}$ are each independently H, alkyl, —(CH$_2$)$_p$—OH, —(CH$_2$)$_p$—OR$^9$, cycloalkyl, cycloalkylalkyl, aryl, or taken together with the nitrogen atom to which they are attached, $R^{10}$ and $R^{11}$ form a 4–7 member heterocycle, optionally interrupted by one or more O, S or NR$^8$ groups;
$R^{12}$ and $R^{12a}$ are each independently H, alkyl, or aryl;
$R^{13}$ is H, alkyl, —C(=O)R$^{14}$, —S(=O)$_2$R$^{14}$, or —C(=O)OR$^{15}$;
$R^{14}$ is alkyl, cycloalkyl, cycloalkylalkyl, alkylcycloalkyl, heteroaryl, heteroalkyl, heteroaralkyl, aryl, or aralkyl;
$R^{15}$ is alkyl, cycloalkyl, alkylcycloalkyl, or aralkyl;
r is the integer 0, 1, 2, 3, or 4;
p is the integer 2, 3, 4, 5, or 6; or
a stereoisomer, prodrug, pharmaceutically acceptable salt, hydrate, solvate, acid salt hydrate, N-oxide or isomorphic crystalline form thereof.

In another embodiment, the invention is directed to pharmaceutical compositions comprising a pharmaceutically acceptable carrier and an effective amount of a compound of formula I. In certain preferred embodiments, the pharmaceutical compositions may further comprise an opioid and/or another active ingredient selected from the group consisting of antibiotics, antivirals, antifungals, anti-inflammatories, anesthetics and mixtures thereof.

In another embodiment, the invention is directed to methods of binding opioid receptors, including κ opioid receptors, in a patient in need thereof, comprising the step of administering to the patient an effective amount of a compound of formula I.

In yet another embodiment, the invention is directed to methods for preventing or treating gastrointestinal dysfunction comprising the step of administering to a patient in need thereof, a composition comprising an effective amount of a compound of formula I.

In other embodiments, the invention is directed to methods for preventing or treating ileus comprising the step of administering to a patient in need thereof, a composition comprising an effective amount of a compound of formula I.

In another embodiment, the invention is directed to methods for preventing or treating pain comprising the step of administering to a patient in need thereof, a composition comprising an effective amount of an opioid and an effective amount of a compound of formula I.

In another embodiment, the invention is directed to methods for preventing or treating pruritic dermatoses and conditions characterized by pruritic dermatosis as a symptom, including allergic dermatitis, atopy, contact dermatitis, psoriasis, eczema, opioid-induced pruritus, and insect bites, comprising the step of administering to a patient in need thereof, a composition comprising an effective amount of a compound of formula I.

In another embodiment, the invention is directed to methods for preventing or treating cerebral edema, comprising the step of administering to a patient in need thereof, a composition comprising an effective amount of a compound of formula I.

In other embodiments, the invention is directed to methods for preventing or treating oxygen supply deficiency of the central nervous system, comprising the step of administering to a patient in need thereof, a composition comprising an effective amount of a compound of formula I.

In another embodiment, the invention is directed to methods for inducing diuresis, comprising the step of administering to a patient in need thereof, a composition comprising an effective amount of a compound of formula I.

In yet another embodiment, the invention is directed to methods for preventing or treating tussis, comprising the step of administering to a patient in need thereof, a composition comprising an effective amount of a compound of formula I.

DETAILED DESCRIPTION OF ILLUSTRATIVE EMBODIMENTS

As employed above and throughout the disclosure, the following terms, unless otherwise indicated, shall be understood to have the following meanings.

As used herein, "alkyl" refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms, herein referred to as "lower alkyl", being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "alkenyl" refers to an alkyl group of at least 2 carbon atoms having one or more double bonds, wherein alkyl is as previously defined. Alkenyl groups can be optionally substituted.

As used herein, "alkynyl" refers to an alkyl group of at least 2 carbon atoms having one or more triple bonds, wherein alkyl is as previously defined. Alkynyl groups can be optionally substituted.

As used herein, "aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

As used herein, "cycloalkylalkyl" refers to alkyl radicals bearing an cycloalkyl substituent and having from about 6 to about 50 carbon atoms (and all combinations and subcombinations of ranges and specific numbers of carbon atoms therein), with from about 6 to about 10 carbon atoms being preferred. Cycloalkylalkyl groups may be monocyclic or include multiple rings, such as for example, bicyclic or fused ring structures. Cycloalkylalkyl groups may be optionally substituted. Non-limiting examples include, for example, cyclohexylmethyl, cyclopropylmethyl, pinan-10-yl, [2.2.1]-bicycloheptan-1-yl, tetrahydronaphtalen-2-yl, and 2-chloro-4-hydroxy-5-methylcyclohexylmethyl.

As used herein, "heteroaryl" refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

As used herein, "cycloalkyl" refers to an optionally substituted, alkyl group having one or more rings in their structures and having from about 3 to about 20 carbon atoms (and all combinations and subcombinations of ranges and specific numbers of carbon atoms therein), with from about 3 to about 10 carbon atoms being preferred. Multi-ring structures may be bridged or fused ring structures. Groups include, but are not limited to, cyclopropyl, cyclobutyl, cyclopentyl, cyclohexyl, cyclooctyl, and adamantyl.

As used herein, "alkylcycloalkyl" refers to an optionally substituted ring system comprising a cycloalkyl group having one or more alkyl substituents. Exemplary alkylcycloalkyl groups include 2-methylcyclohexyl, 3,3-dimethylcyclopentyl, trans-2,3-dimethylcyclooctyl, and 4-methyldecahydronaphthalenyl.

As used herein, "heteroaralkyl" refers to an optionally substituted, heteroaryl substituted alkyl radicals having from about 2 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methylcyclopentanyl.

As used herein, "heterocycloalkyl" refers to an optionally substituted, mono-, di-, tri-, or other multicyclic aliphatic ring system that includes at least one, and preferably from 1 to about 4 sulfur, oxygen, or nitrogen heteroatom ring members. Heterocycloalkyl groups can have from about 3 to about 20 carbon atoms (and all combinations and subcombinations of ranges and specific numbers of carbon atoms therein), with from about 4 to about 10 carbons being preferred. The heterocycloalkyl group may be unsaturated, and may also be fused to aromatic rings. Examples of heterocycloalkyl groups include, for example, tetrahydrofuranyl, tetrahydrothienyl, piperidinyl, pyrrolidinyl, isoxazolidinyl, isothiazolidinyl, pyrazolidinyl, oxazolidinyl, thiazolidinyl, piperazinyl, morpholinyl, piperadinyl, decahydroquinolyl, octahydrochromenyl, octahydro-cyclopenta[c]pyranyl, 1,2,3,4,-tetrahydroquinolyl, octahydro-[2] pyrindinyl, decahydro-cycloocta[c]furanyl, and imidazolidinyl.

As used herein, the term "spiroalkyl" refers to an optionally substituted, alkylene diradical, both ends of which are bonded to the same carbon atom of the parent group to form a spirocyclic group. The spiroalkyl group, taken together with its parent group, as herein defined, has 3 to 20 ring atoms. Preferably, it has 3 to 10 ring atoms. Non-limiting examples of a spiroalkyl group taken together with its parent group include 1-(1-methyl-cyclopropyl)-propan-2-one, 2-(1-phenoxy-cyclopropyl)-ethylamine, and 1-methyl-spiro [4.7]dodecane.

As used herein, "alkoxy" and "alkoxyl" refer to an optionally substituted alkyl-O— group wherein alkyl is as previously defined. Exemplary alkoxy and alkoxyl groups include methoxy, ethoxy, n-propoxy, i-propoxy, n-butoxy, and heptoxy.

As used herein, "aryloxy" and "aryloxyl" refer to an optionally substituted aryl-O— group wherein aryl is as previously defined. Exemplary aryloxy and aryloxyl groups include phenoxy and naphthoxy.

As used herein, "aralkoxy" and "aralkoxyl" refer to an optionally substituted aralkyl-O— group wherein aralkyl is as previously defined. Exemplary aralkoxy and aralkoxyl groups include benzyloxy, 1-phenylethoxy, 2-phenylethoxy, and 3-naphthylheptoxy.

Typically, substituted chemical moieties include one or more substituents that replace hydrogen. Exemplary substituents include, for example, halo (e.g, F, Cl, Br, I), alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), alkoxyl, aryloxyl, aralkoxyl, nitro (—NO2), cyano (—CN), amino (—NH$_2$), —N-substituted amino (—NHR"), —N,N-disubstituted amino (—N(R")R"), carboxyl (—COOH), —C(=O)R", —OR", —C(=O)OR", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), thiol, thiolato (SR"), sulfonic acid (SO$_3$H), phosphonic acid (PO$_3$H), S(=O)$_2$R", S(=O)$_2$NH$_2$, S(=O)$_2$NHR", S(=O)$_2$NR"R", NHS(=O)$_2$R", NR"S(=O)$_2$R", CF$_3$, CF$_2$CF$_3$, NHC(=O) NHR", NHC(=O)NR"R", NR"C(=O)NHR", NR"C(=O) NR"R", NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, for example.

As used herein, an "*" denotes the presence of a chiral center in a molecule, wherein one stereoisomeric form (R or S) predominates, more preferably is substantially enriched, and even more preferably is enantiomerically pure at a specific center in the molecule, but the absolute configuration at this center has not been conclusively established. This can be expressed, for example in a compound's identification number such as 1a*, or 4*, and indicates that the stereochemical configuration of at least one chiral center of the identified compound has not been established. The specific center is identified within a structure by placing the "*" adjacent the chiral center in question, such as, for example, in the structure below.

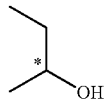

As used herein, "opioid" refers to all agonist and antagonists with morphine-like activity as well as to naturally occurring and synthetic opioid peptides. Non-limiting examples of compounds with morphine-like activity include the family of drugs derived from opium, such as for example, morphine and codeine, thebaine, and a wide variety of semi-synthetic related compounds derived therefrom.

As used herein, "analgesic" refers to pharmaceutical compounds that have the ability to reduce or eliminate pain and/or the perception of pain without a loss of consciousness.

As used herein, "effective amount" refers to an amount of a compound as described herein that may be therapeutically effective to inhibit, prevent or treat the symptoms of particular disease, disorder, condition, or side effect. Such diseases, disorders, conditions, and side effects include, but are not limited to, those pathological conditions associated with the administration of opioids (for example, in connection with the treatment and/or prevention of pain), wherein the treatment or prevention comprises, for example, inhibiting the activity thereof by contacting cells, tissues or receptors with compounds of the present invention. Thus, for example, the term "effective amount", when used in connection with opioids, or opioid replacements, for example, for the treatment of pain, refers to the treatment and/or prevention of the painful condition. The term "effective amount", when used in connection with anti-pruritic compounds, refers to the treatment and/or prevention of symptoms, diseases, disorders, and conditions typically associated with pruritus and other related dermatoses. The term "effective amount", when used in connection with compounds active against gastrointestinal dysfunction, refers to the treatment and/or prevention of symptoms, diseases, disorders, and conditions typically associated with gastrointestinal dysfunction. The term "effective amount", when used in connection with anti-ileus compounds, refers to the treatment and/or prevention of symptoms, diseases, disorders, and conditions typically associated with ileus. The term "effective amount", when used in connection with compounds useful in the treatment and/or prevention of cerebral edema, refers to the treatment and/or prevention of symptoms, diseases, disorders, and conditions typically associated with cerebral edema and other related conditions. The term "effective amount", when used in connection with anti-hypoxia compounds, refers to the treatment and/or prevention of symptoms, diseases, disorders, and conditions typically associated with hypoxia, such as oxygen supply deficiency to the central nervous system. The term "effective amount", when used in connection with anti-tussive compounds, refers to the treatment and/or prevention of tussis. The term "effective amount", when used in connection with diuretic compounds, refers to the inducement of diuresis.

As used herein, "pharmaceutically acceptable" refers to those compounds, materials, compositions, and/or dosage forms that are, within the scope of sound medical judgment, suitable for contact with the tissues of human beings and animals without excessive toxicity, irritation, allergic response, or other problem complications commensurate with a reasonable benefit/risk ratio.

As used herein, "in combination with", "combination therapy" and "combination products" refer, in certain embodiments, to the concurrent administration to a patient of opioids and the compounds of formula I. When administered in combination, each component may be administered at the same time or sequentially in any order at different points in time. Thus, each component may be administered separately but sufficiently closely in time so as to provide the desired therapeutic effect.

As used herein, "dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluene-sulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

As used herein, "patient" refers to animals, including mammals, preferably humans.

As used herein, "stereoisomers" refers to compounds that have identical chemical constitution, but differ as regards the arrangement of the atoms or groups in space.

As used herein, "N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

As used herein, "gastrointestinal dysfunction" refers collectively to maladies of the stomach, small and large intestine. Non-limiting examples of gastrointestinal dysfunction include, for example, irritable bowel syndrome, opioid-bowel dysfunction, post-operative ileus, opioid-induced ileus, colitis, post-operative emesis, opioid-induced emesis, decreased gastric motility, decreased gastric emptying, inhibition of small intestinal propulsion, inhibition of large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, or delayed absorption of orally administered medications or nutritive substances.

As used herein, "pain" refers to the perception or condition of unpleasant sensory or emotional experience, associated with actual or potential tissue damage or described in terms of such damage. "Pain" includes, but is not limited to, two broad categories of pain: acute and chronic pain (Buschmann, H.; Christoph, T; Friderichs, E.; Maul, C.; Sundermann, B; eds.; *Analgesics*, Wiley-VCH, Verlag GMbH & Co. KgaA, Weinheim; 2002; Jain, K. K. "A Guide to Drug Evaluation for Chronic Pain"; *Emerging Drugs*, 5(2), 241–257(2000)). Non-limiting examples of pain include nociceptive pain, inflammatory pain, visceral pain, somatic pain, neuropathic pain, AIDS pain, cancer pain, phantom pain, and psychogenic pain, and pain resulting from hyperalgesia, allodynia and the like.

As used herein, "pruritus" refers to a symptom of a disease, disorder, or condition that is manifested by itching, that is, an uncomfortable sensation due to irritation of a peripheral sensory nerve.

As used herein, "tussis" refers to a coughing condition, and "antitussive" agents refer to those materials that modulate the coughing response.

As used herein, "diuretic" refers to an agent that modulates the water balance in a patient.

As used herein, "pruritic dermatosis" refers to any skin diseases, disorders, or conditions of which itching is a symptom. Non-limiting examples include allergic dermatitis, atopy, contact dermatitis, psoriasis, eczema, opioid-induced pruritus, uremic pruritus, and insect bites.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical; or geometric isomer, except where such stereochemistry is clearly defined.

Accordingly, in one embodiment, the invention provides novel pharmaceutically active compounds of formula I:

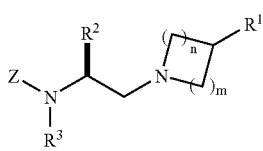

I wherein:
R$^1$ is H or OH;
R$^2$ is alkyl, aralkyl, or aryl;
R$^3$ is alkyl or aralkyl;
n and m are each independently the integer 1 or 2;
Z is:

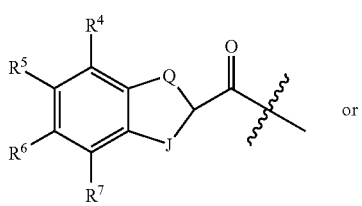

Z$^1$ or

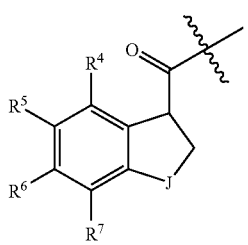

Z$^2$

Q is —O—, —CH$_2$—, or —N(R$^8$)—;
J is —(CH$_2$)$_k$—, —O—(CH$_2$)$_{k-1}$—, —(CH=CH—CH$_2$)—, or —C(A)(B)CH$_2$—, k is the integer 1, and J is —O—(CH$_2$)$_{k-1}$—, then Q is —CH$_2$—;
k is the integer 1, 2, or 3;
A is H and B is alkyl or H, or when taken together, A and B are =O or =CH$_2$;
R$^4$, R$^5$, R$^6$, and R$^7$ are each independently H, alkyl, halo, aryl, heteroaryl, —OH, —OR$^9$, —SO$_2$NR$^{10}$R$^{11}$, —(CH$_2$)$_r$NR$^{12}$R$^{13}$, nitro, —CN, —CF$_3$, —CF$_2$CF$_3$, —OCF$_3$, —SR$^9$, —SO$_2$R$^9$, —(CH$_2$)$_r$C(=O)OR$^9$, —(CH$_2$)$_r$C(=O)NR$^{12}$R$^{12a}$, or —(CH$_2$)$_r$NHC(=O)NR$^{12}$R$^{12a}$, provided that at least two of R$^4$, R$^5$, R$^6$, and R$^7$ are other than —SO$_2$NR$^{10}$R$^{11}$, —(CH$_2$)$_r$NR$^{12}$R$^{13}$, —(CH$_2$)$_r$C(=O)NR$^{12}$R$^{12a}$, or —(CH$_2$)$_r$NHC(=O)NR$^{12}$R$^{12a}$;

R$^8$ is H, alkyl, —C(=O)R$^9$, or —S(=O)$_2$R$^9$;
R$^9$ is alkyl or aralkyl;
R$^{10}$ and R$^{11}$ are each independently H, alkyl, —(CH$_2$)$_p$—OH, —(CH$_2$)$_p$—OR$^9$, cycloalkyl, cycloalkylalkyl, aryl, or taken together with the nitrogen atom to which they are attached, R$^{10}$ and R$^{11}$ form a 4–7 member heterocycle, optionally interrupted by one or more O, S or NR$^8$ groups;
R$^{12}$ and R$^{12a}$ are each independently H, alkyl, or aryl;
R$^{13}$ is H, alkyl, —C(=O)R$^{14}$, —S(=O)$_2$R$^{14}$, or —C(=O)OR$^{15}$;
R$^{14}$ is alkyl, cycloalkyl, cycloalkylalkyl, alkylcycloalkyl, heteroaryl, heteroalkyl, heteroaralkyl, aryl, or aralkyl;
R$^{15}$ is alkyl, cycloalkyl, alkylcycloalkyl, or aralkyl;
r is the integer 0, 1, 2, 3, or 4;
p is the integer 2, 3, 4, 5, or 6; or
a stereoisomer, prodrug, pharmaceutically acceptable salt, hydrate, solvate, acid salt hydrate, N-oxide or isomorphic crystalline form thereof.

In certain preferred embodiments, R$^1$ is —OH. More preferably R$^1$ is —OH and has the configuration shown in the structure below:

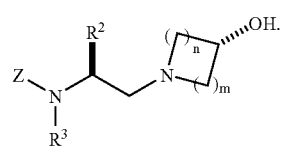

I

In certain preferred embodiments, R$^2$ is aryl. More preferably, R$^2$ is phenyl.

In certain preferred embodiments, R$^3$ is alkyl. More preferably, R$^3$ is C$_{1-5}$ alkyl. Even more preferably, R$^3$ is methyl.

In certain other preferred embodiments, compounds of formula I have formula II:

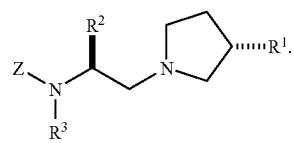

II

More preferably, R$^1$ is —OH. In certain alternate preferred embodiments of formula II compounds, R$^2$ is aryl. More preferably, R$^2$ is phenyl. In certain other alternate preferred embodiments of formula II compounds, R$^3$ is alkyl. More preferably, R$^3$ is methyl.

In yet other alternate preferred embodiments of formula II compounds, Z is:

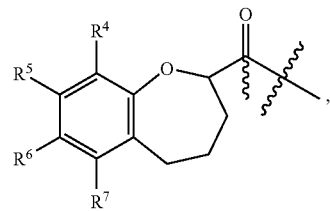

-continued
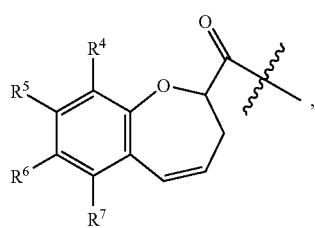
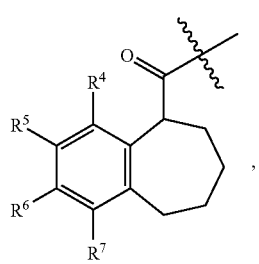
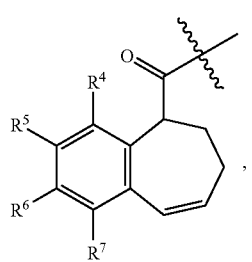
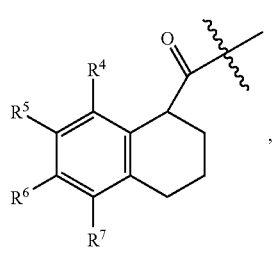
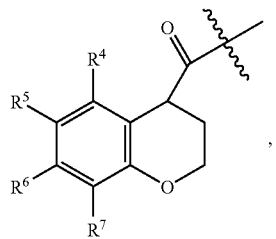
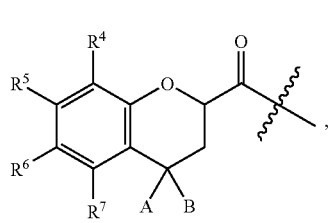
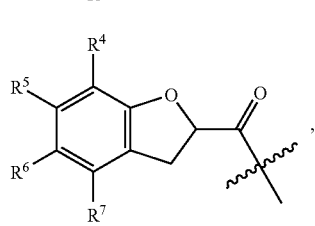
-continued
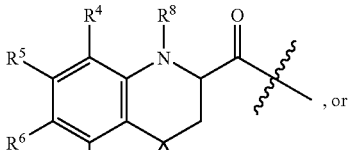
, or
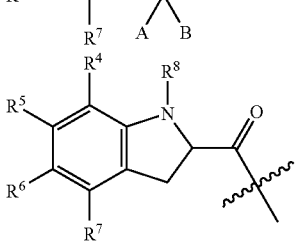
More preferably in the hereinabove formula II compounds, Z is:
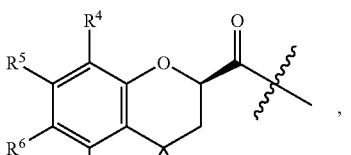
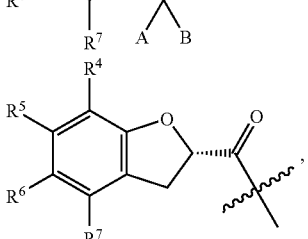
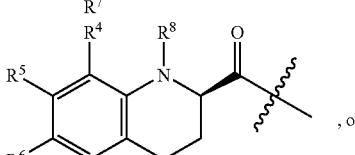
, or
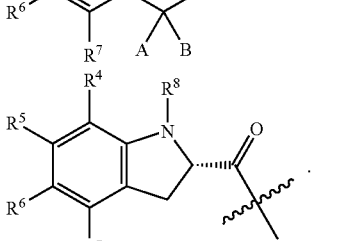
Even more preferably in the hereinabove formula II compounds, Z is:
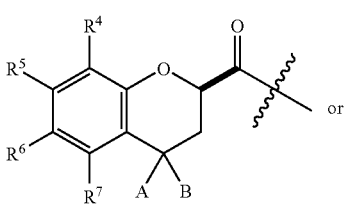
or -continued

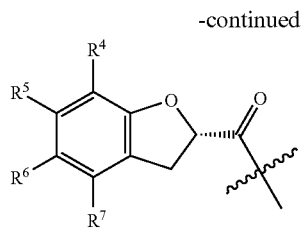

Even more preferably when Z is as shown above, $R^4$ and $R^7$ are H.

Alternately, even more preferably in the hereinabove formula II compounds when Z is:

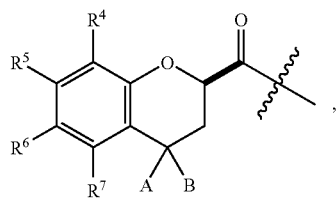

then A and B are H.

In certain other preferred embodiments of formula II compounds, Z is:

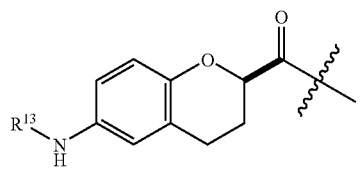

In certain other preferred embodiments of formula II compounds, Z is:

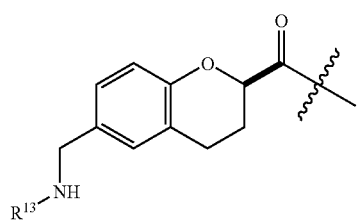

In certain other preferred embodiments of formula II compounds, Z is:

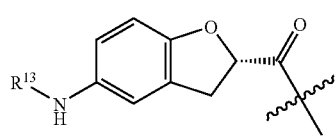

In certain other preferred embodiments of formula II compounds, Z is:

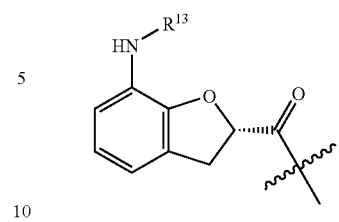

In certain other preferred embodiments of formula II compounds, Z is:

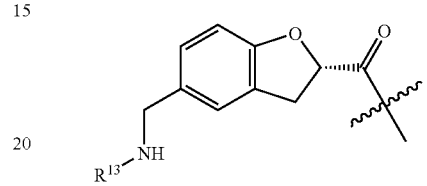

In any of the above teachings, a compound of the invention may be either a compound of one of the formulae herein described, or a stereoisomer, prodrug, pharmaceutically acceptable salt, hydrate, solvate, acid salt hydrate, N-oxide or isomorphic crystalline form thereof.

The compounds employed in the methods of the present invention may exist in prodrug form. As used herein, "prodrug" is intended to include any covalently bonded carriers which release the active parent drug, for example, as according to formula I or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example formula I, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

In certain preferred embodiments, the compounds of the invention do not substantially inhibit cytochrome P450 enzymatic activity. As used herein, the phrase "do not substantially inhibit" means that the activity of the cytochrome P450 is reduced by less than about 25% of its normal physiological activity, preferably less than about 10%, more preferably less than about 5%, even more preferably less than about 1%. Preferably, this lack of effect on inhibition may be measured, as described in the examples, by measuring the inhibition of the cytochrome P450 catalyzed conversion of 7-methoxy-4-(aminomethyl)coumarin (MAMC) to 7-hydroxy-4-(aminomethyl)coumarin (HAMC) for CYP2D6 or the conversion of dibenzylfluorescein (DBF) to fluorescein for CYP2C9 and CYP3A4. In certain preferred embodiments, the compounds exhibit an $IC_{50}$ (CYP) greater than about 1,000 nM and, more preferably, greater than about 10,000 nM, particularly with respect to CYP2D6, CYP2C9 and/or CYP3A4, and most particularly with respect to CYP2D6.

In certain preferred embodiments, the compounds, pharmaceutical compositions and methods of the present invention may involve a peripheral opioid antagonist compound. In preferred form, the peripheral opioid antagonist compounds employed in the methods of the present invention exhibit high levels of activity with respect to peripheral tissue, such as, gastrointestinal tissue, while exhibiting reduced, and preferably substantially no, CNS activity. The term "peripheral" designates that the compound acts primarily on physiological systems and components external to the central nervous system. The phrase "substantially no CNS activity," as used herein, means that less than about 20% of the pharmacological activity of the compounds employed in the present methods is exhibited in the CNS, preferably less than about 15%, more preferably less than about 10%, even more preferably less than about 5% and most preferably 0% of the pharmacological activity of the compounds employed in the present methods is exhibited in the CNS.

Furthermore, it is preferred in certain embodiments of the invention that the compound does not substantially cross the blood-brain barrier and thereby decrease the beneficial activity of the opioid. The phrase "does not substantially cross," as used herein, means that less than about 20% by weight of the compound employed in the present methods crosses the blood-brain barrier, preferably less than about 15% by weight, more preferably less than about 10% by weight, even more preferably less than about 5% by weight and most preferably 0% by weight of the compound crosses the blood-brain barrier. Selected compounds can be evaluated for CNS penetration by determining plasma and brain levels following i.v. administration.

Compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2d. Ed., Wiley & Sons, 1991.

The kappa agonist compounds employed in the methods of the present invention may be administered by any means that results in the contact of the active agent with the agent's site of action in the body of a patient. The compounds may be administered by any conventional means available for use in conjunction with pharmaceuticals, either as individual therapeutic agents or in a combination of therapeutic agents. For example, they may be administered as the sole active agent in a pharmaceutical composition, or they can be used in combination with other therapeutically active ingredients including, for example, opioid analgesic agents. In such combinations, selected compounds of the invention may provide equivalent or even enhanced therapeutic activity such as, for example, pain ameliorization, while providing reduced adverse side effects associated with opioids, such as addiction or pruritus, by lowering the amount of opioid required to achieve a therapeutic effect.

The compounds are preferably combined with a pharmaceutical carrier selected on the basis of the chosen route of administration and standard pharmaceutical practice as described, for example, in *Remington's Pharmaceutical Sciences* (Mack Publishing Co., Easton, Pa., 1980), the disclosures of which are hereby incorporated herein by reference, in their entirety.

In addition to the pharmaceutical carrier, the compounds of formula I may be co-administered with at least one opioid. Suitable opioids include alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol and mixtures thereof.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, rectal, intraocular, intrasynovial, transepithelial including transdermal, ophthalmic, sublingual and buccal; topically including ophthalmic, dermal, ocular, rectal, and nasal inhalation via insulation aerosol.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should preferably contain at least 0.1% of active compound. The percentage of the compositions and preparations may, of course, be varied and may conveniently be, for example, from about 2 to about 6% of the weight of the unit. The amount of active compound in such therapeutically useful compositions is preferably such that a suitable dosage will be obtained. Preferred compositions or preparations according to the present invention may be prepared so that an oral dosage unit form contains from about 0.1 to about 1000 mg of active compound.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or a pharmacologically acceptable salt can be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compound in the required amount, in the appropriate solvent, with various of the other ingredients enumerated above, as required, followed by filtered sterilization. Generally, dispersions may be prepared by incorporating the sterilized active ingredient into a sterile vehicle that contains the basic dispersion medium and the required other ingredients from those enumerated above. In the case of sterile powders for the preparation of sterile injectable solutions, the preferred methods of preparation may include vacuum drying and the freeze-drying technique that yield a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compound, chosen route of administration and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. The therapeutic human dosage, based on physiological studies using rats, may generally range from about 0.01 mg to about 100 mg/kg of body weight per day, and all combinations and subcombinations of ranges therein. Alternatively, the therapeutic human dosage may be from about 0.4 mg to about 10 g or higher, and may be administered in several different dosage units from once to several times a day. Generally speaking, oral administration may require higher dosages.

The compounds of the invention may also be formulated with other optional active ingredients, in addition to the optional opioids, and in addition to the optional pharmaceutical-acceptable carriers. Other active ingredients include, but are not limited to, antibiotics, antivirals, antifungals, anti-inflammatories, including steroidal and non-steroidal anti-inflammatories, anesthetics and mixtures thereof. Such additional ingredients include any of the following:

a. Antibacterial Agents

Aminoglycosides, such as Amikacin, Apramycin, Arbekacin, Bambermycins, Butirosin, Dibekacin, Dihydrostreptomycin, Fortimicin(s), Fradiomycin, Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin;

Amphenicols, such as Azidamfenicol, Chloramphenicol, Chloramphenicol Palmirate, Chloramphenicol Pantothenate, Florfenicol, Thiamphenicol;

Ansamycins, such as Rifamide, Rifampin, Rifamycin and Rifaximin;

β-Lactams;

Carbapenems, such as Imipenem;

Cephalosporins, such as 1-Carba (dethia) Cephalosporin, Cefactor, Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin;

Cephamycins such as Cefbuperazone, Cefmetazole, Cefminox, Cefetan and Cefoxitin;

Monobactams such as Aztreonam, Carumonam and Tigemonan;

Oxacephems such as Flomoxef and Moxolactam;

Penicillins such as Amidinocillin, Amdinocillin, Pivoxil, Amoxicillin, Ampicillan, Apalcillin, Aspoxicillin, Azidocillan, Azlocillan, Bacampicillin, Benzylpenicillinic Acid, Benzylpenicillin, Carbenicillin, Carfecillin, Carindacillin, Clometocillin, Cloxacillin, Cyclacillin, Dicloxacillin, Diphenicillin, Epicillin, Fenbenicillin, Floxicillin, Hetacillin, Lenampicillin, Metampicillin, Methicillin, Mezlocillin, Nafcillin, Oxacillin, Penamecillin, Penethamate Hydriodide, Penicillin G Benethamine, Penicillin G Benzathine, Penicillin G Benzhydrylamine, Penicillin G Calcium, Penicillin G Hydragamine, Penicillin G Potassium, Penicillin G. Procaine, Penicillin N, Penicillin O, Penicillin V, Penicillin V Benzathine, Penicillin V Hydrabamine, Penimepicycline, Phenethicillin, Piperacillin, Pivapicillin, Propicillin, Quinacillin, Sulbenicillin, Talampicillin, Temocillin and Ticarcillin;

Lincosumides such as Clindamycin and Lincomycin;

Macrolides such as Azithromycin, Carbomycin, Clarithromycin, Erythromycin(s) and Derivatives, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramnicidin S, Mikamycin, Polymyxin, Polymyxin β-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin and Zinc Bacitracin;

Tetracyclines such as Spicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; and others such as Cycloserine, Mupirocin, Tuberin.

b. Synthetic Antibacterials 2,4-Diaminopyrimidines such as Brodimoprim, Tetroxoprim and Trimethoprim;

Nitrofurans such as Furaltadone, Furazolium, Nifuradene, Nifuratel, Nifurfoline, Nifurpirinol, Nifurprazine, Nifurtoinol and Nitrofurantoin;

Quinolones and analogs thereof, such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Perfloxacin, Pipemidic Acid, Piromnidic Acid, Rosoxacin, Temafloxacin and Tosufloxacin;

Sulfonamides such as Acetyl Sulfamethoxypyrazine, Acetyl Sulfisoxazole, Azosulfamide, Benzylsulfamide, Chloramine-β, Chloramine-T, Dichloramine-T, Formosulfathiazole, N.sup.2-Formyl-sulfisomidine, N.sup.4-β-D-Glucosylsulfanilamide, Mafenide, 4'-(Methyl-sulfamoyl) sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, sulfamidochrysoidine, Sulfamoxole, Sulfanilarnide, Sulfanilamidomethanesulfonic Acid Triethanolamine Salt, 4-Sulfanilamidosalicyclic Acid, $N^4$-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones, such as Acedapsone, Acediasulfone, Acetosulfone, Dapsone, Diathymosulfone, Glucosulfone, Solasulfone, Succisulfone, Sulfanilic Acid, p-Sulfanilylbenzylamine, p,p'-sulfonyldianiline-N,N'digalactoside, Sulfoxone and Thiazolsulfone;

Others such as Clofoctol, Hexedine, Magainins, Methenamine, Methenamine Anhydromethylene-citrate, Methenamine Hippurate, Methenamine Mandelate, Methenamine Sulfosalicylate, Nitroxoline, Squalamine and Xibomol.

c. Antifungal (Antibiotics)

Polyenes such as Amphotericin-B, Candicidin, Dermostatin, Filipin, Fungichromin, Hachimycin, Hamycin, Lucensomycin, Mepartricin, Natamycin, Nystatin, Pecilocin, Perimycin; and others, such as Azaserine, Griseofulvin, Oligomycins, Pyrrolnitrin, Siccanin, Tubercidin and Viridin.

d. Antifungal (Synthetic)

Allylamines such as Naftifine and terbinafine;

Imidazoles such as Bifonazole, Butoconazole, Chlordantoin, Chlormidazole, Cloconazole, Clotrimazole, Econazole, Enilconazole, Finticonazole, Isoconazole, Ketoconazole, Miconazole, Omoconazole, Oxiconazole Nitrate, Sulconazole and Tioconazole;

Triazoles such as Fluconazole, Itraconazole, Terconazole;

Others such as Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sulbentine, Tenonitrozole, Tolciclate, Tolindate, Tolnaftate, Tricetin, Ujothion, and Undecylenic Acid.

e. Antiglaucoma Agents

Antiglaucoma agents, such as Dapiprazoke, Dichlorphenamide, Dipivefrin and Pilocarpine.

f. Anti-inflammatory Agents

Corticosteroids, aminoarylcarboxylic Acid Derivatives such as Etofenamate, Meclofenamic Acid, Mefanamic Acid, Niflumic Acid;

Arylacetic Acid Derivatives such as Acemetacin, Amfenac Cinmetacin, Clopirac, Diclofenac, Fenclofenac, Fenclorac, Fenclozic Acid, Fentiazac, Glucametacin, Isozepac, Lonazolac, Metiazinic Acid, Oxametacine, Proglumetacin, Sulindac, Tiaramide and Tolmetin;

Arylbutyric Acid Derivatives such as Butibufen and Fenbufen;

Arylcarboxylic Acids such as Clidanac, Ketorolac and Tinoridine;

Arylpropionic Acid Derivatives such as Bucloxic Acid, Carprofen, Fenoprofen, Flunoxaprofen, Ibuprofen, Ibuproxam, Oxaprozin, Piketoprofen, Pirprofen, Pranoprofen, Protizinic Acid and Tiaprofenic Add;

Pyrazoles such as Mepirizole;

Pyrazolones such as Clofezone, Feprazone, Mofebutazone, Oxyphenbutazone, Phenylbutazone, Phenyl Pyrazolidininones, Suxibuzone and Thiazolinobutazone;

Salicylic Acid Derivatives such as Bromosaligenin, Fendosal, Glycol Salicylate, Mesalamine, 1-Naphthyl Salicylate, Olsalazine and Sulfasalazine;

Thiazinecarboxamides such as Droxicam, Isoxicam and Piroxicam;

Others such as e-Acetamidocaproic Acid, S-Adenosylmethionine, 3-Amino-4-hydroxybutyric Acid, Amixetrine, Bendazac, Bucolome, Carbazones, Difenpiramide, Ditazol, Guaiazulene, Heterocyclic Aminoalkyl Esters of Mycophenolic Acid and Derivatives, Nabumetone, Nimesulide, Orgotein, Oxaceprol, Oxazole Derivatives, Paranyline, Pifoxime, 2-substituted-4,6-di-tertiary-butyl-s-hydroxy-1,3-pyrimidines, Proquazone and Tenidap.

g. Antiseptics

Guanidines such as Alexidine, Ambazone, Chlorhexidine and Picloxydine;

Halogens/Halogen Compounds such as Bomyl Chloride, Calcium Iodate, Iodine, Iodine Monochloride, Iodine Trichloride, Iodoform, Povidone-Iodine, Sodium Hypochlorite, Sodium Iodate, Symclosene, Thymol Iodide, Triclocarban, Triclosan and Troclosene Potassium;

Nitrofurans such as Furazolidone, 2-(Methoxymethyl)-5-Nitrofuran, Nidroxyzone, Nifuroxime, Nifurzide and Nitrofurazone;

Phenols such as Acetomeroctol, Chloroxylenol, Hexachlorophene, 1-Naphthyl Salicylate, 2,4,6-Tribromo-m-cresol and 3',4',5-Trichlorosalicylanilide;

Quinolines such as Aminoquinuride, Chloroxine, Chlorquinaldol, Cloxyquin, Ethylhydrocupreine, Halquinol, Hydrastine, 8-Hydroxyquinoline and Sulfate; and others, such as Boric Acid, Chloroazodin, m-Cresyl Acetate, Cupric sulfate and Ichthammol.

h. Antivirals

Purines/Pyrimidinones, such as 2-Acetyl-Pyridine 5-((2-pyridylamino)thiocarbonyl)Thiocarbonohydrazone, Acyclovir, Dideoxyadenosine, dideoxycytidine, Dideoxyinosine, Edoxudine, Floxuridine, Ganciclovir, Idoxuridine, MADU, Pyridinone, Trifluridine, Vidrarbine and Zidovudline;

others such as Acetylleucine Monoethanolamine, Acridinamine, Alkylisooxazoles, Amantadine, Amidinomycin, Cuminaldehyde Thiosemicarbzone, Foscamet Sodium, Kethoxal, Lysozyme, Methisazone, Moroxydine, Podophyllotoxin, Ribavirin, Rimantadine, Stallimycin, Statolon, Thymosins, Tromantadine and Xenazoic Acid.

In certain embodiments, fused bicyclic carboxamide derivatives of the present invention, and particularly fused bicyclic carboxamide derivatives of formula II, wherein $R^1$ is OH and Z is:

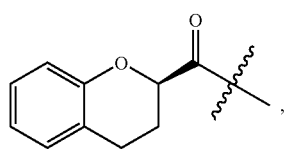,

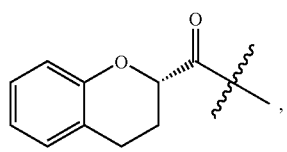,

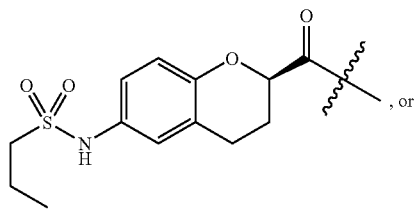, or

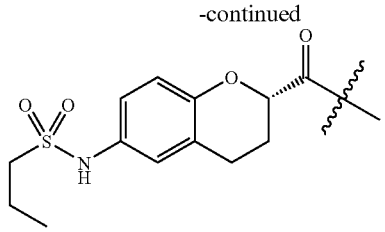

15

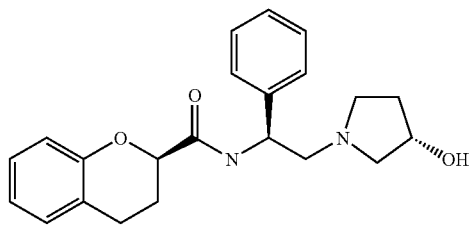

16

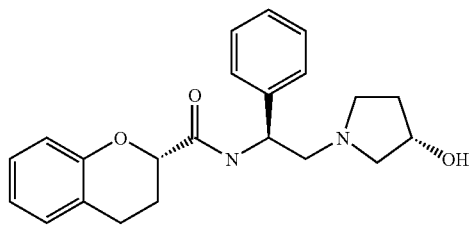

27

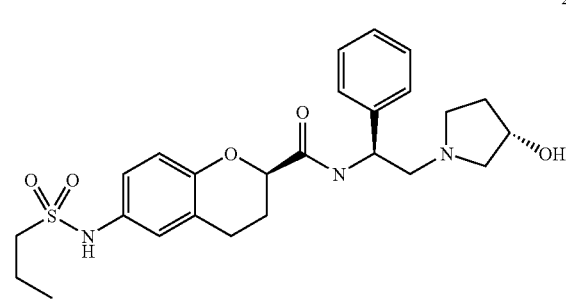

28

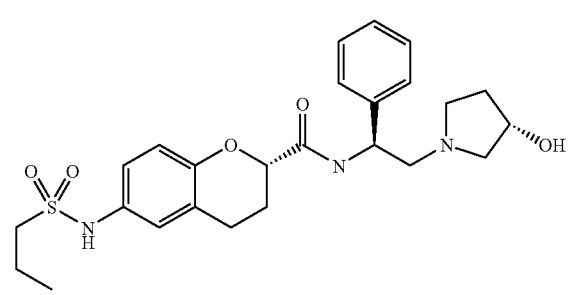

have been characterized in opioid receptor binding assays and show preferential binding to κ opioid receptors relative to μ and δ opioid receptors, as shown in the table below.

| Compound | Ki (κ) (nM) | Ki (μ) (nM) | Ki (δ) (nM) | Ki (CYP2D6) (nM) |
|---|---|---|---|---|
| 15 | 1.6 | >3000 | >3000 | 150 |
| 16 | 31 | >3000 | >3000 | 1400 |
| 27 | 1.6 | 480 | 120 | 6700 |
| 28 | 14 | >3000 | 1000 | 9500 |

In certain embodiments, the invention is directed to methods of binding opioid receptors, including κ opioid receptors, in a patient in need thereof, comprising the step of administering to the patient an effective amount of a compound of formula I. In certain preferred embodiments, the invention is directed to methods of binding κ opioid receptors, wherein said κ opioid receptors are located in the central nervous system. In other preferred embodiments, the invention is directed to methods of binding κ opioid receptors, wherein said κ opioid receptors are located peripherally to the central nervous system. In yet further preferred embodiments, the invention is directed to methods of binding opioid receptors, wherein said binding agonizes the activity of said opioid receptors. In other preferred embodiments, the invention is directed to methods of binding opioid receptors, wherein the compound of formula I does not substantially cross the blood-brain barrier.

In yet another embodiment, the invention is directed to methods for preventing or treating gastrointestinal dysfunction comprising the step of administering to a patient in need thereof, a composition comprising an effective amount of a compound of formula I.

In other embodiments, the invention is directed to methods for preventing or treating ileus comprising the step of administering to a patient in need thereof, a composition comprising an effective amount of a compound of formula I.

In another embodiment, the invention is directed to methods for preventing or treating pain comprising the step of administering to a patient in need thereof, a composition comprising an effective amount of an opioid and an effective amount of a compound of formula I.

In another embodiment, the invention is directed to methods for preventing or treating pruritic dermatoses and conditions characterized by pruritic dermatosis as a symptom, including allergic dermatitis, atopy, contact dermatitis, psoriasis, eczema, opioid-induced pruritus, and insect bites, comprising the step of administering to a patient in need thereof, a composition comprising an effective amount of a compound of formula I.

In another embodiment, the invention is directed to methods for preventing or treating cerebral edema, comprising the step of administering to a patient in need thereof, a composition comprising an effective amount of a compound of formula I.

In other embodiments, the invention is directed to methods for preventing or treating oxygen supply deficiency of the central nervous system, comprising the step of administering to a patient in need thereof, a composition comprising an effective amount of a compound of formula I.

In another embodiment, the invention is directed to methods for inducing diuresis, comprising the step of administering to a patient in need thereof, a composition comprising an effective amount of a compound of formula I.

In yet another embodiment, the invention is directed to methods for preventing or treating tussis, comprising the step of administering to a patient in need thereof, a composition comprising an effective amount of a compound of formula I.

The carboxamide derivatives of the present invention may be prepared according to the general methods depicted in Schemes 1 through 24. Examples of these carboxamides include, but are not limited to, derivatives of: 2,3,4,5-tetrahydro-benzo[b]oxepine-2-carboxamide, 6,7,8,9-tetrahydro-5H-benzocycloheptene-5-carboxamide, 1,2,3,4-tetrahydronaphthalene-1-carboxamide, chroman-2-carboxamide, 2,3-dihydro-benzofuran-2-carboxamide, chroman-4-carboxamide, 2,3-dihydroindole-2-carboxamide and 1,2,3,4-tetrahydro-quinoline-2-carboxamide.

The synthesis of representative benzoxepine carboxamides derivatives $1g_1$*, $1g_2$*, 2 and 3* is shown in Scheme 1. Wittig reaction of commercially available 5-chloro-2-hydroxy-benzaldehyde gave the vinyl sustituted phenol 1a, which was alkylated with ethyl bromoacetate to afford the ester 1b. Allylation of the carbon atom alpha to the ester functionality yielded the corresponding diene 1c, which was subjected to ring closing olefin metathesis using Grubbs catalyst (benzylidene-bis(tricyclohexylphosphine)dichlororuthenium) to provide the key benzoxepine intermediate 1d. Hydrolysis of the ester under basic conditions gave the acid 1e which was hydrogenated to afford the saturated acid 1f. Coupling of 1e, (R,S)-7-Chloro-2,3-dihydro-benzo[b]oxepine-2-carboxylic acid, with 1-(2-methylamino-(S)-2-phenyl-ethyl)-pyrrolidin-(S)-3-ol in the presence of Mukaiyama acylating reagent (2-chloro-1-methylpyridinium iodide) yielded, after chromatography purification over silica gel, two pure diastereomers ($1g_1$* and $1g_2$*) in which the stereochemical integrity of the pyrrolidinol moiety was maintained. Using the same coupling conditions, reaction of 1f, (R,S)-7-Chloro-2,3,4,5-tetrahydro-benzo[b]oxepine-2-carboxylic acid with 1-(2-methylamino-(S)-2-phenyl-ethyl)-pyrrolidin-(S)-3-ol gave 2 as a mixture of two diastereomers. The shorter retention time diastereomer 3* was separable by using silica gel chromatography. The absolute stereochemistry at the 2-position of $1g_1$*, $1g_2$* and 3* has not been established.

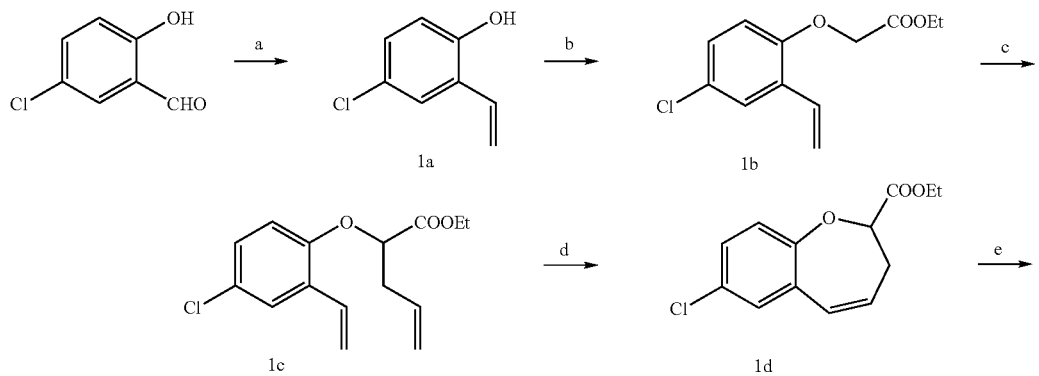

Scheme 1

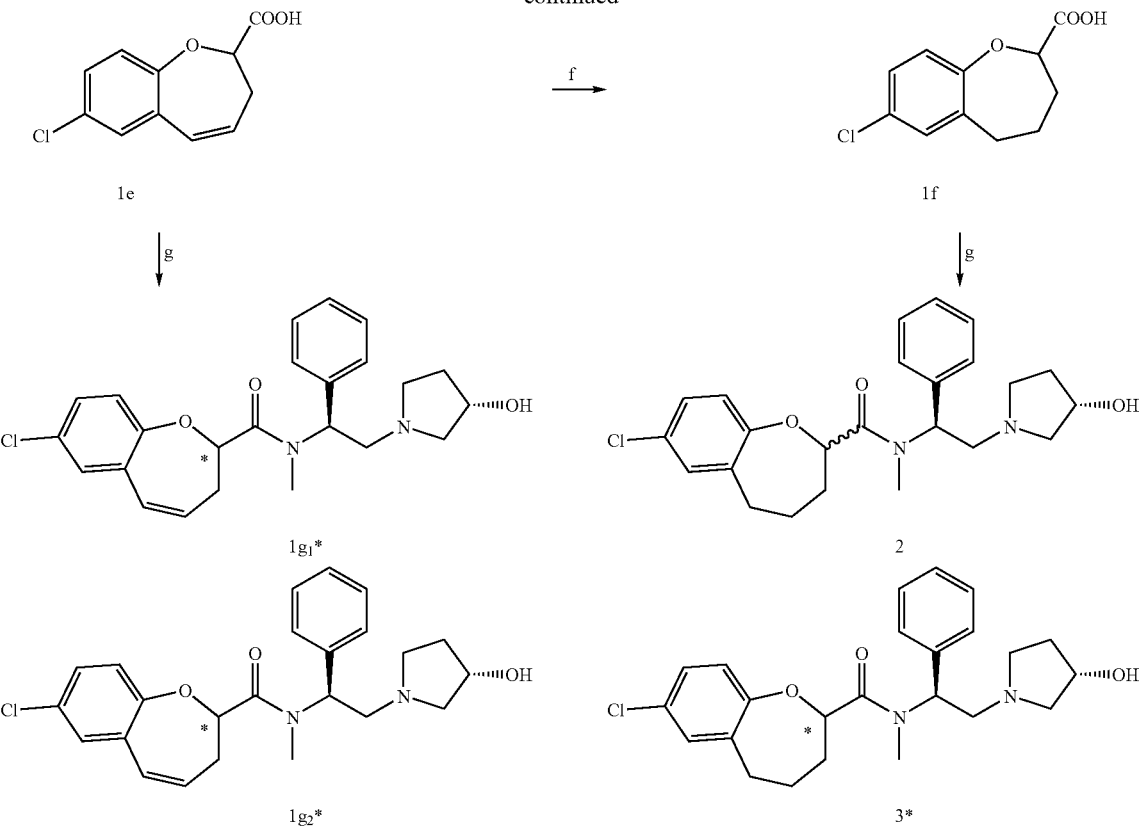
a) Ph₃PCH₃Br, n-BuLi, THF;
b) BrCH₂COOEt, K₂CO₃, acetone;
c) LiHMDS, THF, allyl bromide;
d) Grubbs' catalyst;
e) LiOH, MeOH — THF — H₂O;
f) H₂, 10% Pd/C, ethyl acetate;
g) 2-[(S)-3-hydroxy-pyrrolidin-1-yl]-(S)-1-phenyl-ethyl-methyl-amine dihydrochloride, 2-chloro-1-methyl-pyridinium iodide, Et₃N, dichloromethane.
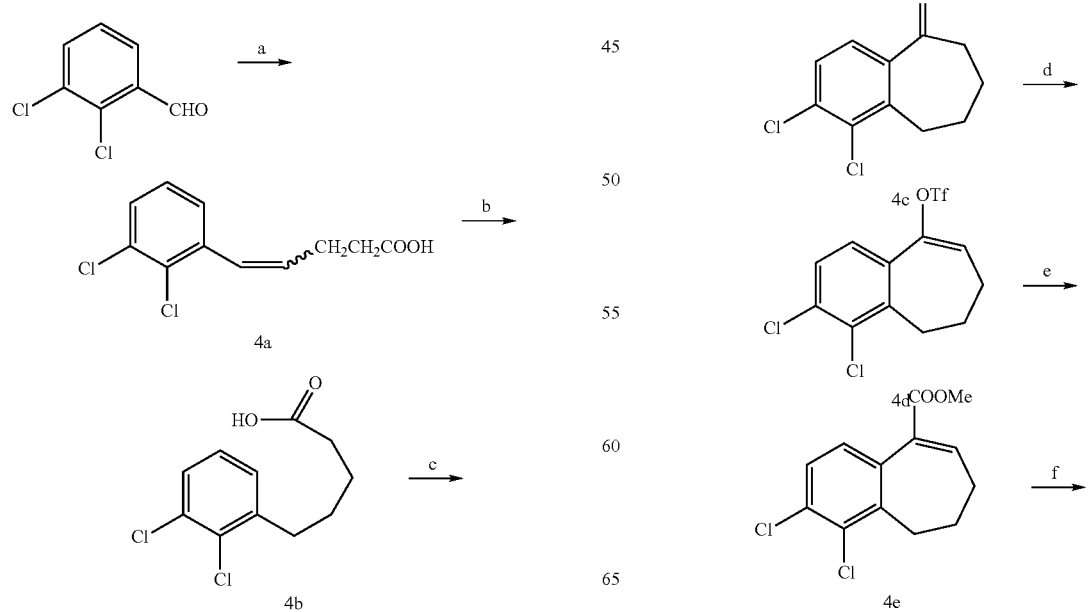

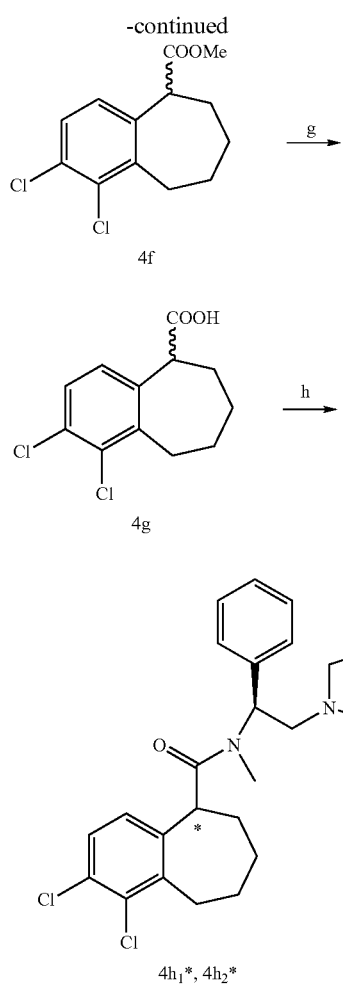

4f

4g

4h₁*, 4h₂* a) BrPh₃PCH₂CH₂COOH, t-BuOK;
b) H₂, Pd/C;
c) i. ClCOCOCl;
   ii. AlCl₃;
d) i. LiHMDS, THF, -78° C.;
   ii. PhNTf₂;
e) Pd(OAc)₂, dppp, CO, MeOH, DMF;
f) H₂, PtO₂;
g) LiOH, MeOH—THF—H₂O;
h) 1-(2-methylamino-(S)-2-phenyl-ethyl)-pyrrolidin-(S)-3-ol, dihydrochloride, 2-chloro-1-methylpyridinium iodide, dichloromethane Scheme 2 outlines the synthesis of representative benzocycloheptene derivatives 4h₁*, 4h₂*. (3-Carboxypropyl) triphenylphosphonium bromide was treated with potassium tert-butoxide and reacted with 2,3-dichlorobenzaldehyde to give the Wittig product 4a. The double bond was reduced by catalytic hydrogenation and the resulting saturated acid 4b was converted to the corresponding acyl chloride by treatment with oxalyl chloride and subsequently cyclized in the presence of aluminum chloride to give the ketone 4c. The ketone was converted to the enol triflate 4d under standard conditions and then subjected to the palladium-catalyzed carbon monoxide insertion reaction to give the α,β-unsaturated ester 4e. Reduction of the double bond by catalytic hydrogenation gave the saturated ester 4f. Basic hydrolysis of 4f afforded the corresponding acid 4g which was coupled with 1-(2-methylamino-(S)-2-phenyl-ethyl)-pyrrolidin-(S)-3-ol using the Mukaiyama acylation method to yield two pure diastereomers, 4h₁* and 4h₂* separable after chromatography on silica gel. The absolute stereochemistry at 5-position of 4h₁* and 4h₂* has not been conclusively established.

The synthesis of tetrahydronaphthalene carboxamide derivatives 5e₁* and 5e₂* is described in Scheme 3. Using the same reaction sequence as described above in Scheme 2, 7-methoxy-1-tetralone was converted to the acid, (R,S)-7-Methoxy-1,2,3,4-tetrahydronaphthalene-1-carboxylic acid 5d which was coupled with 1-(2-methylamino-(S)-2-phenyl-ethyl)-pyrrolidin-(S)-3-ol using the Mukaiyama acylation method to provide the two pure diastereomers 5e₁* and 5e₂*, separable after chromatography on silica gel.

Scheme 3

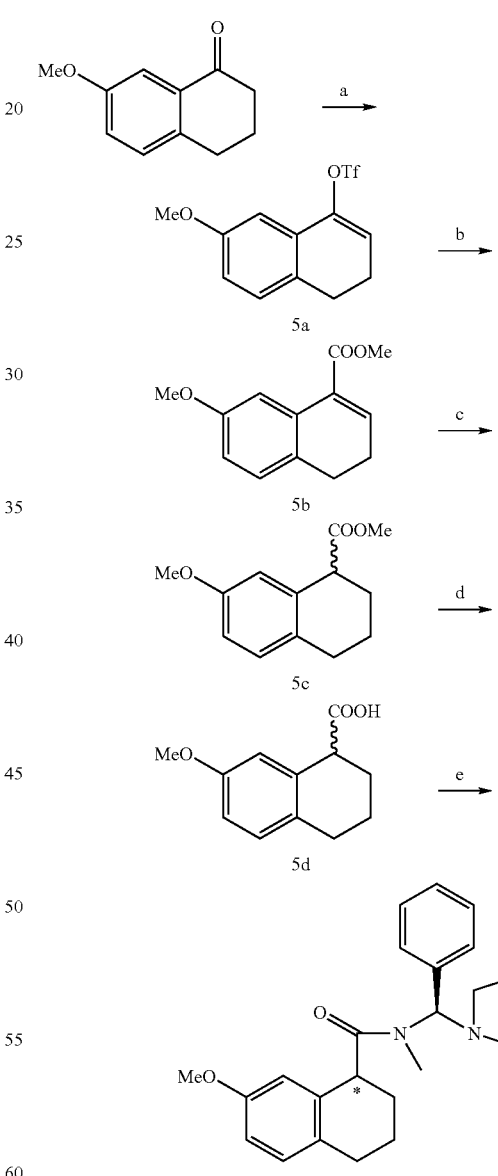

5a

5b

5c

5d

5e₁*, 5e₂* a) i. LiHMDS, THF;
   ii. PhNTf₂;
b) Pd(OAc)₂, dppp, Et₃N, MeOH, DMF, CO
c) H₂, PtO₂;
d) LiOH, MeOH—THF—H₂O;
e) 1-(2-methylamino-(S)-2-phenyl-ethyl)-pyrrolidin-(S)-3-ol, dihydrochloride, 2-chloro-1-methylpyridinium iodide, dichloromethane.

The synthesis of tetrahydronapthalene carboxamide derivatives 6g₁*, 6g₂*, 7a₁* and 7a₂* is described in Scheme 4. 5-Methoxy-1-tetralone was converted to (R,S)-5-Methoxy-3,4-dihydro-naphthalene-1-carboxylic acid methyl ester 6b which was catalytically hydrogenated to give the tetrahydronapthalene ester 6c using analogous chemistry to that described hereinabove for compound 4. Treatment of this ester 6c with sulfur trioxide N,N-dimethylformamide complex followed by reaction with oxalyl chloride gave the crude sulfonyl chloride 6d which was used directly for the next step without further purification. Reaction of the crude sulfonyl chloride with dimethylamine or pyrrolidine (step e) gave the corresponding 8-pyrrolidinylsulfamoyl- or 8-dimethylsulfamoyl- (R,S)-5-methoxy-1,2,3,4-tetrahydronaphthalene-1-carboxylic acid derivative 6e. Basic hydrolysis of the ester in each case gave the acid 6f. Using the Mukaiyama acylation condition described before, the acids obtained from step (f) were converted to 6g₁* and 6g₂* and 7a₁* and 7a₂*, each pair of diastereomers readily separable by column chromatography. The absolute stereochemistry of the individual diastereomers at the position adjacent to the carbonyl has not been conclusively established.

Scheme 4

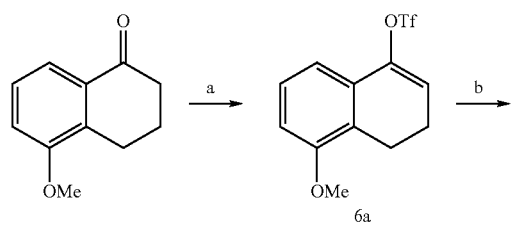

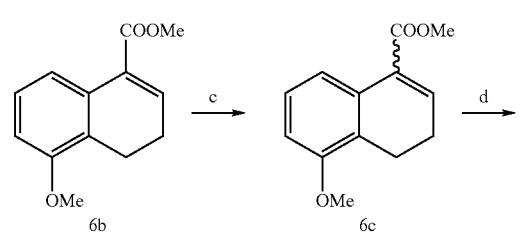

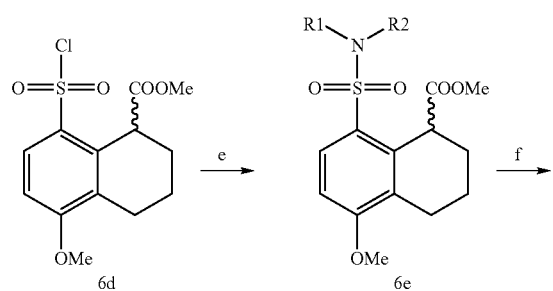

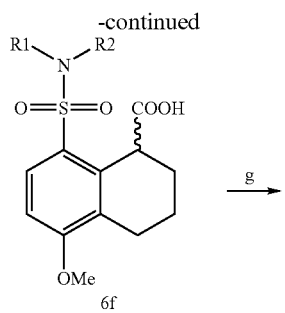

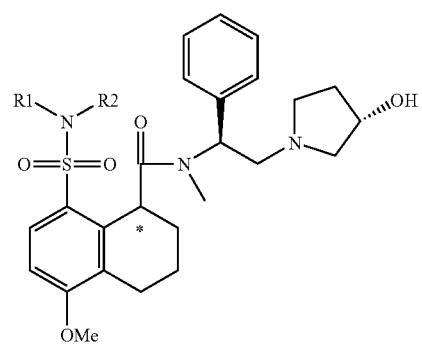

6g₁*, 6g₂*: R1, R2 = ——(CH₂)₄——
7a₁*, 7a₂*: R1 = R2 = CH₃ a) i. LiHMDS, THF;
   ii. PhNTf₂;
b) Pd(OAc)₂, dppp, Et₃N, MeOH, DMF, CO;
c) H₂, Pd/C;
d) i. HCON(CH₃)₂•SO₃;
   ii. ClCOCOCl;
e) (CH₃)₂NH or Pyrrolidine;
f) LiOH, MeOH—THF—H₂O;
g) 1-(2-methylamino-(S)-2-phenyl-ethyl)-pyrrolidin-(S)-3-ol, dihydrochloride, 2-chloro-1-methylpyridinium iodide, dichloromethane The synthesis of a range of chroman-2-carboxamide derivatives, 8 through 53, are illustrated in Schemes 5 through 13. Reaction of 2-bromo4-chloro-phenol with ethyl bromoacetate gave an ester 8a which was treated with lithium bis(trimethylsilyl)amide followed by reaction of the resulting anion with allyl bromide to yield the allylated product 8b.

Palladium catalyzed intramolecular Heck reaction of the bromoolefin 8b afforded the six-membered ring cyclization product 8c. Basic hydrolysis of 8c gave the acid 8d, which when coupled with 1-(2-methylamino-(S)-2-phenyl-ethyl)-pyrrolidin-(S)-3-ol using the Mukaiyama acylation method yielded 8 as a pair of diastereomers (Scheme 5).

Scheme 5

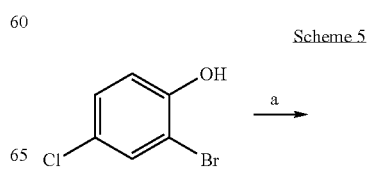

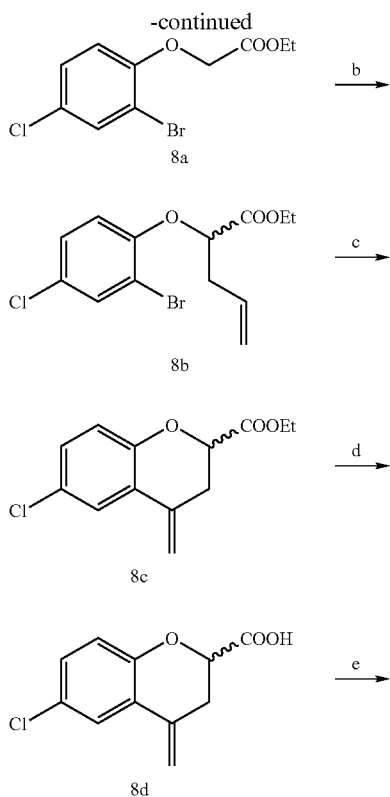
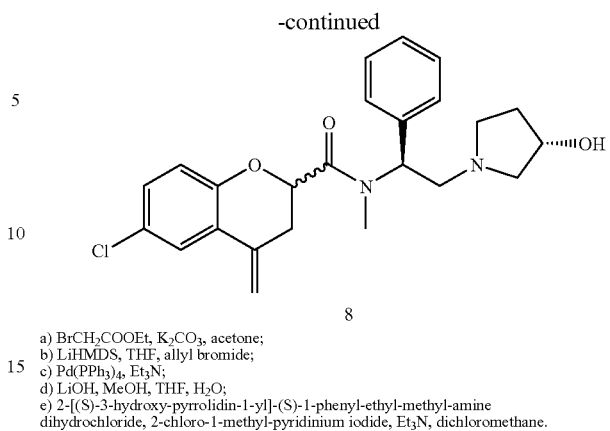

a) BrCH$_2$COOEt, K$_2$CO$_3$, acetone;
b) LiHMDS, THF, allyl bromide;
c) Pd(PPh$_3$)$_4$, Et$_3$N;
d) LiOH, MeOH, THF, H$_2$O;
e) 2-[(S)-3-hydroxy-pyrrolidin-1-yl]-(S)-1-phenyl-ethyl-methyl-amine dihydrochloride, 2-chloro-1-methyl-pyridinium iodide, Et$_3$N, dichloromethane.

Scheme 6 describes the synthesis of chroman carboxamide derivatives 9–13. Reaction of 4-chloroanisole with maleic anhydride in the presence of aluminum chloride (step a) gave the ketoacid 9a which was cyclized under basic conditions to furnish the chroman-2-carboxylic acid derivative 9b. Compound 9b was coupled with 1-(2-methylamino-(S)-2-phenyl-ethyl)-pyrrolidin-(S)-3-ol using the Mukaiyama acylation method to give the two pure diastereomers, 9 and 10. The ketoacid 9b was further reduced with triethylsilane in trifluoroacetic acid to provide the corresponding carboxylic acid 9c which was then coupled with 1-(2-methylamino-(S)-2-phenyl-ethyl)-pyrrolidin-(S)-3-ol using the Mukaiyama acylation method to give a pair of diastereomers, 11, which were chromatographically separated into the two pure diastereomers, 12 and 13.

Scheme 6

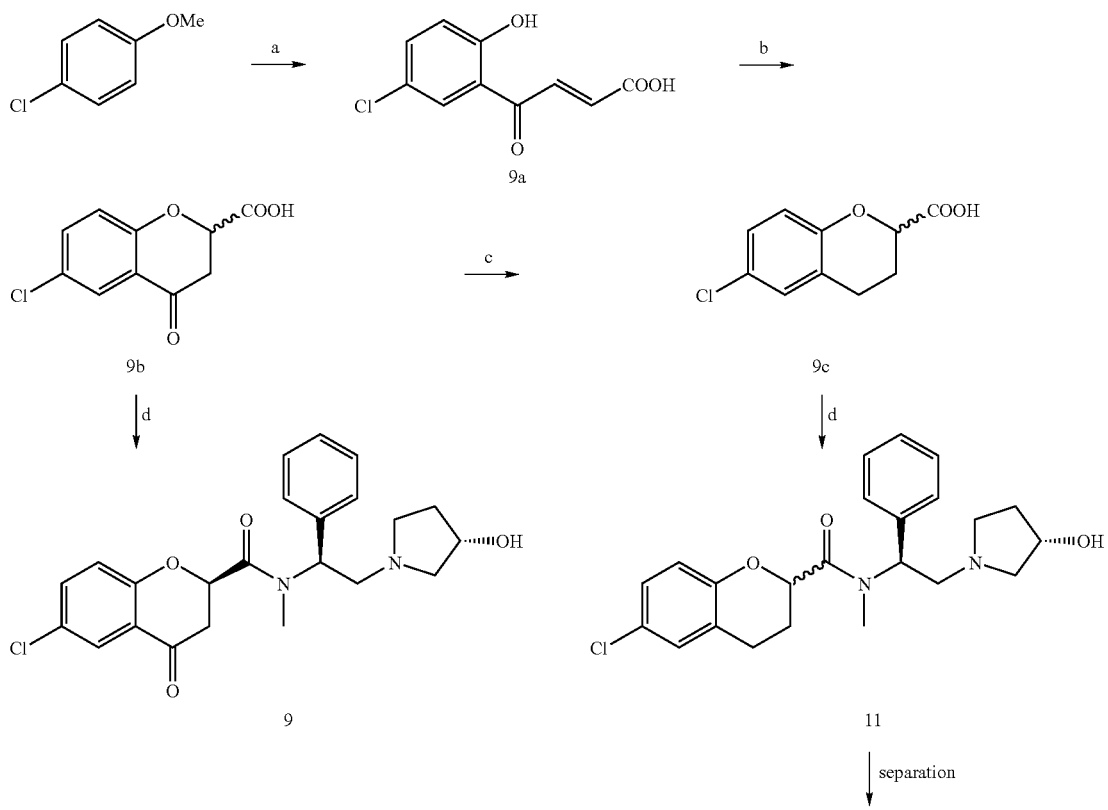

-continued

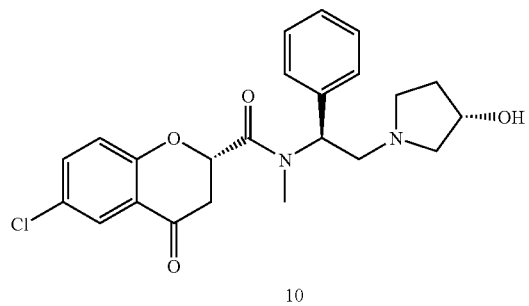

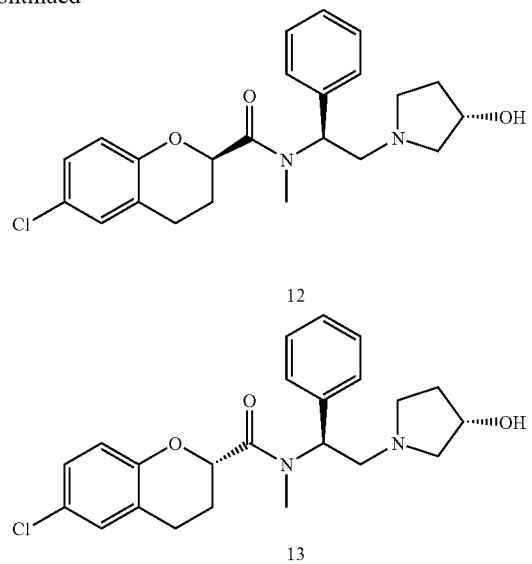

a) Maleic anhydride, AlCl₃;
b) NaOH aq.;
c) Et₃SiH, TFA;
d) 2-[(S)-3-hydroxy-pyrrolidin-1-yl]-(S)-1-phenyl-ethyl-methyl-amine dihydrochloride, 2-chloro-1-methyl-pyridinium iodide, Et₃N, dichloromethane.

The synthesis of chroman-2-carboxamide derivatives 14, 15, and 16 is summarized in Scheme 7. Chroman-2-carboxylic acid 14a was prepared using known methodology (WO 99/32475) from 2'-hydroxyacetophenone. The racemic acid was coupled with 1-(2-methylamino-(S)-2-phenyl-ethyl)-pyrrolidin-(S)-3-ol using the Mukaiyama acylation conditions described above. The enantiomerically pure (R)-chroman-2-carboxylic acid 14c₁ and (S)-chroman-2-carboxylic acid 14c₂ were obtained via chiral separation of the racemic acid. The two pure diastereomers 15 and 16, of mixture 14, were respectively prepared by coupling of the enantiomeric pure (R)-chroman-2-carboxylic acid 14c₁ or (S)-chroman-2-carboxylic acid 14c₂ with 1-(2-methylamino-(S)-2-phenyl-ethyl)-pyrrolidin-(S)-3-ol using TBTU [O-(benzotriazol-1-yl)-N,N,N', N'-tetramethyluronium tetrafluoroborate] as acylating reagent.

Scheme 7

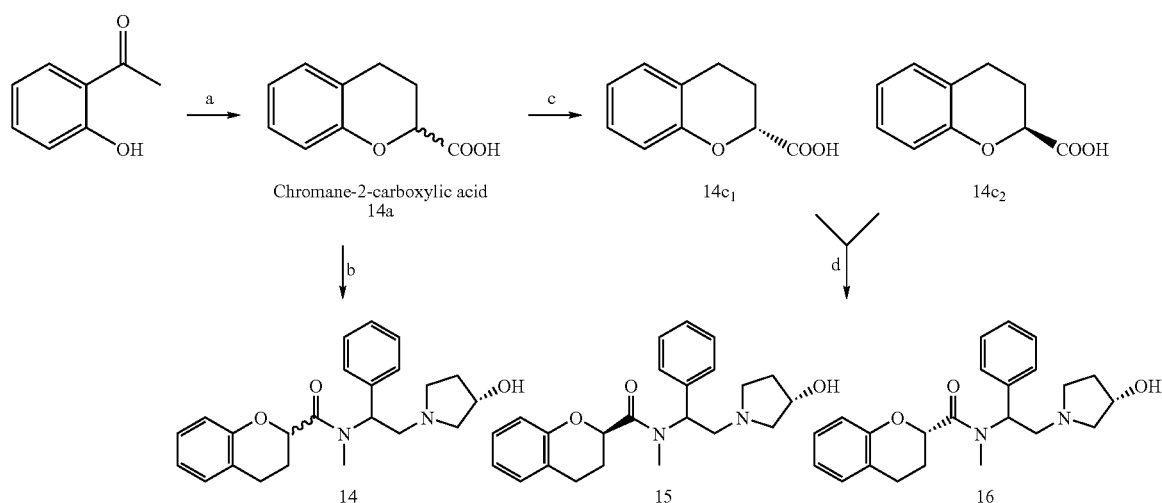

a) i. (COOEt)₂, NaOEt;
   ii. HOAc/HCl;
   iii. H₂, 10% Pd/C, HOAc;
b) 1-(2-methylamino-(S)-2-phenyl-ethyl)-pyrrolidin-(S)-3-ol dihydrochloride, 2-chloro-1-methylpyridinium iodide, dichloromethane
c) Chiral separation;
d) TBTU, i-Pr₂NEt, 1-(2-methylamino-(S)-2-phenyl-ethyl)-pyrrolidin-(S)-3-ol dihydrochloride.

Iodination of chroman-2-carboxylic acid 14a with benzyltrimethylammonium dichloroiodate in the presence of zinc chloride followed by the coupling of the resulting iodoacid 17a with 1-(2-methylamino-(S)-2-phenyl-ethyl)-pyrrolidin-(S)-3-ol using the Mukaiyama acylation condition yielded 17 (Scheme 8). Nigishi coupling of (R,S)-6-iodo-chroman-2-carboxylic acid 17a with 2-thienylzinc bromide in the presence of tetrakis(triphenylphosphine)palladium(0) gave the 6-thiophen substituted product 18a which was coupled with 1-(2-methylamino-(S)-2-phenyl-ethyl)-pyrrolidin-(S)-3-ol using the Mukaiyama acylation conditions described above to give 18 and 19 after chromatographic separation (Scheme 9).

Scheme 8

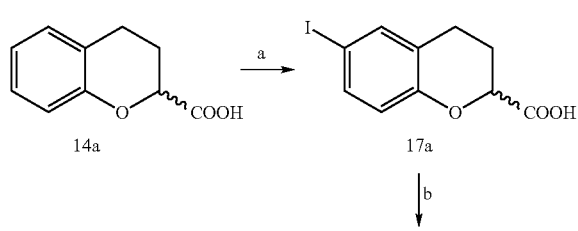

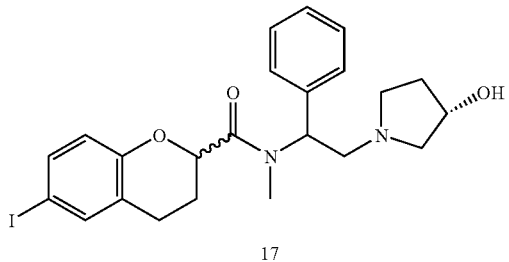

a) PhCH$_2$N(CH$_3$)$_3$ICl$_2$, ZnCl$_2$, HOAc;
b) 1-(2-methylamino-(S)-2-phenyl-ethyl)-pyrrolidin-(S)-3-ol dihydrochloride, 2-chloro-1-methylpyridinium iodide, dichloromethane.

Nitration of chroman-2-carboxylic acid 14a with nitric acid gave the nitroacid 20a which was coupled with 1-(2-methylamino-(S)-2-phenyl-ethyl)-pyrrolidin-(S)-3-ol using the Mukaiyama acylation conditions described above to give 20. Catalytic hydrogenation of 20 afforded 21 (Scheme 10).

Scheme 9

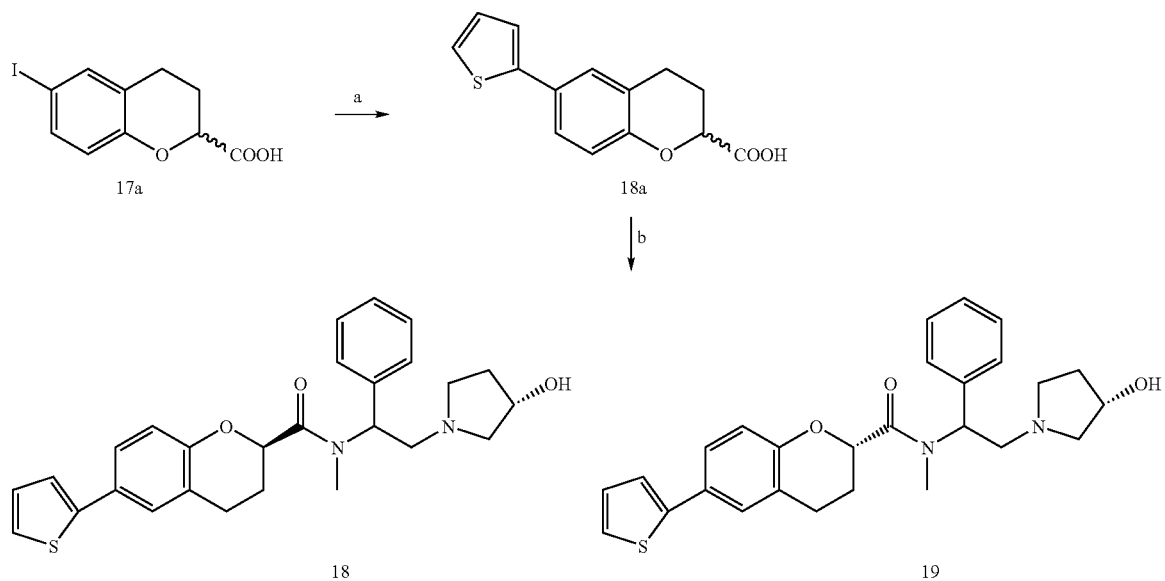

a) Pd(PPh$_3$)$_4$, 2-thienylzinc bromide, THF;
b) 1-(2-methylamino-(S)-2-phenyl-ethyl)-pyrrolidin-(S)-3-ol dihydrochloride, 2-chloro-1-methylpyridinium iodide, dichloromethane.

Scheme 10

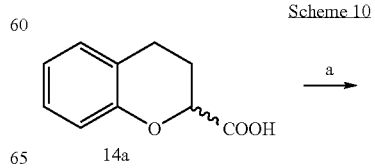

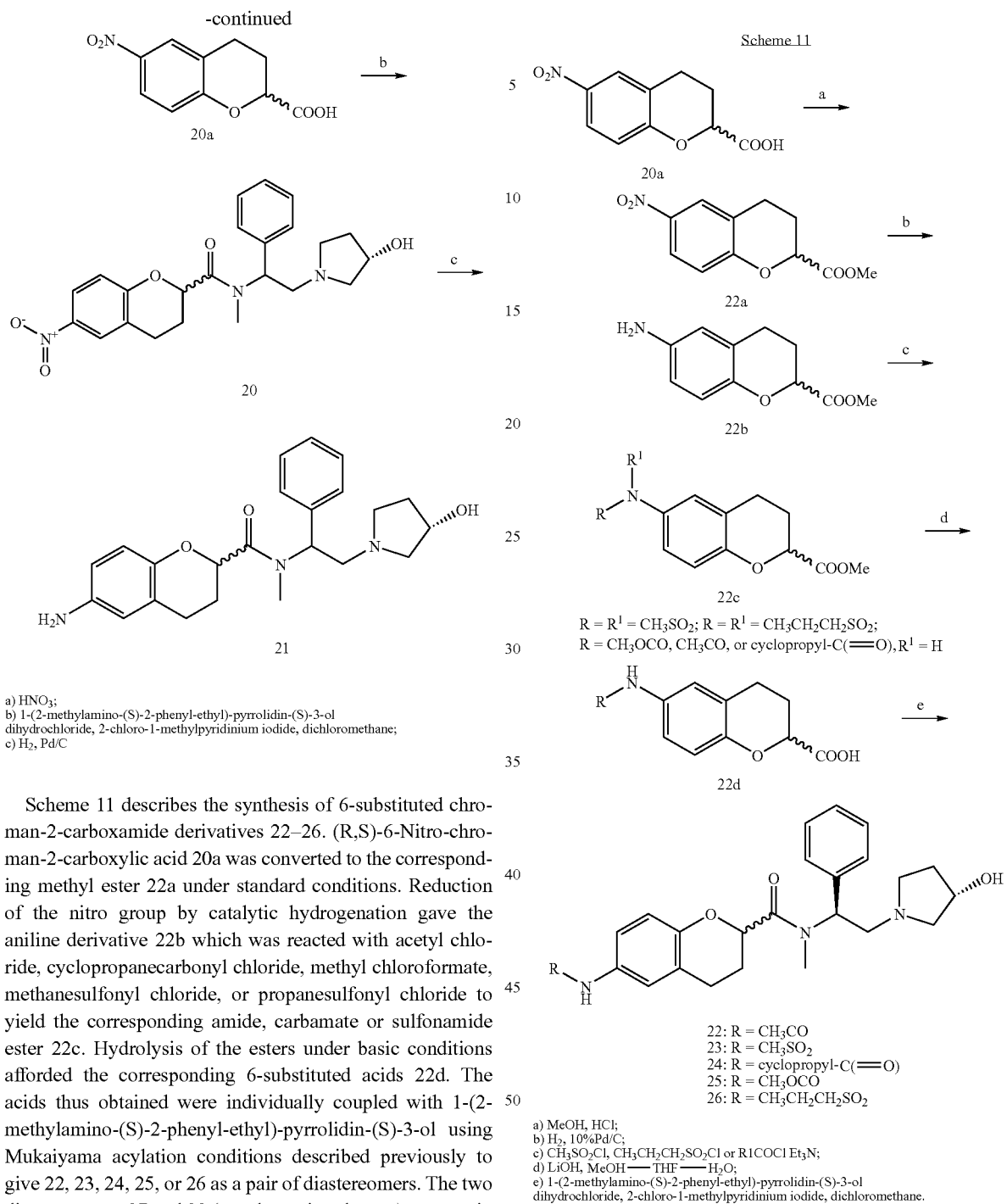

a) HNO₃;
b) 1-(2-methylamino-(S)-2-phenyl-ethyl)-pyrrolidin-(S)-3-ol dihydrochloride, 2-chloro-1-methylpyridinium iodide, dichloromethane;
c) H₂, Pd/C Scheme 11 describes the synthesis of 6-substituted chroman-2-carboxamide derivatives 22–26. (R,S)-6-Nitro-chroman-2-carboxylic acid 20a was converted to the corresponding methyl ester 22a under standard conditions. Reduction of the nitro group by catalytic hydrogenation gave the aniline derivative 22b which was reacted with acetyl chloride, cyclopropanecarbonyl chloride, methyl chloroformate, methanesulfonyl chloride, or propanesulfonyl chloride to yield the corresponding amide, carbamate or sulfonamide ester 22c. Hydrolysis of the esters under basic conditions afforded the corresponding 6-substituted acids 22d. The acids thus obtained were individually coupled with 1-(2-methylamino-(S)-2-phenyl-ethyl)-pyrrolidin-(S)-3-ol using Mukaiyama acylation conditions described previously to give 22, 23, 24, 25, or 26 as a pair of diastereomers. The two diastereomers, 27 and 28 (not shown in schemes), present in 26 were individually prepared from enantiomerically pure (R)-chroman-2-carboxylic acid 14c₁ and (S)-chroman-2-carboxylic acid 14c₂ respectively and reacted as shown in Scheme 11, steps a–d, for 26 to provide each of the (R)- and (S)-6-substituted chroman carboxylic acids. Each of the enantiomeric acids was then coupled with 1-(2-methylamino-(S)-2 -phenyl-ethyl)-pyrrolidin-(S)-3-ol using TBTU [O-(benzotriazol-1-yl)-N,N,N',N'-tetramethyluronium tetrafluoroborate] as acylating reagent to provide the diastereomer 27 or 28.

a) MeOH, HCl;
b) H₂, 10%Pd/C;
c) CH₃SO₂Cl, CH₃CH₂CH₂SO₂Cl or R1COCl Et₃N;
d) LiOH, MeOH — THF — H₂O;
e) 1-(2-methylamino-(S)-2-phenyl-ethyl)-pyrrolidin-(S)-3-ol dihydrochloride, 2-chloro-1-methylpyridinium iodide, dichloromethane.

Scheme 12

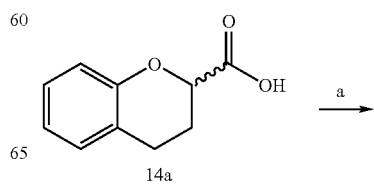

14a

-continued

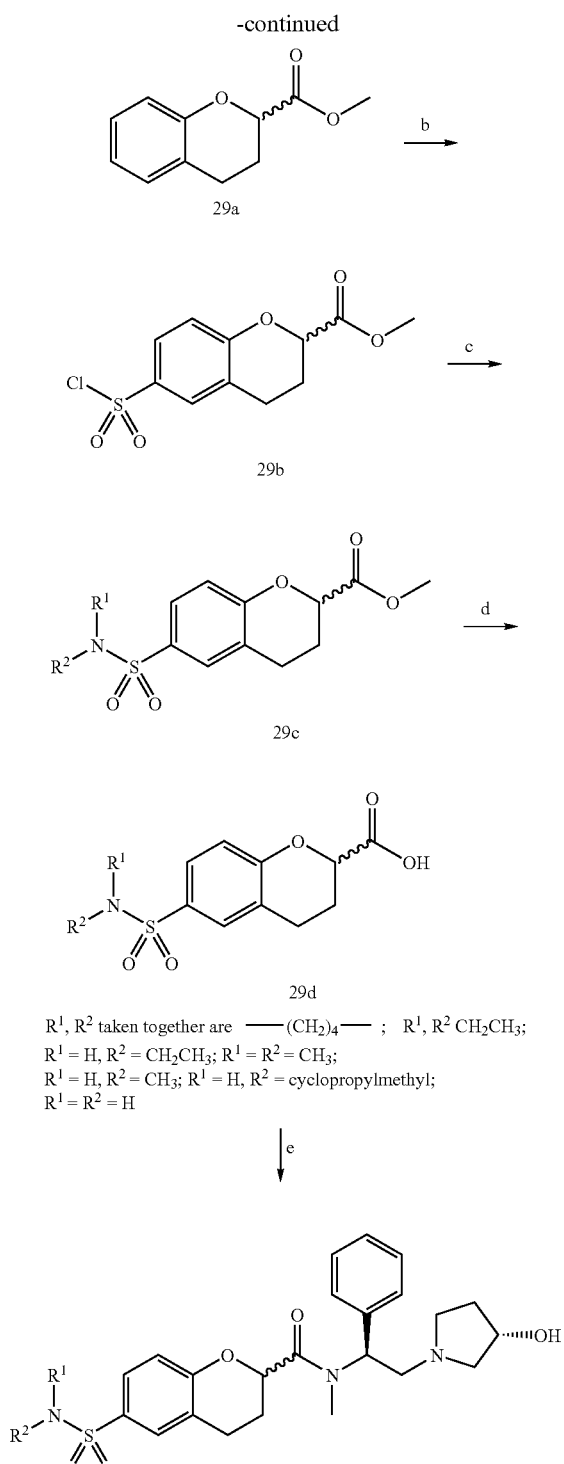

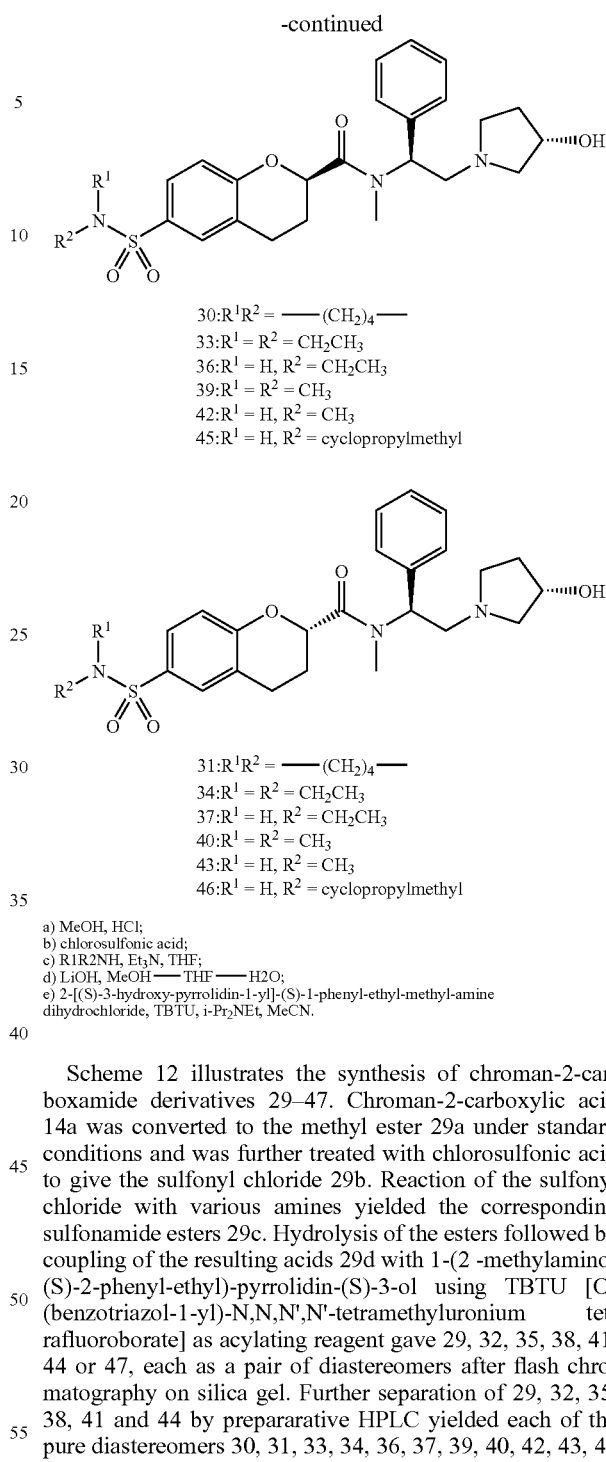

a) MeOH, HCl;
b) chlorosulfonic acid;
c) R1R2NH, Et₃N, THF;
d) LiOH, MeOH—THF—H2O;
e) 2-[(S)-3-hydroxy-pyrrolidin-1-yl]-(S)-1-phenyl-ethyl-methyl-amine dihydrochloride, TBTU, i-Pr₂NEt, MeCN.

Scheme 12 illustrates the synthesis of chroman-2-carboxamide derivatives 29–47. Chroman-2-carboxylic acid 14a was converted to the methyl ester 29a under standard conditions and was further treated with chlorosulfonic acid to give the sulfonyl chloride 29b. Reaction of the sulfonyl chloride with various amines yielded the corresponding sulfonamide esters 29c. Hydrolysis of the esters followed by coupling of the resulting acids 29d with 1-(2-methylamino-(S)-2-phenyl-ethyl)-pyrrolidin-(S)-3-ol using TBTU [O-(benzotriazol-1-yl)-N,N,N',N'-tetramethyluronium tetrafluoroborate] as acylating reagent gave 29, 32, 35, 38, 41, 44 or 47, each as a pair of diastereomers after flash chromatography on silica gel. Further separation of 29, 32, 35, 38, 41 and 44 by prepararative HPLC yielded each of the pure diastereomers 30, 31, 33, 34, 36, 37, 39, 40, 42, 43, 45 and 46.

Scheme 13

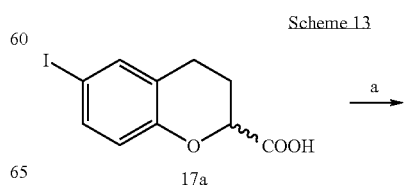

17a

43

-continued

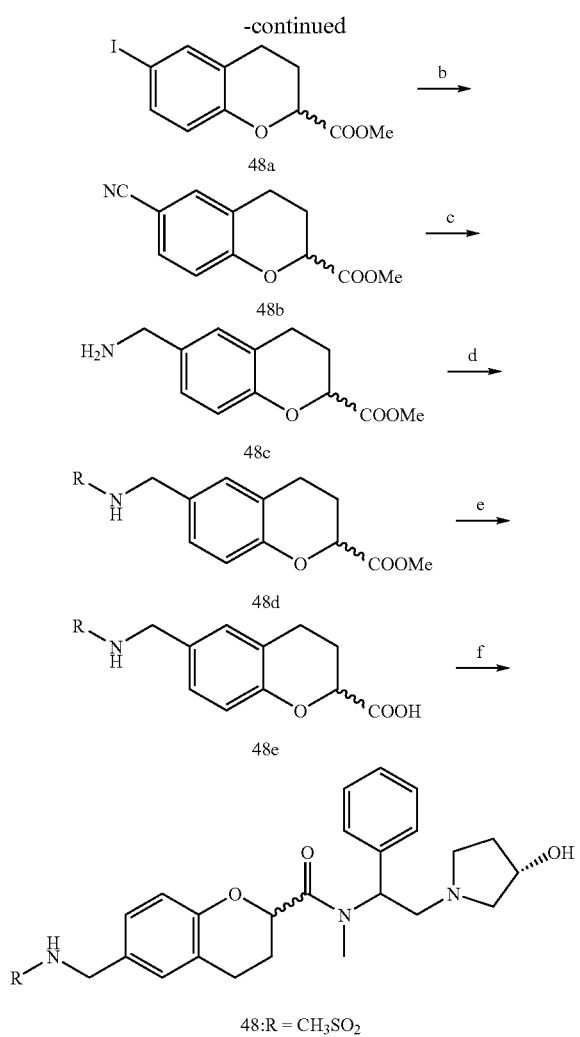

48:R = CH$_3$SO$_2$
51:R = CH$_3$OCO a) MeOH, HCl;
b) CuCN, DMF;
c) H$_2$, Pd/C;
d) CH$_3$SO$_2$Cl or ClCOOMe;
e) LiOH;
f) 1-(2-methylamino-(S)-2-phenyl-ethyl)-pyrrolidin-(S)-3-ol dihydrochloride, 2-chloro-1-methylpyridinium iodide, dichloromethane The synthesis of chroman-2-carboxamide derivatives 48 and 51 is summarized in Scheme 13. (R,S)-6-Iodo-chroman-2-carboxylic acid (17a), described hereinabove, was esterified in methanol 48a and subsequently reacted with copper (I) cyanide in refluxing dimethylforrnamide to afford the cyano-substituted compound 48b. Reduction of the cyano group by catalytic hydrogenation gave the benzylamine derivative 48c which was reacted with methanesulfonyl chloride or methyl chloroformate to yield the sulfonamide or carbamate respectively 48d. Ester hydrolysis of the resulting sulfonamide or carbamate derivative under basic conditions gave the corresponding acid 48e, which was coupled with 1-(2-methylamino-(S)-2-phenyl-ethyl)-pyrrolidin-(S)-3-ol in the presence of the Mukaiyama acylating reagent (2-chloro-1-methylpyridinium iodide) to give 48 or 51 as a pair of diastereomers after chromatographic purification. Utilizing the enantiomerically pure (R)-chroman-2-carboxylic acid 14c$_1$, the same reaction sequence provided the corresponding 6-substituted (R)-chroman-2-carboxylic acid, which was coupled with 1-(2-methylamino-(S)-2-phenyl-

44 ethyl)-pyrrolidin-(S)-3-ol in the presence of TBTU to provide the pure diastereomer with (R)-configuration at the 2-position, 49 or 52 (not shown in schemes), respectively. The other pure diastereomer of 48 or 51 with (S)-configuration at 2-position, 50 or 53 (not shown in schemes), respectively, was obtained using preparative HPLC of diastereomeric mixture 48 or 51.

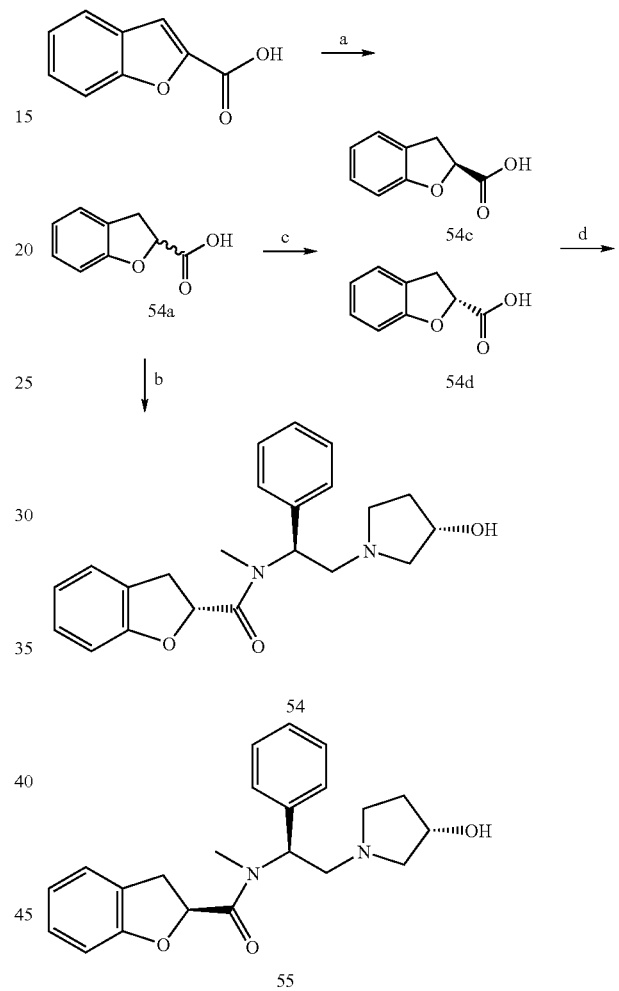

Scheme 14 a) H$_2$ (60–70psi), EtOAc, 10% Pd/C;
b) 1-(2-methylamino-(S)-2-phenyl-ethyl)-pyrrolidin-(S)-3-ol dihydrochloride,2-chloro-1-methylpyridinium iodide, DCM;
c) Chiral separation;
d) TBTU, i-Pr$_2$NEt, 1-(2-methylamino-(S)-2-phenyl-ethyl)-pyrrolidin-(S)-3-ol dihydrochloride.

Scheme 14 describes the synthesis of 2,3-dihydro-benzofuran-based carboxamide derivatives 54 and 55. (R,S)-2,3-Dihydro-benzofuran-2-carboxylic acid 54a was prepared by catalytic hydrogenation of the commercially available benzofuran-2-carboxylic acid. Coupling of the (R,S)-2,3-Dihydro-benzofuran-2-carboxylic acid 54a with 1-(2-methylamino-(S)-2-phenyl-ethyl)-pyrrolidin-(S)-3-ol in the presence of the Mukaiyama acylating reagent (2-chloro-1-methylpyridinium iodide) gave a pair of diastereomers which were separated using flash chromatography on silica gel to provide 54 and 55 as individually pure diastereomers. The same compounds were prepared directly by coupling the (R)- (54c) or (S)-2,3-Dihydro-benzofuran-2-carboxylic acid (54d) (prepared by chiral separation of the (R,S)

material) with 1-(2-methylamino-(S)-2-phenyl-ethyl)-pyrrolidin-(S)-3-ol in the presence of TBTU.

Scheme 15 outlines the synthesis of benzofuran-2-carboxamide derivatives 56 and 59–63. Nitration of (R,S)-2,3-dihydro-benzofuran-2-carboxylic acid 54a with nitric acid gave a mixture of 5- and 7-nitro regioisomers. The crude mixture of acids, used without further purification, was converted to the corresponding esters and was easily separated by flash chromatography over silica gel to give (R,S)-5-nitro-2,3-dihydro-benzofuran-2-carboxylic acid methyl ester 56a$_1$ and (R,S)-7-nitro-2,3-dihydro-benzofuran-2-carboxylic acid methyl ester 56a$_2$ as individual products. The 5-nitro isomer was catalytically hydrogenated to give the corresponding aniline ester derivative 56b. Reaction of the aniline compound with methanesulfonyl chloride, acetyl chloride, cyclopropanecarbonyl chloride or methyl chloroformate furnished the sulfonamide, amide or carbamate, respectively 56c. Each ester derivative was treated with lithium hydroxide to give the corresponding acid 56d. Coupling of each of these acids with 1-(2-methylamino-(S)-2-phenyl-ethyl)-pyrrolidin-(S)-3-ol under Mukaiyama acylation conditions yielded 56 or 59, each as a pair of diastereomers, and 60, 61, 62, and 63 as separated diastereomers after flash chromatography on silica gel.

Utilizing the enantiomerically pure (R)-2,3-dihydro-benzofuran-2-carboxylic acid 54c or (S)-2,3-dihydro-benzofuran-2-carboxylic acid 54d, the same reaction sequence provided the corresponding 5-substituted 2,3-dihydro-benzofuran-2-carboxylic acid, which was coupled with 1-(2-methylamino-(S)-2-phenyl-ethyl)-pyrrolidin-(S)-3-ol in the presence of TBTU to provide either the (2R)- or (2S)-diastereomer 57 or 58, respectively (not shown in schemes).

The (R,S)-7-nitro-2,3-dihydro-benzofuran-2-carboxylic acid methyl ester 56a$_2$ described hereinabove in Scheme 15, was reacted in similar fashion to its 5-nitro derivative 56a$_1$ to yield carboxamides 64, 65, 66, and 67 as pure diastereomers after flash chromatography over silica gel (Scheme 16).

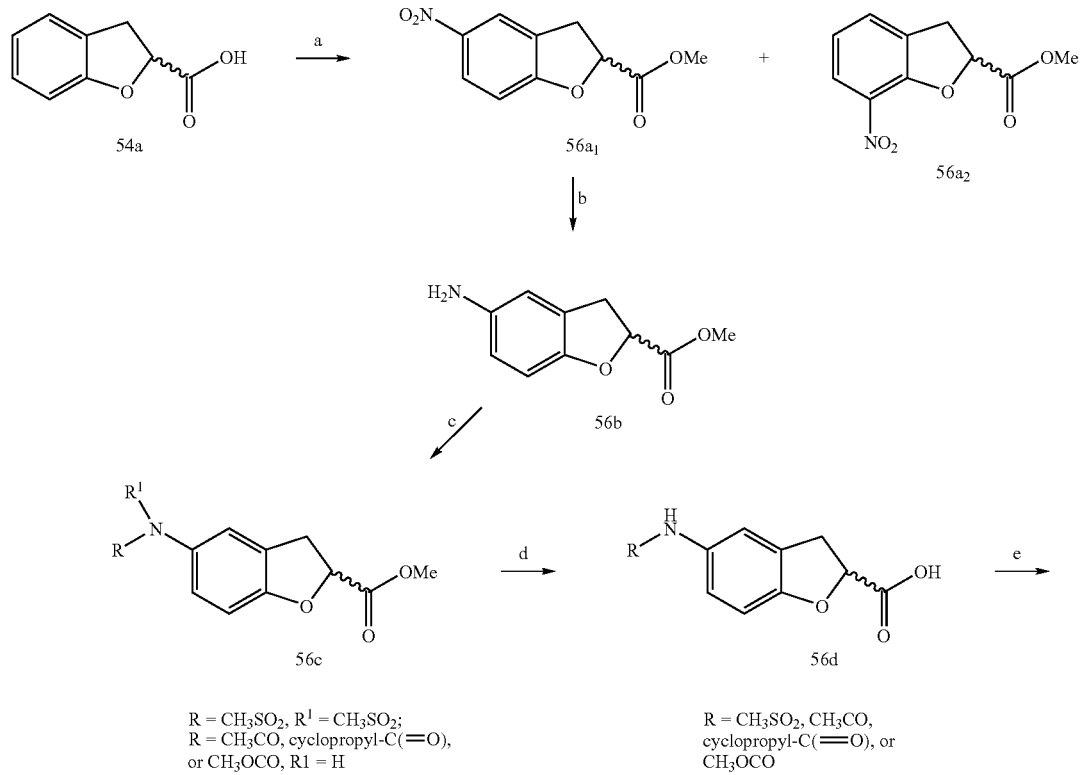

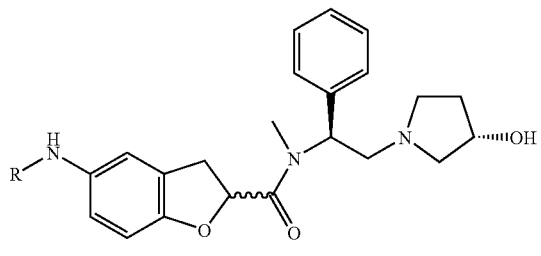

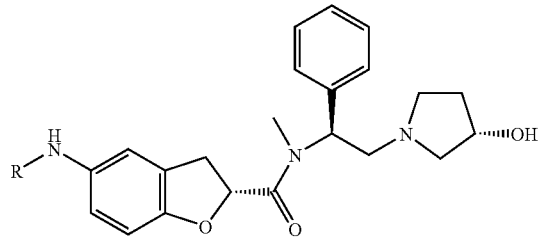

60: R = cyclopropyl-C(═O)
62: R = CH₃OCO

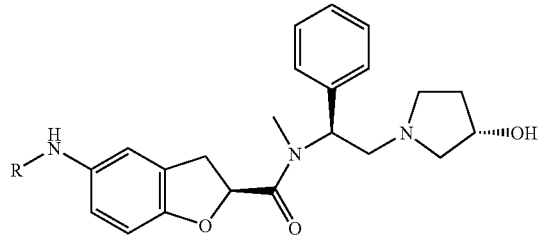

61: R = cyclopropyl-C(═O)
63: R = CH₃OCO a) i. HNO₃; ii. MeOH, HCl; iii. Chromatography;
b) H₂, Pd/C;
c) CH₃SO₂Cl or RCOCl, Et₃N;
d) LiOH, MeOH—THF—H₂O;
e) 1-(2-methylamino-(S)-2-phenyl-ethyl)-pyrrolidin-(S)-3-ol dihydrochloride,
   2-chloro-1-methylpyridinium iodide, dichloromethane

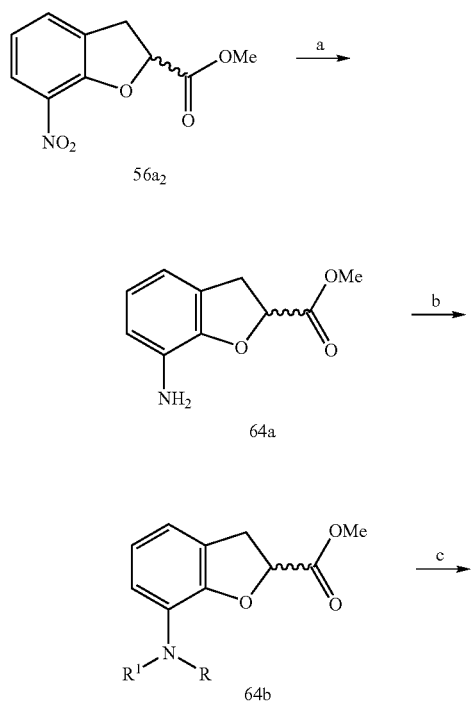

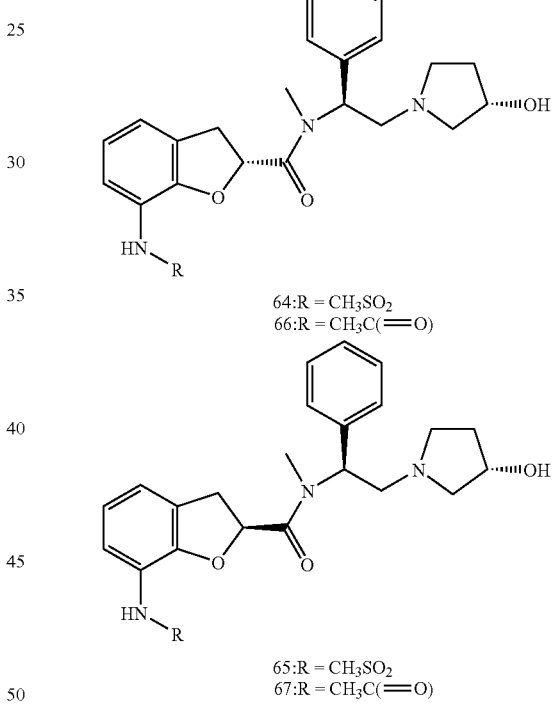

64: R = CH₃SO₂
66: R = CH₃C(═O)

65: R = CH₃SO₂
67: R = CH₃C(═O)

a) H₂, Pd/C;
b) CH₃SO₂Cl or CH₃COCl, Et₃N;
c) LiOH, MeOH—THF—H₂O;
d) 1-(2-methylamino-(S)-2-phenyl-ethyl)-pyrrolidin-(S)-3-ol dihydrochloride,
   2-chloro-1-methylpyridinium iodide, dichloromethane Scheme 17 summarizes the synthesis of 2,3-dihydrobenzofuran-2-carboxamide derivatives 68–72. Esterification of 54a in methanol provided 68a which was chlorosulfonylated with sulfur trioxide/N,N-dimethylformamide complex to afford the sulfonyl chloride 68b. The crude sulfonyl chloride was reacted with pyrrolidine, dimethylamine or methylamine to give the corresponding sulfonamide 68c and the ester group was hydrolyzed to yield the acid 68d. Coupling of the resultant acid with 1-(2-methylamino-(S)-2-phenyl-ethyl)-pyrrolidin-(S)-3-ol under Mukaiyama acylation conditions furnished 68, 69, 70, and 71, each as pure

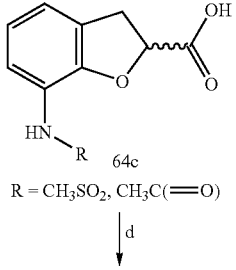

64c
R = CH₃SO₂, CH₃C(═O)

diastereomers, and 72 as a pair of diastereomers after chromatography on silica gel.

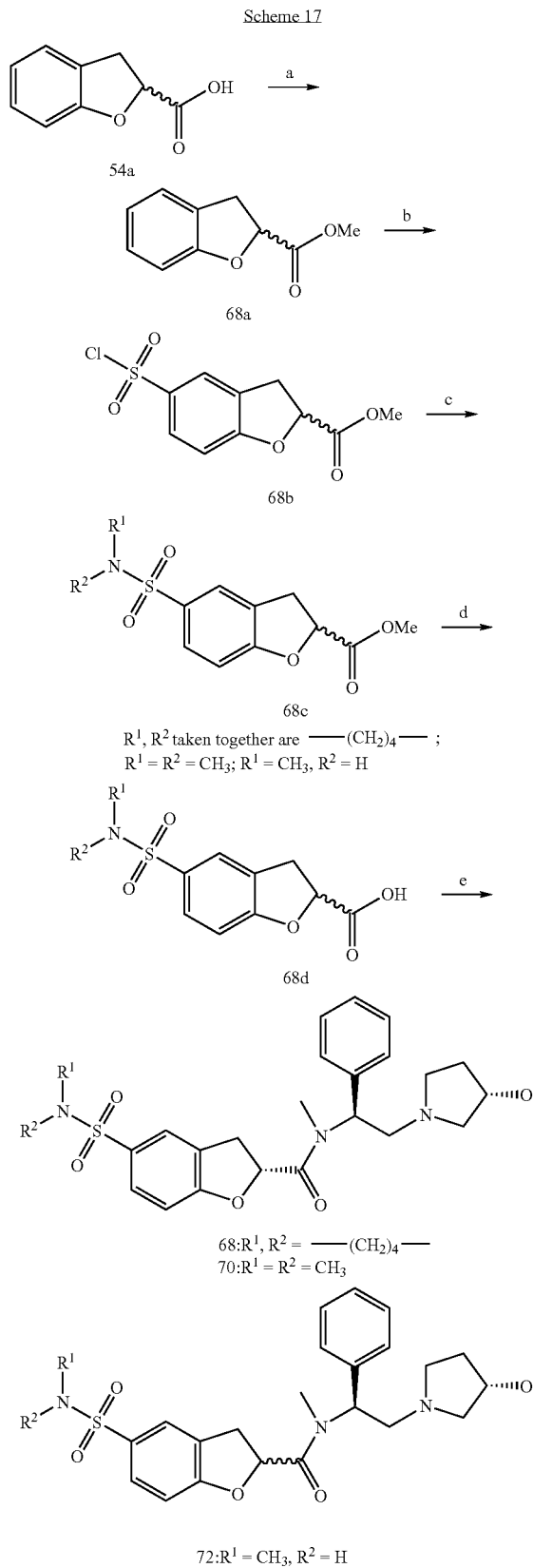

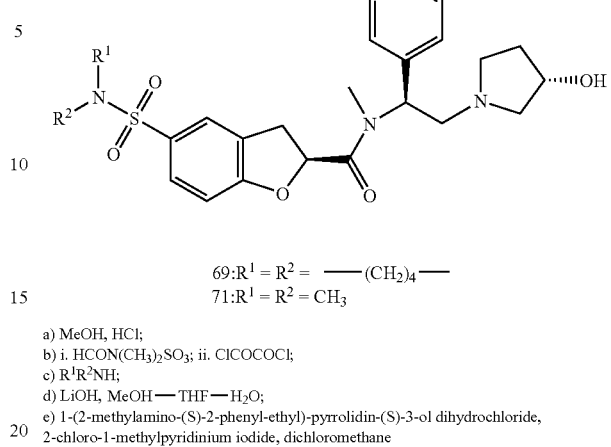

a) MeOH, HCl;
b) i. HCON(CH$_3$)$_2$SO$_3$; ii. ClCOCOCl;
c) R$^1$R$^2$NH;
d) LiOH, MeOH—THF—H$_2$O;
e) 1-(2-methylamino-(S)-2-phenyl-ethyl)-pyrrolidin-(S)-3-ol dihydrochloride, 2-chloro-1-methylpyridinium iodide, dichloromethane Scheme 18 summarizes the synthesis of 2,3-dihydro-benzofuran-2-carboxamide derivatives 73, 76, and 79. Each was prepared from (R,S)-2,3-dihydro-benzofuran-2-carboxylic acid 54a using the reaction sequence for 48 and 51 (Scheme 13). Compounds 74, 75, 77 and 78 (not shown in schemes) were analogously prepared from (R)- or (S)-2,3-dihydro-benzofuran enantiomers 54c or 54d.

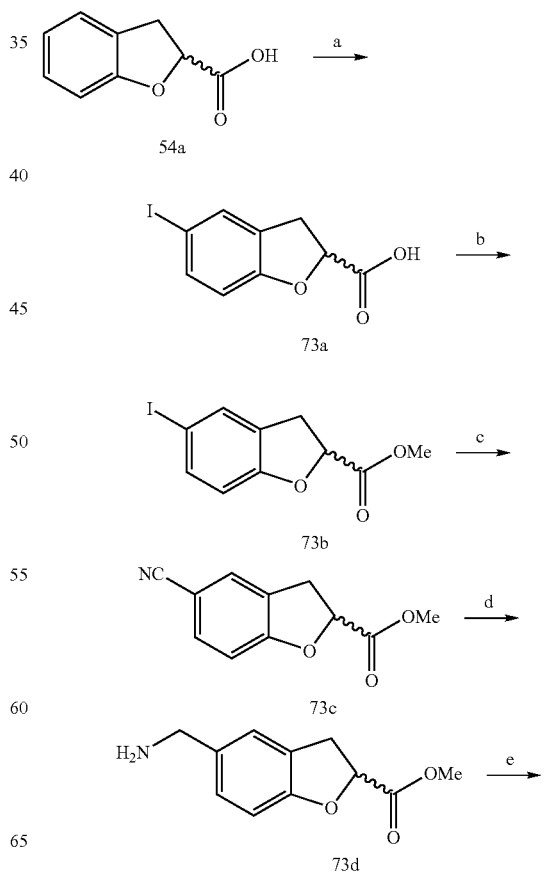

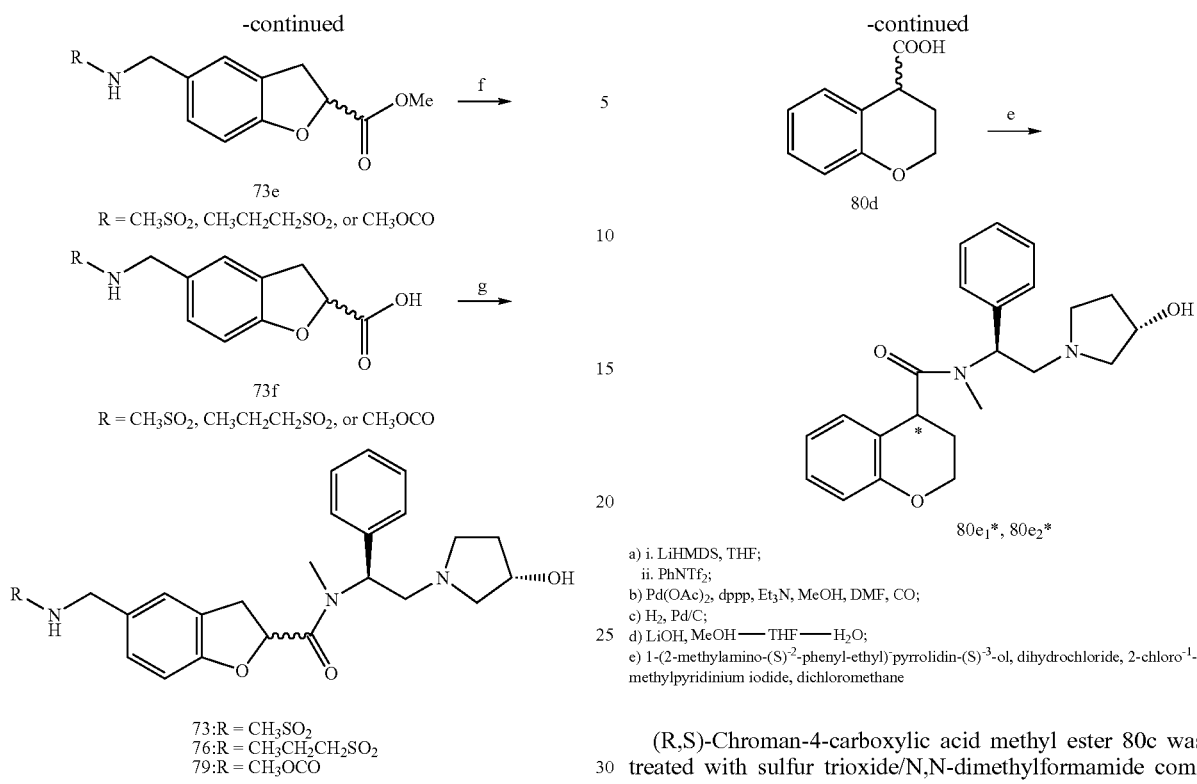

73e
R = CH₃SO₂, CH₃CH₂CH₂SO₂, or CH₃OCO

73f
R = CH₃SO₂, CH₃CH₂CH₂SO₂, or CH₃OCO

73: R = CH₃SO₂
76: R = CH₃CH₂CH₂SO₂
79: R = CH₃OCO a) PhCH₂N(CH₃)₃ICl₂, ZnCl₂, HOAc;
b) MeOH, HCl;
c) CuCN, DMF;
d) H₂, Pd/C;
e) CH₃SO₂Cl or ClCOOMe;
f) LiOH, MeOH——THF——H₂O;
g) 1-(2-methylamino-(S)-2-phenyl-ethyl)-pyrrolidin-(S)-3-ol dihydrochloride, 2-chloro-1-methylpyridinium iodide, dichloromethane Scheme 19 describes the synthesis of chroman-4-carboxamide derivatives 80e₁* and 80e₂*. Using reactions first outlined in Scheme 3, 4-chromanone was transformed into (R,S)chroman-4-carboxylic acid 80d, which was coupled with 1-(2-methylamino-(S)-2-phenyl-ethyl)-pyrrolidin-(S)-3-ol under Mukaiyama acylation conditions to yield 80e₁* and 80e₂* as individual diastereomers after standard silica gel chromatographic separation of the crude reaction product.

80d

80e₁*, 80e₂* a) i. LiHMDS, THF;
   ii. PhNTf₂;
b) Pd(OAc)₂, dppp, Et₃N, MeOH, DMF, CO;
c) H₂, Pd/C;
d) LiOH, MeOH——THF——H₂O;
e) 1-(2-methylamino-(S)-2-phenyl-ethyl)-pyrrolidin-(S)-3-ol, dihydrochloride, 2-chloro-1-methylpyridinium iodide, dichloromethane (R,S)-Chroman-4-carboxylic acid methyl ester 80c was treated with sulfur trioxide/N,N-dimethylformamide complex to afford the sulfonyl chloride 81a which was further reacted with pyrrolidine, N-methylisopropylamine, morpholine, methylamine, dimethylamine or 2-(methylamino)ethanol to give the corresponding sulfonamide esters 81b. Hydrolysis of each of the esters followed by the coupling of the resultant acids 81c with 1-(2-methylamino-(S)-2-phenyl-ethyl)-pyrrolidin-(S)-3-ol under Mukaiyama acylation conditions, which after chromatography on silica gel, yielded 81d₁*, 81d₂*, 82a*, 82b*, 83a*, 83b*, 84a*, 84b*, 85a*, and 85b* as individual diastereomers, and 86 as a pair of diastereomers (Scheme 20).

Scheme 21 describes the synthesis of chroman-4-carboxamide derivatives 87 and 88. Using reactions outlined in Scheme 13 for the preparation of 48 or 51, (R,S)-Chroman-4-carboxylic acid methyl ester 80c was converted to the two 6-substituted chroman-4-carboxylic acid derivatives 87d and each was coupled with 1-(2-methylamino-(S)-2-phenyl-ethyl)-pyrrolidin-(S)-3-ol under Mukaiyama acylation conditions to yield 87 or 88 as a pair of diastereomers.

Scheme 19

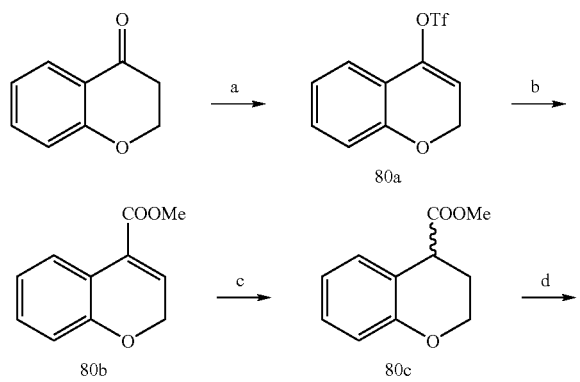

Scheme 20

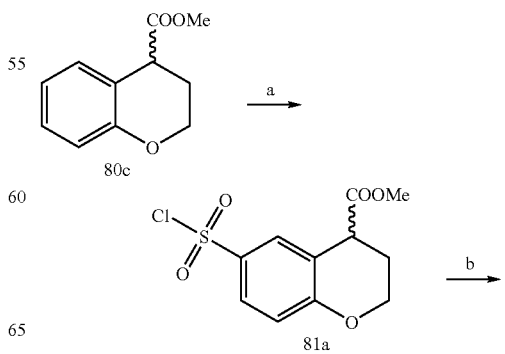

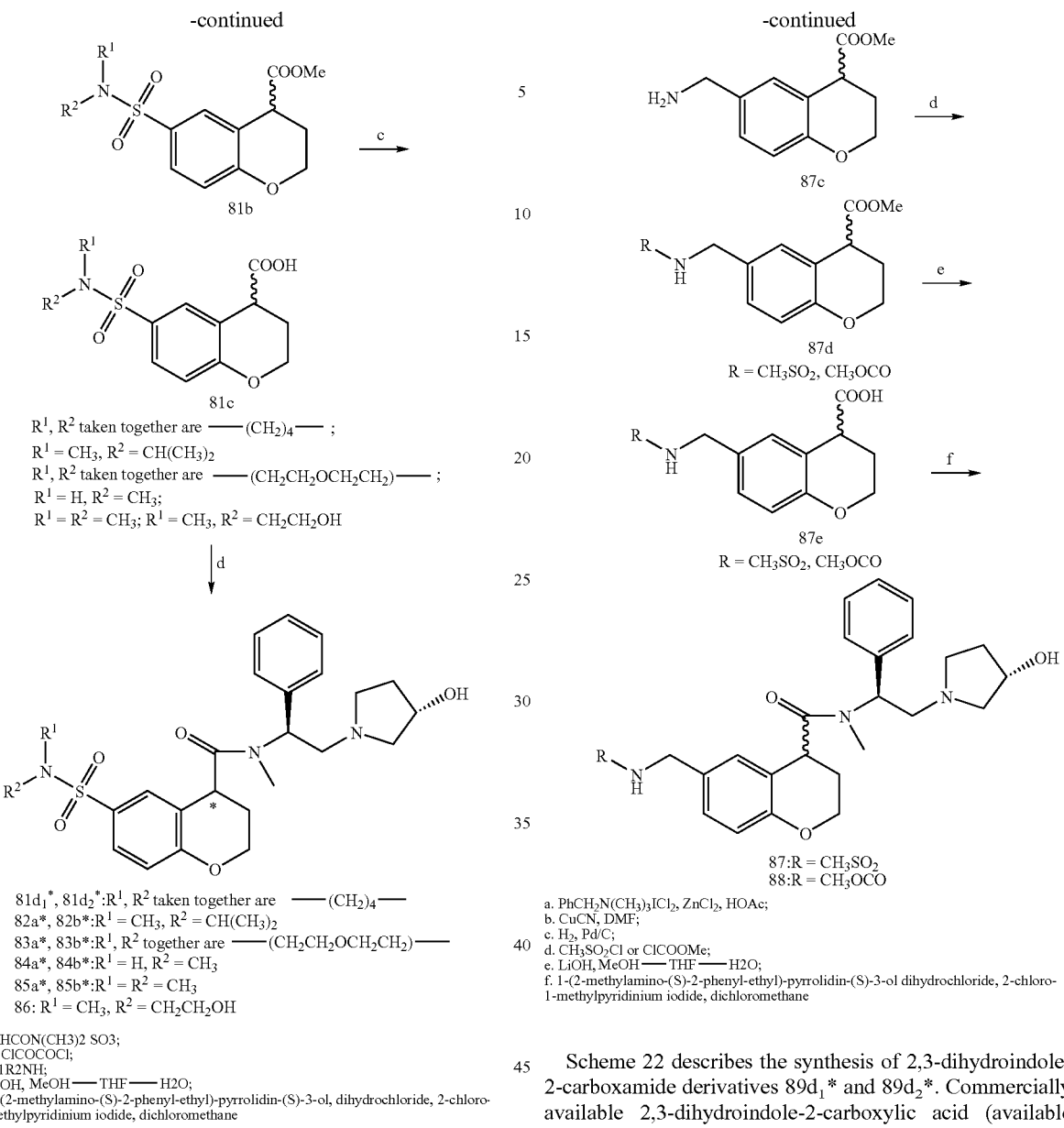

Scheme 22 describes the synthesis of 2,3-dihydroindole-2-carboxamide derivatives 89d$_1$* and 89d$_2$*. Commercially available 2,3-dihydroindole-2-carboxylic acid (available from Aldrich Chemical Company) was converted to the ester 89a and reacted with methyl iodide to give the N-methylated product 89b. Ester hydrolysis afforded the acid 89c, which was coupled with 1-(2-methylamino-(S)-2-phenyl-ethyl)-pyrrolidin-(S)-3-ol in the presence of TBTU to yield a pair of diastereomers. Separation of the mixture by preparative HPLC provided the two individual diastereomers 89d$_1$* and 89d$_2$*.

Treatment of 2,3-dihydroindole-2-carboxylic acid methyl ester 89a with acetyl chloride or methanesulfonyl chloride gave the corresponding acetamide 90a, R=C(=O)CH3 or sulfonamide ester 90a, R=SO$_2$CH$_3$, respectively, which was hydrolyzed with lithium hydroxide to give the corresponding acid 90b (Scheme 23). Coupling of each acid derivative with 1-(2-methylamino-(S)-2-phenyl-ethyl)-pyrrolidin-(S)-3-ol in the presence of TBTU yielded a pair of diastereomers (step c). Separation of each pair by preparative HPLC furnished the individual diastereomers 90c$_1$*, 90c$_2$*, 91c$_1$*, and 91c$_2$*.

Scheme 22

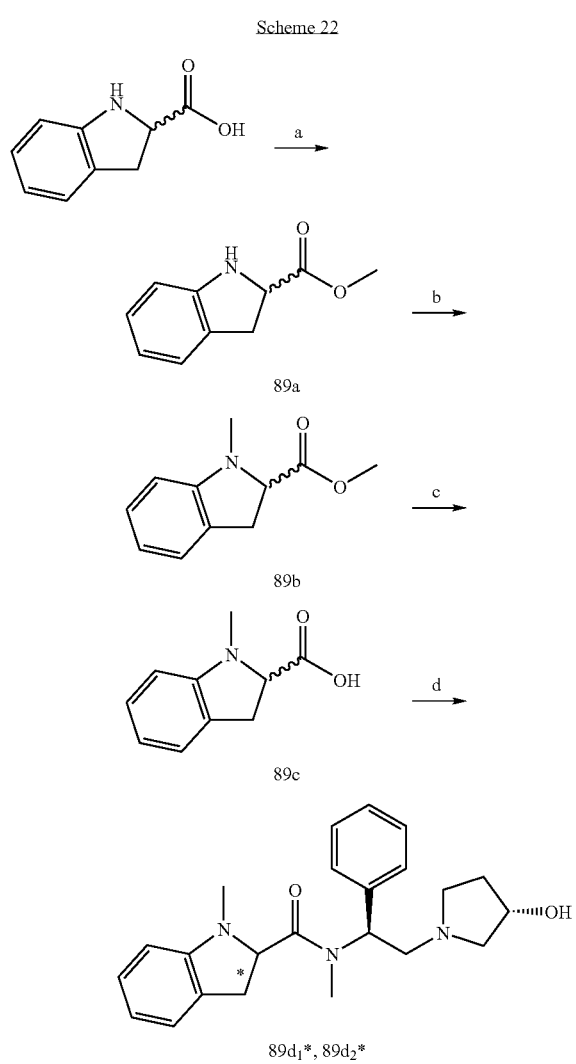

a) MeOH, HCl;
b) MeI, K$_2$CO$_3$, MeCN;
c) 10% HCl aq.;
d) 2-[(S)-3-hydroxy-pyrrolidin-1-yl]-(S)-1-phenyl-ethyl-methyl-amine dihydrochloride, TBTU, i-Pr$_2$NEt, MeCN

Scheme 23

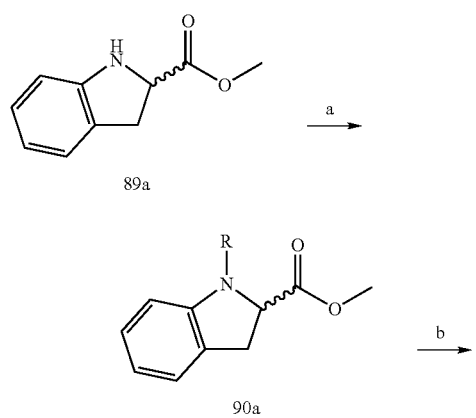

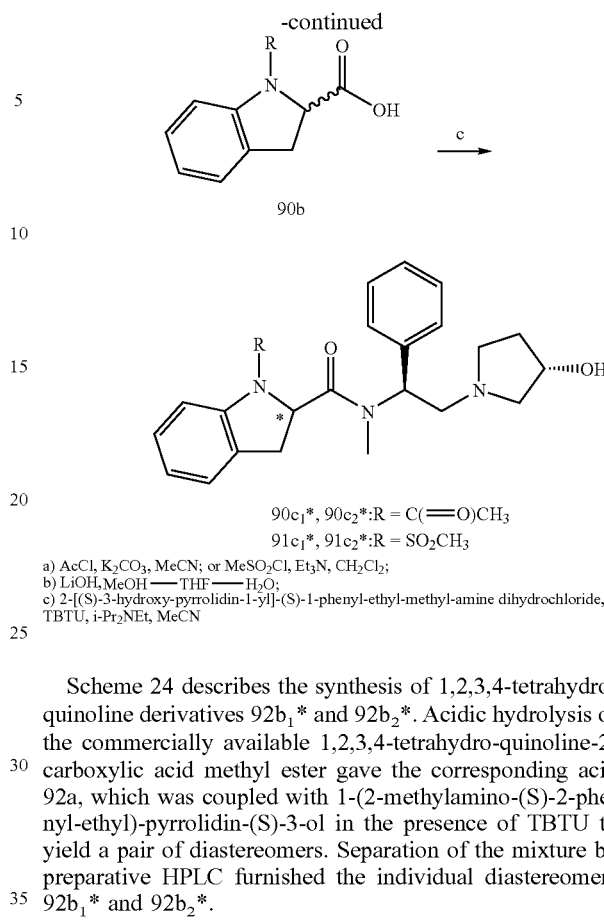

a) AcCl, K$_2$CO$_3$, MeCN; or MeSO$_2$Cl, Et$_3$N, CH$_2$Cl$_2$;
b) LiOH, MeOH — THF — H$_2$O;
c) 2-[(S)-3-hydroxy-pyrrolidin-1-yl]-(S)-1-phenyl-ethyl-methyl-amine dihydrochloride, TBTU, i-Pr$_2$NEt, MeCN Scheme 24 describes the synthesis of 1,2,3,4-tetrahydro-quinoline derivatives 92b$_1$* and 92b$_2$*. Acidic hydrolysis of the commercially available 1,2,3,4-tetrahydro-quinoline-2-carboxylic acid methyl ester gave the corresponding acid 92a, which was coupled with 1-(2-methylamino-(S)-2-phenyl-ethyl)-pyrrolidin-(S)-3-ol in the presence of TBTU to yield a pair of diastereomers. Separation of the mixture by preparative HPLC furnished the individual diastereomers 92b$_1$* and 92b$_2$*.

Scheme 24 a) 10% HCl aq.;
b) 2-[(S)-3-hydroxy-pyrrolidin-1-yl]-(S)-1-phenyl-ethyl-methyl-amine dihydrochloride, TBTU, (iPy)$_2$EtN, MeCN Other features of the invention will become apparent in the course of the following descriptions of exemplary embodiments which are given for illustration of the invention and are not intended to be limiting thereof. The present invention will now be illustrated by reference to the following specific, non-limiting examples. Those skilled in the art of organic synthesis may be aware of still other synthetic routes to the invention compounds. The reagents and intermediates used herein are either commercially available or prepared according to standard literature procedures, unless otherwise described.

EXAMPLES

General Procedure of the Coupling of Acids with 1-(2-methylamino-(S)-2-phenyl-ethyl)-pyrrolidin-(S)-3-ol dihydrochloride:

Method A:

To the solution of the acid in methylene chloride (20 mL) was added 1-(2-methylamino-(S)-2-phenyl-ethyl)-pyrrolidin-(S)-3-ol dihydrochloride (293 mg, 1.0 mmol), triethylamine (0.7 ml, 5 mmol) and finally Mukaiyama acylating reagent: 2-chloro-1-methylpyridinium iodide (307 mg, 1.2 mmol). The reaction mixture was stirred at room temperature overnight and washed with saturated aqueous sodium bicarbonate (2×10 ml), and dried ($Na_2SO_4$). Evaporation of the solvent and purification of the residue by flash chromatography over silica gel (MeOH—$CH_2Cl_2$, 1:50 to 1:10) to yield the target compound.

Method B:

To a suspension of 1-(2-methylamino-(S)-2-phenyl-ethyl)-pyrrolidin-(S)-3-ol dihydrochloride (323 mg, 1.1 mmol) in acetonitrile (40 mL) was added diisopropylethylamine (0.87 mL, 5 mmol) and the acid (1.0 mmol). After 10 minutes at room temperature, the reaction mixture was cooled to 0° C. and TBTU (386 mg, 1.2 mmol) was added portionwise. The reaction mixture was then stirred at room temperature overnight and concentrated. The residue was dissolved in ethyl acetate (50 mL) and washed with saturated sodium bicarbonate (2×30 mL), brine (30 mL) and dried (($Na_2SO_4$)). Evaporation of the solvent and purification of the residue by flash chromatography over silica gel (MeOH—$CH_2Cl_2$, 1:50 to 1:10) to yield the target compound.

Examples $1g_1$*, $1g_2$*, 2, and 3*

Preparation of 7-Chloro-2,3-dihydro-benzo[b]oxepine-2-carboxylic acid {2-[(S)-3-hydroxy-pyrrolidin-1-yl]-(S)-1-phenyl-ethyl}-methyl-amide and (R,S)-7-Chloro-2,3,4,5-tetrahydro-benzo[b]oxepine-2-carboxylic acid {2-[(S)-3-hydroxy-pyrrolidin-1-yl]-(S)-1-phenyl-ethyl}-methyl-amide a) 4-Chloro-2-vinyl-phenol (Ia)

To a stirred suspension of methyltriphenylphosphonium bromide (30 g, 83 mmol) in dry tetrahydrofuran (500 mL) at −78° C. was added slowly n-butyl lithium (100 mL, 1.6 M in hexane, 160 mmol). After 2 hours stirring at −78° C., commercially available 5-chloro-2-hydroxy-benzaldehyde (10 g, 64 mmol, Aldrich Chemical Company) dissolved in 20 mL of tetrahydrofuran was added dropwise. The reaction mixture was stirred another 45 minutes at −78° C. and 2 hours at room temperature. The solvent was removed under reduced pressure; the residue was dissolved in ethyl acetate (200 mL) and poured into 200 mL of saturated sodium bicarbonate aqueous solution to partition the two phases. The aqueous phase was extracted with ethyl acetate two more times and the combined ethyl acetate layers were washed with brine, dried over anhydrous sodium sulfate, filtered and concentrated under reduced pressure. The crude product was purified by flash chromatography (silica gel, ethyl acetate/hexane) to afford 9.16 g (92%) of the title compound. $^1$H NMR (300 MHz, $CDCl_3$) δ 7.35 (s, 1H), 7.09 (t, 1H), 6.85 (dd, 1H), 6.75 (d, 1H), 5.75 (d, 1H), 5.40 (d, 1H), 4.97 (s, 1H).

b) (4-Chloro-2-vinyl-phenoxy)-acetic acid ethyl ester (Ib)

To a stirred solution of compound Ia (5.16 g, 33 mmol) in acetone (400 mL) was added potassium carbonate (6.92 g, 50 mmol) and ethyl bromoacetate (5.5 mL, 50 mmol). The reaction mixture was heated at reflux for 4 hours. After cooling to room temperature, the solids were filtered and the solution was concentrated under reduced pressure. The crude product was purified by flash chromatography (silica gel, ethyl acetate/hexane) to afford 6.5 g (82%) of the title compound. $^1$H NMR (250 MHz, $CDCl_3$) δ 7.48 (s, 1H), 7.15 (t, 1H), 7.05 (dd, 1H), 6.70 (d, 1H), 5.80 (d, 1H), 5.37 (d, 1H), 4.65 (s, 2H), 4.28 (q, 2H), 1.29 (t, 3H).

c) 2-(4-Chloro-2-vinyl-phenoxy)-pent-4-enoic acid ethyl ester (Ic)

Lithium bis(trimethylsilyl)amide (45 mL, 1.0 M in tetrahydrofuran, 45 mmol) was added slowly to a stirred solution of compound Ib (10.81 g, 45 mmol) in dry tetrahydrofuran (600 mL) at −78° C. After 45 minutes at −78° C., allyl bromide (4.50 mL, 52 mmol) was added dropwise. The reaction mixture was stirred another 5 hours at −78° C., then overnight at room temperature. The reaction was quenched with saturated ammonium chloride aqueous solution and the biphasic mnixture was extracted with ethyl acetate. The combined ethyl acetate layers were washed with brine, dried over anhydrous sodium sulfate, filtered and concentrated under reduced pressure. The crude product was purified by flash chromatography (silica gel, ethyl acetate/hexane) to afford 2.70 g (20%) of the title compound. $^1$H NMR (300 MHz, $CDCl_3$) δ 7.46 (s, 1H), 7.15 (t, 1H), 7.09 (dd, 1H), 6.67(d, 1H), 5.90 (m, 1H), 5.67 (d, 1H), 5.33 (d, 1H), 5.19 (dd, 2H), 4.67 (t, 1H), 4.18 (q, 2H), 3.4 (t, 2H), 1.25 (t, 3H).

d) (R,S)-7-Chloro-2,3-dihydro-benzo[b]oxepine-2-carboxylic acid ethyl ester (Id)

Grubbs' catalyst (1.3 g, 1.5 mmol) was added to a stirred solution of compound Ic (1.42 g, 5 mmol) in dry methylene chloride (50 mL) and the reaction mixture was stirred 24 hours at room temperature. The solvent was evaporated and the crude product was purified by flash chromatography (silica gel, ethyl acetate/hexane) to afford 0.42 g (33%) of the title compound. $^1$H NMR (300 MHz, $CDCl_3$) δ 7.12–6.99 (m, 3H), 6.29 (d, 1H), 5.98 (m, 1H), 4.50 (d, 1H), 4.28 (q, 2H), 2.90 (m, 2H), 1.33 (t, 3H).

e) (R,S)-7-Chloro-2,3-dihydro-benzo[b]oxepine-2-carboxylic acid (Ie)

Lithium hydroxide monohydrate (0.30 g, 7.28 mmol) was added to a stirred solution of compound Id (0.42 g, 1.82 mmol) in a mixed solvent of methanol, tetrahydrofuran, and water (10 mL of each) and the mixture was stirred overnight at room temperature. The organic solvents were removed under reduced pressure and the aqueous solution was acidified with 6N hydrochloric acid until pH~1. The resulting acid was then extracted with dichloromethane three times. The combined dichloromethane layers were washed with brine, dried over anhydrous sodium sulfate, filtered, concentrated under reduced pressure and finally dried in vacuo to afford 0.38 g (100%) of the title compound. $^1$H NMR (300 MHz, DMSO-$d_6$) δ 13.07 (s, 1H), 7.37 (s, 1H), 7.24 (d, 1H), 7.02 (d, 1H), 6.38 (d, 1H), 6.04 (m, 1H), 4.59 (t, 1H), 2.83 (m, 2H).

f) (R,S)-7-Chloro-2,3,4,5-tetrahydro-benzo[b]oxepine-2-carboxylic acid (If)

Ten wt. % (dry basis) palladium on activated carbon wet (380 mg, 20% wt. equiv.) was added to a stirred solution of compound Ie (190 g, 0.84 mmol) in ethyl acetate (10 mL) at room temperature under a nitrogen atmosphere. After evacuation of the reaction flask, a hydrogen-filled balloon was attached and the mixture was stirred overnight at room temperature. The catalyst was removed by filtration through a pad of Celite and the clear solution was concentrated under reduced pressure and dried in vacuo to yield 177 mg (94%) of the title compound. $^1$H NMR (300 MHz, DMSO) δ 12.86 (s, 1H), 7.31 (s, 1H), 7.22 (d, 1H), 6.99 (d, 1H), 4.18 (d, 1H), 2.78 (t, 2H), 2.18 (m, 1H), 1.95 (m, 2H), 1.53 (m, b, 1H).

g) 7-Chloro-2,3-dihydro-benzo[b]oxepine-2-carboxylic acid [2-(3-hydroxy-pyrrolidin-1-yl)-1-phenyl-ethyl]-methyl-amide ($1g_1$*, $1g_2$*) and (R,S)-7-Chloro-2,3,4,5-tetrahydro-benzo[b]oxepine-2-carboxylic acid [2-(3-hydroxy-pyrrolidin-1-yl)-1-phenyl-ethyl]-methyl-amide (2, 3*)

Using the general coupling method A, compound 1e (0.18 g, 0.8 mmol) was coupled with 2-[(S)-3-hydroxy-pyrrolidin-1-yl]-(S)-1-phenyl-ethyl-methyl-amine dihydrochloride (0.21 g, 0.73 mmol) to give $1g_1$* (115 mg, 33.7%) with a shorter retention time in LC/MS and $1g_2$* (52 mg, 15%) with longer retention time in LC/MS. $1g_1$*: $^1$H NMR (300 MHz, CDCl$_3$) δ 7.49–7.29 (m, 5H), 7.16 (d, 1H), 7.1 (dd, 1H), 6.99 (d, 1H), 6.29 (d, 1H), 6.12 (m, 2H), 4.65 (d, 1H), 4.27 (brs, 1H), 3.35–3.08 (m, 3H), 2.96–2.67 (m, 7H), 2.45–2.08 (m, 3H), 1.79 (m, 1H); $^1$); MS: [M+1]$^+$: 427. $1g_2$*: $^1$H NMR (300 MHz, CDCl$_3$) δ 7.49–7.28 (m, 5H), 7.17 (d, 1H), 7.05 (dd, 1H), 6.88 (d, 1H), 6.30 (d, 1H), 6.11 (m, 2H), 4.73 (d, 1H), 4.35 (bs, 1H), 3.3–3.05 (m, 3H), 3.0–2.6 (m, 7H), 2.45–2.1 (m, 3H), 1.85 (m, 1H); ); MS: [M+1]$^+$: 427.

Using the same coupling method, the compound 1f, (R,S)-7-Chloro-2,3,4,5-tetrahydro-benzo[b]oxepine-2-carboxylic acid (0.177 g, 0.78 mmol) was coupled with 2-[(S)-3-hydroxy-pyrrolidin-1-yl]-(S)-1-phenyl-ethyl-methyl-amine dihydrochloride (0.21 g, 0.73 mmol) to give 2 (248 mg, 83%). $^1$H NMR (300 MHz, CDCl$_3$) δ 7.55–7.28 (m, 5H), 7.2–6.85 (m, 3H), 6.13 (m, 1H), 4.44 (m, 1H), 4.31 (b,s, 1H), 3.4–2.6 (m, 10H), 2.55–2.05 (m, 6H), 1.79 (m, 1H), 1.57 (m, 1H); MS: [M+1]$^+$: 429.

Compound 3* the diastereomer within 2 with shorter retention time in the LC/MS analysis was obtained after chromatography on silica gel. $^1$H NMR (300 MHz, CDCl$_3$) δ 7.5–7.28 (m, 5H), 7.1 (m, 2H), 6.96 (d, 1H), 6.12 (m, 1H), 4.4 (d, 1H), 4.3 (brs, 1H), 3.35–2.6 (m, 10H), 2.5–2.1 (m, 6H), 1.81 (m, 1H), 1.55 (m, 1H); MS: [M+1]$^+$: 429.

Examples $4h_1$* and $4h_2$*

Preparation of 1,2-Dichloro-6,7,8,9-tetrahydro-5H-benzocycloheptene-5-carboxylic acid [2-(3-hydroxy-pyrrolidin-1-yl)-1-phenyl-ethyl]-methyl-amide a) 5-(2,3-Dichloro-phenyl)-pent-4-enoic acid (4a)

(3-Carboxypropyl) triphenylphosphonium bromide (18.1 g, 42 mmol) was dissolved in anhydrous tetrahydrofuran (250 ml), treated dropwise with potassium tert-butoxide (92.4 mL, 1.0 M in tetrahydrofuran, 92.4 mmol) and stirred for 1.5 hours at 0° C. A solution of commercially available 2,3-dichlorobenzaldehyde (Aldrich Chemical Company) (5.25 g, 30 mmol) in tetrahydrofuran (50 ml) was added dropwise at 0° C., and the reaction mixture was stirred at room temperature overnight. The reaction was quenched with 1N HCl (150 ml) and extracted with ethyl acetate (3×200 ml). The organic layer was dried (Na$_2$SO$_4$) and concentrated. The residue was purified by flash chromatography over silica gel (hexane-ethyl acetate, 2:1) to give the title compound (7.30 g, ~100%). $^1$H NMR (300 MHz, CDCl$_3$) δ: 7.4–5.85 (m, 5H), 2.96–2.65 (m, 4H).

b) 5-(2,3-Dichloro-phenyl)-pentanoic acid (4b)

Compound 4a (12.5 g, 51.2 mmol) was dissolved in ethyl acetate (500 mL) and hydrogenated at 1 atm in the presence of 10% Pd/C (2.0 g) for 5 h. Filtration followed by evaporation of the solvent afforded the title compound (12.6 g, ~100%). $^1$H NMR (300 MHz, CDCl$_3$) δ: 7.32–7.10 (m, 3H), 2.82 (t, 2H), 2.42 (t, 2H), 1.75 (m, 4H).

c) 1,2-Dichloro-6,7,8,9-tetrahydro-benzocyclohepten-5-one (4c)

Compound 4b (10.5 g, 42.7 mmol) was treated with oxalyl chloride ( 130 mL, 2.0 M in methylene chloride, 260 mmol) at room temperature for 4 hours and then concentrated. The residue was dissolved in anhydrous methylene chloride (600 ml) and aluminum chloride (11.6 g, 87 mmol) was added. The reaction mixture was stirred at room temperature overnight and quenched with 1N HCl (200 mL). The organic layer was separated and the aqueous layer was extracted with methylene chloride (2×100 mL). The combined organic layers were dried (Na$_2$SO$_4$) and concentrated. The residue was purified by flash chromatography on silica gel (hexane-ethyl acetate, 5:1) to yield the title compound (8.67 g, 89.1%). $^1$H NMR (300 MHz, CDCl$_3$) δ: 7.46 (d, 1H), 7.40 (d, 1H), 3.15 (t, 2H), 2.70 (m, 2H), 2.90–2.80 (m, 4H).

d) Trifluoro-methanesulfonic acid 1,2-dichloro-8,9-dihydro-7H-benzocyclohepten-5-yl ester (4d)

Lithium bis(trimethylsilyl)amide (20 mL, 1.0M in tetrahydrofuran, 20 mmol) was added at −78° C. to a solution of compound 4c (4.2 g, 18.4 mmol) in tetrahydrofuran (150 mL). After 40 minutes, a solution of N-phenyltrifluoromethanesulfonimide (7.2 g, 20 mmol) in tetrahydrofuran (40 mL) was added dropwise. The reaction mixture was then stirred at 0° C. for 2.5 h, quenched by addition of water (80 mL), and extracted with a mixture of hexane and ether (1:1, 3×100 mL). The organic extracts were washed with water (2×100 mL), brine (100 mL) and dried (Na$_2$SO$_4$). Evaporation of the solvent gave the crude title compound (6.7 g, ~100%) which was used without further purification. $^1$H NMR (300 MHz, CDCl$_3$) δ: 7.42 (d, 1H), 7.32 (d, 1H), 6.31 (t, 1H), 3.00 (t, 2H), 2.10–2.20 (m, 4H).

e) 1,2-Dichloro-8,9-dihydro-7H-benzocycloheptene-5-carboxylic acid methyl ester (4e)

To a solution of compound 4d (6.7 g, 18.4 mmol) in dimethylformamide (40 mL) was added methanol (30 mL), triethylamine (4.18 mL, 30 mmol), 1,3-bis(diphenylphosphino)propane (619 mg, 1.5 mmol) and palladium acetate (338 mg, 1.5 mmol). Carbon monoxide was introduced and bubbled through the reaction mixture at 65–70° C. for 4 hours. The reaction mixture was cooled to room temperature and diluted with a mixed solvent (hexane-ether, 1:1, 250 mL), washed with 1N HCl (2×100 mL), brine (100 mL) and dried (Na$_2$SO$_4$). Evaporation of the solvent followed by flash chromatography on silica gel (hexane-ethyl acetate, 30:1 to 2:1) to yield the title compound (4.1 g, 82.4%). $^1$H NMR (300 MHz, CDCl$_3$) δ: 7.53 (t, 1H), 7.38 (d, 1H), 7.21(d, 1H), 3.82 (s, 3H), 2.88 (t, 2H), 2.22 (m, 2H), 1.99 (m, 2H).

f) 1,2-Dichloro-6,7,8,9-tetrahydro-5H-benzocycloheptene-5-carboxylic acid methyl ester (4f)

Compound 4e (1.35 g, 5 mmol) was dissolved in ethyl acetate (60 mL) and hydrogenated in the presence of platinum oxide using a hydrogen balloon. After 3.5 hours at room temperature, the reaction mixture was filtered and concentrated to give the title compound which was used without further purification for the next step. $^1$H NMR (300 MHz, CDCl$_3$) δ: 7.22 (d, 1H), 6.86 (d, 1H), 3.90 (dd, 1H), 3.74 (s, 3H), 3.14 (m, 1H), 2.97 (m, 1H), 2.10–1.42 (m, 6H).

g) 1,2-Dichloro-6,7,8,9-tetrahydro-5H-benzocycloheptene-5-carboxylic acid (4g)

Compound 4f was dissolved in a mixed solvent (methanol-tetrahydrofuran-water, 30-30-30 ml), and treated with lithium hydroxide (1.05 g, 25 mmol). The reaction mixture was stirred at room temperature overnight and concentrated, acidified with 3N HCl and extracted with ethyl acetate (3×50 mL) to yield the title compound (1.18 g, 91.5% for two steps). $^1$H NMR (300 MHz, CDCl$_3$) δ: 7.24 (d, 1H), 6.95 (d, 1H), 3.96 (dd, 1H), 3.26 (m, 1H), 2.94 (m, 1H), 2.17–1.50 (m, 6H).

h) 1,2-Dichloro-6,7,8,9-tetrahydro-5H-benzocycloheptene-5-carboxylic acid [2-{(S)-3-hydroxy-pyrrolidin-1-yl)}-1-(S)-phenyl-ethyl]-methyl-amide (4h$_1$*, 4h$_2$*)

By using the general Method A, pure 4h$_1$* (260 mg, 56.5%) with longer retention time in LC/MS and 4h$_2$* (120 mg, 26.1%) with shorter retention time in LC/MS were prepared. 4h$_1$*: $^1$H NMR (300 MHz, CDCl$_3$) δ: 7.31 (m, 7H), 6.28 (m, 1H), 4.41 (m, 1H), 4.01 (m, 1H), 3.59 (m, 1H), 3.28 (m, 2H), 3.0–1.33 (m, 17H); MS: [M+1]$^+$: 461. 4h$_2$*: $^1$H NMR (300 MHz, CDCl$_3$) δ: 7.35–6.64 (m, 7H), 6.22 (m, 1H), 4.36 (m, 1H), 4.03 (m, 1H), 3.54 (m, 1H), 3.40–1.30 (m, 19H); MS: [M+1]$^+$: 461.

Examples 5e$_1$* and 5e$_2$*

Preparation of 7-Methoxy-1,2,3,4-tetrahydro-naphthalene-1-carboxylic acid [2-{(S)-3-hydroxy-pyrrolidin-1-yl}-(S)-1-phenyl-ethyl]-methyl-amide a) Trifluoro-methanesulfonic acid 7-methoxy-3,4-dihydro-naphthalen-1-yl ester (5a)

Commercially available 7-methoxy-1-tetralone (3.24 g, 18.4 mmol) (Aldrich Chemical Company) was converted to 5a using the same procedure as for the preparation of Example 4d. $^1$H NMR (300 MHz, CDCl$_3$) δ: 7.12 (d, 1H), 6.92 (d, 1H), 6.81 (dd, 1H), 6.05 (t, 1H), 3.82 (s, 3H), 2.81 (t, 1H), 2.50 (m, 1H).

b) 7-Methoxy-3,4-dihydro-naphthalene-1-carboxylic acid methyl ester (5b)

Compound 5a was converted to the title compound (3.3 g, 82.2% overall yield) by using the same procedure as for the preparation of 4e. $^1$H NMR (300 MHz, CDCl$_3$) δ: 7.46 (d, 1H), 7.19 (t, 1H), 7.06 (d, 1H), 7.67 (dd, 1H), 3.85 (s, 3H), 3.81 (s, 3H), 2.70 (t, 1H), 2.40 (m, 1H).

c) 7-Methoxy-1,2,3,4-tetrahydro-naphthalene-1-carboxylic acid methyl ester (5c)

Compound 5b (3.3 g, 15.1 mmol) was hydrogenated in ethyl acetate (150 mL) using platinum oxide (1.5 g) as catalyst for 3.5 hours at room temperature. Filtration, concentration and purification of the residue by flash chromatography over silica gel (Hexane-ethyl acetate, 30:1 to 6:1) gave the title compound (2.33 g, 70%). $^1$H NMR (300 MHz, CDCl$_3$) δ: 7.02 (d, 1H), 6.75 (dd, 1H), 6.71 (d, 1H), 3.81 (t, 1H), 3.76 (s, 3H), 3.71 (s, 3H), 2.77 (m, 2H), 2.20–1.75 (m, 4H).

d) (R,S)-7-Methoxy-1,2,3,4-tetrahydro-naphthalene-1-carboxylic acid (5d)

Compound 5c (2.2 g, 10 mmol) was hydrolyzed by lithium hydroxide (2.10 g, 50 mmol) to the title acid (2.03 g, ~100%). $^1$H NMR (300 MHz, DMSO-d$_6$) δ: 12.38 (s, 1H), 6.99 (d, 1H), 6.74 (dd, 1H), 6.69 (d, 1H), 3.68 (s, 3H), 3.66 (m, 1H), 2.64 (m, 2H), 2.05–1.68 (m, 4H).

e) 7-Methoxy-1,2,3,4-tetrahydro-naphthalene-1-carboxylic acid [2-{(S)-3-hydroxy-pyrrolidin-1-yl}-(S)-1-phenyl-ethyl]-methyl-amide (5e$_1$*, 5e$_2$*)

By using the general Method A for the amide formation, 5e$_1$* (600 mg, 49%) with longer retention time in LC/MS and 5e$_2$* (310 mg, 25.3%) with shorter retention time in LC/MS were obtained. 5e$_1$*: $^1$H NMR (400 MHz, DMSO-d$_6$) δ: 7.50–6.58 (m, 8H), 5.92, 5.32 (m, total 1H), 4.75–4.63 (m, 1H), 4.32–4.10 (m, 2H), 3.68–1.55 (m, 20H); MS: [M+1]$^+$: 409. 5e$_2$*: $^1$H NMR (400 MHz, DMSO-d$_6$) δ: 7.38–6.32 (m, 8H), 5.90, 5.38 (m, total 1H), 4.70–4.16 (m, 3H), 3.70–1.55 (m, 20H); MS: [M+1]$^+$: 409.

Example 6g$_1$* and 6g$_2$*

Preparation of 5-Methoxy-8-(pyrrolidine-1-sulfonyl)-1,2,3,4-tetrahydro-naphthalene-1-carboxylic acid [2-{(S)-3-hydroxy-pyrrolidin-1-yl}-(S)-1-phenyl-ethyl]-methyl-amide a) Trifluoro-methanesulfonic acid 5-methoxy-3,4-dihydro-naphthalen-1-yl ester (6a)

By using the same procedure as described above in 4d, commercially available 5-methoxy-1-tetralone (16.2 g, 92.05 mmol) (Aldrich Chemical Company) was converted to the title enol triflate which was used for the next step without further purification. $^1$H NMR (400 MHz, CDCl$_3$) δ: 7.18 (t, 1H), 6.94 (d, 1H), 6.83 (d, 1H), 5.95 (t, 1H), 3.79 (s, 3H), 2.81 (m, 2H), 2.41 (m, 2H).

b) (R,S)-5-Methoxy-3,4-dihydro-naphthalene-1-carboxylic acid methyl ester (6b)

The crude material 6a from the preceding step was converted to the title compound (16.3 g, 81.2%) by using the same procedure as described in Example 4e. $^1$H NMR (400 MHz, CDCl$_3$) δ: 7.38–7.14 (m, 3H), 6.82 (d, 1H), 3.83 (s, 3H), 2.78 (t, 2H), 2.36 (m, 2H).

c) (R,S)-5-Methoxy-1,2,3,4-tetrahydro-naphthalene-1-carboxylic acid methyl ester (6c)

Compound 6b (9.68 g, 44 mmol) was dissolved in ethyl acetate (400 mL) and hydrogenated in the presence of 10% Pd/C (2.0 g) using a hydrogen balloon. The reaction mixture was stirred at room temperature overnight, filtered and concentrated to give crude product (9.68 g, ~100%) which was used for the next step without further purification. $^1$H NMR (400 MHz, CDCl$_3$) δ: 7.10 (t, 1H), 6.78 (d, 1H), 6.71 (d, 1H), 3.82 (s, 3H), 3.70 (s, 3H), 2.65 (m, 2H), 2.10–1.78 (m, 4H).

d) (R,S)-8-Chlorosulfonyl-5-methoxy-1,2,3,4-tetrahydro-naphthalene-1-carboxylic acid methyl ester (6d)

To a solution of compound 6c (8.8 g, 40 mmol) was in 1,2-dichloroethane (80 mL) was added sulfur trioxide N,N-dimethylformamide complex (7.14 g, 46.6 mmol). The reaction mixture was stirred at 75° C. overnight and then cooled to room temperature. Oxalyl chloride (4.2 ml, 48 mmol) was added dropwise to the above reaction mixture and heated to 65° C. for 3.5 hours and then cooled to 0° C. with an ice-bath and quenched by slowly adding water (30 mL). The organic layer was separated, washed with water (2×30 mL), dried (Na$_2$SO$_4$) and evaporated to give crude sulfonyl chloride which was used directly in the next step.

e) (R,S)-5-Methoxy-8-pyrrolidine-1-sulfamoyl-1,2,3,4-tetrahydro-naphthalene-1-carboxylic acid methyl ester (6e)

Compound 6d (2.23 g, 7 mmol) in methylene chloride (10 mL) was added to a solution of pyrrolidine (7.0 mL, 2.0 M in tetrahydrofuran, 14 mmol) in methylene chloride (60 mL) containing triethylamine (1.96 mL, 14 mmol) at 0° C. The reaction mixture was stirred for 45 minutes and washed with 1N hydrochloric acid (30 mL) and saturated aqueous sodium bicarbonate (30 mL), and dried (Na$_2$SO$_4$). Evaporation of the solvent and purification of the residue by flash chromatography over silica gel (hexane-ethyl acetate, 3:1) yielded the title sulfonamide (1.9 g, 83%). $^1$H NMR (400 MHz, CDCl$_3$) δ: 7.90 (d, 1H), 6.82 (d, 1H), 4.66 (m, 1H), 3.90 (s, 3H), 3.68 (s, 3H), 2.90 (dd, 1H), 2.66 (s, 6H), 2.53 (m, 1H), 2.29 (m, 1H), 1.87 (m, 2H), 1.63 (m, 1H).

f) (R,S)-5-Methoxy-8-pyrrolidine-1-sulfamoyl-1,2,3,4-tetrahydro-naphthalene-1-carboxylic acid (6f)

Compound 6e (1.8 g, 5.5 mmol) was dissolved in methanol (80 mL) and to this solution was added 6N aqueous potassium hydroxide (50 mL, 300 mmol). The reaction mixture was refluxed for 3 h, concentrated, acidified with 6N hydrochloric acid to pH 1–2, and extracted with ethyl acetate (3×100 mL). The organic extracts was dried (Na$_2$SO$_4$), and concentrated to give the title acid (1.7 g, 98.7%). $^1$H NMR (400 MHz, DMSO-d$_6$) δ: 12.21 (s, 1H), 7.73 (d, 1H), 7.04 (d, 1H), 4.40 (m, 1H), 3.88 (s, 3H), 2.73 (dd, 1H), 2.58 (s, 6H), 2.51 (m, 1H), 2.19 (m, 1H), 1.88–1.60 (m, 3H). The structure of this acid was confirmed to be para-sulfonamide substituted regio-isomer by an NOE experiment. Irradiation of the methoxy proton at 3.88 ppm caused enhancement of one aromatic proton at 7.04 ppm, indicating close proximity of these protons which is consistent only with the structure of para-sulfonylated compound.

g) 5-Methoxy-8-(pyrrolidine-1-sulfonyl)-1,2,3,4-tetrahydro-naphthalene-1-carboxylic acid [2-{(S)-3-hydroxy-pyrrolidin-1-yl}-(S)-1-phenyl-ethyl]-methyl-amide (6g$_1$*, 6g$_2$*)

Compound 6f (1.04 g, 3.3 mmol) was coupled with 1-(2-methylamino-2-phenyl-ethyl)-pyrrolidin-3-ol dihydrochloride (879 mg, 3.0 mmol) in the presence of triethylamine (2.1 ml, 15 mmol) and 2-chloro-1-methylpyridinium iodide (921 mg, 3.6 mmol) as described in general Method A except that the reaction mixture was refluxed for 6 hours and then stirred at room temperature overnight. Typical work-up yielded 6g$_1$* (330 mg, 21.4%) with longer retention time in LC/MS and 6g$_2$* (380 mg, 24.6%) with shorter retention time in LC/MS. 6g$_1$*: $^1$H NMR (400 MHz, DMSO-d$_6$) δ: 7.68–7.30 (m, 6H), 7.03 (d, 1H), 5.69 (m, 1H), 4.82–4.63 (m, 2H), 4.19 (m, 1H), 3.90 (s, 3H), 3.00–1.50 (m, 23H); MS: [M+1]$^+$: 516. 6g$_2$*: $^1$H NMR (400 MHz, DMSO-d$_6$) δ: 7.68 (d, 1H), 7.40–7.30 (m, 5H), 7.03 (d, 1H), 5.69 (m, 1H), 4.87 (m, 1H), 4.68 (m, 1H), 4.18 (m, 1H), 3.89 (s, 3H), 3.18 (m, 1H), 2.90–2.50 (m, 9H), 2.35 (s, 6H), 2.23–2.52 (m, 7H); MS: [M+1]$^+$: 516.

In like manner to the preparation of 6g$_1$* and 6g$_2$*, diastereomers of 8-dimethylsulfamoyl-5-methoxy-1,2,3,4-tetrahydro-naphthalene-1-carboxylic acid [2-{(S)-3-hydroxy-pyrrolidin-1-yl}-(S)-1-phenyl-ethyl]-methyl-amide 7a$_1$* (with longer retention time in LC/MS) and 7a$_2$* (with shorter retention time in LC/MS): were prepared. 7a$_1$*. $^1$H NMR (400 MHz, DMSO-d$_6$) δ: 7.67–7.30 (m, 6H), 7.03 (d, 1H), 5.69 (m, 1H), 4.84–4.58 (m, 2H), 4.18 (m, 1H), 3.89 (s, 3H), 3.19–1.50 (m, 25H); MS: [M+1]$^+$: 542. 7a$_2$*: $^1$H NMR (400 MHz, DMSO-d$_6$) δ: 7.68 (d, 1H), 7.38–7.25 (m, 5H), 7.04 (d, 1H), 5.69 (m, 1H), 4.90 (m, 1H), 4.68 (m, 1H), 4.19 (m, 1H), 3.89 (s, 3H), 3.12–1.52 (m, 25H); MS: [M+1]$^+$: 542.

Example 8

Preparation of (R,S)-6-Chloro-4-methylene-chroman-2-carboxylic acid {2-[(S)-3-hydroxy-pyrrolidin-1-yl]-(S)-1-phenyl-ethyl}-methyl-amide a) (2-Bromo-4-chloro-phenoxy)-acetic acid ethyl ester (8a)

To a stirred solution of commercially available 2-bromo-4-chloro-phenol (Aldrich Chemical Company) (10.05 g, 48.4 mmol) in acetone (300 mL) was added potassium carbonate (10.03 g, 72.6 mmol) and ethyl bromoacetate (8.0 mL, 72.3 mmol). The reaction mixture was heated at reflux overnight. After cooling to room temperature, the solids were filtered and the solution was concentrated under reduced pressure. The crude product was purified by flash chromatography (silica gel, ethyl acetate/hexane) to afford 13.98 g (98%) of the title compound. $^1$H NMR (300 MHz, CDCl$_3$) δ 7.58 (s, 1H), 7.22 (d, 1H), 6.76 (d, 1H), 4.72 (s, 2H), 4.25 (q, 2H), 1.29 (t, 3H)

b) 2-(2-Bromo-4-chloro-phenoxy)-pent-4-enoic acid ethyl ester (8b)

Lithium bis(trimethylsilyl)amide (17.1 mL, 1.0 M solution in tetrahydrofuran, 17.1 mmol) was added slowly to a stirred solution of compound 8a (5.02 g, 17.1 mmol) in dry tetrahydrofuran (100 mL) at −78° C. After 45 minutes at −78° C., allyl bromide (1.8 mL, 20.6 mmol) was added dropwise. The reaction mixture was stirred at −78° C. for another 5 hours, and then at room temperature overnight. The reaction was quenched with saturated ammonium chloride solution and the biphasic mixture was extracted with ethyl acetate. The combined ethyl acetate layers were washed with brine, dried over anhydrous sodium sulfate, filtered and concentrated under reduced pressure. The crude product was purified by flash chromatography (silica gel, ethyl acetate/hexane) to afford 1.37 g (24%) of the title compound. $^1$H NMR (300 MHz, CDCl$_3$) δ 7.58 (s, 1H), 7.20 (d, 1H), 6.73 (d, 1H), 5.98 (m, 1H), 5.24 (m, 2H), 4.66 (t, 1H), 4.23 (q, 2H), 2.81 (m, 2H), 1.28 (t, 3H)

c) (R,S)-6-Chloro-4-methylene-chroman-2-carboxylic acid ethyl ester (8c)

Palladium tetrakis(triphenylphosphine) (0.52 g, 0.45 mmol) was added to a stirred solution of compound 8b (2.97 g, 8.9 mmol) in dry triethylamine (50 mL) under nitrogen atmosphere and the mixture was refluxed overnight. After cooled down to room temperature, the mixture was partitioned by the addition of 1M hydrochloric acid (50 mL) and dichloromethane (50 mL). The aqueous phase was extracted with dichloromethane three more times. The combined dichloromethane layers were washed with saturated sodium bicarbonate (50 mL), brine (50 mL), dried over anhydrous sodium sulfate, filtered and concentrated under reduced pressure. The crude product was purified by flash chromatography (silica gel, ethyl acetate/hexane) to afford 0.88 g (39%) of the title compound. $^1$H NMR (300 MHz, CDCl$_3$) δ 7.50 (s, 1H), 7.27 (d, 1H), 6.96 (d, 1H), 5.57 (s, 1H), 5.07 (s, 1H), 4.81 (t, 1H), 2.94 (m, 2H), 1.29 (t, 3H)

d) (R,S)-6-Chloro-4-methylene-chroman-2-carboxylic acid (8d)

To a stirred solution of compound 8c (0.95 g, 3.76 mmol) in a mixed solvent of methanol, tetrahydrofuran, and water (20 mL of each) was added lithium hydroxide monohydrate (0.63 g, 15 mmol) and the mixture was stirred overnight at room temperature. The organic solvents were removed under reduced pressure and the aqueous solution was acidified with 6N hydrochloric acid until pH~1. The resulting acid was then extracted with dichloromethane three times. The combined dichloromethane layers were washed with brine, dried over anhydrous sodium sulfate, filtered, concentrated under reduced pressure and finally dried in vacuo to afford 0.81 g (95%) of the title compound. $^1$H NMR (300 MHz, CDCl$_3$) δ 7.52 (s, 1H), 7.16 (d, 1H), 6.94 (d, 1H), 5.61 (s, 1H), 5.11 (s, 1H), 4.88 (t, 1H), 3.03 (m, 1H), 2.92 (m, 1H).

e) (R,S)-6-Chloro-4-methylene-chroman-2-carboxylic acid {2-[(S)-3-hydroxy-pyrrolidin-1-yl]-(S)-1-phenyl-ethyl}-methyl-amide (8)

Using the coupling method A, compound 8d (0.38 g, 1.68 mmol) was coupled with 2-[(S)-3-hydroxy-pyrrolidin-1-yl]-(S)-1-phenyl-ethyl-methyl-amine dihydrochloride (0.45 g, 1.53 mmol) to yield 8 (510 mg, 78%). ¹H NMR (400 MHz, CDCl₃) δ 7.65–7.27 (m, 6H), 7.13 (m, 1H), 6.87 (m, 1H), 6.08 (m, 1H), 5.59 (s, 1H), 5.06 (m, 1H), 4.92 (m, 1H), 4.3 (b,s, 1H), 3.35–2.6 (m, 8H), 2.5–1.7 (m, 6H); MS: [M+1]⁺: 427.

Examples 9, 10, and 11

Preparation of (R) and (S)-6-Chloro-4-oxo-chroman-2-carboxylic acid {2-[(S)-3-hydroxy-pyrrolidin-1-yl]-(S)-1-phenyl-ethyl}-methyl-amide, and (R,S)-6-Chloro-chroman-2-carboxylic acid {2-[(S)-3-hydroxy-pyrrolidin-1-yl]-(S)-1-phenyl-ethyl}-methyl-amide a) 4-(5-Chloro-2-hydroxy-phenyl)-4-oxo-but-2-enoic acid (9a)

Maleic anhydride (3.68 g, 37.5 mmol) and anhydrous aluminum chloride (10 g, 75 mmol) were dissolved 1,2-dichloroethane (35 mL) by heating at 50° C. for 15 minutes and then 4-chloroanisole (4.11 mL, 32.9 mmol) was added dropwise. The mixture was refluxed for 1 hour and poured into conc. hydrochloric acid (20 mL) with cracked ice (130 g). The resulting solids were filtered, washed with water, dichloromethane and dried under vacumn to afford 5.46 g (73%) of the title compound. ¹H NMR (300 MHz, DMSO-d₆) δ 13.12 (brs, 1H), 11.32 (s, 1H), 7.90 (d, 1H), 7.76 (s, 1H), 7.58 (d, 1H), 7.09 (d, 1H), 6.68 (d, 1H).

b) (R,S)-6-Chloro-4-oxo-chroman-2-carboxylic acid (9b)

To a stirred suspension of compound 9a (step a) (5.16 g, 22.8 mmol) in water (150 mL) was added dropwise 1N sodium hydroxide aqueous solution (24 mL, 24 mmol). After heating to 100° C., the mixture was cooled down to room temperature and acidified with concentrated hydrogen chloride acid until pH~1. The resulting residues were filtered, washed with water and dried in vacuo to afford 4.61 g (89%) of the title compound. ¹H NMR (300 MHz, DMSO-d₆) δ 13.55 (b, 1H), 7.72 (s, 1H), 7.16 (d, 1H), 7.21 (d, 1H), 5.42 (t, 1H), 3.20 (dd, 1H), 3.0 (dd, 1H).

c) (R,S)-6-Chloro-chroman-2-carboxylic acid (9c)

To a stirred suspension of compound 9b (1.13 g, 5 mmol) in trifluoroacetic acid (5 mL) was added dropwise triethylsilane (2.4 mL, 12.5 mmol). The mixture was stirred at 55° C. for three days. After cooled down to 25° C., the excess triethylsilane and solvent were removed under reduced pressure and the residue was dissolved in 1N sodium hydroxide. The aqueous solution was washed with ethyl ether, acidified with 6N hydrogen chloride acid until pH~1, and extracted with ethyl acetate. The combined extracts were washed with water, brine, dried over anhydrous sodium sulfate, filtered, concentrated under reduced pressure, and dried in vacuo to afford 0.95 g (90%) of the title compound. ¹H NMR (300 MHz, DMSO-d₆) δ 13.08 (b, 1H), 7.15 (m, 2H), 6.86 (d, 1H), 4.83 (t, 1H), 2.82 (m, 1H), 2.76 (m, 1H), 2.11 (m, 2H).

d) 6-Chloro-4-oxo-(R)-chroman-2-carboxylic acid {2-[(S)-3-hydroxy-pyrrolidin-1-yl]-(S)-1-phenyl-ethyl}-methyl-amide and (R,S)-6-Chloro-chroman-2-carboxylic acid {2-[(S)-3-hydroxy-pyrrolidin-1-yl]-(S)-1-phenyl-ethyl}-methyl-amide Using coupling method A, compound 9b (1.0 g, 4.4 mmol) was coupled with 2-[(S)-3-hydroxy-pyrrolidin-1-yl]-(S)-1-phenyl-ethyl-methyl-amine dihydrochloride (1.18 g, 4 mmol) to give 9 (0.61 g, 36%) with shorter retention time in LC/MS and 10 (0.89 g, 52%) with longer retention time in LC/MS. 9: ¹H NMR (300 MHz, CDCl₃) δ 7.9 (s, 1H), 7.45 (d, 1H), 7.3 (m, 3H), 7.2 (m, 2H), 6.95 (d, 1H), 6.0 (m, 1H), 5.59 (t, 1H), 4.32 (brs, 1H), 3.35–2.6 (m, 10H), 2.45 (m, 1H), 2.2 (m, 2H), 1.88 (m, 1H); MS: [M+1]⁺: 429. 10: ¹H NMR (200 MHz, CDCl₃) δ 7.9 (s, 1H), 7.5–7.25 (m, 6H), 7.0 (d, 1H), 6.15 (t, 1H), 5.95 (m, 1H), 4.2 (b,s, 1H), 3.4–2.5 (m, 10H), 2.25–1.95 (m, 2H), 1.85–1.5 (m, 2H); MS: [M+1]⁺: 429. The absolute stereochemistry for 9 and 10 were assigned based on their retention times in LC/MS (see 15, 16 for details).

In the same manner, the acid obtained from 9c, (R,S)-6-Chloro-chroman-2-carboxylic acid (1.3 g, 6.1 mmol) was coupled with 2-[(S)-3-hydroxy-pyrrolidin-1-yl]-(S)-1-phenyl-ethyl-methyl-amine dihydrochloride (1.63 g, 5.5 mmol) to give 11 (1.83 g, 80%) as a diastereomer mixture. ¹H NMR (400 MHz, CDCl₃) δ: 7.44–7.24 (m, 5H), 7.11–6.57 (m, 3H), 6.17–6.01, 5.5–4.8 (m, 2H), 4.36–4.15 (b, s, 1H), 3.3–1.6 (m, 16H); MS: [M+1]⁺: 415.

Examples 12 and 13

Preparation of (R)-6-Chloro-chroman-2-carboxylic acid {2-[(S)-3-hydroxy-pyrrolidin-1-yl]-(S)-1-phenyl-ethyl}-methyl-amide and (S)-6-Chloro-chroman-2-carboxylic acid {2-[(S)-3-hydroxy-pyrrolidin-1-yl]-(S)-1-phenyl-ethyl}-methyl-amide Compounds 12 and 13 were obtained by preparative separation of 11 and the stereochemistry at 2-position was assigned based on their retention times in LC/MS (see Example 15, 16 for details).

Column: Michrom BioResources Inc. Magic C18 Macro Bullet
Temperature: 40° C. Flow: 1.0 mL/min
Detector: PDA 200 nm to 300 nm, total scan
Mass Detector: Singe quadrupole with Electrospray Ionization
Mobile Phase A: 10 mM Ammonium Acetate, pH 4.5
Mobile Phase B: Acetonitrile
Gradient (linear): 100% A to 99% B in 3.2 minutes, hold at 99% B until 3.6 minutes.
Instrument(s): HPLC: ThermoFinnigan Surveyor
Mass Spectrometer: ThermoFinnigan AQA
Compound 12: (R)-6-Chloro-chroman-2-carboxylic acid {2-[(S)-3-hydroxy-pyrrolidin-1-yl]-(S)-1-phenyl-ethyl}-methyl-amide ¹H NMR (400 MHz, CDCl₃) δ: 7.58–6.71 (m, 8H), 6.45–6.05 (m, 1H), 5.5–1.7 (m, 18H); MS: [M+1]⁺: 415.
Compound 13: (S)-6-Chloro-chroman-2-carboxylic acid {2-[(S)-3-hydroxy-pyrrolidin-1-yl]-(S)-1-phenyl-ethyl}-methyl-amide ¹H NMR (400 MHz, CDCl₃) δ: 7.48–7.28 (m, 3H), 7.25–6.95 (m, 4H), 6.68 (d, 1H), 6.4–6.2 (m, 1H), 5.0–1.95 (m, 18H); MS: [M+1]⁺: 415.

Example 14

Preparation of (R,S)-Chroman-2-carboxylic acid {2-[(S)-3-hydroxy-pyrrolidin-1-yl]-(S)-1-phenyl-ethyl}-methyl-amide (R,S)-Chroman-2-carboxylic acid 14a (588 mg, 3.3 mmol) was prepared using a literature method see (G. Ladouceur, et al., WO 99/32475). m.p: 97.5–99° C.; ¹H NMR (400 MHz, DMSO-d₆) δ: 13.00 (s, 1H), 7.06 (m, 2H), 6.80 (m, 2H), 4.77 (dd, 1H), 2.76 (m, 1H), 2.66 (m, 1H), 2.10 (m, 2H).

(R,S)-Chroman-2-carboxylic acid (588 mg, 3.3 mmol) was coupled with 1-(2-methylamino-(S)-2-phenyl-ethyl)-pyrrolidin-(S)-3-ol dihydrochloride (879 mg, 3.0 mmol)

using the general method A to yield 14 (900 mg, 79%) as a mixture of diastereomers. $^1$H NMR (400 MHz, DMSO-$d_6$) δ: 7.40–6.60 (m, 9H), 5.78, 5.35 (m, total 1H), 5.23–5.16 (m, 1H), 4.66 (m, 1H), 4.15 (m, 1H), 3.15–1.50 (m, 15H); MS: [M+1]$^+$: 381.

Examples 15 and 16

Preparation of (R)-Chroman-2-carboxylic acid {2-[(S)-3-hydroxy-pyrrolidin-1-yl]-(S)-1-phenyl-ethyl}-methyl-amide and (S)-Chroman-2-carboxylic acid {2-[(S)-3-hydroxy-pyrrolidin-1-yl]-(S)-1-phenyl-ethyl}-methyl-amide Compounds 15 and 16, the two pure diastereomers of 14 were prepared by coupling of the corresponding enantiomeric pure (R)-chroman-2-carboxylic acid 14c$_1$ {[α]$_D$=−5.97 (c=1.039, MeOH, 20° C.)}, and (S)-chroman-2-carboxylic acid 14c$_2$ {[α]$_D$=+5.95 (c=1.058, MeOH, 20° C.)}, obtained via chiral separation of the racemic acid, with 1-(2-methylamino-(S)-2-phenyl-ethyl)-pyrrolidin-(S)-3-ol dihydrochloride using general method B.

Compound 15 with a (R)-configuration at 2-position had shorter retention time in LC/MS, and compound 16 with a (S)-configuration at 2-position had a longer retention time in LC/MS. This phenomenon is also consistent with other substituted analogs, 27, 28, 49, 50 and 52, 53. Based on this phenomenon, the stereochemistry of the 2-position of the remaining analogs, 9, 10, 12, 13, 18, 19, 30, 31, 33, 34, 36, 37, 39, 40, 42, 43 and 45, 46 which were obtained by preparative HPLC separation of the corresponding diastereomer mixtures, were assigned.

Example 17

Preparation of 6-Iodo-(R,S)-chroman-2-carboxylic acid {2-[(S)-3-hydroxy-pyrrolidin-1-yl]-(S)-1-phenyl-ethyl}-methyl-amide a) (R,S)-6-Iodo-chroman-2-carboxylic acid (17a)

The title acid was prepared using the literature procedure (WO99/32475). To a solution of chroman-2-carboxylic acid 14a (6 g, 33.7 mmol) in acetic acid (180 mL) was added anhydrous zinc chloride (6 g, 44 mol) and folllowed by benzyltrimethylammonium dichloroiodate (12.5 g, 95%, 34 mmol). The reaction mixture was stirred at room temperature overnight and quenched with water (400 mL), extracted with methylene chloride (3×300 mL), dried (Na$_2$SO$_4$) and concentrated. The residue was dissolved in methylene chloride (200 mL) and washed with 10% aqueous sodium thiosulfate (80 mL), brine (80 mL) and dried (Na$_2$SO$_4$), concentrated to give the title acid (8.8 g, 86%). $^1$H NMR (400 MHz, DMSO-$d_6$) δ: 13.02 (s, 1H), 7.39 (m, 2H), 6.65 (d, 1H), 4.81 (m, 1H), 2.79 (m, 1H), 2.76–2.60 (m, 2H), 2.10 (m, 2H).

b) 6-Iodo-(R,S)-chroman-2-carboxylic acid {2-[(S)-3-hydroxy-pyrrolidin-1-yl]-(S)-1-phenyl-ethyl}-methyl-amide Using the general method A, compound 17a (1.0 g, 3.3 mmol) was coupled with 1-(2-methylamino-(S)-2-phenyl-ethyl)-pyrrolidin-(S)-3-ol dihydrochloride (879 mg, 3 mmol) to give 17 (1.2 g, 79%) as a diastereomer mixture. $^1$H NMR (400 MHz, DMSO-$d_6$) δ: 7.30 (m, 7H), 6.61 (m, 1H), 5.75, 5.26–5.15 (m, total 2H), 4.67 (m, 1H), 4.13 (m, 1H), 3.12–1.50 (m, 13H); MS: [M+1]$^+$: 507.

Examples 18 and 19

Preparation of 6-Thiophen-2-yl-(R)-chroman-2-carboxylic acid {2-[(S)-3-hydroxy-pyrrolidin-1-yl]-(S)-1-phenyl-ethyl}-methyl-amide and 6-Thiophen-2-yl-(S)-chroman-2-carboxylic acid {2-[(S)-3-hydroxy-pyrrolidin-1-yl]-(S)-1-phenyl-ethyl}-methyl-amide a) (R,S)-6-Thiophen-2-yl-chroman-2-carboxylic acid (18a)

To a solution of 6-iodo-chroman-2-carboxylic acid 17a (2.13 g, 7 mmol) in tetrahydrofuran (50 mL), 2-thienylzinc bromide (36.4 mL, 0.5 M, 18.2 mmol) was added under a nitrogen atmosphere at room temperature. This was followed by addition of tetrakis(triphenylphosphine)palladium (0) (578 mg, 0.5 mmol). The reaction mixture was heated to 50° C. and stirred overnight. After cooling to room temperature, the reaction was quenched with 1N HCl (50 mL), extracted with ethyl acetate (3×80 mL), dried (Na$_2$SO$_4$), and concentrated to give the title acid (1.56 g, 85.7%). $^1$H NMR (400 MHz, DMSO-$d_6$) δ: 13.08 (s, 1H), 7.42–7.35 (m, 4H), 7.07 (dd, 1H), 6.85 (d, 1H), 4.83 (dd, 1H), 2.80–2.70 (m, 2H), 2.13 (m, 2H).

In a like manner, coupling of (R,S)-6-thiophen-2-yl-chroman-2-carboxylic acid 18a with 1-(2-methylamino-(S)-2-phenyl-ethyl)-pyrrolidin-(S)-3-ol dihydrochloride (879 mg, 3 mmol) using the general method A gave a mixture of diastereomers which were separated under standard chromatographic conditions (silica gel, methanol-methylene, 1:50–1:10) to yield the diastereomerically pure 18 (500 mg, 36%) with a shorter retention time in LC/MS and 19 (600 mg, 43.3%) with a longer retention time in LC/MS. 18: $^1$H NMR (400 MHz, DMSO-$d_6$) δ: 7.40–6.65 (m, 11H), 5.75, 5.28–5.15 (m, 2H), 4.65 (m, 1H, 4.06 (m, 1H), 3.0–1.5 (m, 15H); MS: [M+1]$^+$: 463. 19: $^1$H NMR (400 MHz, DMSO-$d_6$) δ: 7.40–6.80 (m, 11H). 5.75, 5.28 (m, total 1H), 5.22 (m, 1H), 4.68 (m, 1H), 4.16 (m, 1H), 3.12–1.50 (m, 15H); MS: [M+1]$^+$: 463.

Example 20

Preparation of 6-Nitro-(R,S)-chroman-2-carboxylic acid {2-[(S)-3-hydroxy-pyrrolidin-1-yl]-(S)-1-phenyl-ethyl}-methyl-amide a) (R,S)-6-Nitro-chroman-2-carboxylic acid (20a)

(R,S)-Chroman-2-carboxylic acid 14a was nitrated using the literature procedure (WO 99/32475). To a solution of nitric acid (70%, 250 mL) at 0° C. was added portionwise chroman-2-carboxylic acid (15 g, 84.3 mmol). The reaction mixture was stirred for 1 hours and poured into ice (600 g). the solid was collected by filtration, washed with cold water (2×100 mL), and dried under vacuum to give the title acid (11.56 g, 61.5%). $^1$H NMR (400 MHz, DMSO-$d_6$) δ: 13.25 (brs, 1H), 8.02 (m, 2H), 7.02 (d, 1H), 5.01 (t, 1H), 2.92 (m, 1H), 2.75 (m, 1H), 2.20 (m, 2H).

b) 6-Nitro-(R,S)-chroman-2-carboxylic acid {2-[(S)-3-hydroxy-pyrrolidin-1-yl]-(S)-1-phenyl-ethyl}-methyl-amide Using the general method A, (R,S)-6-nitro-chroman-2-carboxylic acid 20a (1.48 g, 6.6 mmol) was coupled with 1-(2-methylamino-(S)-2-phenyl-ethyl)-pyrrolidin-(S)-3-ol dihydrochloride (1.76 g, 6.0 mmol) to give 20 as a mixture of diastereomers. $^1$H NMR (400 MHz, DMSO-$d_6$) δ: 8.00 (m, 2H), 7.39–6.85 (m, 6H), 5.75–5.28 (m, 2H), 4.65 (m, 1H), 4.12 (m, 1H), 3.16–1.50 (m, 15H); MS: [M+1]$^+$: 426.

Example 21

Preparation of 6-Amino-(R,S)-chroman-2-carboxylic acid {2-[(S)-3-hydroxy-pyrrolidin-1-yl]-(S)-1-phenyl-ethyl}-methyl-amide Compound 21 (1.2 g, ~100%) was prepared by hydrogenation of 20 (1.3 g, 3.06 mmol) over 10% Pd/C (300 mg) using a hydrogen balloon. $^1$H NMR (400 MHz, DMSO-$d_6$) δ: 7.45–7.25 (m, 5H), 6.52–6.30 (m, 3H), 5.98–4.88 (m, 3H), 4.28 (m, 1H), 3.16–1.50 (m, 17H); MS: [M+1]$^+$: 396.

Example 22

Preparation of 6-Acetylamino-(R,S)-chroman-2-carboxylic acid {2-[(S)-3-hydroxy-pyrrolidin-1-yl]-(S)-1-phenyl-ethyl}-methyl-amide a) (R,S)-6-Nitro-chroman-2-carboxylic acid methyl ester (22a)

To a solution of 6-nitro-chroman-2-carboxylic acid 20a (14.0 g, 62.8 mmol) in methanol (400 mL) was added hydrogen chloride (200 mL, 2.0 M in ether). The reaction mixture was stirred at room temperature overnight and concentrated to give the title ester (14.8 g, ~100%). $^1$H NMR (400 MHz, CDCl$_3$) δ: 8.04 (m, 2H), 7.02 (d, 1H), 4.89 (dd, 1H), 3.83 (s, 3H), 2.87 (m, 2H), 2.30 (m, 2H).

b) (R,S)-6-Amino-chroman-2-carboxylic acid methyl ester (22b)

Compound 22a (14.8 g, 62.8 mmol) was dissolved in a mixture of solvent (methylene chloride, 80 mL and methanol, 500 mL) and hydrogenated in the presence of 10% Pd/C (4.5 g) to afford the title compound (12.9 g, ~100%). $^1$H NMR (400 MHz, DMSO-$d_6$) δ: 6.58 (d, 1H), 6.48 (dd, 1H), 6.42 (d, 1H), 6.02 (brs, 2H), 4.77 (m, 1H), 3.68 (s, 3H), 2.68 (m, 1H), 2.53 (m, 1H), 2.10 (m, 1H), 2.00(m, 1H).

c) (R,S)-6-Acetylamino-chroman-2-carboxylic acid methyl ester (22c)

To a solution of compound 22b (2.07 g, 10 mmol) in methylene chloride (100 mL) at 0° C. was added triethylamine (3.5 mL, 25 mmol) and followed by dropwise addition of acetyl chloride (1.07 mL, 15 mmol). The reaction mixture was stirred for 1 hour and washed with saturated sodium bicarbonate (2×50 mL). The organic layer was dried (Na$_2$SO$_4$) and concentrated. The residue was purified by flash chromatography over silica gel (ethyl acetate-methylene chloride, 1:1) to give the title compound (2.24 g, 90%). $^1$H NMR (400 MHz, CDCl$_3$) δ: 7.33 (d, 1H), 7.28 (s, 1H), 7.02 (dd, 1H), 6.85 (d, 1H), 4.69 (m, 1H), 3.78 (s, 3H), 2.75 (m, 2H), 2.23–2.16 (m, 2H), 2.11 (s, 3H).

d) (R,S)-6-Acetylamino-chroman-2-carboxylic acid (22d)

Compound 22c (2.2 g, 8.84 mmol) was hydrolyzed with lithium hydroxide (1.89 g, 45 mmol) to yield the title acid (1.93 g, 93%). $^1$H NMR (400 MHz, DMSO-$d_6$) δ: 12.96 (s, 1H), 9.70 (s, 1H), 7.31 (d, 1H), 7.20 (dd, 1H), 6.72 (d, 1H), 4.73 (m, 1H), 2.76 (m, 1H), 2.60 (m, 1H), 2.11–2.02 (m, 2H), 1.97 (s, 3H).

e) 6-Acetylamino-(R,S)-chroman-2-carboxylic acid {2-[(S)-3-hydroxy-pyrrolidin-1-yl]-(S)-1-phenyl-ethyl}-methyl-amide Using the general method A, coupling of 22d (776 mg, 3.3 mmol) with 1-(2-methylamino-(S)-2-phenyl-ethyl)-pyrrolidin-(S)-3-ol dihydrochloride (879 mg, 3.3 mmol) yielded 22 (1.1 g, 83.9%) as a diastereomeric mixture. $^1$H NMR (400 MHz, DMSO-$d_6$) δ: 9.71 (s, 1H), 7.40–7.15 (m, 7H), 6.67–6.53 (m, 1H), 5.73, 5.30 (m, total 1H), 5.12–5.01 (m, 1H), 4.65 (m, 1H), 4.10 (m, 1H), 3.10–1.50 (m, 18H); MS: [M+1]$^+$: 438.

Examples 23–26

Preparation of 6-Methanesulfonylamino-(R,S)-chroman-2-carboxylic acid {2-[(S)-3-hydroxy-pyrrolidin-1-yl]-(S)-1-phenyl-ethyl}-methyl-amide, 6-(Cyclopropanecarbonyl-amino)-(R,S)-chroman-2-carboxylic acid {2-[(S)-3-hydroxy-pyrrolidin-1-yl]-(S)-1-phenyl-ethyl}-methyl-amide, (2-{[2-({S}-3-Hydroxy-pyrrolidin-1-yl)-{S}-1-phenyl-ethyl]-methyl-carbamoyl}-(R,S)-chroman-6-yl)-carbamic acid methyl ester, and 6-(Propane-1-sulfonylamino)- (R,S)-chroman-2-carboxylic acid {2-[(S)-3-hydroxy-pyrrolidin-1-yl]-(S)-1-phenyl-ethyl}-methyl-amide Following the same reaction sequence as for Compounds 22, Compounds 23–26 were prepared.

Compound 23: 6-Methanesulfonylamino-(R,S)-chroman-2-carboxylic acid {2-[(S)-3-hydroxy-pyrrolidin-1-yl]-(S)-1-phenyl-ethyl}-methyl-amide $^1$H NMR (400 MHz, DMSO-$d_6$) δ: 9.30 (s, 1H), 7.40–6.59 (m, 8H), 5.75, 5.3–5.05 (m, 2H), 4.68 (m, 1H), 4.15 (m, 1H), 3.10–1.50 (m, 18H); MS: [M+1]$^+$: 474.

Compound 24: 6-(Cyclopropanecarbonyl-amino)-(R,S)-chroman-2-carboxylic acid {2-[(S)-3-hydroxy-pyrrolidin-1-yl]-(S)-1-phenyl-ethyl}-methyl-amide $^1$H NMR (400 MHz, DMSO-$d_6$) δ: 9.97 (s, 1H), 7.42–7.20 (m, 7H), 6.70–6.54 (m, 1H), 5.78, 5.35–5.05 (m, 2H), 4.69 (m, 1H), 4.15 (m, 1H), 3.15–1.50 (m, 16H), 0.75 (m, 4H); MS: [M+1]$^+$: 464.

Compound 25: (2-{[2-({S}-3-Hydroxy-pyrrolidin-1-yl)-{S}-1-phenyl-ethyl]-methyl-carbamoyl}-(R,S)-chroman-6-yl)-carbamic acid methyl ester $^1$H NMR (400 MHz, DMSO-$d_6$) δ: 9.35 (s, 1H), 7.43–7.15 (m, 7H), 6.71–6.55 (m, 1H), 5.78, 5.32 (m, total 1H), 5.10 (m, 1H), 4.68 (m, 1H), 4.15 (m, 1H), 3.63 (s, 3H), 3.10–1.50 (m,15H); MS: [M+1]$^+$: 454.

Compound 26: 6-(Propane-1-sulfonylamino)-(R,S)-chroman-2-carboxylic acid {2-[(S)-3-hydroxy-pyrrolidin-1-yl]-(S)-1-phenyl-ethyl}-methyl-amide. $^1$H NMR (400 MHz, DMSO-$d_6$) δ 9.38 (s, 1H), 7.35 (m, 5H), 6.95 (m, 2H), 6.75–6.58 (m, 1H), 5.75, 5.30–5.08 (m, 2H), 4.68 (m, 1H), 4.14 (m, 1H), 3.10–1.50 (m, 18H), 0.95 (t, 3H); MS: [M+1]$^+$: 502.

Example 27 and 28

Preparation of 6-(Propane-1-sulfonylamino)-(R)-chroman-2-carboxylic acid {2-[(S)-3-hydroxy-pyrrolidin-1-yl]-(S)-1-phenyl-ethyl}-methyl-amide and 6-(Propane-1-sulfonyl amino)-(S)-chroman-2-carboxylic acid {2-[(S)-3-hydroxy-pyrrolidin-1-yl]-(S)-1-phenyl-ethyl}-methyl-amide Employing the same procedure used in the preparation of 26, (R)-Chroman-2-carboxylic acid 14c$_1$ and (S)-Chroman-2-carboxylic acid 14c$_2$ were converted to the corresponding substituted chiral acids: (R)-6-(Propane-1-sulfonylamino)-chroman-2-carboxylic acid and (S)-6-(Propane-1-sulfonylamino)-chroman-2-carboxylic acid. These substituted acids were then coupled with 1-(2-methylamino-(S)-2-phenyl-ethyl)-pyrrolidin-(S)-3-ol dihydrochloride using the general coupling method B to provide 27 and 28.

(R)-6-(Propane-1-sulfonylamino)-chroman-2-carboxylic acid and (S)-6-(Propane-1-sulfonylamino)-chroman-2-carboxylic acid: $^1$H NMR (400 MHz, DMSO-d$_6$) δ: 13.02 (s, 1H), 9.38 (s, 1H), 6.92 (m, 2H), 6.78 (d, 1H), 4.75 (m, 1H), 2.98 (m, 2H), 2.75 (m, 1H), 2.60 (m, 1H), 2.10–2.00 (m, 2H), 1.68 (m, 2H), 0.95 (s, 3H) (The two acids are enantiomers with identical NMR spectra)

Compound 27: 6-(Propane-1-sulfonylamino)-(R)-chroman-2-carboxylic acid {2-[(S)-3-hydroxy-pyrrolidin-1-yl]-(S)-1-phenyl-ethyl}-methyl-amide $^1$H NMR (400 MHz, CDCl$_3$) δ 7.31 (m, 5H), 6.96–6.80 (m, 3H), 6.40 (brs, 1H), 6.05, 5.32 (m, total 1H), 5.00–4.95 (m, 1H), 4.30 (brs, 1H), 3.22–1.65 (m, 19H), 1.02 (t, 3H); MS: [M+1]$^+$: 502; 27 had shorter retention time in LC/MS.

Compound 28: 6-(Propane-1-sulfonylamino)-(S)-chroman-2-carboxylic acid {2-[(S)-3-hydroxy-pyrrolidin-1-yl]-(S)-1-phenyl-ethyl}-methyl-amide $^1$H NMR (400 MHz, DMSO-d$_6$) δ 7.32 (m, 5H), 7.00–6.85 (m, 3H), 6.50 (m, 1H), 6.08, 5.45 (m, total 1H), 5.08, 4.86 (m, total 1H), 4.32, 4.17 (m, total 1H), 3.23–1.65 (m, 19H), 1.02 (t, 3H); MS: [M+1]$^+$: 502; 28 had longer retention time in LC/MS.

Example 29

Preparation of (R,S)-6-(Pyrrolidine-1-sulfonyl)-chroman-2-carboxylic acid {2-[(S)-3-hydroxy-pyrrolidin-1-yl]-(S)-1-phenyl-ethyl}-methyl-amide a) (R,S)-Chroman-2-carboxylic acid methyl ester (29a)

To a stirred solution of compound 14a (15 g, 84.2 mmol) in dry methanol (250 mL) was added hydrogen chloride (4.0 M solution in dioxane, 60 mL) and the mixture was stirred overnight at room temperature. The solvents were removed under reduced pressure, the residue was dissolved in ether (300 mL) and washed with 1N sodium bicarbonate (2×100 mL), brine (1×100 mL), dried over anhydrous sodium sulfate, filtered, concentrated under reduced pressure, and dried in vacuo to afford the title compound (15.05 g, 93%). $^1$H NMR (400 MHz, CDCl$_3$) δ 7.15–6.83 (m, 4H), 4.76 (dd, 1H), 3.79 (s, 3H), 2.8 (m, 2H), 2.25 (m, 2H).

b) (R,S)-6-Chlorosulfonyl-chroman-2-carboxylic acid methyl ester (29b)

Compound 29a (13.07 g, 71 mmol) was added portionwise to a cooled solution (0° C.) of chlorosulfonic acid (70 mL). After 30 minutes at 0° C. and 30 minutes at room temperature, the mixture was added to ice (800 g) dropwise. The resulting solids were collected by filtration, washed with water, and dried in vacuo. This yielded 11.46 g (58%) of the title compound. $^1$H NMR (400 MHz, CDCl$_3$) δ 7.8 (dd, 1H), 7.75 (d, 1H), 7.08 (d, 1H), 4.9 (t, 1H), 3.81 (s, 3H), 2.85 (m, 2H), 2.3 (m, 2H).

c) (R,S)-6-(Pyrrolidine-1-sulfonyl)-chroman-2-carboxylic acid methyl ester (29c)

A mixture of triethylamine (2.1 mL, 15 mmol) and pyrrolidine (0.5 mL, 6 mmol) was added dropwise to a stirred solution of compound 29b (1.45 g, 5 mmol) in dry tetrahydrofuran (30 mL) at 0° C. After 30 minutes at 0° C. and then warmed to room temperature, the solvent was removed, and the residue was partitioned by the addition of 1N hydrochloric acid (50 mL) and ethyl acetate (50 mL). The aqueous layer was extracted with ethyl acetate two more times and the combined ethyl acetate layers was washed with brine (1×50 mL), dried over anhydrous sodium sulfate, filtered, concentrated under reduced pressure. The crude product was purified by flash chromatography (silica gel, ethyl acetate/hexane) to afford 1.54 g (95%) of the title product. $^1$H NMR (400 MHz, CDCl$_3$) δ 7.6 (dd, 1H), 7.55 (d, 1H), 7.03 (d, 1H), 4.85 (t, 1H), 3.81 (s, 3H), 3.25 (m, 4H), 2.85 (m, 2H), 2.3 (m, 2H), 1.78 (m, 4H).

d) (R,S)-6-(Pyrrolidine-1-sulfonyl)-chroman-2-carboxylic acid (29d)

To a stirred solution of the mixture from Example 29c (1.52 g, 4.71 mmol) in a mixed solvent of methanol, tetrahydrofuran, and water (20 mL of each) was added lithium hydroxide monohydrate (0.80 g, 19 mmol) and the mixture was stirred overnight at room temperature. The organic solvents were removed under reduced pressure and the aqueous solution was acidified with 6N hydrochloric acid until pH ~1. The resulting solids were collected by filtration, washed with water, and dried in vacuo to afford 1.36 g (93%) of the title compound. $^1$H NMR (400 MHz, CDCl$_3$) δ 7.6 (dd, 1H), 7.55 (d, 1H), 7.03 (d, 1H), 4.85 (t, 1H), 3.25 (m, 4H), 2.85 (m, 2H), 2.3 (m, 2H), 1.78 (m, 4H).

e) (R,S)-6-(Pyrrolidine-1-sulfonyl)-chroman-2-carboxylic acid {2-[(S)-3-hydroxy-pyrrolidin-1-yl]-(S)-1-phenyl-ethyl}-methyl-amide Using the coupling method B, the title compound 29 was prepared: 1.36 g (80%). $^1$H NMR (400 MHz, CDCl$_3$) δ 7.58 (m, 2H), 7.43–7.3 (m, 5H), 7.0 (m, 1H), 6.08 (dd, 1H), 5.05 (m, 1H), 4.3 (b, s, 1H), 3.32–2.6 (m, 14H), 2.4–2.05 (m, 4H), 1.9–1.65 (m, 6H); MS: [M+1]$^+$: 514.

Examples 30 and 31

Preparation of (R)-6-(Pyrrolidine-1-sulfonyl)-chroman-2-carboxylic acid {2-[(S)-3-hydroxy-pyrrolidin-1-yl]-(S)-1-phenyl-ethyl}-methyl-amide and (S)-6-(Pyrrolidine-1-sulfonyl)-chroman-2-carboxylic acid {2-[(S)-3-hydroxy-pyrrolidin-1-yl]-(S)-1-phenyl-ethyl}-methyl-amide Compounds 30 and 31 were obtained by preparative HPLC separation of 29 (See the preparation of compounds 12 and 13 for details).

Compound 30: (R)-6-(Pyrrolidine-1-sulfonyl)-chroman-2-carboxylic acid {2-[(S)-3-hydroxy-pyrrolidin-1-yl]-(S)-1-phenyl-ethyl}-methyl-amide. $^1$H NMR (400 MHz, CDCl$_3$) δ: 7.65–7.0 (m, 8H), 7.18 (m, 2H), 6.55–5.7 (m, 2H), 5.2–3.7 (m, 5H), 3.5–1.7 (m, 19H); MS: [M+1]$^+$: 514.

Compound 31: (S)-6-(Pyrrolidine-1-sulfonyl)-chroman-2-carboxylic acid {2-[(S)-3-hydroxy-pyrrolidin-1-yl]-(S)-1-phenyl-ethyl}-methyl-amide. $^1$H NMR (400 MHz, CDCl$_3$) δ: 7.63–7.35 (m, 5H), 7.18 (m, 2H), 6.85 (m, 1H), 6.48–5.5 (m, 3H), 5.1–2.75 (m, 16H), 2.5–2.05 (m, 4H), 1.86 (m, 4H); MS: [M+1]$^+$: 514.

Examples 32–47

Following the same procedure utilized in the preparation of 29 and its separated diastereomers 30 and 31, compounds 32–47 were prepared.

Compound 32: (R,S)-6-Diethylsulfamoyl-chroman-2-carboxylic acid {2-[(S)-3-hydroxy-pyrrolidin-1-yl]-(S)-1-phenyl-ethyl}-methyl-amide $^1$H NMR (400 MHz, CDCl$_3$) δ 7.53 (m, 2H), 7.41–7.28 (m, 5H), 6.95 (m, 1H), 6.05 (dd, 1H), 5.0 (m, 1H), 4.25 (b, s, 1H), 3.28–2.6 (m, 14H), 2.35–2.05 (m, 4H), 1.9–1.65 (m, 2H), 1.15 (m, 6H); MS: [M+1]$^+$: 516.

Compound 33: (R)-6-Diethylsulfamoyl-chroman-2-carboxylic acid {2-[(S)-3-hydroxy pyrrolidin-1-yl]-(S)-1-phenyl-ethyl}-methyl-amide Compound 34: (S)-6-Diethylsulfamoyl-chroman-2-carboxylic acid {2-[(S)-3-hydroxy-pyrrolidin-1-yl]-(S)-1-phenyl-ethyl}-methyl-amide Compound 35: (R,S)-6-Ethylsulfamoyl)-chroman-2-carboxylic acid {2-[(S)-3-hydroxy-pyrrolidin-1-yl]-(S)-1-phenyl-ethyl}-methyl-amide ¹H NMR (400 MHz, CDCl₃) δ 7.51 (m, 2H), 7.45–7.3 (m, 5H), 6.98 (m, 1H), 6.08 (m, 1H), 5.05 (m, 1H), 4.4–4.15 (m, 2H), 3.35–2.6 (m, 12H), 2.5–2.05 (m, 4H), 1.88–1.62 (m, 2H), 1.15 (t, 3H); MS: [M+1]⁺: 488.

Compound 36: (R)-6-Ethylsulfamoyl)-chroman-2-carboxylic acid {2-[(S)-3-hydroxy-pyrrolidin-1-yl]-(S)-1-phenyl-ethyl}-methyl-amide Compound 37: (S)-6-Ethylsulfamoyl)-chroman-2-carboxylic acid {2-[(S)-3-hydroxy-pyrrolidin-1-yl]-(S)-1-phenyl-ethyl}-methyl-amide Compound 38: (R,S)-6-Dimethylsulfamoyl)-chroman-2-carboxylic acid {2-[(S)-3-hydroxy-pyrrolidin-1-yl]-(S)-1-phenyl-ethyl}-methyl-amide 1H NMR (400 MHz, CDCl₃) δ 7.51 (m, 2H), 7.42–7.28 (m, 5H), 6.99 (m, 1H), 6.06 (dd, 1H), 5.04 (m, 1H), 4.25 (b, s, 1H), 3.3–2.6 (m, 16H), 2.55–2.0 (m, 4H), 1.9–1.6 (m, 2H); MS: [M+1]⁺: 488.

Compound 39: (R)-6-Dimethylsulfamoyl)-chroman-2-carboxylic acid {2-[(S)-3-hydroxy-pyrrolidin-1-yl]-(S)-1-phenyl-ethyl}-methyl-amide Compound 40: (S)-6-Dimethylsulfamoyl)-chroman-2-carboxylic acid {2-[(S)-3-hydroxy-pyrrolidin-1-yl]-(S)-1-phenyl-ethyl}-methyl-amide Compound 41: (R,S)-6-Methylsulfamoyl)-chroman-2-carboxylic acid {2-[(S)-3-hydroxy-pyrrolidin-1-yl]-(S)-1-phenyl-ethyl}-methyl-amide 1H NMR (400 MHz, CDCl₃) δ 7.56 (m, 2H), 7.45–7.3 (m, 5H), 6.93 (m, 1H), 6.06 (m, 1H), 5.05 (m, 1H), 4.45–4.15 (m, 2H), 3.35–1.4 (m, 20H), 0.9 (m, 1H), 0.48 (m, 2H). MS: [M+1]⁺: 474.

Compound 42: (R)-6-Methylsulfamoyl)-chroman-2-carboxylic acid {2-[(S)-3-hydroxy-pyrrolidin-1-yl]-(S)-1-phenyl-ethyl}-methyl-amide Compound 43: (S)-6-Methylsulfamoyl)-chroman-2-carboxylic acid {2-[(S)-3-hydroxy-pyrrolidin-1-yl]-(S)-1-phenyl-ethyl}-methyl-amide Compound 44: (R,S)-6-(Cyclopropylmethyl-sulfamoyl)-chroman-2-carboxylic acid {2-[(S)-3-hydroxy-pyrrolidin-1-yl]-(S)-1-phenyl-ethyl}-methyl-amide ¹H NMR (400 MHz, CDCl₃) δ 7.56 (m, 2H), 7.45–7.3 (m, 5H), 6.96 (m, 1H), 6.06 (m, 1H), 5.05 (m, 1H), 4.6–4.15 (m, 2H), 3.35–1.6 (m, 19H); MS: [M+1]⁺: 514.

Compound 45: (R)-6-(Cyclopropylmethyl-sulfamoyl)-chroman-2-carboxylic acid {2-[(S)-3-hydroxy-pyrrolidin-1-yl]-(S)-1-phenyl-ethyl}-methyl-amide Compound 46: (S)-6-(Cyclopropylmethyl-sulfamoyl)-chroman-2-carboxylic acid {2-[(S)-3-hydroxy-pyrrolidin-1-yl]-(S)-1-phenyl-ethyl}-methyl-amide Compound 47: (R,S)-6-Sulfamoyl-chroman-2-carboxylic acid {2-[(S)-3-hydroxy-pyrrolidin-1-yl]-(S)-1-phenyl-ethyl}-methyl-amide ¹H NMR (400 MHz, CDCl₃) δ 7.65 (m, 2H), 7.45–7.3 (m, 5H), 6.96 (m, 1H), 6.05 (m, 1H), 5.1 (m, 1H), 4.7 (b, s, 2H), 4.35 (b, s, 1H), 3.35–2.65 (m, 8H), 2.5–2.1 (m, 3H), 1.85–1.5 (m, 5H); MS: [M+1]⁺: 460.

Example 48

Preparation of (R,S)-6-(Methane sulfonylamino-methyl)-chroman-2-carboxylic acid {2-[(S)-3-hydroxy-pyrrolidin-1-yl]-(S)-1-phenyl-ethyl}-methyl-amide a) (R,S)-6-Iodo-chroman-2-carboxylic acid methyl ester (48a)

Compound 17a, (R,S)-6-Iodo-chroman-2-carboxylic acid (8.0 g, 26.3 mmol) was converted to the title compound (8.36 g, ~100%) under the same reaction conditions as described for the preparation of 22a. ¹H NMR (400 MHz, CDCl₃) δ: 7.36 (m, 2H), 6.70 (d, 1H), 4.72 (m, 1H), 3.79 (s, 3H), 2.75 (m, 2H), 2.20 (m, 2H).

b) (R,S)-6-Cyano-chroman-2-carboxylic acid methyl ester (48b)

To a solution of compound 48a (8.0 g, 25.2 mmol) in dimethylformamide (30 mL) was added copper (I) cyanide (2.88 g, 32 mmol) under a nitrogen atmosphere. The reaction mixture was heated to reflux overnight, cooled to room temperature and quenched with an aqueous solution of iron (III) chloride (5.19 g, 32 mmol, in 100 mL water). The mixture was vigorously stirred for 30 minutes and extracted with a mixture of solvent (ethyl acetate-ether-hexane, 1:1:1, 3×100 mL). The combined organic layers were washed with brine (100 mL), dried (Na₂SO₄) and concentrated. The residue was purified by flash chromatography over silica gel (ethyl acetate-hexane, 1:3) to give the title compound (4.86 g, 89%). ). ¹H NMR (400 MHz, CDCl₃) δ: 7.36 (m, 2H), 6.70 (d, 1H),7.42 (dd, 1H), 7.36 (d, 1H), 6.98 (d, 1H), 3.80 (s, 3H), 2.80 (m, 2H), 2.25 (m, 2H).

c) (R,S)-6-Aminomethyl-chroman-2-carboxylic acid methyl ester hydrochloride (48c)

Compound 48b (4.8 g, 22.12 mmol) in methanol (200 mL) containing concentrated HCl (7.0 mL) and 10% Pd/C (3.0 g) was hydrogenated using a hydrogen balloon at room temperature overnight. Filtration and evaporation of the solvent gave the title compound as hydrochloride salt (5.65 g, ~100%). ¹H NMR (400 MHz, CDCl₃) δ: 8.46 (brs, 2H), 7.22 (m, 2H), 6.85 (d, 1H), 4.95 (m, 1H), 3.85 (m, 2H), 3.69 (s, 3H), 2.78 (m, 1H), 2.58 (m, 1H), 2.10 (m, 2H).

d) (R,S)-6-(Methanesulfonylamino-methyl)-chroman-2-carboxylic acid methyl ester (48d)

To a solution of compound 48c (step c) (2.57 g, 10 mmol) in methylene chloride (100 mL) at 0° C. was added triethylamine (8.4 mL, 60 mmol) followed by dropwise addition of methanesufonyl chloride (2.33 mL, 30 mmol). The reaction mixture was stirred at room temperature for 3 hours and washed with saturated sodium bicarbonate (2×50 mL), dried (Na₂SO₄). Evaporation of the solvent and purification by flash chromatography over silica gel (methylene chloride-ethyl acetate-hexane, 1:1:1) afforded the title compound (2.5 g, 83.6%). ¹H NMR (400 MHz, CDCl₃) δ: 7.07 (dd, 1H), 7.02 (d, 1H), 6.91 (d, 1H), 4.76 (m, 1H), 4.43 (brs, 1H), 4.21 (d, 2H), 3.80 (s, 3H), 2.90 (s, 3H), 2.79 (m, 2H), 2.21 (m, 2H).

e) (R,S)-6-(Methanesulfonylamino-methyl)-chroman-2-carboxylic acid (48e)

Hydrolysis of compound 48d (2.3 g, 7.7 mmol) by lithium hydroxide (1.77 g, 42 mmol) yielded the title acid (2.19 g, 100%). ¹H NMR (400 MHz, DMSO-d₆) δ: 13.00 (s, 1H), 7.40 (t, 1H), 7.02 (m, 2H), 6.77 (d, 1H), 4.77 (m, 1H), 4.00 (d, 2H), 2.83 (s, 3H), 2.78 (m, 1H), 2.60 (m, 1H), 2.10 (m, 2H).

f) (R,S)-6-(Methane sulfonylamino-methyl)-chroman-2-carboxylic acid {2-[(S)-3-hydroxy-pyrrolidin-1-yl]-(S)-1-phenyl-ethyl}-methyl-amide Using the general coupling method A, compound 48e (941 mg, 3.3 mmol) was coupled with 1-(2-methylamino-(S)-2-phenyl-ethyl)-pyrrolidin-(S)-3-ol dihydrochloride (879 mg, 3.0 mmol) to yield 48 (1.3 g, 89%). ¹H NMR (400 MHz, DMSO-d₆) δ: 7.35 (m, 6H), 7.05 (m, 2H), 6.75–6.60 (m, 1H), 5.78, 5.34 (m, total 1H), 5.15 (m, 1H), 4.67 (m, 1H), 4.15 (m, 1H), 4.02 (m, 2H), 3.12–1.50 (m, 18H); MS: [M+1]⁺: 488.

Examples 49 and 50

Preparation of (R)-6-(Methane sulfonylamino-methyl)-chroman-2-carboxylic acid {2-[(S)-3-hydroxy-pyrrolidin-1-yl]-(S)-1-phenyl-ethyl}-methyl-amide and (S)-6-(Methane sulfonylamino-methyl)-chroman-2-carboxylic acid {2-[(S)-3-hydroxy-pyrrolidin-1-yl]-(S)-1-phenyl-ethyl}-methyl-amide Compound 49 was prepared by the same procedure used for the preparation of the compound 48 except that enantiomerically pure (R)-chroman-2-carboxylic acid (14c$_1$) was substituted as the starting material for the racemic acid and the general coupling method B was employed in the final amide formation reaction to avoid the racemization of the chiral acid.

Compound 49 $^1$H NMR (400 MHz, CDCl$_3$) δ: 7.34 (m, 5H), 7.06 (d, 2H), 6.86–6.60 (d, 1H), 6.05, 5.48 (m, total 1H), 5.10 (m, 1H), 4.92 (dd, 1H), 4.20 (d, 2H), 4.08 (m, 1H), 3.25 (t, 1H), 3.20–1.50 (m, 18H); MS: [M+1]$^+$: 488.

Compound 50, the other diastereomer with longer retention time in LC/MS was obtained by preparative HPLC separation of compound 48. Compound 50: (S)-6-(Methane sulfonylamino-methyl)-chroman-2-carboxylic acid {2-[(S)-3-hydroxy-pyrrolidin-1-yl]-(S)-1-phenyl-ethyl}-methyl-amide 1H NMR (400 MHz, CDCl$_3$) δ: 7.4 (m, 3H), 7.2 (m, 2H), 7.15 (m, 2H), 6.75 (m, 1H), 6.35–6.2 (m, 1H), 5.0–1.95 (m, 24H); MS: [M+1]$^+$: 488.

Example 51

Preparation of (2-{[2-({S}-3-Hydroxy-pyrrolidin-1-yl)-{S}-1-phenyl-ethyl]-(R,S)-methyl-carbamoyl}-chroman-6-ylmethyl)-carbamic acid methyl ester Compound 51 was prepared by the same procedure used for the preparation of 48, except that methyl chloroformate was substituted for the methanesulfonyl chloride in step (d) to form the carbamate. Compound 48d (carbamate) was hydrolysed and the resulting acid 48e was coupled with 1-(2-methylamino-(S)-2-phenyl-ethyl)-pyrrolidin-(S)-3-ol dihydrochloride using the general coupling method A.

(R,S)-6-(Methoxycarbonylamino-methyl)-chroman-2-carboxylic acid 48e: $^1$H NMR (400 MHz, DMSO-d$_6$) δ: 12.98 (s, 1H), 7.58 (t, 1H), 6.93 (m, 2H), 6.72 (d, 1H), 4.73 (m, 1H), 4.05 (d, 2H), 3.52 (s, 3H), 2.75 (m, 1H), 2.60 (m, 1H), 2.10 (m, 2H).

Compound 51: $^1$H NMR (400 MHz, DMSO-d$_6$) δ: 7.58–6.90 (m, 8H), 6.70–6.52 (m, 1H), 5.75, 5.30 (m, total 1H), 5.11 (m, 1H), 4.65 (m, 1H), 4.12–4.04 (m, 3H), 3.53 (s, 3H), 3.10–1.48 (m, 15H); MS: [M+1]$^+$: 468.

Examples 52 and 53

Preparation of (2-{[2-({S}-3-Hydroxy-pyrrolidin-1-yl)-{S}-1-phenyl-ethyl]-(R)-methyl-carbamoyl}-chroman-6-ylmethyl)-carbamic acid methyl ester and (2-{[2-({S}-3-Hydroxy-pyrrolidin-1-yl)-{S}-1-phenyl-ethyl]-(S)-methyl-carbamoyl}-chroman-6-ylmethyl)-carbamic acid methyl ester Compound 52 was prepared by the same procedure used for the preparation of 50 except that enantiomerically pure (R)-chroman-2-carboxylic acid (14c$_1$) was employed as the starting material instead of the racemic acid and the general coupling method B was employed in the final amide formation reaction to avoid the racemization of the chiral acid. $^1$H NMR (400 MHz, CDCl$_3$) δ: 7.33 (m, 5H), 7.03 (d, 2H), 6.85 (d, 1H), 6.07, 5.45 (m, total 1H), 5.18 (m, 1H), 4.88 (dd, 1H), 4.25 (d, 2H), 4.10 (m, 1H), 3.72 (s, 3H), 3.25 (t, 1H), 3.13–1.50 (m, 15H); MS: [M+1]$^+$: 468.

Compound 53, the other diastereomer with longer retention time in LC/MS was obtained by preparative HPLC separation of 51.

Compound 53: (2-{[2-({S}-3-Hydroxy-pyrrolidin-1-yl)-{S}-1-phenyl-ethyl]-(S)-methyl-carbamoyl}-chroman-6-yl-methyl)-carbamic acid methyl ester $^1$H NMR (400 MHz, CDCl$_3$) δ: 7.3 (m, 3H), 7.18 (m, 2H), 7.0 (m, 2H), 6.73 (m, 1H), 6.3 (dd, 1H), 5.1–2.0 (m, 24H); MS: [M+1]$^+$: 468.

Examples 54 and 55

Preparation of (R)-2,3-Dihydro-benzofuran-2-carboxylic acid-{2-[(S)-3-hydroxy-pyrrolidin-1-yl]-(S)-1-phenyl-ethyl}-methyl-amide and (S)-2,3-Dihydro-benzofuran-2-carboxylic acid-{2-[(S)-3-hydroxy-pyrrolidin-1-yl]-(S)-1-phenyl-ethyl}-methyl-amide a) (R,S)-2,3-Dihydro-benzofuran-2-carboxylic acid (54a)

Commercially available benzofuran-2-carboxylic acid (Aldrich Chemical Company) (27 g, 167.7 mmol) was dissolved in ethyl acetate (300 mL) and hydrogenated in the presence of 10% Pd/C (20 g) at 65–70 psi for 2 days. After filtration of the solution and evaporation of the solvent, a mixture of solvent (ethyl acetate-hexane, 1:6) was added to the residue. The title compound was obtained as a crystalline solid by filtration (20.23 g, 74%). m.p: 116–117° C.; $^1$H NMR (300 MHz, CDCl$_3$) δ: 11.05 (brs, 1H), 7.17 (m, 2H), 6.91 (m, 2H), 5.24 (dd, 1H), 3.63 (dd, 1H), 3.42 (dd, 1H).

b) (R)-2,3-Dihydro-benzofuran-2-carboxylic acid-{2-[(S)-3-hydroxy-pyrrolidin-1-yl]-(S)-1-phenyl-ethyl}-methyl-amide(54) and (S)-2,3-Dihydro-benzofuran-2-carboxylic acid-{2-[(S)-3-hydroxy-pyrrolidin-1-yl]-(S)-1-phenyl-ethyl}-methyl-amide (55)

Using the general coupling method A, (R,S)-2,3-Dihydro-benzofuran-2-carboxylic acid 54a (181 mg, 1.1 mmol) was coupled with 1-(2-methylamino-(S)-2-phenyl-ethyl)-pyrrolidin-(S)-3-ol dihydrochloride (293 mg, 1.0 mmol) to yield a mixture of diastereomers (100 mg, 27.3%), and the two diastereomers were isolated in pure form after flash chromatography on silica gel: 54 (140 mg, 38.3%) with shorter retention time in LC/MS and 55 (70 mg, 19.1%) with longer retention time in LC/MS. 54: $^1$H NMR (300 MHz, CDCl$_3$) δ: 7.35 (m, 5H), 7.22–7.15 (m, 2H), 6.10, 5.65–5.46 (m, 2H), 4.33–3.75 (m, 2H), 3.40–1.70 (m, 13H); MS: [M+1]$^+$: 367. 55: $^1$H NMR (300 MHz, CDCl$_3$) δ: 7.32 (m, 5H), 7.18 (m, 2H), 6.86 (m, 2H), 6.08, 5.47 (m, total 2H), 4.30 (m, 1H), 3.85–1.65 (m, 14H); MS: [M+1]$^+$: 367.

Compound 54, prepared as described immediately above, having shorter retention time in LC/MS as compared with 55, was identical with the product obtained from the coupling of the (R)-2,3-Dihydro-benzofuran-2-carboxylic acid 54c with 1-(2-methylamino-(S)-2-phenyl-ethyl)-pyrrolidin-(S)-3-ol dihydrochloride by using the general coupling method B, and 55, having the longer retention time in LC/MS, was identical with the product obtained from the Method B coupling of the (S)-2,3-dihydro-benzofuran-2-carboxylic acid 54d with 1-(2-methylamino-(S)-2-phenyl-ethyl)-pyrrolidin-(S)-3-ol dihydrochloride. The two enantiomeric pure acids: (R)-2,3-dihydro-benzofuran-2-carboxylic acid, [α]$_D$=+22.07 (c=0.1006, EtOH, 20° C.) and (S)-2,3-dihydro-benzofuran-2-carboxylic acid, [α]$_D$=−21.5

(c=0.1026, EtOH, 20° C.) were obtained by chiral separation of the racemic 2,3-dihydro-benzofuran-2-carboxylic acid. (Column: Chiralpak AD-H; Eluent: $CO_2$/Methanol–90/10; Temperature: 30° C.; Detection: UV 254 nm)

This phenomenon that the diastereomer with a (R)-configuration at 2-position had shorter retention time in LC/MS and the other diastereomer with a (S)-configuration at 2-position had longer retention time in LC/MS was also consistent with other substituted analogs 57, 58, 62, 63, 74, 75 and 77, 78 which were prepared from enantiomerically pure acid. Based on this trend, the stereochemistry of the 2-position of the remaining analogs 60, 61, 64, 65, 66, 67, 68, 69 and 70, 71 which were obtained by standard chromatography separation of the corresponding diastereomer mixtures over silica gel, was assigned.

Example 56

Preparation of (R,S)-5-Methanesulfonylamino-2,3-dihydro-benzofuran-2-carboxylic-acid-{2-[(S)-3-hydroxy-pyrrolidin-1-yl]-(S)-1-phenyl-ethyl}-methyl-amide a) (R,S)-5-Nitro-2,3-dihydro-benzofuran-2-carboxylic acid methyl ester ($56a_1$) and (R,S)-7-Nitro-2,3-dihydro-benzofuran-2-carboxylic acid methyl ester ($56a_2$)

(R,S)-2,3-Dihydro-benzofuran-2-carboxylic acid 54a (26g, 158.5 mmol) was added portionwise to nitric acid (480 mL, 70%) at 0° C. The reaction mixture was stirred for 80 min, quenched by addition ice-water (600 mL) and extracted with methylene chloride (4×700 mL). The combined organic layers were dried ($Na_2SO_4$) and concentrated. The residue was dissolved in methanol (600 mL) and hydrogen chloride (300 mL, 2.0 M in ether) was added. The reaction mixture was stirred at room temperature overnight and concentrated. Purification of the residue by flash chromatography over silica gel (ethyl acetate-hexane, 1:3) gave two regioisomers: (R,S)-5-nitro-2,3-dihydro-benzofuran-2-carboxylic acid methyl ester $56a_1$ (16g, 45.3%) as the major isomer and (R,S)-7-nitro-2,3-dihydro-benzofuran-2-carboxylic acid methyl ester $56a_2$ (4.3 g, 12.2%) as the minor isomer. The structural assignment of the isomers was based on the coupling pattern of the aromatic protons in $^1$HNMR spectra.

(R,S)-5-Nitro-2,3-dihydro-benzofuran-2-carboxylic acid methyl ester, ($56a_1$) $^1$H NMR (400 MHz, $CDCl_3$) δ: 8.12 (dd, 1H), 8.08 (d, 1H), 6.93 (d, 1H), 5.35 (dd, 1H), 3.82 (s, 3H), 3.62 (dd, 1H), 3.45 (dd, 1H).

(R,S)-7-Nitro-2,3-dihydro-benzofuran-2-carboxylic acid methyl ester, ($56a_2$) $^1$H NMR (400 MHz, $CDCl_3$) δ: 7.92 (d, 1H), 7.43 (d, 1H), 6.98 (t, 1H), 5.45 (dd, 1H), 3.80 (s, 3H), 3.65 (dd, 1H), 3.44 (dd, 1H).

b) (R,S)-5-Amino-2,3-dihydro-benzofuran-2-carboxylic acid methyl ester (56b)

Hydrogenation of $56a_1$: 5-Nitro-2,3-dihydro-benzofuran-2-carboxylic acid methyl ester (4.5 g, 20 mmol) by the same reaction conditions used for the preparation of 22b yielded the title compound (3.85 g, 100%) which was used directly in the next step without further purification. $^1$H NMR (400 MHz, DMSO-$d_6$) δ: 6.56 (m, 2H), 6.40 (d, 1H), 5.25 (brs, 2H), 5.21 (dd, 1H), 3.68 (s, 3H), 3.45 (dd, 1H), 3.16 (dd, 1H).

c) (R,S)-5-Bismethanesulfonylamino-2,3-dihydro-benzofuran-2-carboxylic acid methyl ester (56c)

To a solution of the compound from Example 56b (step b) (1.93 g, 10 mmol) in methylene chloride (100 mL) was added at 0° C. triethylamine (6.3 mL, 45 mmol) followed by dropwise addition of methanesulfonyl chloride (2.33 mL, 30 mmol). The reaction mixture was stirred at room temperature overnight, washed with saturated sodium bicarbonate and dried ($Na_2SO_4$). Evaporation of the solvent and purification of the residue by flash chromatography over silica gel (ethyl acetate-methylene chloride-hexane, 1:1:2) gave the title compound (2.1 g, 60.2%). $^1$H NMR (400 MHz, $CDCl_3$) δ: 7.38 (d, 1H), 7.27 (dd, 1H), 6.93 (d, 1H), 5.48 (dd, 1H), 3.72 (s, 3H), 3.64 (dd, 1H), 3.50 (s, 6H), 3.32 (dd, 1H).

b) (R,S)-5-Methanesulfonylamino-2,3-dihydro-benzofuran-2-carboxylic acid (56d)

Hydrolysis of compound 56c (1.9 g, 5.44 mmol) with lithium hydroxide (2.28 g, 54 mmol) yielded the title acid (1.32 g, 94.3%). $^1$H NMR (400 MHz, DMSO-$d_6$) δ: 13.11 (s, 1H), 9.32 (s, 1H), 7.09 (d, 1H), 6.96 (dd, 1H), 6.80 (d, 1H), 5.22 (dd, 1H), 3.55 (dd, 1H), 3.23 (dd, 1H), 2.88 (s, 3H).

c) (R,S)-5-Methanesulfonylamino-2,3-dihydro-benzofuran-2-carboxylic-acid-{2-[(S)-3-hydroxy-pyrrolidin-1-yl]-(S)-1-phenyl-ethyl}-methyl-amide (56)

Using the general coupling method A, compound 56d (849 mg, 3.3 mmol) was coupled with 1-(2-methylamino-(S)-2-phenyl-ethyl)-pyrrolidin-(S)-3-ol dihydrochloride (879 mg, 3.0 mmol) to yield 56 (1.16 g, 84.2%) as a mixture of diastereomers. $^1$H NMR (400 MHz, DMSO-$d_6$) δ: 9.28 (s, 1H), 7.40–7.30 (m, 5H), 7.10–6.70 (m, 3H), 5.82–5.28 (m, 2H), 4.70 (m, 1H), 4.15 (m, 1H), 3.50–1.48 (m, 16H); MS: $[M+1]^+$: 460.

Examples 57 and 58

Preparation of (R)-5-Methanesulfonylamino-2,3-dihydro-benzofuran-2-carboxylic-acid-{2-[(S)-3-hydroxy-pyrrolidin-1-yl]-(S)-1-phenyl-ethyl}-methyl-amide and (S)-5-Methane sulfonylamino-2,3-dihydro-benzofuran-2-carboxylic-acid-{2-[(S)-3-hydroxy-pyrrolidin-1-yl]-(S)-1-phenyl-ethyl}-methyl-amide Compounds 57 and 58 were individually prepared by the same procedure used for the preparation of the compound 56 except that the enantiomerically pure acids: (R)-2,3-dihydro-benzofuran-2-carboxylic acid (54c) and (S)-2,3-Dihydro-benzofuran-2-carboxylic acid (54d) were substituted respectively as starting material for racemic acid and the general coupling method B was employed in the final amide formation reaction to avoid the racemization of the chiral acid.

Compound 57: (R)-5-Methanesulfonylamino-2,3-dihydro-benzofuran-2-carboxylic-acid-{2-[(S)-3-hydroxy-pyrrolidin-1-yl]-(S)-1-phenyl-ethyl}-methyl-amide $^1$H NMR (400 MHz, DMSO-$d_6$) δ 9.30 (s, 1H), 7.40–7.30 (m, 5H), 7.10 (m, 1H), 6.95 (m, 1H), 6.78, 6.73 (2d, total 1H), 5.82–5.30 (m, 2H), 4.69 (m, 1H), 4.15 (m, 1H), 3.50–1.51 (m, 16H); MS: $[M+1]^+$: 460; In LC/MS, this diastereomer had shorter retention time.

Compound 58: (S)-5-Methanesulfonylamino-2,3-dihydro-benzofuran-2-carboxylic-acid-{2-[(S)-3-hydroxy-pyrrolidin-1-yl]-(S)-1-phenyl-ethyl}-methyl-amide $^1$H NMR (400 MHz, DMSO-$d_6$) δ: 9.30 (s, 1H), 7.40–7.30 (m, 5H), 7.10 (m, 1H), 6.96 (m, 1H), 6.76 (d, 1H), 5.74, 5.30 (m, total 2H), 4.69 (m, 1H), 4.15 (m, 1H), 3.50–1.50 (m, 16H); MS: $[M+1]^+$: 460; In LC/MS, this diastereomer had longer retention time.

Examples 59–63

Preparation of (2-{[2-({S}-3-Hydroxy-pyrrolidin-1-yl)-{S}-1-phenyl-ethyl]-(S)-methyl-carbamoyl}-2,3-dihydro-benzofuran-5-yl)-carbamic acid methyl ester, (R)-5-(Cyclopropanecarbonyl-amino)-2,3-dihydro-benzofuran-2-carboxylic acid-{2-[(S)-3-hydroxy-pyrrolidin-1-yl]-(S)-1-phenyl-ethyl}-methyl-amide, (S)-5-(Cyclopropanecarbonyl-amino)-2,3-dihydro-benzofuran-2-carboxylic acid-{2-[(S)-3-hydroxy-pyrrolidin-1-yl]-(S)-1-phenyl-ethyl}-methyl-amide, (2-{[2-({S}-3-Hydroxy-pyrrolidin-1-yl)-{S}-1-phenyl-ethyl]-(R)-methyl-carbamoyl}-2,3-dihydro-benzofuran-5-yl)-carbamic acid methyl ester, and (R,S)-5 -Acetylamino-2,3-dihydro-benzofuran-2-carboxylic acid-{2-[(S)-3-hydroxy-pyrrolidin-1-yl]-(S)-1-phenyl-ethyl}-methyl-amide Following the same reaction sequence utilized for 56, compounds 59–63 were prepared. The assignment of the 2-position absolute stereochemistry of 60, 61 and 62, 63 was based on their retention times in LC/MS as described in Example 54, 55. Compounds 62 and 63 were prepared by two approaches: using the racemic acid as the starting material and separation of the diastereomeric mixture by chromatography over silica gel in the last step, and using the enantiomerically pure acid to carry the 2-position stereochemistry through to the final product. Compound 62, with shorter retention in LC/MS was identical with the pure diastereomer obtained from (R)-2,3-dihydro-benzofuran-2-carboxylic acid (54c), and compound 63, with longer retention time in LC/MS, was identical with the pure diastereomer obtained from (S)-2,3-dihydro-benzofuran-2-carboxylic acid (54d). This further confirmed the stereochemistry assignment based on retention time in LC/MS.

Compound 59: (R,S)-5-Acetylamino-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-$d_6$) δ 9.75 (s, 1H), 7.50–7.20 (m, 7H), 6.70 (m, 1H), 5.76–5.31 (m, 2H), 4.69 (m, 1H), 4.15 (m, 1H), 3.50–2.25 (m, 11H), 1.98 (s, 3H), 1.93 (m, 1H), 1.50 (m, 1H); MS: [M+1]$^+$: 424.

Compound 60: (R)-5-(Cyclopropanecarbonyl-amino)-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-$d_6$) δ 10.00 (s, 1H), 7.48–7.20 (m, 7H), 6.71, 6.68 (2d, total 1H), 5.80–5.30 (m, 2H), 4.68 (m, 1H), 4.15 (m, 1H), 3.50–1.50 (m, 14H), 0.75 (m, 4H); MS: [M+1]$^+$: 450.

Compound 61: (S)-5-(Cyclopropanecarbonyl-amino)-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-$d_6$) δ 10.00 (s, 1H), 7.48–7.22 (m, 7H), 6.70 (d, 1H), 5.75–5.60, 5.30 (m, 2H), 4.68 (m, 1H), 4.15 (m, 1H), 3.50–1.45 (m, 14H), 0.75 (m, 4H); MS: [M+1]$^+$: 450.

Compound 62: (2-{[2-({S}-3-Hydroxy-pyrrolidin-1-yl)-{S}-1-phenyl-ethyl]-(R)-methyl-carbamoyl}-2,3-dihydro-benzofuran-5-yl)-carbamic acid methyl ester $^1$H NMR (400 MHz, DMSO-$d_6$) δ: 9.40 (s, 1H), 7.40–7.10 (m, 7H), 6.71, 6.68 (2d, total 1H), 5.78–5.31 (m, 2H), 4.69 (m, 1H), 4.16 (m, 1H), 3.62 (s, 3H), 3.50–2.25 (m, 11H), 1.92 (m, 1H), 1.50 (m,1H); MS: [M+1]$^+$: 440.

Compound 63: (2-{[2-({S}-3-Hydroxy-pyrrolidin-1-yl)-{S}-1-phenyl-ethyl]-(S)-methyl-carbamoyl}-2,3-dihydro-benzofuran-5-yl)-carbamic acid methyl ester $^1$H NMR (400 MHz, DMSO-$d_6$) δ: 9.40 (s, 1H), 7.40–7.10 (m, 7H), 6.70 (d, 1H), 5.75–5.66, 5.30 (m, total 2H), 4.66 (m, 1H), 4.16 (m, 1H), 3.62 (s, 3H), 3.50–2.25 (m, 11H), 1.95 (m, 1H), 1.49 (m, 1H); MS: [M+1]$^+$: 440.

Examples 64 and 65

Preparation of (R)-7-Methanesulfonylamino-2,3-dihydro-benzofuran-2-carboxylic acid-{2-[(S)-3-hydroxy-pyrrolidin-1-yl]-(S)-1-phenyl-ethyl}-methyl-amide and (S)-7-Methane sulfonylamino-2,3-dihydro-benzofuran-2-carboxylic acid-{2-[(S)-3-hydroxy-pyrrolidin-1-yl]-(S)-1-phenyl-ethyl}-methyl-amide Following the same procedure used for the preparation of 56, (R,S)-7-nitro-2,3-dihydro-benzofuran-2-carboxylic acid methyl ester (56$a_2$) (4.3 g, 19.3 mmol) was carried through hydrogenation (64a), sulfonylation (64b), hydrolysis (64c) and coupling with 1-(2-methylamino-(S)-2-phenyl-ethyl)-pyrrolidin-(S)-3-ol dihydrochloride to yield 64 and 65 as pure diastereomers after flash chromatography on silica gel.

(R,S)-7-Amino-2,3-dihydro-benzofuran-2-carboxylic acid methyl ester (64a) $^1$H NMR (400 MHz, DMSO-$d_6$) δ: 6.60 (d, 1H), 6.45 (m, 1H), 5.27 (dd, 1H), 4.93 (brs, 2H), 3.70 (s, 3H), 3.50 (dd, 1H), 3.20 (dd, 1H).

(R,S)-7-Bismethanesulfonylamino-2,3-dihydro-benzofuran-2-carboxylic acid methyl ester (64b) $^1$H NMR (400 MHz, DMSO-$d_6$) δ: 7.32 (d, 1H), 7.28 (d, 1H), 6.93 (t, 1H), 3.70 (s+m, 4H), 3.60 (s, 3H), 3.53 (s, 3H), 3.40 (dd, 1H).

(R,S)-7-Methanesulfonylamino-2,3-dihydro-benzofuran-2-carboxylic acid (64c) $^1$H NMR (400 MHz, DMSO-$d_6$) δ 13.18 (s, 1H), 9.27 (s, 1H), 7.10 (d, 1H), 7.02 (d, 1H), 6.82 (t, 1H), 5.30 (dd, 1H), 3.60 (dd, 1H), 3.29 (dd, 1H), 3.02 (s, 3H).

Compound 64: (R)-7-Methanesulfonylamino-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-$d_6$) δ 9.21 (s, 1H), 7.35 (m, 5H), 7.11–6.82 (m, 3H), 5.92–5.72, 5.27 (m 2H), 4.70 (m, 1H), 4.16 (m, 1H), 3.6–1.48 (m, 16H); MS: [M+1]$^+$: 460; In LC/MS, this diastereomer had shorter retention time.

Compound 65: (S)-7-Methanesulfonylamino-2,3-dihydro-benzofuran-2-carboxylic acid-{2-[(S)-3-hydroxy-pyrrolidin-1-yl]-(S)-1-phenyl-ethyl}-methyl-amid $^1$H NMR (400 MHz, DMSO-$d_6$) δ 9.22 7.50–7.30 (m, 5H), 7.15–6.82 (m, 3H), 5.92–5.72, 5.30 (m, total 2H), 4.70 (m, 1H), 4.18 (m, 1H), 3.53 (m, 1H), 3.20–1.50 (m, 15H); MS: [M+1]$^+$: 460; In LC/MS, this diastereomer had longer retention time.

Examples 66 and 67

Preparation of (R)-7-Acetylamino-2,3-dihydro-benzofuran-2-carboxylic-{2-[(S)-3-hydroxy-pyrrolidin-1-yl]-(S)-1-phenyl-ethyl}-methyl-amide and (S)-7-Acetylamino-2,3-dihydro-benzofuran-2-carboxylic-{2-[(S)-3-hydroxy-pyrrolidin-1-yl]-(S)-1-phenyl-ethyl}-methyl-amide Following the same procedure as for the preparation of Example 64 and 65 except using acetyl chloride instead of methanesulfonyl chloride, 66 and 67 were prepared.

Compound 66: (R)-7-Acetylamino-2,3-dihydro-benzofuran-2-carboxylic-{2-[(S)-3-hydroxy-pyrrolidin-1-yl]-

(S)-1-phenyl-ethyl}-methyl-amide $^1$H NMR (400 MHz, DMSO-d$_6$) δ: 9.38, 9.30 (2s, total 1H), 7.63–7.30 (m, 6H), 6.93 (d, 1H), 6.76 (t, 1H), 5.75, 5.30 (m, total 1H), 4.68 (m, 1H), 4.15 (m, 1H), 3.60 (m, 1H), 3.30–1.48 (m, 15H); MS: [M+1]$^+$: 424; In LC/MS, this diastereomer had shorter retention time.

Compound 67: (R)-7-Acetylamino-2,3-dihydro-benzofuran-2-carboxylic-{2-[(S)-3-hydroxy-pyrrolidin-1-yl]-(S)-1-phenyl-ethyl}-methyl-amide $^1$H NMR (400 MHz, DMSO-d$_6$) δ: 9.38, 9.30 (2s, total 1H), 7.63–7.25 (m, 6H), 7.00, 6.93 (2d, total 1H), 6.78 (m, 1H), 5.85–5.66, 5.334 (m, total 2H), 4.70 (m, 1H), 4.16 (m, 1H), 3.51–1.50 (m, 16H); MS: [M+1]$^+$: 424; In LC/MS, this diastereomer had longer retention time.

Examples 68 and 69

Preparation of (R)-5-(Pyrrolidine-1-sulfonyl)-2,3-dihydro-benzofuran-2-carboxylic-{2-[(S)-3-hydroxy-pyrrolidin-1-yl]-(S)-1-phenyl-ethyl}-methyl-amide and (S)-5-(Pyrrolidine-1-sulfonyl)-2,3-dihydro-benzofuran-2-carboxylic-{2-[(S)-3-hydroxy-pyrrolidin-1-yl]-(S)-1-phenyl-ethyl}-methyl-amide a) (R,S)-2,3-Dihydro-benzofuran-2-carboxylic acid methyl ester (68a)

To a solution of (R,S)-2,3-Dihydro-benzofuran-2-carboxylic acid 54a (18 g) in methanol was added hydrogen chloride (200 mL, 2.0 M in ether). The reaction mixture was stirred at room temperature overnight and concentrated to give the title compound (19 g, 97.2%). $^1$H NMR (400 MHz, CDCl$_3$) δ: 7.16 (m, 2H), 6.89 (m, 2H), 5.20 (dd, 1H), 3.80 (s, 3H), 3.55 (dd, 1H), 3.37 (dd, 1H).

b) (R,S)-5-Chlorosulfonyl-2,3-dihydro-benzofuran-2-carboxylic acid methyl ester (68b)

(R,S)-2,3-Dihydro-benzofuran-2-carboxylic acid methyl ester 68a (7.12 g, 40 mmol) was converted to the title sulfonyl chloride (11 g, ~100%) by using the same procedure as described for 6d. $^1$H NMR (400 MHz, CDCl$_3$) δ: 7.88 (dd, 1H), 7.85 (d, 1H), 7.03 (d, 1H), 3.84 (s, 3H), 3.68 (dd, 1H), 3.49 (dd, 1H).

c) (R,S)-5-(Pyrrolidine-1-sulfonyl)-2,3-dihydro-benzofuran-2-carboxylic acid methyl ester (68c)

The title compound (2.16 g, 99.2%) was prepared by reaction of 68b (1.94 g, 7 mmol) with pyrrolidine using the same reaction conditions as described for 29c. $^1$H NMR (400 MHz, CDCl$_3$) δ: 7.68 (m, 2H), 6.98 (d, 1H), 3.82 (s, 3H), 3.62 (dd, 1H), 3.42 (dd, 1H), 3.21 (t, 4H), 1.78 (m, 4H).

d) (R,S)-5-(Pyrrolidine-1-sulfonyl)-2,3-dihydro-benzofuran-2-carboxylic acid (68d)

Hydrolysis of 68c (2.0 g, 6.43 mmol) with lithium hydroxide (1.35 g, 32 mmol) gave the title acid (1.90 g, 100%). $^1$H NMR (400 MHz, DMSO-d$_6$) δ: 13.28 (s, 1H), 7.66 (d, 1H), 7.60 (dd, 1H), 7.03 (d, 1H), 5.39 (dd, 1H), 3.62 (dd, 1H), 3.35 (dd, 1H), 3.10 (t, 4H), 1.65 (m, 4H).

e) (R)-5-(Pyrrolidine-1-sulfonyl)-2,3-dihydro-benzofuran-2-carboxylic-{2-[(S)-3-hydroxy-pyrrolidin-1-yl]-(S)-1-phenyl-ethyl}-methyl-amide and (S)-5-(Pyrrolidine-1-sulfonyl)-2,3-dihydro-benzofuran-2-carboxylic-{2-[(S)-3-hydroxy-pyrrolidin-1-yl]-(S)-1-phenyl-ethyl}-methyl-amide Using the general coupling method A, (R,S)-5-(Pyrrolidine-1-sulfonyl)-2,3-dihydro-benzofuran-2-carboxylic acid (68d) (981 mg, 3.3 mmol) was coupled with 1-(2-methylamino-(S)-2-phenyl-ethyl)-pyrrolidin-(S)-3-ol dihydrochloride (879 mg, 3.0 mmol) to yield two pure diastereomers: Compound 68 (250 mg, 16.7%) with shorter retention time in LC/MS and compound 69 (370 mg, 24.7%) with longer retention time in LC/MS, and a mixture of the pair of diastereomers (700 mg, 46.8%).

Compound 68: $^1$H NMR (400 MHz, DMSO-d$_6$) δ: 7.68–7.30 (m, 7H), 7.01, 6.98 (2d, total 1H), 6.02–5.71, 5.25 (m, total 2H), 4.69 (m, 1H), 4.15 (m, 1H), 3.55 (m, 1H), 3.25–2.25 (m, 14H), 1.92 (m, 1H), 1.68 (m, 4H), 1.50 (m, 1H); MS: [M+1]$^+$: 500.

Compound 69: $^1$H NMR (400 MHz, DMSO-d$_6$) δ: 7.61–7.28 (m, 7H), 7.00 (d, 1H), 6.00–5.75, 5.28 (m, total 2H), 4.70 (m, 1H), 4.15 (m, 1H), 3.62–3.43 (m, 2H), 3.18–2.30 (m, 13H), 1.93 (m, 1H), 1.64 (m, 4H), 1/45 (m, 1H); MS: [M+1]$^+$: 500.

Examples 70–72

Preparation of (R)-5-Dimethylsulfamoyl-2,3-dihydro-benzofuran-2-carboxylic acid-{2-[(S)-3-hydroxy-pyrrolidin-1-yl]-(S)-1-phenyl-ethyl}-methyl-amide, (S)-5-Dimethylsulfamoyl-2,3-dihydro-benzofuran-2-carboxylic acid-{2-[(S)-3-hydroxy-pyrrolidin-1-yl]-(S)-1-phenyl-ethyl}-methyl-amide, and (R,S)-5-Methylsulfamoyl-2,3-dihydro-benzofuran-2-carboxylic acid-{2-[(S)-3-hydroxy-pyrrolidin-1-yl]-(S)-1-phenyl-ethyl}-methyl-amide Compounds 70, 71, and 72 were prepared by the same procedure used for the preparation of 68 and 69 described above.

Compound 70: (R)-5-Dimethylsulfamoyl-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-d$_6$) δ: 7.63–7.30 (m, 7H), 7.04, 7.00 (2d, total 1H), 6.04–5.73, 5.26 (m, total 2H), 4.69 (m, 1H), 4.15 (m, 1H), 3.55 (m, 1H), 3.30–2.25 (m, 14H), 1.95 (m, 1H), 1.50 (m, 1H); MS: [M+1]$^+$: 474. In LC/MS, this diastereomer had shorter retention time.

Compound 71: (S)-5-Dimethylsulfamoyl-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-d$_6$) δ 7.60–7.30 (m, 7H), 7.05 (d, 1H), 6.01–5.72, 5.28 (m, total 2H), 4.68 (m, 1H), 4.15 (m, 1H), 3.63 (m, 1H), 3.42 (m, 1H), 3.18–2.66 (m, 7H), 2.56 (s, 6H), 2.36 (m, 2H), 1.95 (m, 1H), 1.46 (m, 1H); MS: [M+1]$^+$: 474; In LC/MS, this diastereomer had longer retention time.

Compound 72: (R,S)-5-Methylsulfamoyl-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-d$_6$) δ 7.65–7.22 (m, 7H), 7.00, 6.95 (2d, total 1H), 6.01–5.72, 5.28 (m, total 2H), 4.70 (m, 1H), 4.16 (m, 1H), 3.55–2.40 (m, 10H), 2.38 (d, 3H), 2.30 (m, 1H), 1.95 (m, 1H), 1.48 (m, 1H); MS: [M+1]$^+$: 460.

Example 73

Preparation of (R,S)-5-(Methanesulfonylaminomethyl)-2,3-dihydro-benzofuran-2-carboxylic acid-{2-[(S)-3-hydroxy-pyrrolidin-1-yl]-(S)-1-phenyl-ethyl}-methyl-amide (R,S)-2,3-Dihydro-benzofuran-2-carboxylic acid (54a) was carried through the same reaction sequence used for the preparation of 48 to prepare 73: a) iodination; b) methyl ester formation; c) cyanide substitution; d) hydrogenation; e) conversion to sulfonamide; f) hydrolysis of the ester and finally e) coupling with 1-(2-methylamino-(S)-2-phenyl-ethyl)-pyrrolidin-(S)-3-ol dihydrochloride using general coupling method A.

a) (R,S)-5-Iodo-2,3-dihydro-benzofuran-2-carboxylic acid (73a) $^1$H NMR (400 MHz, DMSO-d$_6$) δ: 13.40 (brs, 1H), 7.52 (d, 1H), 7.41 (dd, 1H), 6.70 (d, 1H), 5.23 (dd, 1H), 3.52 (dd, 1H), 3.22 (dd, 1H).

b) (R,S)-5-Iodo-2,3-dihydro-benzofuran-2-carboxylic acid methyl ester (73b) $^1$H NMR (400 MHz, CDCl$_3$) δ: 7.45 (m, 2H), 6.68 (d, 1H), 5.20 (dd, 1H), 3.82 (s, 3H), 3.52 (dd, 1H), 3.35 (dd, 1H).

c) (R,S)-5-Cyano-2,3-dihydro-benzofuran-2-carboxylic acid methyl ester (73c) $^1$H NMR (400 MHz, CDCl$_3$) δ: 7.48 (m, 2H), 6.95 (d, 1H), 5.30 (dd, 1H), 3.82 (s, 3H), 3.60 (dd, 1H), 3.41 (dd, 1H).

d) (R,S)-5-Aminomethyl-2,3-dihydro-benzofuran-2-carboxylic acid methyl ester hydrochloride (73d) $^1$H NMR (400 MHz, DMSO-d$_6$) δ: 8.40 (brs, 2H), 7.36 (d, 1H), 7.27 (dd, 1H), 6.89 (d, 1H), 5.40 (dd, 1H), 3.90 (brs, 2H), 3.80 (s, 3H), 3.59 (dd, 1H), 3.28 (dd, 1H).

e) (R,S)-5-(Methanesulfonylamino-methyl)-2,3-dihydro-benzofuran-2-carboxylic acid methyl ester (73e) $^1$H NMR (400 MHz, CDCl$_3$) δ: 7.18 (d, 1H), 7.10 (dd, 1H), 6.83 (d, 1H), 5.22 (dd, 1H), 4.83 (t, 1H), 4.20 (d, 2H), 3.80 (s, 3H), 3.53 (dd, 1H), 3.35 (dd, 1H), 2.86 (s, 3H).

f) (R,S)-5-(Methanesulfonylamino-methyl)-2,3-dihydro-benzofuran-2-carboxylic acid (73f) $^1$H NMR (400 MHz, DMSO-d$_6$) δ: 13.10 (s, 1H), 7.44 (t, 1H), 7.20 (d, 1H), 7.08 (dd, 1H), 6.80 (d, 1H), 5.22 (dd, 1H), 4.05 (d, 2H), 3.53 (dd, 1H), 3.22 (dd, 1H), 2.85 (s, 3H).

g) (R,S)-5-(Methanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide (73) $^1$H NMR (400 MHz, DMSO-d$_6$) δ: 7.42–7.06 (m, 8H), 6.76, 6.71 (2d, total 1H), 5.82–5.65, 5.30 (m, total 2H), 4.70 (m, 1H), 4.20–4.05 (m, 3H), 3.50–2.25 (m, 14H), 1.95 (m, 1H), 1.50 (m, 1H); MS: [M+1]$^+$: 474.

Examples 74 and 75

Preparation of (R)-5-(Methanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide and (S)-5-(Methanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide Compounds 74 and 75, the two pure diastereomers of 73, were prepared by the same procedure used for the preparation of 73 except that the enantiomerically pure (R)-2,3-Dihydro-benzofuran-2-carboxylic acid (54c) or (S)-2,3-Dihydro-benzofuran-2-carboxylic acid (54d) were substituted for racemic acid starting material.

Compound 74: (R)-5-(Methanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-d$_6$) δ: 7.42–7.06 (m, 8H), 6.76, 6.70 (2d, total 1H), 5.82–5.65, 5.32 (m, tatal 2H), 4.69 (m, 1H), 4.20–4.05 (m, 3H), 3.55–2.20 (14H), 1.93 (m, 1H), 1.50 (m, 1H); MS: [M+1]$^+$: 474; In LC/MS, this diastereomer had shorter retention time.

Compound 75: (S)-5-(Methanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-d$_6$) δ: 7.42–7.06 (m, 6H), 7.18 (d, 1H), 7.05 (dd, 1H), 6.78 (d, 1H), 5.75, 5.30 (m, total 2H), 4.68 (m, 1H), 4.16 (m, 1H), 4.05 (d, 2H), 3.50 (m, 1H), 3.40–2.28 (m, 13H), 1.95 (m, 1H), 1.50 (m, 1H); MS: [M+1]$^+$: 474; In LC/MS, this diastereomer had longer retention time.

Example 76

Preparation of (R,S)-5-(Propanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide Compound 76 was prepared by the same reaction sequence used for the preparation of 73 except that 1-propanesulfonyl chloride was substituted for methanesulfonyl chloride in step (e).

(R,S)-5-(Propanesulfonylamino-methyl)-2,3-dihydro-benzofuran-2-carboxylic acid (73f, R=propanesulfonyl): $^1$H NMR (400 MHz, DMSO-d$_6$) δ: 13.10 (s, 1H), 7.50 (t, 1H), 7.19 (d, 1H), 7.08 (dd, 1H), 6.78 (d, 1H), 5.22 (dd, 1H), 4.04 (d, 2H), 3.51 (dd, 1H), 3.22 (dd, 1H), 2.85 (t, 2H), 1.60 (m, 2H), 0.90 (t, 3H).

Compound 76: $^1$H NMR (400 MHz, DMSO-d$_6$) δ: 7.48 (t, 1H), 7.40–7.06 (m, 7H), 6.76, 6.71 (2d, total 1H), 5.82–5.65, 5.30 (m, total 2H), 4.69 (m, 1H), 4.20–4.05 (m, 3H), 3.50–2.28 (m, 13H), 1.95 (m, 1H), 1.60 (m, 2H), 1.50 (m, 1H), 0.90 (t, 3H); MS: [M+1]$^+$: 502.

Examples 77 and 78

Preparation of (R)-5-(Propanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide and (S)-5-(Propanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide Compounds 77 and 78, the two pure diastereomers of Example 76, were prepared by the same procedure used for the preparation of 76 except that enantiomerically pure (R)-2,3-Dihydro-benzofuran-2-carboxylic acid (54c) and (S)-2,3-Dihydro-benzofuran-2-carboxylic acid (54d) were substituted for racemic acid as the starting material.

Compound 77: $^1$H NMR (400 MHz, DMSO-d$_6$) δ: 7.48 (t, 1H), 7.40–7.05 (m, 7H), 6.75, 6.70 (2d, total 1H), 5.83–5.65, 5.30 (m, total 2H), 4.70 (m, 1H), 4.20–4.03 (m, 3H), 3.50–2.28 (m, 13H), 1.93 (m, 1H), 1.60 (m, 2H), 1.50 (m, 1H), 0.90 (t, 3H); MS: [M+1]$^+$: 502; In LC/MS, this diastereomer had shorter retention time.

Compound 78: $^1$H NMR (400 MHz, DMSO-d$_6$) δ: 7.50 (t, 1H), 7.38–7.30 (m, 5H), 7.18 (d, 1H), 7.05 (dd, 1H), 5.73, 5.30 (m, total 1H), 4.70 (m, 1H), 4.15 (m, 1H), 4.02 (d, 2H), 3.50 (m, 1H), 3.40–2.28 (m, 12H), 1.95 (m, 1H), 1.60 (m, 2H), 1.50 (m, 1H), 0.90 (t, 3H); MS: [M+1]$^+$: 502; In LC/MS, this diastereomer had longer retention time.

Example 79

Preparation of (2-{[2-({S}-3-Hydroxy-pyrrolidin-1-yl)-{S}-1-phenyl-ethyl]-methyl-carbamoyl}-(R,S)-2,3-dihydro-benzofuran-5-ylmethyl)-carbamic acid methyl ester (79)

Compound 79 was prepared by the same reaction sequence used for the preparation of 73 except that methyl chloroformate was substituted for methanesulfonyl chloride in step (e).

(R,S)-5-(Methoxycarbonylamino-methyl)-2,3-dihydro-benzofuran-2-carboxylic acid (73f, R=CH3OC(=O)): $^1$H NMR (400 MHz, DMSO-$d_6$) δ: 13.08 (s, 1H), 7.60 (t, 1H), 7.10 (d, 1H), 6.99 (dd, 1H), 6.75 (d, 1H), 5.20 (dd, 1H), 4.09 (d, 2H), 3.51 (s+m, 4H), 3.20 (dd, 1H). Example 79: $^1$H NMR (400 MHz, DMSO-$d_6$) δ: 7.58 (t, 1H), 7.40–7.25 (m, 5H), 7.10–7.68 (m, 3H), 5.80–5.65, 5.30 (m, total 2H), 4.70 (m, 1H), 4.20–4.08 (m, 3H), 3.52 (s, 3H), 3.45–2.28 (m, 11H), 1.95 (m, 1H), 1.50 (m, 1H); MS: [M+1]$^+$: 454.

Examples 80e$_1$* and 80e$_2$*

Preparation of Chroman-4-carboxylic acid-{2-[(S)-3-hydroxy-pyrrolidin-1-yl]-(S)-1-phenyl-ethyl}-methyl-amide a) Trifluoro-methanesulfonic acid 2H-chromen-4-yl ester (80a)

Commercially available 4-chromanone (Aldrich Chemical Company) (17.8 g, 120.3 mmol) was converted to the title compound using the same procedure described in Example 4 (step d) and the crude was used without further purification. $^1$H NMR (300 MHz, CDCl$_3$) δ: 7.10 (t, 1H), 7.28–6.86 (m, 4H), 5.78 (t, 1H), 5.00 (d, 1H).

b) 2H-Chromene-4-carboxylic acid methyl ester (80b)

Compound 80a was converted to the title compound (11.5 g, 50.3% overall yield) using the same procedure as described in Example 4 (step e). $^1$H NMR (300 MHz, CDCl$_3$) δ: 7.90 (dd, 1H), 7.17 (dd, 1H), 6.96–6.86 (m, 3H), 4.82 (d, 1H), 3.85 (s, 3H).

c) (R,S)-Chroman-4-carboxylic acid methyl ester (80c)

Compound 80b was hydrogenated in ethyl acetate (600 ml) in the presence of 10% Pd/C (2.2 g) to give the title compound (11.0 g, ~100%). $^1$H NMR (300 MHz, CDCl$_3$) δ: 7.22–7.15 (m, 2H), 6.87 (m, 2H), 4.28 (m, 2H), 3.79 (m, 1H), 3.73 (s, 3H), 2.32 (m, 1H), 2.10 (m, 1H).

d) (R,S)-Chroman-4-carboxylic acid (80d)

Compound 80c (1.21 g, 6.3 mmol) was hydrolyzed with lithium hydroxide (1.35 g, 32 mmol) to give the title acid (1.05 g, 93.4%). $^1$H NMR (300 MHz, CDCl$_3$) δ: 12.66 (s, 1H), 7.20–7.13 (m, 2H), 6.87–6.78 (m, 2H), 4.18 (m, 2H), 3.75 (t, 1H), 2.16–2.03 (m, 2H).

e) Chroman-4-carboxylic acid-{2-[(S)-3-hydroxy-pyrrolidin-1-yl]-(S)-1-phenyl-ethyl}-methyl-amide (80e$_1$* and 80e$_2$*)

Using general coupling Method A, compound 80d (588 mg, 3.3 mmol) was coupled with 1-(2-methylamino-(S)-2-phenyl-ethyl)-pyrrolidin-(S)-3-ol dihydrochloride (879 mg, 3.0 mmol) to yield, after chromatographic separation, 80e$_1$*_(260 mg, 22.8%) with longer retention time in LC/MS, and 80e$_2$* (520 mg, 45.6%) with shorter retention time in LC/MS. 80e$_1$*: $^1$H NMR (400 MHz, DMSO-$d_6$) δ: 7.38–6.75 (m, 9H), 5.85, 5.45 (m, total 1H), 4.76–4.18 (m, 5H), 3.22–1.50 (m, 13H); MS: [M+1]$^+$: 381. 80e$_2$*: $^1$H NMR (400 MHz, DMSO-$d_6$) δ: 7.45–6.75 (m, 9H), 5.95, 5.39 (m, total 1H), 4.71 (m, 1H), 4.48–4.10 (m, 4H), 3.08–1.57 (m, 13H); MS: [M+1]$^+$: 381.

Examples 81d$_1$* and 81d$_2$*

Preparation of 6-(Pyrrolidine-1-sulfonyl)-chroman4-carboxylic acid-{2-[(S)-3-hydroxy-pyrrolidin-1-yl]-(S)-1-phenyl-ethyl}-methyl-amide a) (R,S)-6-Chlorosulfonyl-chroman-4-carboxylic acid methyl ester (81a)

(R,S)-Chroman-4-carboxylic acid methyl ester 80c (7.0 g, 36.5 mmol) was chlorosulfonylated to give the title sulfonyl chloride (81a) (10.5 g, ~100%) using the same procedure described for compound 6d. $^1$H NMR (400 MHz, CDCl$_3$) δ: 7.98 (d, 1H), 7.82 (dd, 1H), 6.98 (d, 1H), 4.38 (m, 2H), 3.86 (m, 1H), 3.78 (s, 3H), 2.45 (m, 1H), 2.13 (m, 1H).

b) (R,S)-6-(Pyrrolidine-1-sulfonyl)-chroman-4-carboxylic acid methyl ester (81b, R$_1$ and R$_2$ taken together are —(CH$_2$)$_4$—)

A solution of compound 81a (4.35 g, 15 mmol) in methylene chloride (20 mL) was added to a solution of pyrrolidine (1.6 mL, 19.2 mmol) in methylene chloride (120 mL) containing triethylamine (4.18 mL, 30 mmol) at 0° C. The reaction mixture was stirred for 40 minutes and washed with 1N hydrochloric acid (50 mL) and saturated aqueous NaHCO$_3$ (50 mL), dried (Na$_2$SO$_4$), and concentrated. The residue was purified by flash chromatography over silica gel (hexane-ethyl acetate, 2:1) to afford the title compound (4.5 g, 92.3%). $^1$H NMR (400 MHz, CDCl$_3$) δ: 7.78 (d, 1H), 7.59 (dd, 1H), 6.95 (d, 1H), 4.30 (m, 2H), 3.85 (m, 1H), 3.76 (s, 3H), 3.21 (m, 4H), 2.38 (m, 1H), 2.13 (m, 1H), 1.76 (m, 4H).

c) (R,S)-6-(Pyrrolidine-1-sulfonyl)-chroman-4-carboxylic acid (81c, R$_1$ and R$_2$ taken together are —(CH$_2$)$_4$—)

Compound 81b (4.3 g, 13.2 mmol) was hydrolyzed with lithium hydroxide at room temperature to give the acid 81c, (R$_1$ and R$_2$ taken together are —(CH$_2$)$_4$—) (4.05 g, 98.5%). $^1$H NMR (400 MHz, DMSO-$d_6$) δ: 12.89 (s, 1H), 7.72 (d, 1H), 7.57 (dd, 1H), 6.98 (d, 1H), 4.32 (m, 1H), 4.15 (m, 1H), 3.95 (m, 1H), 3.08 (m, 4H), 2.22 (m, 1H), 2.08 (m, 1H), 1.63 (m, 4H).

d) 6-(Pyrrolidine-1-sulfonyl)-chroman-4-carboxylic acid-{2-[(S)-3-hydroxy-pyrrolidin-1-yl]-(S)-1-phenyl-ethyl}-methyl-amide (81d$_1$* and 81d$_2$*)

Using the general coupling Method A, compound 81c (step c) (1.03 g, 3.3 mmol) was coupled with 1-(2-methylamino-(S)-2-phenyl-ethyl)-pyrrolidin-(S)-3-ol dihydrochloride (879 mg, 3.0 mmol) to yield pure example 81d$_1$* (800 mg, 52%) with longer retention time in LC/MS and compound 81d$_2$* (265 mg, 17.2%) with shorter retention time in LC/MS, and a mixture of 81d$_1$* and 81d$_2$* (200 mg, 13%). 81d$_1$*: $^1$H NMR (400 MHz, (d, 1H), 4.85 (t, 1H), 3.25 (m, 4H), 2.85 (m, 2H), 2.3 (m, 2H), 1.78 (m, 4H).

e) (R,S)-6-(Pyrrolidine-1-sulfonyl)-chroman-2-carboxylic acid {2-[(S)-3-hydroxy-pyrrolidin-1-yl]-(S)-1-phenyl-ethyl}-methyl-amide Using the coupling method B, the title compound 29 was prepared: 1.36 g (80%). $^1$H NMR (400 MHz, CDCl$_3$) δ 7.58 (m, 2H), 7.43–7.3 (m, 5H), 7.0 (m, 1H), 6.08 (dd, 1H), 5.05 (m, 1H), 4.3 (b, s, 1H), 3.32–2.6 (m, 14H), 2.4–2.05 (m, 4H), 1.9–1.65 (m, 6H); MS: [M+1]$^+$: 514.

Examples 30 and 31

Preparation of (R)-6-(Pyrrolidine-1-sulfonyl)-chroman-2-carboxylic acid {2-[(S)-3-hydroxy-pyrrolidin-1-yl]-(S)-1-phenyl-ethyl}-methyl-amide and (S)-6-(Pyrrolidine-1-sulfonyl)-chroman-2-carboxylic acid {2-[(S)-3-hydroxy-pyrrolidin-1-yl]-(S)-1-phenyl-ethyl}-methyl-amide Compounds 30 and 31 were obtained by preparative HPLC separation of 29 (See the preparation of compounds 12 and 13 for details).

Compound 30: (R)-6-(Pyrrolidine-1-sulfonyl)-chroman-2-carboxylic acid {2-[(S)-3-hydroxy-pyrrolidin-1-yl]-(S)-1-phenyl-ethyl}-methyl-amide.
$^1$H NMR (400 MHz, CDCl$_3$) δ: 7.65–7.0 (m, 8H), 7.18 (m, 2H), 6.55–5.7 (m, 2H), 5.2–3.7 (m, 5H), 3.5–1.7 (m, 19H); MS: [M+1]$^+$: 514.

Compound 31: (S)-6-(Pyrrolidine-1-sulfonyl)-chroman-2-carboxylic acid {2-[(S)-3hydroxy-pyrrolidin-1-yl]-(S)-1-phenyl-ethyl}-methyl-amide.
$^1$H NMR (400 MHz, CDCl$_3$) δ: 7.63–7.35 (m, 5H), 7.18 (m, 2H), 6.85 (m, 1H), 6.48–5.5 (m, 3H), 5.1–2.75 (m, 16H), 2.5–2.05 (m, 4H), 1.86 (m, 4H); MS: [M+1]$^+$: 514.

Examples 32–47

Following the same procedure utilized in the preparation of 29 and its separated diastereomers 30 and 31, compounds 32–47 were prepared.

Compound 32: (R,S)-6-Diethylsulfamoyl)-chroman-2-carboxylic acid {2-[(S)-3-hydroxy-pyrrolidin-1-yl]-(S)-1-phenyl-ethyl}-methyl-amide $^1$H NMR (400 MHz, CDCl$_3$) δ 7.53 (m, 2H), 7.41–7.28 (m, 5H), 6.95 (m, 1H), 6.05 (dd, 1H), 5.0 (m, 1H), 4.25 (b, s, 1H), 3.28–2.6 (m, 14H), 2.35–2.05 (m, 4H), 1.9–1.65 (m, 2H), 1.15 (m, 6H); MS: [M+1]$^+$: 516.

Compound 33: (R)-6-Diethylsulfamoyl)-chroman-2-carboxylic acid {2-[(S)-3-hydroxy pyrrolidin-1-yl]-(S)-1-phenyl-ethyl}-methyl-amide Compound 34: (S)-6-Diethylsulfamoyl)-chroman-2-carboxylic acid {2-[(S)-3-hydroxy-pyrrolidin-1-yl]-(S)-1-phenyl-ethyl}-methyl-amide Compound 35: (R,S)-6-Ethylsulfamoyl)-chroman-2-carboxylic acid {2-[(S)-3-hydroxy-pyrrolidin-1-yl]-(S)-1-phenyl-ethyl}-methyl-amide $^1$H NMR (400 MHz, CDCl$_3$) δ 7.51 (m, 2H), 7.45–7.3 (m, 5H), 6.98 (m, 1H), 6.08 (m, 1H), 5.05 (m, 1H), 4.4–4.15 (m, 2H), 3.35–2.6 (m, 12H), 2.5–2.05 (m, 4H), 1.88–1.62 (m, 2H), 1.15 (t, 3H); MS: [M+1]$^+$: 488.

Compound 36: (R)-6-Ethylsulfamoyl)-chroman-2-carboxylic acid {2-[(S)-3-hydroxy-pyrrolidin-1-yl]-(S)-1-phenyl-ethyl}-methyl-amide Compound 37: (S)-6-Ethylsulfamoyl)-chroman-2-carboxylic acid {2-[(S)-3-hydroxy-pyrrolidin-1-yl]-(S)-1-phenyl-ethyl}-methyl-amide Compound 38: (R,S)-6-Dimethylsulfamoyl)-chroman-2-carboxylic acid {2-[(S)-3-hydroxy-pyrrolidin-1-yl]-(S)-1-phenyl-ethyl}-methyl-amide 1H NMR (400 MHz, CDCl$_3$) δ 7.51 (m, 2H), 7.42–7.28 (m, 5H), 6.99 (m, 1H), 6.06 (dd, 1H), 5.04 (m, 1H), 4.25 (b, s, 1H), 3.3–2.6 (m, 16H), 2.55–2.0 (m, 4H), 1.9–1.6 (m, 2H); MS: [M+1]$^+$: 488.

Compound 39: (R)-6-Dimethylsulfamoyl)-chroman-2-carboxylic acid {2-[(S)-3-hydroxy-pyrrolidin-1-yl]-(S)-1-phenyl-ethyl}-methyl-amide Compound 40: (S)-6-Dimethylsulfamoyl)-chroman-2-carboxylic acid {2-[(S)-3-hydroxy-pyrrolidin-1-yl]-(S)-1-phenyl-ethyl}-methyl-amide Compound 41: (R,S)-6-Methylsulfamoyl)-chroman-2-carboxylic acid {2-[(S)-3-hydroxy-pyrrolidin-1-yl]-(S)-1-phenyl-ethyl}-methyl-amide 1H NMR (400 MHz, CDCl$_3$) δ 7.56 (m, 2H), 7.45–7.3 (m, 5H), 6.93 (m, 1H), 6.06 (m, 1H), 5.05 (m, 1H), 4.45–4.15 (m, 2H), 3.35–1.4 (m, 20H), 0.9 (m, 1H), 0.48 (m, 2H). MS: [M+1]$^+$: 474.

Compound 42: (R)-6-Methylsulfamoyl)-chroman-2-carboxylic acid {2-[(S)-3-hydroxy-pyrrolidin-1-yl]-(S)-1-phenyl-ethyl}-methyl-amide Compound 43: (S)-6-Methylsulfamoyl)-chroman-2-carboxylic acid {2-[(S)-3-hydroxy-pyrrolidin-1-yl]-(S)-1-phenyl-ethyl}-methyl-amide Compound 44: (R,S)-6-(Cyclopropylmethyl-sulfamoyl)-chroman-2-carboxylic acid {2-[(S)-3-hydroxy-pyrrolidin-1-yl]-(S)-1-phenyl-ethyl}-methyl-amide $^1$H NMR (400 MHz, CDCl$_3$) δ 7.56 (m, 2H), 7.45–7.3 (m, 5H), 6.96 (m, 1H), 6.06 (m, 1H), 5.05 (m, 1H), 4.6–4.15 (m, 2H), 3.35–1.6 (m, 19H); MS: [M+1]$^+$: 514.

Compound 45: (R)-6-(Cyclopropylmethyl-sulfamoyl)-chroman-2-carboxylic acid {2-[(S)-3-hydroxy-pyrrolidin-1-yl]-(S)-1-phenyl-ethyl}-methyl-amide Compound 46: (S)-6-(Cyclopropylmethyl-sulfamoyl)-chroman-2-carboxylic acid {2-[(S)-3-hydroxy-pyrrolidin-1-yl]-(S)-1-phenyl-ethyl}-methyl-amide Compound 47: (R,S)-6-Sulfamoyl-chroman-2-carboxylic acid {2-[(S)-3-hydroxy-pyrrolidin-1-yl]-(S)-1-phenyl-ethyl}-methyl-amide $^1$H NMR (400 MHz, CDCl$_3$) δ 7.65 (m, 2H), 7.45–7.3 (m, 5H), 6.96 (m, 1H), 6.05 (m, 1H), 5.1 (m, 1H), 4.7 (b, s, 2H), 4.35 (b, s, 1H), 3.35–2.65 (m, 8H), 2.5–2.1 (m, 3H), 1.85–1.5 (m, 5H); MS: [M+1]$^+$: 460.

Example 48

Preparation of (R,S)-6-(Methane sulfonylaminomethyl)-chroman-2-carboxylic acid {2-[(S)-3-hydroxy-pyrrolidin-1-yl]-(S)-1-phenyl-ethyl}-methyl-amide a) (R,S)-6-Iodo-chroman-2-carboxylic acid methyl ester (48a)

Compound 17a, (R,S)-6-Iodo-chroman-2-carboxylic acid (8.0 g, 26.3 mmol) was converted to the title compound (8.36 g, ~100%) under the same reaction conditions as described for the preparation of 22a. $^1$H NMR (400 MHz, CDCl$_3$) δ: 7.36 (m, 2H), 6.70 (d, 1H), 4.72 (m, 1H), 3.79 (s, 3H), 2.75 (m, 2H), 2.20 (m, 2H).

b) (R,S)-6-Cyano-chroman-2-carboxylic acid methyl ester (48b)

To a solution of compound 48a (8.0 g, 25.2 mmol) in dimethylformamide (30 mL) was added copper (I) cyanide (2.88 g, 32 mmol) under a nitrogen atmosphere. The reaction mixture was heated to reflux overnight, cooled to room temperature and quenched with an aqueous solution of iron (III) chloride (5.19 g, 32 mmol, in 100 mL water). The mixture was vigorously stirred for 30 minutes and extracted with a mixture of solvent (ethyl acetate-ether-hexane, 1:1:1, 3×100 mL). The combined organic layers were washed with brine (100 mL), dried (Na$_2$SO$_4$) and concentrated. The residue was purified by flash chromatography over silica gel (ethyl acetate-hexane, 1:3) to give the title compound (4.86 g, 89%). ). $^1$H NMR (400 MHz, CDCl$_3$) δ: 7.36 (m, 2H), 6.70 (d, 1H), 7.42 (dd, 1H), 7.36 (d, 1H), 6.98 (d, 1H), 3.80 (s, 3H), 2.80 (m, 2H), 2.25 (m, 2H).

c) (R,S)-6-Aminomethyl-chroman-2-carboxylic acid methyl ester hydrochloride (48c)

Compound 48b (4.8 g, 22.12 mmol) in methanol (200 mL) containing concentrated HCl (7.0 mL) and 10% Pd/C (3.0 g) was hydrogenated using a hydrogen balloon at room temperature overnight. Filtration and evaporation of the solvent gave the title compound as hydrochloride salt (5.65 g, ~100%). $^1$H NMR (400 MHz, CDCl$_3$) δ: 8.46 (brs, 2H), 7.22 (m, 2H), 6.85 (d, 1H), 4.95 (m, 1H), 3.85 (m, 2H), 3.69 (s, 3H), 2.78 (m, 1H), 2.58 (m, 1H), 2.10 (m, 2H).

d) (R,S)-6-(Methanesulfonylamino-methyl)-chroman-2-carboxylic acid methyl ester (48d)

To a solution of compound 48c (step c) (2.57 g, 10 mmol) in methylene chloride (100 mL) at 0° C. was added triethylamine (8.4 mL, 60 mmol) followed by dropwise addition of methanesufonyl chloride (2.33 mL, 30 mmol). The reaction mixture was stirred at room temperature for 3 hours and washed with saturated sodium bicarbonate (2×50 mL), dried (Na$_2$SO$_4$). Evaporation of the solvent and purification by flash chromatography over silica gel (methylene chloride-ethyl acetate-hexane, 1:1:1) afforded the title compound (2.5 g, 83.6%). $^1$H NMR (400 MHz, CDCl$_3$) δ: 7.07 (dd, 1H), 7.02 (d, 1H), 6.91 (d, 1H), 4.76 (m, 1H), 4.43 (brs, 1H), 4.21 (d, 2H), 3.80 (s, 3H), 2.90 (s, 3H), 2.79 (m, 2H), 2.21 (m, 2H).

e) (R,S)-6-(Methanesulfonylamino-methyl)-chroman-2-carboxylic acid (48e)

Hydrolysis of compound 48d (2.3 g, 7.7 mmol) by lithium hydroxide (1.77 g, 42 mmol) yielded the title acid (2.19 g, 100%). $^1$H NMR (400 MHz, DMSO-d$_6$) δ: 13.00 (s, 1H), 7.40 (t, 1H), 7.02 (m, 2H), 6.77 (d, 1H), 4.77 (m, 1H), 4.00 (d, 2H), 2.83 (s, 3H), 2.78 (m, 1H), 2.60 (m, 1H), 2.10 (m, 2H).

f) (R,S)-6-(Methane sulfonylamino-methyl)-chroman-2-carboxylic acid {2-[(S)-3-hydroxy-pyrrolidin-1-yl]-(S)-1-phenyl-ethyl}-methyl-amide Using the general coupling method A, compound 48e (941 mg, 3.3 mmol) was coupled with 1-(2-methylamino-(S)-2-phenyl-ethyl)-pyrrolidin-(S)-3-ol dihydrochloride (879 mg, 3.0 mmol) to yield 48 (1.3 g, 89%). $^1$H NMR (400 MHz, DMSO-d$_6$) δ: 7.35 (m, 6H), 7.05 (m, 2H), 6.75–6.60 (m, 1H), 5.78, 5.34 (m, total 1H), 5.15 (m, 1H), 4.67 (m, 1H), 4.15 (m, 1H), 4.02 (m, 2H), 3.12–1.50 (m, 18H); MS: [M+1]$^+$: 488.

Examples 49 and 50

Preparation of (R)-6-(Methane sulfonylamino-methyl)-chroman-2-carboxylic acid {2-[(S)-3-hydroxy-pyrrolidin-1-yl]-(S)-1-phenyl-ethyl}-methyl-amide and (S)-6-(Methane sulfonylamino-methyl)-chroman-2-carboxylic acid {2-[(S)-3-hydroxy-pyrrolidin-1-yl]-(S)-1-phenyl-ethyl}-methyl-amide Compound 49 was prepared by the same procedure used for the preparation of the compound 48 except that enantiomerically pure (R)-chroman-2-carboxylic acid (14c$_1$) was substituted as the starting material for the racemic acid and the general coupling method B was employed in the final amide formation reaction to avoid the racemization of the chiral acid.

Compound 49 $^1$H NMR (400 MHz, CDCl$_3$) δ: 7.34 (m, 5H), 7.06 (d, 2H), 6.86–6.60 (d, 1H), 6.05, 5.48 (m, total 1H), 5.10 (m, 1H), 4.92 (dd, 1H), 4.20 (d, 2H), 4.08 (m, 1H), 3.25 (t, 1H), 3.20–1.50 (m, 18H); MS: [M+1]$^+$: 488.

Compound 50, the other diastereomer with longer retention time in LC/MS was obtained by preparative HPLC separation of compound 48. Compound 50: (S)-6-(Methane sulfonylamino-methyl)-chroman-2-carboxylic acid {2-[(S)-3-hydroxy-pyrrolidin-1-yl]-(S)-1-phenyl-ethyl}-methyl-amide 1H NMR (400 MHz, CDCl$_3$) δ: 7.4 (m, 3H), 7.2 (m, 2H), 7.15 (m, 2H), 6.75 (m, 1H), 6.35–6.2 (m, 1H), 5.0–1.95 (m, 24H); MS: [M+1]$^+$: 488.

Example 51

Preparation of (2-{[2-({S}-3-Hydroxy-pyrrolidin-1-yl)-{S}-1-phenyl-ethyl]-(R,S)-methyl-carbamoyl}-chroman-6-ylmethyl)-carbamic acid methyl ester Compound 51 was prepared by the same procedure used for the preparation of 48, except that methyl chloroformate was substituted for the methanesulfonyl chloride in step (d) to form the carbamate. Compound 48d (carbamate) was hydrolysed and the resulting acid 48e was coupled with 1-(2-methylamino-(S)-2-phenyl-ethyl)-pyrrolidin-(S)-3-ol dihydrochloride using the general coupling method A.

(R,S)-6-(Methoxycarbonylamino-methyl)-chroman-2-carboxylic acid 48e: $^1$H NMR (400 MHz, DMSO-d$_6$) δ: 12.98 (s, 1H), 7.58 (t, 1H), 6.93 (m, 2H), 6.72 (d, 1H), 4.73 (m, 1H), 4.05 (d, 2H), 3.52 (s, 3H), 2.75 (m, 1H), 2.60 (m, 1H), 2.10 (m, 2H).

Compound 51: $^1$H NMR (400 MHz, DMSO-d$_6$) δ: 7.58–6.90 (m, 8H), 6.70–6.52 (m, 1H), 5.75, 5.30 (m, total 1H), 5.11 (m, 1H), 4.65 (m, 1H), 4.12–4.04 (m, 3H), 3.53 (s, 3H), 3.10–1.48 (m, 15H); MS: [M+1]$^+$: 468.

Examples 52 and 53

Preparation of (2-{[2-({S}-3-Hydroxy-pyrrolidin-1-yl)-{S}-1-phenyl-ethyl]-(R)-methyl-carbamoyl}-chroman-6-ylmethyl)-carbamic acid methyl ester and (2-{[2-({S}-3-Hydroxy-pyrrolidin-1-yl)-{S}-1-phenyl-ethyl]-(S)-methyl-carbamoyl}-chroman-6-ylmethyl)-carbamic acid methyl ester Compound 52 was prepared by the same procedure used for the preparation of 50 except that enantiomerically pure (R)-chroman-2-carboxylic acid (14c$_1$) was employed as the starting material instead of the racemic acid and the general coupling method B was employed in the final amide formation reaction to avoid the racemization of the chiral acid. $^1$H NMR (400 MHz, CDCl$_3$) δ: 7.33 (m, 5H), 7.03 (d, 2H), 6.85 (d, 1H), 6.07, 5.45 (m, total 1H), 5.18 (m, 1H), 4.88 (dd, 1H), 4.25 (d, 2H), 4.10 (m, 1H), 3.72 (s, 3H), 3.25 (t, 1H), 3.13–1.50 (m, 15H); MS: [M+1]$^+$: 468.

Compound 53, the other diastereomer with longer retention time in LC/MS was obtained by preparative HPLC separation of 51.

Compound 53: (2-{[2-({S}-3-Hydroxy-pyrrolidin-1-yl)-{S}-1-phenyl-ethyl]-(S)-methyl-carbamoyl}-chroman-6-ylmethyl)-carbamic acid methyl ester $^1$H NMR (400 MHz, CDCl$_3$) δ: 7.3 (m, 3H), 7.18 (m, 2H), 7.0 (m, 2H), 6.73 (m, 1H), 6.3 (dd, 1H), 5.1–2.0 (m, 24H); MS: [M+1]$^+$: 468.

Examples 54 and 55

Preparation of (R)-2,3-Dihydro-benzofuran-2-carboxylic acid-{2-[(S)-3-hydroxy-pyrrolidin-1-yl]-(S)-1-phenyl-ethyl}-methyl-amide and (S)-2,3-Dihydro-benzofuran-2-carboxylic acid-{2-[(S)-3-hydroxy-pyrrolidin-1-yl]-(S)-1-phenyl-ethyl}-methyl-amide a) (R,S)-2,3-Dihydro-benzofuran-2-carboxylic acid (54a)

Commercially available benzofuran-2-carboxylic acid (Aldrich Chemical Company) (27 g, 167.7 mmol) was dissolved in ethyl acetate (300 mL) and hydrogenated in the presence of 10% Pd/C (20 g) at 65–70 psi for 2 days. After filtration of the solution and evaporation of the solvent, a mixture of solvent (ethyl acetate-hexane, 1:6) was added to the residue. The title compound was obtained as a crystalline solid by filtration (20.23 g, 74%). m.p: 116–117° C.; $^1$H NMR (300 MHz, CDCl$_3$) δ: 11.05 (brs, 1H), 7.17 (m, 2H), 6.91 (m, 2H), 5.24 (dd, 1H), 3.63 (dd, 1H), 3.42 (dd, 1H).

b) (R)-2,3-Dihydro-benzofuran-2-carboxylic acid-{2-[(S)-3-hydroxy-pyrrolidin-1-yl]-(S)-1-phenyl-ethyl}-methyl-amide(54) and (S)-2,3-Dihydro-benzofuran-2-carboxylic acid-{2-[(S)-3-hydroxy-pyrrolidin-1-yl]-(S)-1-phenyl-ethyl}-methyl-amide (55)

Using the general coupling method A, (R,S)-2,3-Dihydro-benzofuran-2-carboxylic acid 54a (181 mg, 1.1 mmol) was coupled with 1-(2-methylamino-(S)-2-phenyl-ethyl)-pyrrolidin-(S)-3-ol dihydrochloride (293 mg, 1.0 mmol) to yield a mixture of diastereomers (100 mg, 27.3%), and the two diastereomers were isolated in pure form after flash chromatography on silica gel: 54 (140 mg, 38.3%) with shorter retention time in LC/MS and 55 (70 mg, 19.1%) with longer retention time in LC/MS. 54: $^1$H NMR (300 MHz, CDCl$_3$) δ: 7.35 (m, 5H), 7.22–7.15 (m, 2H), 6.10, 5.65–5.46 (m, 2H), 4.33–3.75 (m, 2H), 3.40–1.70 (m, 13H); MS: [M+1]$^+$: 367. 55: $^1$H NMR (300 MHz, CDCl$_3$) δ: 7.32 (m, 5H), 7.18 (m, 2H), 6.86 (m, 2H), 6.08, 5.47 (m, total 2H), 4.30 (m, 1H), 3.85–1.65 (m, 14H); MS: [M+1]$^+$: 367.

Compound 54, prepared as described immediately above, having shorter retention time in LC/MS as compared with 55, was identical with the product obtained from the coupling of the (R)-2,3-Dihydro-benzofuran-2-carboxylic acid 54c with 1-(2-methylamino-(S)-2-phenyl-ethyl)-pyrrolidin-(S)-3-ol dihydrochloride by using the general coupling method B, and 55, having the longer retention time in LC/MS, was identical with the product obtained from the Method B coupling of the (S)-2,3-dihydro-benzofuran-2-carboxylic acid 54d with 1-(2-methylamino-(S)-2-phenyl-ethyl)-pyrrolidin-(S)-3-ol dihydrochloride. The two enantiomeric pure acids: (R)-2,3-dihydro-benzofuran-2-carboxylic acid, [α]$_D$=+22.07 (c=0.1006, EtOH, 20° C.) and (S)-2,3-dihydro-benzofuran-2-carboxylic acid, [α]$_D$=−21.5 (c=0.1026, EtOH, 20° C.) were obtained by chiral separation of the racemic 2,3-dihydro-benzofuran-2-carboxylic acid. (Column: Chiralpak AD-H; Eluent: CO$_2$/Methanol–90/10; Temperature: 30° C.; Detection: UV 254 nm)

This phenomenon that the diastereomer with a (R)-configuration at 2-position had shorter retention time in LC/MS and the other diastereomer with a (S)-configuration at 2-position had longer retention time in LC/MS was also consistent with other substituted analogs 57, 58, 62, 63, 74, 75 and 77, 78 which were prepared from enantiomerically pure acid. Based on this trend, the stereochemistry of the 2-position of the remaining analogs 60, 61, 64, 65, 66, 67, 68, 69 and 70, 71 which were obtained by standard chromatography separation of the corresponding diastereomer mixtures over silica gel, was assigned.

Example 56

Preparation of (R,S)-5-Methanesulfonylamino-2,3-dihydro-benzofuran-2-carboxylic-acid-{2-[(S)-3-hydroxy-pyrrolidin-1-yl]-(S)-1-phenyl-ethyl}-methyl-amide a) (R,S)-5-Nitro-2,3-dihydro-benzofuran-2-carboxylic acid methyl ester (56a$_1$) and (R,S)-7-Nitro-2,3-dihydro-benzofuran-2-carboxylic acid methyl ester (56a$_2$)

(R,S)-2,3-Dihydro-benzofuran-2-carboxylic acid 54a (26g, 158.5 mmol) was added portionwise to nitric acid (480 mL, 70%) at 0° C. The reaction mixture was stirred for 80 min, quenched by addition ice-water (600 mL) and extracted with methylene chloride (4×700 mL). The combined organic layers were dried (Na$_2$SO$_4$) and concentrated. The residue was dissolved in methanol (600 mL) and hydrogen chloride (300 mL, 2.0 M in ether) was added. The reaction mixture was stirred at room temperature overnight and concentrated. Purification of the residue by flash chromatography over silica gel (ethyl acetate-hexane, 1:3) gave two regioisomers: (R,S)-5-nitro-2,3-dihydro-benzofuran-2-carboxylic acid methyl ester 56a$_1$ (16g, 45.3%) as the major isomer and (R,S)-7-nitro-2,3-dihydro-benzofuran-2-carboxylic acid methyl ester 56a$_2$ (4.3 g, 12.2%) as the minor isomer. The structural assignment of the isomers was based on the coupling pattern of the aromatic protons in $^1$HNMR spectra.

(R,S)-5-Nitro-2,3-dihydro-benzofuran-2-carboxylic acid methyl ester, (56a$_1$) $^1$H NMR (400 MHz, CDCl$_3$) δ: 8.12 (dd, 1H), 8.08 (d, 1H), 6.93 (d, 1H), 5.35 (dd, 1H), 3.82 (s, 3H), 3.62 (dd, 1H), 3.45 (dd, 1H).

(R,S)-7-Nitro-2,3-dihydro-benzofuran-2-carboxylic acid methyl ester, (56a$_2$) $^1$H NMR (400 MHz, CDCl$_3$) δ: 7.92 (d, 1H), 7.43 (d, 1H), 6.98 (t, 1H), 5.45 (dd, 1H), 3.80 (s, 3H), 3.65 (dd, 1H), 3.44 (dd, 1H).

b) (R,S)-5-Amino-2,3-dihydro-benzofuran-2-carboxylic acid methyl ester (56b)

Hydrogenation of 56a$_1$: 5-Nitro-2,3-dihydro-benzofuran-2-carboxylic acid methyl ester (4.5 g, 20 mmol) by the same reaction conditions used for the preparation of 22b yielded the title compound (3.85 g, 100%) which was used directly in the next step without further purification. $^1$H NMR (400 MHz, DMSO-d$_6$) δ: 6.56 (m, 2H), 6.40 (d, 1H), 5.25 (brs, 2H), 5.21 (dd, 1H), 3.68 (s, 3H), 3.45 (dd, 1H), 3.16 (dd, 1H).

c) (R,S)-5-Bismethanesulfonylamino-2,3-dihydro-benzofuran-2-carboxylic acid methyl ester (56c)

To a solution of the compound from Example 56b (step b) (1.93 g, 10 mmol) in methylene chloride (100 mL) was added at 0° C. triethylamine (6.3 mL, 45 mmol) followed by dropwise addition of methanesulfonyl chloride (2.33 mL, 30 mmol). The reaction mixture was stirred at room temperature overnight, washed with saturated sodium bicarbonate and dried (Na$_2$SO$_4$). Evaporation of the solvent and purification of the residue by flash chromatography over silica gel (ethyl acetate-methylene chloride-hexane, 1:1:2) gave the title compound (2.1 g, 60.2%). $^1$H NMR (400 MHz, CDCl$_3$) δ: 7.38 (d, 1H), 7.27 (dd, 1H), 6.93 (d, 1H), 5.48 (dd, 1H), 3.72 (s, 3H), 3.64 (dd, 1H), 3.50 (s, 6H), 3.32 (dd, 1H).

b) (R,S)-5-Methanesulfonylamino-2,3-dihydro-benzofuran-2-carboxylic acid (56d)

Hydrolysis of compound 56c (1.9 g, 5.44 mmol) with lithium hydroxide (2.28 g, 54 mmol) yielded the title acid (1.32 g, 94.3%). $^1$H NMR (400 MHz, DMSO-d$_6$) δ: 13.11 (s, 1H), 9.32 (s, 1H), 7.09 (d, 1H), 6.96 (dd, 1H), 6.80 (d, 1H), 5.22 (dd, 1H), 3.55 (dd, 1H), 3.23 (dd, 1H), 2.88 (s, 3H).

c) (R,S)-5-Methanesulfonylamino-2,3-dihydro-benzofuran-2-carboxylic-acid-{2-[(S)-3-hydroxy-pyrrolidin-1-yl]-(S)-1-phenyl-ethyl}-methyl-amide (56)

Using the general coupling method A, compound 56d (849 mg, 3.3 mmol) was coupled with 1-(2-methylamino-(S)-2-phenyl-ethyl)-pyrrolidin-(S)-3-ol dihydrochloride (879 mg, 3.0 mmol) to yield 56 (1.16 g, 84.2%) as a mixture of diastereomers. $^1$H NMR (400 MHz, DMSO-$d_6$) δ: 9.28 (s, 1H), 7.40–7.30 (m, 5H), 7.10–6.70 (m, 3H), 5.82–5.28 (m, 2H), 4.70 (m, 1H), 4.15 (m, 1H), 3.50–1.48 (m, 16H); MS: [M+1]$^+$: 460.

Examples 57 and 58

Preparation of (R)-5-Methanesulfonylamino-2,3-dihydro-benzofuran-2-carboxylic-acid-{2-[(S)-3-hydroxy-pyrrolidin-1-yl]-(S)-1-phenyl-ethyl}-methyl-amide and (S)-5-Methane sulfonylamino-2,3-dihydro-benzofuran-2-carboxylic-acid-{2-[(S)-3-hydroxy-pyrrolidin-1-yl]-(S)-1-phenyl-ethyl}-methyl-amide Compounds 57 and 58 were individually prepared by the same procedure used for the preparation of the compound 56 except that the enantiomerically pure acids: (R)-2,3-dihydro-benzofuran-2-carboxylic acid (54c) and (S)-2,3-Dihydro-benzofuran-2-carboxylic acid (54d) were substituted respectively as starting material for racemic acid and the general coupling method B was employed in the final amide formation reaction to avoid the racemization of the chiral acid.

Compound 57: (R)-5-Methanesulfonylamino-2,3-dihydro-benzofuran-2-carboxylic-acid-{2-[(S)-3-hydroxy-pyrrolidin-1-yl]-(S)-1-phenyl-ethyl}-methyl-amide $^1$H NMR (400 MHz, DMSO-$d_6$) δ 9.30 (s, 1H), 7.40–7.30 (m, 5H), 7.10 (m, 1H), 6.95 (m, 1H), 6.78, 6.73 (2d, total 1H), 5.82–5.30 (m, 2H), 4.69 (m, 1H), 4.15 (m, 1H), 3.50–1.51 (m, 16H); MS: [M+1]$^+$: 460; In LC/MS, this diastereomer had shorter retention time.

Compound 58: (S)-5-Methanesulfonylamino-2,3-dihydro-benzofuran-2-carboxylic-acid-{2-[(S)-3-hydroxy-pyrrolidin-1-yl]-(S)-1-phenyl-ethyl}-methyl-amide $^1$H NMR (400 MHz, DMSO-$d_6$) δ: 9.30 (s, 1H), 7.40–7.30 (m, 5H), 7.10 (m, 1H), 6.96 (m, 1H), 6.76 (d, 1H), 5.74, 5.30 (m, total 2H), 4.69 (m, 1H), 4.15 (m, 1H), 3.50–1.50 (m, 16H); MS: [M+1]$^+$: 460; In LC/MS, this diastereomer had longer retention time.

Examples 59–63

Preparation of (2-{[2-({S}-3-Hydroxy-pyrrolidin-1-yl)-{S}-1-phenyl-ethyl]-(S)-methyl-carbamoyl}-2,3-dihydro-benzofuran-5-yl)-carbamic acid methyl ester, (R)-5-(Cyclopropanecarbonyl-amino)-2,3-dihydro-benzofuran-2-carboxylic acid-{2-[(S)-3-hydroxy-pyrrolidin-1-yl]-(S)-1-phenyl-ethyl}-methyl-amide, (S)-5-(Cyclopropanecarbonyl-amino)-2,3-dihydro-benzofuran-2-carboxylic acid-{2-[(S)-3-hydroxy-pyrrolidin-1-yl]-(S)-1-phenyl-ethyl}-methyl-amide, (2-{[2-({S}-3-Hydroxy-pyrrolidin-1-yl)-{S}-1-phenyl-ethyl]-(R)-methyl-carbamoyl}-2,3-dihydro-benzofuran-5-yl)-carbamic acid methyl ester, and (R,S)-5 -Acetylamino-2,3-dihydro-benzofuran-2-carboxylic acid-{2-[(S)-3-hydroxy-pyrrolidin-1-yl]-(S)-1-phenyl-ethyl}-methyl-amide Following the same reaction sequence utilized for 56, compounds 59–63 were prepared. The assignment of the 2-position absolute stereochemistry of 60, 61 and 62, 63 was based on their retention times in LC/MS as described in Example 54, 55. Compounds 62 and 63 were prepared by two approaches: using the racemic acid as the starting material and separation of the diastereomeric mixture by chromatography over silica gel in the last step, and using the enantiomerically pure acid to carry the 2-position stereochemistry through to the final product. Compound 62, with shorter retention in LC/MS was identical with the pure diastereomer obtained from (R)-2,3-dihydro-benzofuran-2-carboxylic acid (54c), and compound 63, with longer retention time in LC/MS, was identical with the pure diastereomer obtained from (S)-2,3-dihydro-benzofuran-2-carboxylic acid (54d). This further confirmed the stereochemistry assignment based on retention time in LC/MS.

Compound 59: (R,S)-5-Acetylamino-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-$d_6$) δ 9.75 (s, 1H), 7.50–7.20 (m, 7H), 6.70 (m, 1H), 5.76–5.31 (m, 2H), 4.69 (m, 1H), 4.15 (m, 1H), 3.50–2.25 (m, 11H), 1.98 (s, 3H), 1.93 (m, 1H), 1.50 (m, 1H); MS: [M+1]$^+$: 424.

Compound 60: (R)-5-(Cyclopropanecarbonyl-amino)-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-$d_6$) δ 10.00 (s, 1H), 7.48–7.20 (m, 7H), 6.71, 6.68 (2d, total 1H), 5.80–5.30 (m, 2H), 4.68 (m, 1H), 4.15 (m, 1H), 3.50–1.50 (m, 14H), 0.75 (m, 4H); MS: [M+1]$^+$: 450.

Compound 61: (S)-5-(Cyclopropanecarbonyl-amino)-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-$d_6$) δ 10.00 (s, 1H), 7.48–7.22 (m, 7H), 6.70 (d, 1H), 5.75–5.60, 5.30 (m, 2H), 4.68 (m, 1H), 4.15 (m, 1H), 3.50–1.45 (m, 14H), 0.75 (m, 4H); MS: [M+1]$^+$: 450.

Compound 62: (2-{[2-({S}-3-Hydroxy-pyrrolidin-1-yl)-{S}-1-phenyl-ethyl]-(R)-methyl-carbamoyl}-2,3-dihydro-benzofuran-5-yl)-carbamic acid methyl ester $^1$H NMR (400 MHz, DMSO-$d_6$) δ: 9.40 (s, 1H), 7.40–7.10 (m, 7H), 6.71, 6.68 (2d, total 1H), 5.78–5.31 (m, 2H), 4.69 (m, 1H), 4.16 (m, 1H), 3.62 (s, 3H), 3.50–2.25 (m, 11H), 1.92 (m, 1H), 1.50 (m,1H); MS: [M+1]$^+$: 440.

Compound 63: (2-{[2-({S}-3-Hydroxy-pyrrolidin-1-yl)-{S}-1-phenyl-ethyl]-(S)-methyl-carbamoyl}-2,3-dihydro-benzofuran-5-yl)-carbamic acid methyl ester $^1$H NMR (400 MHz, DMSO-$d_6$) δ: 9.40 (s, 1H), 7.40–7.10 (m, 7H), 6.70 (d, 1H), 5.75–5.66, 5.30 (m, total 2H), 4.66 (m, 1H), 4.16 (m, 1H), 3.62 (s, 3H), 3.50–2.25 (m, 11H), 1.95 (m, 1H), 1.49 (m, 1H); MS: [M+1]$^+$: 440.

Examples 64 and 65

Preparation of (R)-7-Methanesulfonylamino-2,3-dihydro-benzofuran-2-carboxylic acid-{2-[(S)-3-hydroxy-pyrrolidin-1-yl]-(S)-1-phenyl-ethyl}-methyl-amide and (S)-7-Methane sulfonylamino-2,3-dihydro-benzofuran-2-carboxylic acid-{2-[(S)-3-hydroxy-pyrrolidin-1-yl]-(S)-1-phenyl-ethyl}-methyl-amide Following the same procedure used for the preparation of 56, (R,S)-7-nitro-2,3-dihydro-benzofuran-2-carboxylic acid methyl ester (56a$_2$) (4.3 g, 19.3 mmol) was carried through hydrogenation (64a), sulfonylation (64b), hydrolysis (64c) and coupling with 1-(2-methylamino-(S)-2-phenyl-ethyl)-pyrrolidin-(S)-3-ol dihydrochloride to yield 64 and 65 as pure diastereomers after flash chromatography on silica gel.

(R,S)-7-Amino-2,3-dihydro-benzofuran-2-carboxylic acid methyl ester (64a) $^1$H NMR (400 MHz, DMSO-$d_6$) δ: 6.60 (d, 1H), 6.45 (m, 1H), 5.27 (dd, 1H), 4.93 (brs, 2H), 3.70 (s, 3H), 3.50 (dd, 1H), 3.20 (dd, 1H).

(R,S)-7-Bismethanesulfonylamino-2,3-dihydro-benzofuran-2-carboxylic acid methyl ester (64b) $^1$H NMR (400

MHz, DMSO-d$_6$) δ: 7.32 (d, 1H), 7.28 (d, 1H), 6.93 (t, 1H), 3.70 (s+m, 4H), 3.60 (s, 3H), 3.53 (s, 3H), 3.40 (dd, 1H).

(R,S)-7-Methanesulfonylamino-2,3-dihydro-benzofuran-2-carboxylic acid (64c) $^1$H NMR (400 MHz, DMSO-d$_6$) δ 13.18 (s, 1H), 9.27 (s, 1H), 7.10 (d, 1H), 7.02 (d, 1H), 6.82 (t, 1H), 5.30 (dd, 1H), 3.60 (dd, 1H), 3.29 (dd, 1H), 3.02 (s, 3H).

Compound 64: (R)-7-Methanesulfonylamino-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-d$_6$) δ 9.21 (s, 1H), 7.35 (m, 5H), 7.11–6.82 (m, 3H), 5.92–5.72, 5.27 (m 2H), 4.70 (m, 1H), 4.16 (m, 1H), 3.6–1.48 (m, 16H); MS: [M+1]$^+$: 460; In LC/MS, this diastereomer had shorter retention time.

Compound 65: (S)-7-Methanesulfonylamino-2,3-dihydro-benzofuran-2-carboxylic acid-{2-[(S)-3-hydroxy-pyrrolidin-1-yl]-(S)-1-phenyl-ethyl}-methyl-amid $^1$H NMR (400 MHz, DMSO-d$_6$) δ 9.227.50–7.30 (m, 5H), 7.15–6.82 (m, 3H), 5.92–5.72, 5.30 (m, total 2H), 4.70 (m, 1H), 4.18 (m, 1H), 3.53 (m, 1H), 3.20–1.50 (m, 15H); MS: [M+1]$^+$: 460; In LC/MS, this diastereomer had longer retention time.

Examples 66 and 67

Preparation of (R)-7-Acetylamino-2,3-dihydro-benzofuran-2-carboxylic-{2-[(S)-3-hydroxy-pyrrolidin-1-yl]-(S)-1-phenyl-ethyl}-methyl-amide and (S)-7-Acetylamino-2,3-dihydro-benzofuran-2-carboxylic-{2-[(S)-3-hydroxy-pyrrolidin-1-yl]-(S)-1-phenyl-ethyl}-methyl-amide Following the same procedure as for the preparation of Example 64 and 65 except using acetyl chloride instead of methanesulfonyl chloride, 66 and 67 were prepared.

Compound 66: (R)-7-Acetylamino-2,3-dihydro-benzofuran-2-carboxylic-{2-[(S)-3-hydroxy-pyrrolidin-1-yl]-(S)-1-phenyl-ethyl}-methyl-amide $^1$H NMR (400 MHz, DMSO-d$_6$) δ: 9.38, 9.30 (2s, total 1H), 7.63–7.30 (m, 6H), 6.93 (d, 1H), 6.76 (t, 1H), 5.75, 5.30 (m, total 1H), 4.68 (m, 1H), 4.15 (m, 1H), 3.60 (m, 1H), 3.30–1.48 (m, 15H); MS: [M+1]$^+$: 424; In LC/MS, this diastereomer had shorter retention time.

Compound 67: (R)-7-Acetylamino-2,3-dihydro-benzofuran-2-carboxylic-{2-[(S)-3-hydroxy-pyrrolidin-1-yl]-(S)-1-phenyl-ethyl}-methyl-amide $^1$H NMR (400 MHz, DMSO-d$_6$) δ: 9.38, 9.30 (2s, total 1H), 7.63–7.25 (m, 6H), 7.00, 6.93 (2d, total 1H), 6.78 (m, 1H), 5.85–5.66, 5.334 (m, total 2H), 4.70 (m, 1H), 4.16 (m, 1H), 3.51–1.50 (m, 16H); MS: [M+1]$^+$: 424; In LC/MS, this diastereomer had longer retention time.

Examples 68 and 69

Preparation of (R)-5-(Pyrrolidine-1-sulfonyl)-2,3-dihydro-benzofuran-2-carboxylic-{2-[(S)-3-hydroxy-pyrrolidin-1-yl]-(S)-1-phenyl-ethyl}-methyl-amide and (S)-5-(Pyrrolidine-1-sulfonyl)-2,3-dihydro-benzofuran-2-carboxylic-{2-[(S)-3-hydroxy-pyrrolidin-1-yl]-(S)-1-phenyl-ethyl}-methyl-amide a) (R,S)-2,3-Dihydro-benzofuran-2-carboxylic acid methyl ester (68a)

To a solution of (R,S)-2,3-Dihydro-benzofuran-2-carboxylic acid 54a (18 g) in methanol was added hydrogen chloride (200 mL, 2.0 M in ether). The reaction mixture was stirred at room temperature overnight and concentrated to give the title compound (19 g, 97.2%). $^1$H NMR (400 MHz, CDCl$_3$) δ: 7.16 (m, 2H), 6.89 (m, 2H), 5.20 (dd, 1H), 3.80 (s, 3H), 3.55 (dd, 1H), 3.37 (dd, 1H).

b) (R,S)-5-Chlorosulfonyl-2,3-dihydro-benzofuran-2-carboxylic acid methyl ester (68b)

(R,S)-2,3-Dihydro-benzofuran-2-carboxylic acid methyl ester 68a (7.12 g, 40 mmol) was converted to the title sulfonyl chloride (11 g, ~100%) by using the same procedure as described for 6d. $^1$H NMR (400 MHz, CDCl$_3$) δ: 7.88 (dd, 1H), 7.85 (d, 1H), 7.03 (d, 1H), 3.84 (s, 3H), 3.68 (dd, 1H), 3.49 (dd, 1H).

c) (R,S)-5-(Pyrrolidine-1-sulfonyl)-2,3-dihydro-benzofuran-2-carboxylic acid methyl ester (68c)

The title compound (2.16 g, 99.2%) was prepared by reaction of 68b (1.94 g, 7 mmol) with pyrrolidine using the same reaction conditions as described for 29c. $^1$H NMR (400 MHz, CDCl$_3$) δ: 7.68 (m, 2H), 6.98 (d, 1H), 3.82 (s, 3H), 3.62 (dd, 1H), 3.42 (dd, 1H), 3.21 (t, 4H), 1.78 (m, 4H).

d) (R,S)-5-(Pyrrolidine-1-sulfonyl)-2,3-dihydro-benzofuran-2-carboxylic acid (68d)

Hydrolysis of 68c (2.0 g, 6.43 mmol) with lithium hydroxide (1.35 g, 32 mmol) gave the title acid (1.90 g, 100%). $^1$H NMR (400 MHz, DMSO-d$_6$) δ: 13.28 (s, 1H), 7.66 (d, 1H), 7.60 (dd, 1H), 7.03 (d, 1H), 5.39 (dd, 1H), 3.62 (dd, 1H), 3.35 (dd, 1H), 3.10 (t, 4H), 1.65 (m, 4H).

e) (R)-5-(Pyrrolidine-1-sulfonyl)-2,3-dihydro-benzofuran-2-carboxylic-{2-[(S)-3-hydroxy-pyrrolidin-1-yl]-(S)-1-phenyl-ethyl}-methyl-amide and (S)-5-(Pyrrolidine-1-sulfonyl)-2,3-dihydro-benzofuran-2-carboxylic-{2-[(S)-3-hydroxy-pyrrolidin-1-yl]-(S)-1-phenyl-ethyl}-methyl-amide Using the general coupling method A, (R,S)-5-(Pyrrolidine-1-sulfonyl)-2,3-dihydro-benzofuran-2-carboxylic acid (68d) (981 mg, 3.3 mmol) was coupled with 1-(2-methylamino-(S)-2-phenyl-ethyl)-pyrrolidin-(S)-3-ol dihydrochloride (879 mg, 3.0 mmol) to yield two pure diastereomers: Compound 68 (250 mg, 16.7%) with shorter retention time in LC/MS and compound 69 (370 mg, 24.7%) with longer retention time in LC/MS, and a mixture of the pair of diastereomers (700 mg, 46.8%).

Compound 68: $^1$H NMR (400 MHz, DMSO-d$_6$) δ: 7.68–7.30 (m, 7H), 7.01, 6.98 (2d, total 1H), 6.02–5.71, 5.25 (m, total 2H), 4.69 (m, 1H), 4.15 (m, 1H), 3.55 (m, 1H), 3.25–2.25 (m, 14H), 1.92 (m, 1H), 1.68 (m, 4H), 1.50 (m, 1H); MS: [M+1]$^+$: 500.

Compound 69: $^1$H NMR (400 MHz, DMSO-d$_6$) δ: 7.61–7.28 (m, 7H), 7.00 (d, 1H), 6.00–5.75, 5.28 (m, total 2H), 4.70 (m, 1H), 4.15 (m, 1H), 3.62–3.43 (m, 2H), 3.18–2.30 (m, 13H), 1.93 (m, 1H), 1.64 (m, 4H), 1/45 (m, 1H); MS: [M+1]$^+$: 500.

Examples 70–72

Preparation of (R)-5-Dimethylsulfamoyl-2,3-dihydro-benzofuran-2-carboxylic acid-{2-[(S)-3-hydroxy-pyrrolidin-1-yl]-(S)-1-phenyl-ethyl}-methyl-amide, (S)-5-Dimethylsulfamoyl-2,3-dihydro-benzofuran-2-carboxylic acid-{2-[(S)-3-hydroxy-pyrrolidin-1-yl]-(S)-1-phenyl-ethyl}-methyl-amide, and (R,S)-5-Methylsulfamoyl-2,3-dihydro-benzofuran-2-carboxylic acid-{2-[(S)-3-hydroxy-pyrrolidin-1-yl]-(S)-1-phenyl-ethyl}-methyl-amide Compounds 70, 71, and 72 were prepared by the same procedure used for the preparation of 68 and 69 described above.

Compound 70: (R)-5-Dimethylsulfamoyl-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-d$_6$) δ: 7.63–7.30 (m, 7H), 7.04, 7.00 (2d, total 1H), 6.04–5.73, 5.26 (m, total 2H), 4.69 (m, 1H), 4.15 (m, 1H), 3.55 (m, 1H), 3.30–2.25 (m, 14H), 1.95 (m, 1H), 1.50 (m, 1H); MS: [M+1]$^+$: 474. In LC/MS, this diastereomer had shorter retention time.

Compound 71: (S)-5-Dimethylsulfamoyl-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-d$_6$) δ 7.60–7.30 (m, 7H), 7.05 (d, 1H), 6.01–5.72, 5.28 (m, total 2H), 4.68 (m, 1H), 4.15 (m, 1H), 3.63 (m, 1H), 3.42 (m, 1H), 3.18–2.66 (m, 7H), 2.56 (s, 6H), 2.36 (m, 2H), 1.95 (m, 1H), 1.46 (m, 1H); MS: [M+1]$^+$: 474; In LC/MS, this diastereomer had longer retention time.

Compound 72: (R,S)-5-Methylsulfamoyl-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-d$_6$) δ 7.65–7.22 (m, 7H), 7.00, 6.95 (2d, total 1H), 6.01–5.72, 5.28 (m, total 2H), 4.70 (m, 1H), 4.16 (m, 1H), 3.55–2.40 (m, 10H), 2.38 (d, 3H), 2.30 (m, 1H), 1.95 (m, 1H), 1.48 (m, 1H); MS: [M+1]$^+$: 460.

Example 73

Preparation of (R,S)-5-(Methanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide (R,S)-2,3-Dihydro-benzofuran-2-carboxylic acid (54a) was carried through the same reaction sequence used for the preparation of 48 to prepare 73: a) iodination; b) methyl ester formation; c) cyanide substitution; d) hydrogenation; e) conversion to sulfonamide; f) hydrolysis of the ester and finally e) coupling with 1-(2-methylamino-(S)-2-phenyl-ethyl)-pyrrolidin-(S)-3-ol dihydrochloride using general coupling method A.

a) (R,S)-5-Iodo-2,3-dihydro-benzofuran-2-carboxylic acid (73a) $^1$H NMR (400 MHz, DMSO-d$_6$) δ: 13.40 (brs, 1H), 7.52 (d, 1H), 7.41 (dd, 1H), 6.70 (d, 1H), 5.23 (dd, 1H), 3.52 (dd, 1H), 3.22 (dd, 1H).

b) (R,S)-5-Iodo-2,3-dihydro-benzofuran-2-carboxylic acid methyl ester (73b)
$^1$H NMR (400 MHz, CDCl$_3$) δ: 7.45 (m, 2H), 6.68 (d, 1H), 5.20 (dd, 1H), 3.82 (s, 3H), 3.52 (dd, 1H), 3.35 (dd, 1H).

c) (R,S)-5-Cyano-2,3-dihydro-benzofuran-2-carboxylic acid methyl ester (73c)
$^1$H NMR (400 MHz, CDCl$_3$) δ: 7.48 (m, 2H), 6.95 (d, 1H), 5.30 (dd, 1H), 3.82 (s, 3H), 3.60 (dd, 1H), 3.41 (dd, 1H).

d) (R,S)-5-Aminomethyl-2,3-dihydro-benzofuran-2-carboxylic acid methyl ester hydrochloride (73d) $^1$H NMR (400 MHz, DMSO-d$_6$) δ: 8.40 (brs, 2H), 7.36 (d, 1H), 7.27 (dd, 1H), 6.89 (d, 1H), 5.40 (dd, 1H), 3.90 (brs, 2H), 3.80 (s, 3H), 3.59 (dd, 1H), 3.28 (dd, 1H).

e) (R,S)-5-(Methanesulfonylamino-methyl)-2,3-dihydro-benzofuran-2-carboxylic acid methyl ester (73e) $^1$H NMR (400 MHz, CDCl$_3$) δ: 7.18 (d, 1H), 7.10 (dd, 1H), 6.83 (d, 1H), 5.22 (dd, 1H), 4.83 (t, 1H), 4.20 (d, 2H), 3.80 (s, 3H), 3.53 (dd, 1H), 3.35 (dd, 1H), 2.86 (s, 3H).

f) (R,S)-5-(Methanesulfonylamino-methyl)-2,3-dihydro-benzofuran-2-carboxylic acid (73f) $^1$H NMR (400 MHz, DMSO-d$_6$) δ: 13.10 (s, 1H), 7.44 (t, 1H), 7.20 (d, 1H), 7.08 (dd, 1H), 6.80 (d, 1H), 5.22 (dd, 1H), 4.05 (d, 2H), 3.53 (dd, 1H), 3.22 (dd, 1H), 2.85 (s, 3H).

g) (R,S)-5-(Methanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide (73) $^1$H NMR (400 MHz, DMSO-d$_6$) δ: 7.42–7.06 (m, 8H), 6.76, 6.71 (2d, total 1H), 5.82–5.65, 5.30 (m, total 2H), 4.70 (m, 1H), 4.20–4.05 (m, 3H), 3.50–2.25 (m, 14H), 1.95 (m, 1H), 1.50 (m, 1H); MS: [M+1]$^+$: 474.

Examples 74 and 75

Preparation of (R)-5-(Methanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide and (S)-5-(Methanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide Compounds 74 and 75, the two pure diastereomers of 73, were prepared by the same procedure used for the preparation of 73 except that the enantiomerically pure (R)-2,3-Dihydro-benzofuran-2-carboxylic acid (54c) or (S)-2,3-Dihydro-benzofuran-2-carboxylic acid (54d) were substituted for racemic acid starting material.

Compound 74: (R)-5-(Methanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-d$_6$) δ: 7.42–7.06 (m, 8H); 6.76, 6.70 (2d, total 1H), 5.82–5.65, 5.32 (m, tatal 2H), 4.69 (m, 1H), 4.20–4.05 (m, 3H), 3.55–2.20 (14H), 1.93 (m, 1H), 1.50 (m, 1H); MS: [M+1]$^+$: 474; In LC/MS, this diastereomer had shorter retention time.

Compound 75: (S)-5-(Methanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide $^1$H NMR (400 MHz, DMSO-d$_6$) δ: 7.42–7.06 (m, 6H), 7.18 (d, 1H), 7.05 (dd, 1H), 6.78 (d, 1H), 5.75, 5.30 (m, total 2H), 4.68 (m, 1H), 4.16 (m, 1H), 4.05 (d, 2H), 3.50 (m, 1H), 3.40–2.28 (m, 13H), 1.95 (m, 1H), 1.50 (m, 1H); MS: [M+1]$^+$: 474; In LC/MS, this diastereomer had longer retention time.

Example 76

Preparation of (R,S)-5-(Propanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide Compound 76 was prepared by the same reaction sequence used for the preparation of 73 except that 1-propanesulfonyl chloride was substituted for methanesulfonyl chloride in step (e).

(R,S)-5-(Propanesulfonylamino-methyl)-2,3-dihydro-benzofuran-2-carboxylic acid (73f, R=propanesulfonyl): $^1$H NMR (400 MHz, DMSO-d$_6$) δ: 13.10 (s, 1H), 7.50 (t, 1H), 7.19 (d, 1H), 7.08 (dd, 1H), 6.78 (d, 1H), 5.22 (dd, 1H), 4.04 (d, 2H), 3.51 (dd, 1H), 3.22 (dd, 1H), 2.85 (t, 2H), 1.60 (m, 2H), 0.90 (t, 3H).

Compound 76: $^1$H NMR (400 MHz, DMSO-d$_6$) δ: 7.48 (t, 1H), 7.40–7.06 (m, 7H), 6.76, 6.71 (2d, total 1H), 5.82–5.65, 5.30 (m, total 2H), 4.69 (m, 1H), 4.20–4.05 (m, 3H), 3.50–2.28 (m, 13H), 1.95 (m, 1H), 1.60 (m, 2H), 1.50 (m, 1H), 0.90 (t, 3H); MS: [M+1]$^+$: 502.

Examples 77 and 78

Preparation of (R)-5-(Propanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide and (S)-5-(Propanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide Compounds 77 and 78, the two pure diastereomers of Example 76, were prepared by the same procedure used for the preparation of 76 except that enantiomerically pure (R)-2,3-Dihydro-benzofuran-2-carboxylic acid (54c) and (S)-2,3-Dihydro-benzofuran-2-carboxylic acid (54d) were substituted for racemic acid as the starting material.

Compound 77: $^1$H NMR (400 MHz, DMSO-$d_6$) δ: 7.48 (t, 1H), 7.40–7.05 (m, 7H), 6.75, 6.70 (2d, total 1H), 5.83–5.65, 5.30 (m, total 2H), 4.70 (m, 1H), 4.20–4.03 (m, 3H), 3.50–2.28 (m, 13H), 1.93 (m, 1H), 1.60 (m, 2H), 1.50 (m, 1H), 0.90 (t, 3H); MS: [M+1]$^+$: 502; In LC/MS, this diastereomer had shorter retention time.

Compound 78: $^1$H NMR (400 MHz, DMSO-$d_6$) δ: 7.50 (t, 1H), 7.38–7.30 (m, 5H), 7.18 (d, 1H), 7.05 (dd, 1H), 5.73, 5.30 (m, total 1H), 4.70 (m, 1H), 4.15 (m, 1H), 4.02 (d, 2H), 3.50 (m, 1H), 3.40–2.28 (m, 12H), 1.95 (m, 1H), 1.60 (m, 2H), 1.50 (m, 1H), 0.90 (t, 3H); MS: [M+1]$^+$: 502; In LC/MS, this diastereomer had longer retention time.

Example 79

Preparation of (2-{[2-({S}-3-Hydroxy-pyrrolidin-1-yl)-{S}-1-phenyl-ethyl]-methyl-carbamoyl}-(R,S)-2,3-dihydro-benzofuran-5-ylmethyl)-carbamic acid methyl ester (79)

Compound 79 was prepared by the same reaction sequence used for the preparation of 73 except that methyl chloroformate was substituted for methanesulfonyl chloride in step (e).

(R,S)-5-(Methoxycarbonylamino-methyl)-2,3-dihydro-benzofuran-2-carboxylic acid (73f, R=CH3OC(=O)): $^1$H NMR (400 MHz, DMSO-$d_6$) δ: 13.08 (s, 1H), 7.60 (t, 1H), 7.10 (d, 1H), 6.99 (dd, 1H), 6.75 (d, 1H), 5.20 (dd, 1H), 4.09 (d, 2H), 3.51 (s+m, 4H), 3.20 (dd, 1H). Example 79: $^1$H NMR (400 MHz, DMSO-$d_6$) δ: 7.58 (t, 1H), 7.40–7.25 (m, 5H), 7.10–7.68 (m, 3H), 5.80–5.65, 5.30 (m, total 2H), 4.70 (m, 1H), 4.20–4.08 (m, 3H), 3.52 (s, 3H), 3.45–2.28 (m, 11H), 1.95 (m, 1H), 1.50 (m, 1H); MS: [M+1]$^+$: 454.

Examples 80e$_1$* and 80e$_2$*

Preparation of Chroman-4-carboxylic acid-{2-[(S)-3-hydroxy-pyrrolidin-1-yl]-(S)-1-phenyl-ethyl}-methyl-amide a) Trifluoro-methanesulfonic acid 2H-chromen-4-yl ester (80a)

Commercially available 4-chromanone (Aldrich Chemical Company) (17.8 g, 120.3 mmol) was converted to the title compound using the same procedure described in Example 4 (step d) and the crude was used without further purification. $^1$H NMR (300 MHz, CDCl$_3$) δ: 7.10 (t, 1H), 7.28–6.86 (m, 4H), 5.78 (t, 1H), 5.00 (d, 1H).

b) 2H-Chromene-4-carboxylic acid methyl ester (80b)

Compound 80a was converted to the title compound (11.5 g, 50.3% overall yield) using the same procedure as described in Example 4 (step e). $^1$H NMR (300 MHz, CDCl$_3$) δ: 7.90 (dd, 1H), 7.17 (dd, 1H), 6.96–6.86 (m, 3H), 4.82 (d, 1H), 3.85 (s, 3H).

c) (R,S)-Chroman-4-carboxylic acid methyl ester (80c)

Compound 80b was hydrogenated in ethyl acetate (600 ml) in the presence of 10% Pd/C (2.2 g) to give the title compound (11.0 g, ~100%). $^1$H NMR (300 MHz, CDCl$_3$) δ: 7.22–7.15 (m, 2H), 6.87 (m, 2H), 4.28 (m, 2H), 3.79 (m, 1H), 3.73 (s, 3H), 2.32 (m, 1H), 2.10 (m, 1H).

d) (R,S)-Chroman-4-carboxylic acid (80d)

Compound 80c (1.21 g, 6.3 mmol) was hydrolyzed with lithium hydroxide (1.35 g, 32 mmol) to give the title acid (1.05 g, 93.4%). $^1$H NMR (300 MHz, CDCl$_3$) δ: 12.66 (s, 1H), 7.20–7.13 (m, 2H), 6.87–6.78 (m, 2H), 4.18 (m, 2H), 3.75 (t, 1H), 2.16–2.03 (m, 2H).

e) Chroman-4-carboxylic acid-{2-[(S)-3-hydroxy-pyrrolidin-1-yl]-(S)-1-phenyl-ethyl}-methyl-amide (80e$_1$* and 80e$_2$*)

Using general coupling Method A, compound 80d (588 mg, 3.3 mmol) was coupled with 1-(2-methylamino-(S)-2-phenyl-ethyl)-pyrrolidin-(S)-3-ol dihydrochloride (879 mg, 3.0 mmol) to yield, after chromatographic separation, 80e$_1$* (260 mg, 22.8%) with longer retention time in LC/MS, and 80e$_2$* (520 mg, 45.6%) with shorter retention time in LC/MS. 80e$_1$*: $^1$H NMR (400 MHz, DMSO-$d_6$) δ: 7.38–6.75 (m, 9H), 5.85, 5.45 (m, total 1H), 4.76–4.18 (m, 5H), 3.22–1.50 (m, 13H); MS: [M+1]$^+$: 381. 80e$_2$*: $^1$H NMR (400 MHz, DMSO-$d_6$) δ: 7.45–6.75 (m, 9H), 5.95, 5.39 (m, total 1H), 4.71 (m, 1H), 4.48–4.10 (m, 4H), 3.08–1.57 (m, 13H); MS: [M+1]$^+$: 381.

Examples 81d$_1$* and 81d$_2$*

Preparation of 6-(Pyrrolidine-1-sulfonyl)-chroman4-carboxylic acid-{2-[(S)-3-hydroxy-pyrrolidin-1-yl]-(S)-1-phenyl-ethyl}-methyl-amide a) (R,S)-6-Chlorosulfonyl-chroman-4-carboxylic acid methyl ester (81a)

(R,S)-Chroman-4-carboxylic acid methyl ester 80c (7.0 g, 36.5 mmol) was chlorosulfonylated to give the title sulfonyl chloride (81a) (10.5 g, ~100%) using the same procedure described for compound 6d. $^1$H NMR (400 MHz, CDCl$_3$) δ: 7.98 (d, 1H), 7.82 (dd, 1H), 6.98 (d, 1H), 4.38 (m, 2H), 3.86 (m, 1H), 3.78 (s, 3H), 2.45 (m, 1H), 2.13 (m, 1H).

b) (R,S)-6-(Pyrrolidine-1-sulfonyl)-chroman-4-carboxylic acid methyl ester (81b, R$_1$ and R$_2$ taken together are —(CH$_2$)$_4$—)

A solution of compound 81a (4.35 g, 15 mmol) in methylene chloride (20 mL) was added to a solution of pyrrolidine (1.6 mL, 19.2 mmol) in methylene chloride (120 mL) containing triethylamine (4.18 mL, 30 mmol) at 0° C. The reaction mixture was stirred for 40 minutes and washed with 1N hydrochloric acid (50 mL) and saturated aqueous NaHCO$_3$ (50 mL), dried (Na$_2$SO$_4$), and concentrated. The residue was purified by flash chromatography over silica gel (hexane-ethyl acetate, 2:1) to afford the title compound (4.5 g, 92.3%). $^1$H NMR (400 MHz, CDCl$_3$) δ: 7.78 (d, 1H), 7.59 (dd, 1H), 6.95 (d, 1H), 4.30 (m, 2H), 3.85 (m, 1H), 3.76 (s, 3H), 3.21 (m, 4H), 2.38 (m, 1H), 2.13 (m, 1H), 1.76 (m, 4H).

c) (R,S)-6-(Pyrrolidine-1-sulfonyl)-chroman-4-carboxylic acid (81c, $R_1$ and $R_2$ taken together are —$(CH_2)_4$—)

Compound 81b (4.3 g, 13.2 mmol) was hydrolyzed with lithium hydroxide at room temperature to give the acid 81c, ($R_1$ and $R_2$ taken together are —$(CH_2)_4$—) (4.05 g, 98.5%).
$^1$H NMR (400 MHz, DMSO-$d_6$) δ: 12.89 (s, 1H), 7.72 (d, 1H), 7.57 (dd, 1H), 6.98 (d, 1H), 4.32 (m, 1H), 4,15 (m, 1H), 3.95 (m, 1H), 3.08 (m, 4H), 2.22 (m, 1H), 2.08 (m, 1H), 1.63 (m, 4H).

d) 6-(Pyrrolidine-1-sulfonyl)-chroman-4-carboxylic acid-{2-[(S)-3-hydroxy-pyrrolidin-1-yl]-(S)-1-phenyl-ethyll-methyl-amide (81d$_1$* and 81d$_2$*)

Using the general coupling Method A, compound 81c (step c) (1.03 g, 3.3 mmol) was coupled with 1-(2-methy-lamino-(S)-2-phenyl-ethyl)-pyrrolidin-(S)-3-ol dihydrochloride (879 mg, 3.0 mmol) to yield pure example 81d$_1$* (800 mg, 52%) with longer retention time in LC/MS and compound 81d$_2$* (265 mg, 17.2%) with shorter retention time in LC/MS, and a mixture of 81d$_1$* and 81d$_2$* (200 mg, 13%). 81d$_1$*: $^1$H NMR (400 MHz, DMSO-$d_6$) δ: 7.52–6.96 (m, 8H), 5.80, 5.43 (m, total 1H), 4.75–4.20 (m, 4H), 3.10–1.65 (m, 22H); MS: [M+1]$^+$: 514. 81d$_2$*: $^1$H NMR (400 MHz, DMSO-$d_6$) δ: 7.53–7.32 (m, 7H), 6.96 (d, 1H), 5.85, 5.43 (m, total 1H), 4.68–4.15 (m, 4H), 3.45–1.50 (m, 22H); MS: [M+1]$^+$: 514.

Examples 82a*, 82b*, 83a*, 83b*, 84a*, 84b*, 85a*, 85b* and 86

In a manner analogous to compounds 81d$_1$* and 81d$_2$*, compounds 82a*, 82b*, 83a*, 83b*, 84a*, 84b*, 85a*, 85b* and 86 were prepared.

Compound Mixture 82a*, 82b*: 6-(Isopropyl-methyl-sulfamoyl)-chroman-4-carboxylic acid-{2-[(S)-3-hydroxy-pyrrolidin-1-yl]-(S)-1-phenyl-ethyl}-methyl-amide Compound 82a* (with longer retention time in LC/MS):
$^1$H NMR (400 MHz, DMSO-$d_6$) δ: 7.50–6.95 (m, 8H), 5.80, 5.43 (m, total 1H), 4.75–3.92 (m, 5H), 3.15–1.56 (m, 17H), 0.88 (m, 6H); MS: [M+1]$^+$: 516.

Compound 82b* (with shorter retention time in LC/MS):
$^1$H NMR (400 MHz, DMSO-$d_6$) δ: 7.49–7.30 (m, 7H), 6.95 (d, 1H), 5.85, 5.43 (m, total 1H), 4.70–3.98 (m, 5H), 3.45–1.50 (m, 22H), 0.88 (m, 6H); MS: [M+1]$^+$: 516.

Compound Mixture 83a*, 83b*: 6-(Morpholine-4-sulfonyl)-chroman-4-carboxylic acid-{2-[(S)-3-hydroxy-pyrrolidin-1-yl]-(S)-1-phenyl-ethyl}-methyl-amide Compound 83a* (with longer retention time in LC/MS):
$^1$H NMR (400 MHz, DMSO-$d_6$) δ: 7.48–6.98 (m, 8H), 5.80, 5.43 (m, total 1H), 4.73–4.18 (m, 4H), 3.60 (m, 4H), 3.12–1.55 (m, 18H); MS: [M+1]$^+$: 530.

Compound 83b* (with shorter retention time in LC/MS):
$^1$H NMR (400 MHz, DMSO-$d_6$) δ: 7.48–7.30 (m, 7H), 6.99 (d, 1H), 5.85, 5.43 (m, total 1H), 4.72–4.18 (m, 4H), 3.60 (m, 4H), 3.45–1.50 (m, 18H); MS: [M+1]$^+$: 530.

Compound Mixture 84a*, 84b*: 6-(Methyl-sulfamoyl)-chroman-4-carboxylic acid-{2-[(S)-3-hydroxy-pyrrolidin-1-yl]-(S)-1-phenyl-ethyl}-methyl-amide Compound 84a* (with longer retention time in LC/MS):
$^1$H NMR (400 MHz, DMSO-$d_6$) δ: 7.50–6.95 (m, 9H), 5.80, 5.43 (m, total 1H), 4.73–4.20 (m, 4H), 3.10–1.55 (m, 17H); MS: [M+1]$^+$: 474.

Compound 84b* (with shorter retention time in LC/MS):
$^1$H NMR (400 MHz, DMSO-$d_6$) δ: 7.50–7.23 (m, 8H), 6.96 (d, 1H), 5.85, 5.43 (m, total 1H), 4.78–4.15 (m, 4H), 3.45–1.50 (m, 17H); MS: [M+1]$^+$: 474.

Compound Mixture 85a*, 85b*: 6-(Dimethyl-sulfamoyl)-chroman-4-carboxylic acid-{2-[(S)-3-hydroxy-pyrrolidin-1-yl]-(S)-1-phenyl-ethyl}-methyl-amide Compound 85a* (with longer retention time in LC/MS):
$^1$H NMR (400 MHz, DMSO-$d_6$) δ 7.48–6.99 (m, 8H), 5.80, 5.43 (m, total 1H), 3.10–1.55 (m, 20H); MS: [M+1]$^+$: 488.

Compound 85b* (with shorter retention time in LC/MS):
$^1$H NMR (400 MHz, DMSO-$d_6$) δ: 7.48–7.30 (m, 7H), 6.98 (d, 1H), 5.85, 5.43 (m, total 1H), 4.70–4.15 (m, 4H), 3.45–1.50 (m, 20H); MS: [M+1]$^+$: 488.

Compound 86: 6-[(2-Hydroxy-ethyl)-methyl-sulfamoyl]-(R,S)-chroman-4-carboxylic acid-{2-[(S)-3-hydroxy-pyrrolidin-1-yl]-(S)-1-phenyl-ethyl}-methyl-amide $^1$H NMR (400 MHz, DMSO-$d_6$) δ: 7.48–6.98 (m, 8H), 5.84, 5.43 (m, total 1H), 4.80–4.15 (m, 5H), 3.48 (m, 2H), 3.20–1.50 (m, 19H); MS: [M+1]$^+$: 518.

Examples 87 and 88

Preparation of 6-(Methanesulfonylamino-methyl)-(R,S)-chroman-4-carboxylic acid-{2-[(S)-3-hydroxy-pyrrolidin-1-yl]-(S)-1-phenyl-ethyl}-methyl-amide and (4-{[2-({S}-3-Hydroxy-pyrrolidin-1-yl)-{S}-1-phenyl-ethyl]-methyl-carbamoyl}-(R,S)-chroman-6-ylmethyl)-carbamic acid methyl ester Chroman-4-carboxylic acid methyl ester 80c was carried through the same reaction sequence used for the preparation of 48 or 51: a) iodination, b) cyanide substitution, c) reduction, d) sulfonamide or carbamate formation, e) ester hydrolysis and f) acid coupling with 1-(2-methylamino-2-phenyl-ethyl)-pyrrolidin-3-ol dihydrochloride using general coupling method A to yield 87 and 88 as a mixture of diastereomers.

a) (R,S)-6-Iodo-chroman-4-carboxylic acid methyl ester (87a)
$^1$H NMR (400 MHz, CDCl$_3$) δ: 7.54 (d, 1H), 7.40 (dd, 1H), 6.60 (d, 1H), 4.23 (m, 2H), 3.76 (s+m, 4H), 2.30 (m, 1H), 2.08 (m, 1H).

b) (R,S)-6-Cyano-chroman-4-carboxylic acid methyl ester (87b)
$^1$H NMR (400 MHz, CDCl$_3$) δ: 7.59 (d, 1H), 7.43 (dd, 1H), 6.88 (d, 1H), 4.31 (m, 1H), 3.78 (s+m, 4H), 2.38 (m, 1H), 2.10 (m, 1H).

c) (R,S)-6-Aminomethyl-chroman-4-carboxylic acid methyl ester hydrochloride (87c)
$^1$H NMR (400 MHz, DMSO-$d_6$) δ: 8.52 (brs, 2H), 7.34 (m, 2H), 6.82 (d, 1H), 4.18 (m, 2H), 3.89 (m, 2H), 3.70 (s+m, 4H), 2.18–2.10 (m, 2H).

d) (R,S)-6-(Methanesulfonylamino-methyl)-chroman-4-carboxylic acid methyl ester (87d, R=methanesulfonyl) $^1$H NMR (400 MHz, CDCl$_3$) δ: 7.20 (d, 1H), 7.12 (dd, 1H), 4.76 (t, 1H), 4.22 (m, 4H), 3.79 (m, 1H), 3.75 (s, 3H), 2.85 (s, 3H), 2.32 (m, 1H), 2.12 (m, 1H).

(R,S)-6-(Methoxycarbonylamino-methyl)-chroman-4-carboxylic acid methyl ester ester (87d, R=methoxycarbonyl) $^1$HNMR (400 MHz, CDCl$_3$) δ: 7.12 (m, 2H), 6.80 (d, 1H), 4.95 (brs, 1H), 4.25 (m, 4H), 3.78 (m, 1H), 3.75 (s, 3H), 3.70 (s, 3H), 2.32 (m, 1H), 2.11 (m, 1H).

e) (R,S)-6-(Methanesulfonylamino-methyl)-chroman-4-carboxylic acid (87e, R=methanesulfonyl) $^1$H NMR (400 MHz, DMSO-$d_6$) δ: 12.67 (s, 1H), 7.47 (t, 1H), 7.19 (d, 1H), 7.10 (dd, 1H), 6.78 (d, 1H), 4.15 (m, 2H), 4.04 (d, 2H), 3.75 (m, 1H), 2.80 (s, 3H), 2.16 (m, 1H), 2.03 (m, 1H).

(R,S)-6-(Methoxycarbonylamino-methyl)-chroman-4-carboxylic acid (87e, R=methoxycarbonyl) $^1$H NMR (400 MHz, DMSO-$d_6$) δ: 12.62 (s, 1H), 7.60 (t, 1H), 7.09 (d, 1H), 7.02 (dd, 1H), 6.72 (d, 1H), 4.16–4.08 (m, 4H), 3.72 (m, 1H), 3.53 (s, 3H), 2.15 (m, 1H), 2.02 (m, 1H).

f) 6-(Methanesulfonylamino-methyl)-(R,S)-chroman-4-carboxylic acid-{2-[(S)-3-hydroxy-pyrrolidin-1-yl]-(S)-1-phenyl-ethyl}-methyl-amide 87 $^1$H NMR (400 MHz, DMSO-$d_6$) δ: 7.46–7.68 (m, 9H), 5.88, 5.42 (m, total 1H), 4.80–3.95 (m, 6H), 3.33–1.56 (m, 17H); MS: [M+1]$^+$: 488.

4-{[2-({S}-3-Hydroxy-pyrrolidin-1-yl)-{S}-1-phenyl-ethyl]-methyl-carbamoyl}-(R,S)-chroman-6-ylmethyl)-carbamic acid methyl ester 88 $^1$H NMR (400 MHz, DMSO-$d_6$) δ: 7.45–7.58 (m, 9H), 5.85, 5.40 (m, total 1H), 4.78–3.97 (m, 6H), 3.32–1.56 (m, 17H); MS: [M+1]$^+$: 468.

Examples 89d$_1$* and 89d$_2$*

Preparation of 1-Methyl-2,3-dihydro-1H-indole-2-carboxylic acid {2-[(S)-3-hydroxy-pyrrolidin-1-yl]-(S)-1-phenyl-ethyl}-methyl-amide a) (R,S)-2,3-Dihydro-1H-indole-2-carboxylic acid methyl ester (89a)

To a stirred solution of commercially available (R,S)-2,3-dihydro-1H-indole-2-carboxylic acid (Aldrich Chemical Company) (3.26 g, 20 mmol) in methanol (100 mL) was added hydrogen chloride (50 mL, 4.0 M solution in dioxane) and the mixture was stirred overnight at room temperature. The organic solvents were removed under reduced pressure; the residue was dissolved in dichloromethane (100 mL), washed with 1N sodium carbonate (3×50 mL), brine (50 mL), dried over anhydrous sodium sulfate, filtered, concentrated under reduced pressure and finally dried in vacuo to afford the title compound (3.37 g, 95%). $^1$H-NMR (400 MHz, CDCl$_3$) δ: 7.07 (m, 2H), 6.64 (m, 2H), 4.48 (dd, 1H), 3.76 (s, 3H), 3.45–3.27 (m, 2H).

b) (R,S)-1-Methyl-2,3-dihydro-1H-indole-2-carboxylic acid methyl ester (89b)

Compound 89a (0.95 g, 5.36 mmol), potassium carbonate (2.22 g, 16.08 mmol), and iodomethane (1.19 g, 8.04 mmol) in acetonitrile (30 mL) were stirred at refluxing temperature overnight. The solids were filtered; the filtrate was diluted with water (100 mL) and extracted with dichloromethane (4×50 mL). The combined extracts were washed with brine (100 mL), dried over anhydrous sodium sulfate, filtered, and concentrated under reduced pressure. The crude product was purified by flash chromatography over silica gel to afford the title compound (0.98 g, 96%). $^1$H-NMR (400 MHz, CDCl$_3$) δ: 7.11 (t, 1H), 7.04 (d, 1H), 6.71 (t, 1H), 6.52 (d, 1H), 4.05 (m, 1H), 3.81 (s, 3H), 3.35 (m, 1H), 3.15 (m, 1H), 2.85 (s, 3H).

c) (R,S)-1-Methyl-2,3-dihydro-1H-indole-2-carboxylic acid (89c)

An aqueous solution of 10% hydrochloric acid (30 mL) containing compound 89b (0.56 g, 2.93 mmol) was stirred at reflux for 4 hours. Water was removed under reduced pressure and the residue was dried in vacuo to give the title compound (0.61 g, 98%) as the hydrochloride salt. $^1$H-NMR (400 MHz, DMSO-$d_6$) δ: 7.02 (m, 2H), 6.59 (t, 1H), 6.47 (d, 1H), 4.03 (dd, 1H), 3.28 (m, 1H), 2.96 (m, 1H), 2.75 (s, 3H).

d) 1-Methyl-2,3-dihydro-1H-indole-2-carboxylic acid {2-[(S)-3-hydroxy-pyrrolidin-1-yl]-(S)-1-phenyl-ethyl}-methyl-amide (89d)

Coupling of compound 89c with 1-(2-methylamino-(S)-2-phenyl-ethyl)-pyrrolidin-(S)-3-ol using general coupling method B gave a mixture of diastereomers (400 mg) which was separated by preparative HPLC to provide the two pure diastereomers 89d$_1$* and 89d$_2$* in a quantity of 196 mg and 156 mg respectively. Their absolute stereochemistry at the 2-position was not established.

Compound 89d$_1$*: 1-Methyl-2,3-dihydro-1H-indole-2-carboxylic acid {2-[(S)-3-hydroxy-pyrrolidin-1-yl]-(S)-1-phenyl-ethyl}-methyl-amide $^1$H NMR (400 MHz, CDCl$_3$) δ: 7.47–7.26(m, 5H), 7.09 (t, 1H), 7.01 (d, 1H), 6.65 (t, 1H), 6.49 (d, 1H), 6.16, 5.19 (dd, 1H), 4.52, 4.35 (t, 1H), 4.29 (brs, 1H), 3.39 (dd, 1H), 3.29–2.86 (m, 3H), 2.86 (s, 3H), 2.79–2.62 (m, 6H), 2.47, 2.27 (m, 1H), 2.13 (m, 1H), 1.9–1.6 (m, 2H); MS: [M+1]$^+$: 380.

Compound 89d$_2$*: 1-Methyl-2,3-dihydro-1H-indole-2-carboxylic acid {2-[(S)-3-hydroxy-pyrrolidin-1-yl]-(S)-1-phenyl-ethyl}-methyl-amide $^1$H NMR (400 MHz, CDCl$_3$) δ: 7.45–7.22 (m, 5H), 7.09 (t, 1H), 7.01 (d, 1H), 6.66 (t, 1H), 6.48 (d, 1H), 6.17, 5.14 (dd, 1H), 5.28, 4.44–4.23, 4.02, (m, 2H), 3.57, 3.39–2.57 (m, 13H), 2.53–2.11 (m, 2H), 2.02–1.65 (m, 2H); MS: [M+1]$^+$: 380.

Examples 90c$_1$* and 90c$_2$*

Preparation of 1-Acetyl-2,3-dihydro-1H-indole-2-carboxylic acid {2-[(S)-3-hydroxy-pyrrolidin-1-yl]-(S)-1-phenyl-ethyl}-methyl-amide a) (R,S)-1-Acetyl-2,3-dihydro-1H-indole-2-carboxylic acid methyl ester (90a, R=CH$_3$C(=O))

The mixture from Example 89a (0.66 g, 3.72 mmol), potassium carbonate (1.54 g, 11.16 mmol) in acetonitrile (20 mL) at 0° C. was added dropwise acetyl chloride (0.4 mL, 5.59 mmol). After 30 minutes at 0° C., the mixture was warmed to room temperature and stirred overnight. The reaction mixture were filtered; the filtrate was diluted with water (100 mL) and extracted with dichloromethane (4×50 mL). The combined extracts were washed with brine (100 mL), dried (Na$_2$SO$_4$) and concentrated under reduced pressure to afford the title compound (0.75 g, 92%). $^1$H-NMR (400 MHz, CDCl$_3$) δ: 8.22 (d, 0.5H), 7.27–7.12 (m, 2.5H), 7.03 (t, 1H), 5.18, 4.92 (dd, 1H), 3.77, 3.74 (s, 3H), 3.63, 3.47 (m, 1H), 3.26, 3.12 (m, 1H), 2.49, 2.17 (s, 3H).

b) (R,S)-1-Acetyl-2,3-dihydro-1H-indole-2-carboxylic acid (90b, R=CH$_3$C(=O))

To a stirred solution of the mixture from Example 90a (0.70 g, 3.19 mmol) in a mixed solvent of methanol (20 mL), tetrahydrofuran (20 mL) and water (20 mL) was added lithium hydroxide monohydrate (0.536 g, 12.77 mmol) and the mixture was stirred overnight at room temperature. The organic solvents were removed under reduced pressure and the aqueous solution was acidified with 6N hydrochloric acid until about pH 1. The resulting solids was collected by filtration, washed with water, and dried in vacuo to afford the title compound (0.41 g, 63%). $^1$H-NMR (400 MHz, DMSO-$d_6$) δ: 13.34 (brs, 1H), 8.04 (d, 0.8H), 7.33–7.13 (m, 2.2H), 7.0 (t, 1H), 5.15, 4.93 (dd, 1H), 3.64–3.44 (m, 1H), 3.17, 2.97 (m, 1H), 2.39, 2.07 (s, 3H).

c) 1-Acetyl-2,3-dihydro-1H-indole-2-carboxylic acid {2-[(S)-3-hydroxy-pyrrolidin-1-yl]-(S)-1-phenyl-ethyl}-methyl-amide Coupling of the compound from Example 90b (R=CH$_3$C(=O)) with 1-(2-methylamino-(S)-2-phenyl-ethyl)-pyrrolidin-(S)-3-ol using general coupling method B gave a mixture of diastereomers (400 mg) which was separated by preparative HPLC to give the two pure diastereomers 90c$_1$* and 90c$_2$* in a quantity of 180 mg and 72 mg respectively. Their absolute stereochemistry at 2-position was not established.

Compound 90c$_1$*: 1-Acetyl-2,3-dihydro-1H-indole-2-carboxylic acid {2-[(S)-3-hydroxy-pyrrolidin-1-yl]-(S)-1-phenyl-ethyl}-methyl-amide $^1$H-NMR (400 MHz, CDCl$_3$) δ: 8.32, 7.46–6.95 (m, 9H), 6.04, 5.34 (dd, 1H), 5.75, 5.47, 5.15 (dd, 1H), 4.36, 4.26 (brs, 1H), 3.68, 3.49 (m, 1H), 3.33–2.05 (m, 14H), 1.91–1.55 (m, 2H); MS: [M+1]$^+$: 408.

Compound 90c$_2$*: 1-Acetyl-2,3-dihydro-1H-indole-2-carboxylic acid {2-[(S)-3-hydroxy-pyrrolidin-1-yl]-(S)-1-phenyl-ethyl}-methyl-amide $^1$H NMR (400 MHz, CDCl$_3$) δ: 8.3, 7.46–6.92 (m, 9H), 6.24 (m, 1H), 5.36–5.18 (m, 1H), 4.65 (brs, 1H), 4.26–2.05 (m, 17H); MS: [M+1]$^+$: 408.

Examples 91c$_1$* and 91c$_2$*

Preparation of 1-Methanesulfonyl-2,3-dihydro-1H-indole-2-carboxylic acid {2-[(S)-3-hydroxy-pyrrolidin-1-yl]-(S)-1-phenyl-ethyl}-methyl-amide a) (R,S)-1-Methanesulfonyl-2,3-dihydro-1H-indole-2-carboxylic acid methyl ester (90a, R=methanesulfonyl)

To a stirred solution of compound 89a (0.57 g, 3.2 mmol), and triethylamine (0.9 mL, 6.4 mmol) in dichloromethane (30 mL) at 0° C. was added methanesulfonyl chloride (0.27 mL, 3.52 mmol) dropwise. The mixture was warmed to and stirred at room temperature overnight. Water (60 mL) was added and the two layers were separated. The aqueous phase was extracted with dichloromethane (3×30 mL) and the combined organic extracts were washed with acidic brine (pH 1), dried (Na$_2$SO$_4$) and concentrated under to give the crude title product (0.79 g). This crude product was directly used for the next step without further purification.

b) (R,S)-1- Methanesulfonyl-2,3-dihydro-1H-indole-2-carboxylic acid (90b, R=methanesulfonyl)

Basic hydrolysis of compound 91a (0.79 g) with lithium hydroxide monohydrate (0.54 g, 12.8 mmol) gave the title acid (0.62 g, 80% overall yield). $^1$H-NMR (400 MHz, DMSO-d$_6$) δ: 13.07 (brs, 1H), 7.33–7.19 (m, 3H), 7.05 (m, 1H), 4.95 (dd, 1H), 3.65 (m, 1H), 3.17–3.06 (m, 4H).

c) 1-Methanesulfonyl-2,3-dihydro-1H-indole-2-carboxylic acid {2-[(S)-3-hydroxy-pyrrolidin-1-yl]-(S)-1-phenyl-ethyl}-methyl-amide Coupling of compound 91b (0.60 g, 2.5 mmol) with 2-[(S)-3-hydroxy-pyrrolidin-1-yl]-(S)-1-phenyl-ethyl-methyl-amine dihydrochloride (0.88 g, 3.0 mmol) using general coupling method B provided the diastereomeric mixture of the title compound. Preparative HPLC separation of the mixture (150 mg) provided two pure diastereomers 91c$_1$* (25 mg) and 91c$_2$* (28 mg). The absolute stereochemistry at the 2-position was not established.

Compound 91c$_1$*: $^1$H NMR (400 MHz, CDCl$_3$) δ: 7.49–6.99 (m, 9H), 6.28 (m, 1H), 5.29–5.11 (m, 1H), 4.6 (brs, 1H), 4.25–2.69 (m, 15H), 2.45–1.97 (m, 2H); MS: [M+1]$^+$: 444.

Compound 91c$_2$*: $^1$H-NMR (400 MHz, CDCl$_3$) δ: 7.49–6.98 (m, 9H), 6.28 (m, 1H), 5.3 (m, 1H), 4.68 (brs, 1H), 4.47–2.08 (m, 17H); MS: [M+1]$^+$: 444.

Example 92b$_1$* and 92b$_2$*

Preparation of 1,2,3,4-Tetrahydro-quinoline-2-carboxylic acid {2-[(S)-3-hydroxy-pyrrolidin-1-yl]-(S)-1-phenyl-ethyl}-methyl-amide a) (R,S)-1,2,3,4-Tetrahydro-quinoline-2-carboxylic acid (92a)

A suspension of commercially available (R,S)-1,2,3,4-tetrahydro-quinoline-2-carboxylic acid ethyl ester hydrochloride (Aldrich Chemical Company) (0.483 g, 2 mmol) in 10% hydrochloric acid (10 mL) was stirred at reflux for 4 h. Water was removed under reduced pressure and the resulting solids were collected by filtration, washed with ether, and dried in vacuo to afford the crude title compound (0.45 g) as hydrochloride salt, which was used directly in the next step without further purification.

b) 1,2,3,4-Tetrahydro-quinoline-2-carboxylic acid {2-[(S)-3-hydroxy-pyrrolidin-1-yl]-(S)-1-phenyl-ethyl}-methyl-amide (92b$_1$* and 92b$_2$*)

Coupling of compound 92a (0.45 g, 2 mmol) and 2-[(S)-3-hydroxy-pyrrolidin-1-yl]-(S)-1-phenyl-ethyl-methyl-amine dihydrochloride (0.70 g, 2.4 mmol) using general coupling method B gave the product as a mixture of diastereomers, which was purified by flash chromatograraphy over silica gel (methanol/methylene chloride) to yield one diastereomer with >96% purity by LC/MS (92b$_1$*) and 250 mg of the mixture of the diastereomers containing mostly the other isomer. Preparative HPLC separation of the mixture (100 mg) provided 62 mg of the other diastereomer with >98% purity by LC/MS (92b$_2$*).

Compound 92b$_1$*: $^1$H NMR (400 MHz, CDCl$_3$) δ: 7.48–7.25 (m, 5H), 7.0 (m, 2H), 6.68 (m, 2H), 6.11, 5.17 (dd, 1H), 4.52 (brs, 1H), 4.33 (m, 1H), 4.21 (m, 1H), 3.19 (m, 2H), 2.91–2.68 (m, 8H), 2.39–2.24 (m, 3H), 1.83–1.53 (m, 3H); MS: [M+1]$^+$: 380.

Compound 92b$_2$*: $^1$H NMR (400 MHz, CDCl$_3$) δ: 7.39–7.25 (m, 5H), 7.01 (m, 2H), 6.68 (m, 2H), 6.13, 5.23 (dd, 1H), 4.66–4.17 (m, 3H), 3.27 (m, 1H), 3.18 (m, 1H), 2.95–2.62 (m, 8H), 2.35–1.51 (m, 6H); MS: [M+1]$^+$: 380.

TABLE 1

Derivatives of 2,3,4,5-Tetrahydro-benzo[b]oxepine-2-carboxylic acid

| Example | Name | Structure | [M + 1]$^+$ |
|---|---|---|---|
| 1g$_1$* | 7-Chloro-2,3-dihydro-benzo[b]oxepine-2-carboxylic acid [2{(S)-3-hydroxy-pyrrolidin-1-yl}-(S)-1-phenyl-ethyl]-methyl-amide | 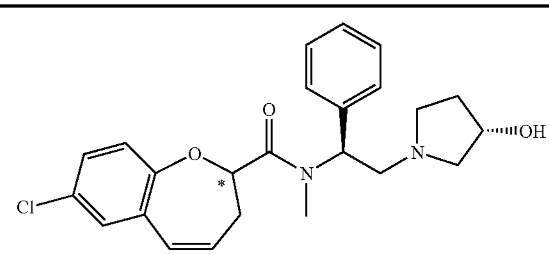 | 427 |

TABLE 1-continued

Derivatives of 2,3,4,5-Tetrahydro-benzo[b]oxepine-2-carboxylic acid

| Example | Name | Structure | [M + 1]+ |
|---|---|---|---|
| 1g$_2$* | 7-Chloro-2,3-dihydro-benzo[b]oxepine-2-carboxylic acid [2-{(S)-3-hydroxy-pyrrolidin-1-yl}-(S)-1-phenyl-ethyl]-methyl-amide | 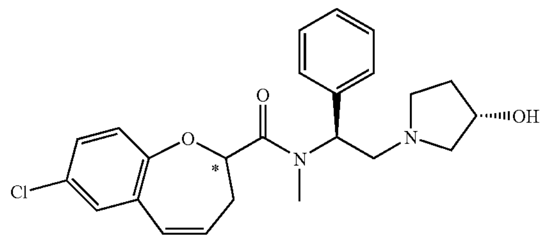 | 427 |
| 2 | (R,S)-7-Chloro-2,3,4,5-tetrahydro-benzo[b]oxepine-2-carboxylic acid [(S)-2-(3-hydroxy-pyrrolidin-1-yl)-(S)-1-phenyl-ethyl]-methyl-amide | 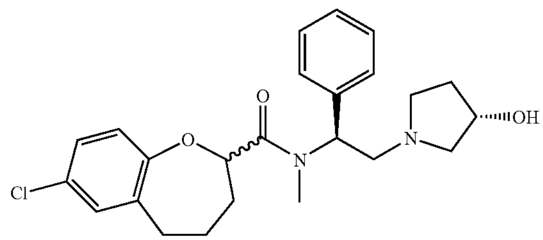 | 429 |
| 3* | 7-Chloro-2,3,4,5-tetrahydro-benzo[b]oxepine-2-carboxylic acid [(S)-2-(3-hydroxy-pyrrolidin-1-yl)-(S)-1-phenyl-ethyl]-methyl-amide | 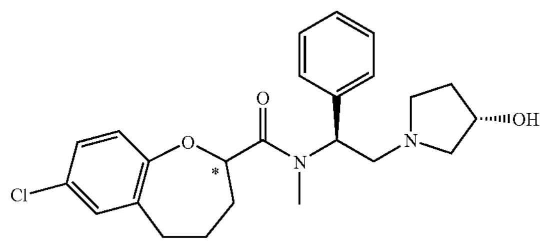 | 429 |

TABLE 2

Derivatives of 6,7,8,9-Tetrahydro-5H-benzocycloheptene-5-carboxylic acid

| Example | Name | Structure | [M + 1]+ |
|---|---|---|---|
| 4h$_1$* | 1,2-Dichloro-6,7,8,9-tetrahydro-5H-benzocycloheptene-5-carboxylic acid {2-[(S)-3-hydroxy-pyrrolidin-1-yl]-(S)-1-phenyl-ethyl}-methyl-amide | 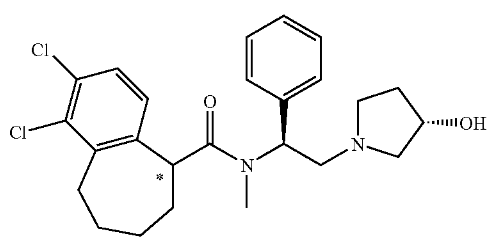 | 461 |
| 4h$_2$* | 1,2-Dichloro-6,7,8,9-tetrahydro-5H-benzocycloheptene-5-carboxylic acid {2-[(S)-3-hydroxy-pyrrolidin-1-yl]-(S)-1-phenyl-ethyl}-methyl-amide | 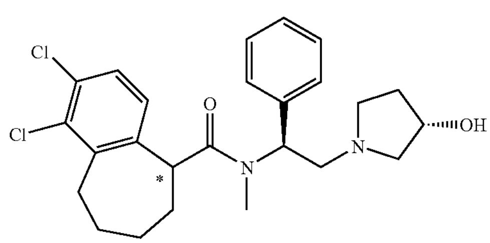 | 461 |

TABLE 3

Derivatives of 1,2,3,4-Tetrahydro-naphthalene-1-carboxylic acid

| Example | Name | Structure | [M + 1]+ |
|---|---|---|---|
| 5e$_1$* | 7-Methoxy-1,2,3,4-tetrahydro-naphthalene-1-carboxylic acid {2-[(S)-3-hydroxy-pyrrolidin-1-yl]-(S)-1-phenyl-ethyl}-methyl-amide | 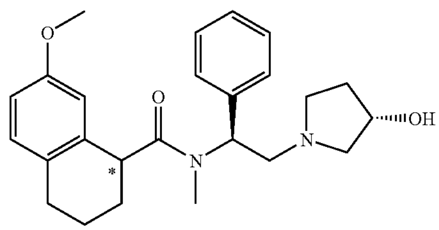 | 409 |
| 5e$_2$* | 7-Methoxy-1,2,3,4-tetrahydro-naphthalene-1-carboxylic acid {2-[(S)-3-hydroxy-pyrrolidin-1-yl]-(S)-1-phenyl-ethyl}-methyl-amide | 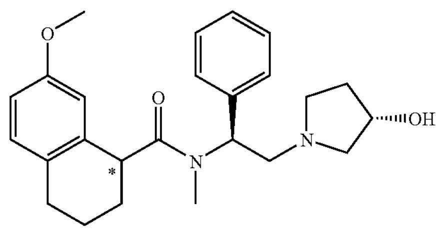 | 409 |
| 6g$_1$* | 5-Methoxy-8-(pyrrolidine-1-sulfonyl)-1,2,3,4-tetrahydro-naphthalene-1-carboxylic acid {2-[(S)-3-hydroxy-pyrrolidin-1-yl]-(S)-1-phenyl-ethyl}-methyl-amide | 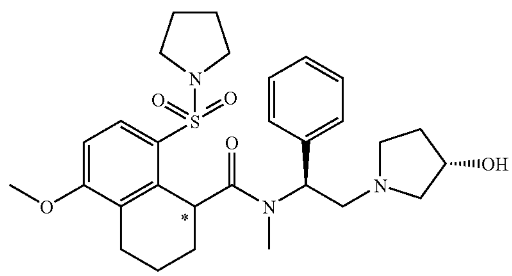 | 542 |
| 6g$_2$* | 5-Methoxy-8-(pyrrolidine-1-sulfonyl)-1,2,3,4-tetrahydro-naphthalene-1-carboxylic acid {2-[(S)-3-hydroxy-pyrrolidin-1-yl]-(S)-1-phenyl-ethyl}-methyl-amide | 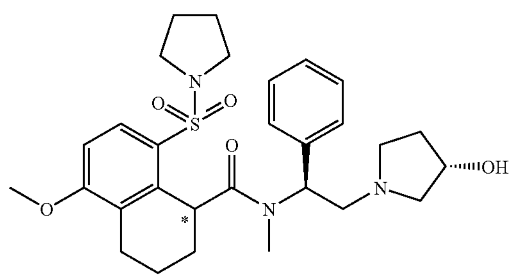 | 542 |
| 7a$_1$* | 8-Dimethylsulfamoyl-5-methoxy-1,2,3,4-tetrahydro-naphthalene-1-carboxylic acid {2-[(S)-3-hydroxy-pyrrolidin-1-yl]-(S)-1-phenyl-ethyl}-methyl-amide | 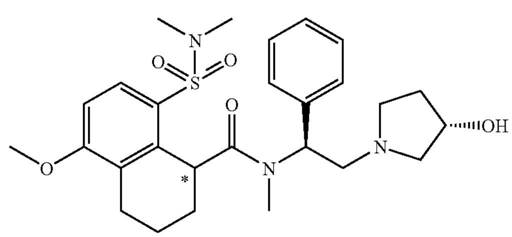 | 516 |
| 7a$_2$* | 8-Dimethylsulfamoyl-5-methoxy-1,2,3,4-tetrahydro-naphthalene-1-carboxylic acid {2-[(S)-3-hydroxy-pyrrolidin-1-yl]-(S)-1-phenyl-ethyl}-methyl-amide | 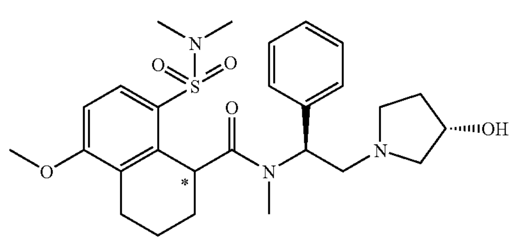 | 516 |

TABLE 4

Derivatives of Chroman-2-carboxylic acid

| Example | Name | Structure | [M + 1]⁺ |
|---|---|---|---|
| 8 | (R,S)-6-Chloro-4-methylene-chroman-2-carboxylic acid {2-[(S)-3-hydroxy-pyrrolidin-1-yl]-(S)-1-phenyl-ethyl}-methyl-amide | 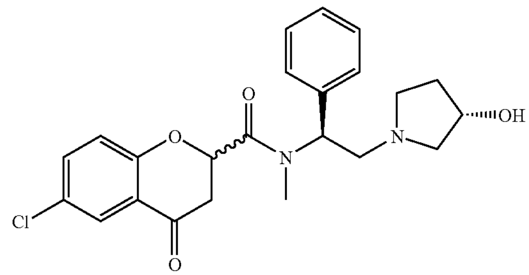 | 427 |
| 9 | (R)-6-Chloro-4-oxo-chroman-2-carboxylic acid {2-[(S)-3-hydroxy-pyrrolidin-1-yl]-(S)-1-phenyl-ethyl}-methyl-amide | 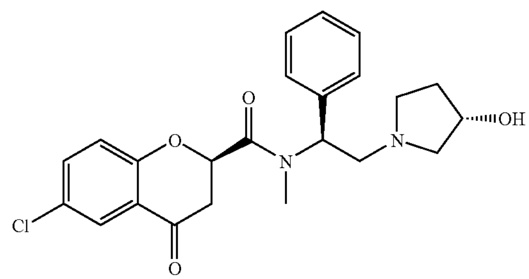 | 429 |
| 10 | (S)-6-Chloro-4-oxo-chroman-2-carboxylic acid {2-[(S)-3-hydroxy-pyrrolidin-1-yl]-(S)-1-phenyl-ethyl}-methyl-amide | 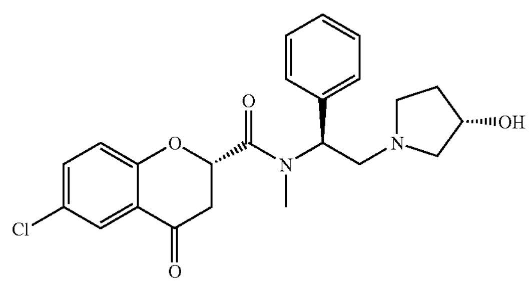 | 429 |
| 11 | (R,S)-6-Chloro-chroman-2-carboxylic acid {2-[(S)-3-hydroxy-pyrrolidin-1-yl]-(S)-1-phenyl-ethyl}-methyl-amide | 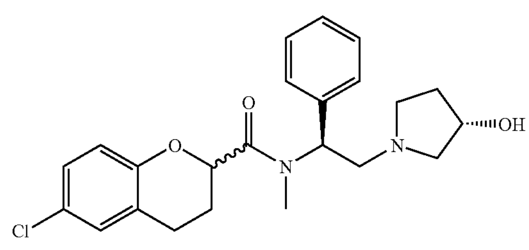 | 415 |
| 12 | (R)-6-Chloro-chroman-2-carboxylic acid {2-[(S)-3-hydroxy-pyrrolidin-1-yl]-(S)-1-phenyl-ethyl}-methyl-amide | 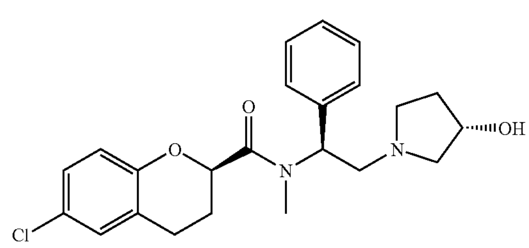 | 415 |

TABLE 4-continued

Derivatives of Chroman-2-carboxylic acid

| Example | Name | Structure | [M + 1]+ |
|---|---|---|---|
| 13 | (S)-6-Chloro-chroman-2-carboxylic acid {2-[(S)-3-hydroxy-pyrrolidin-1-yl]-(S)-1-phenyl-ethyl}-methyl-amide | 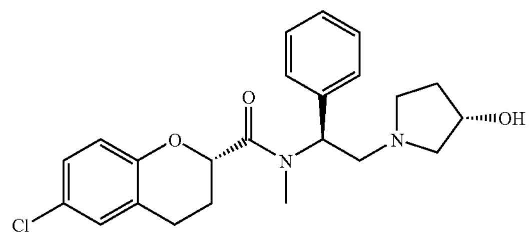 | 415 |
| 14 | (R,S)-Chroman-2-carboxylic acid {2-[(S)-3-hydroxy-pyrrolidin-1-yl]-(S)-1-phenyl-ethyl}-methyl-amide | 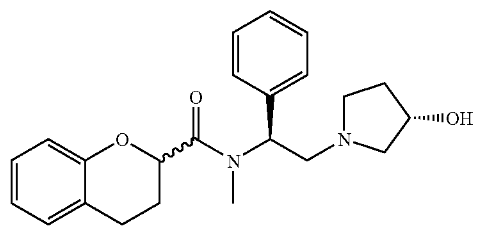 | 382 |
| 15 | (R)-Chroman-2-carboxylic acid {2-[(S)-3-hydroxy-pyrrolidin-1-yl]-(S)-1-phenyl-ethyl}-methyl-amide | 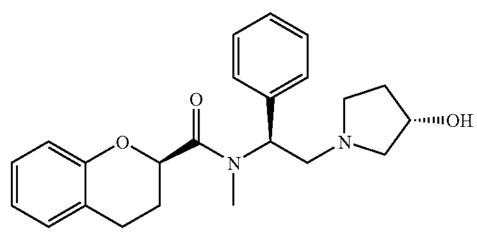 | 381 |
| 16 | (S)-Chroman-2-carboxylic acid {2-[(S)-3-hydroxy-pyrrolidin-1-yl]-(S)-1-phenyl-ethyl}-methyl-amide | 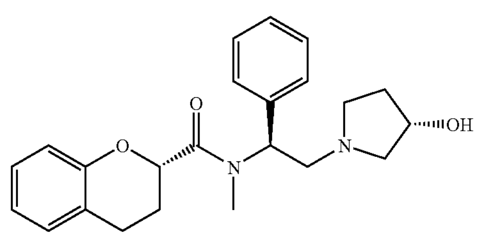 | 381 |
| 17 | (R,S)-6-Iodo-chroman-2-carboxylic acid {2-[(S)-3-hydroxy-pyrrolidin-1-yl]-(S)-1-phenyl-ethyl}-methyl-amide | 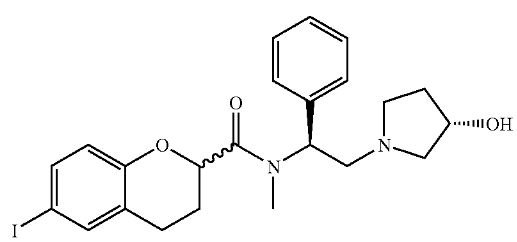 | 507 |
| 18 | (R)-6-Thiophen-2-yl-chroman-2-carboxylic acid {2-[(S)-3-hydroxy-pyrrolidin-1-yl]-(S)-1-phenyl-ethyl}-methyl-amide | 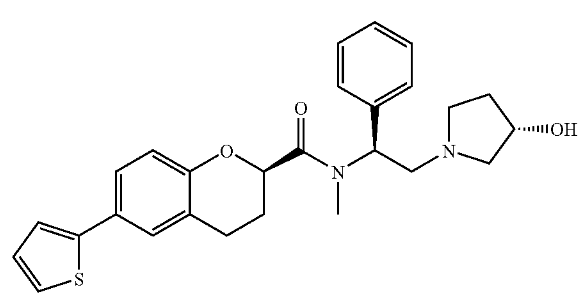 | 463 |

TABLE 4-continued

Derivatives of Chroman-2-carboxylic acid

| Example | Name | Structure | [M + 1]+ |
|---|---|---|---|
| 19 | (S)-6-Thiophen-2-yl-chroman-2-carboxylic acid {2-[(S)-3-hydroxy-pyrrolidin-1-yl]-(S)-1-phenyl-ethyl}-methyl-amide | 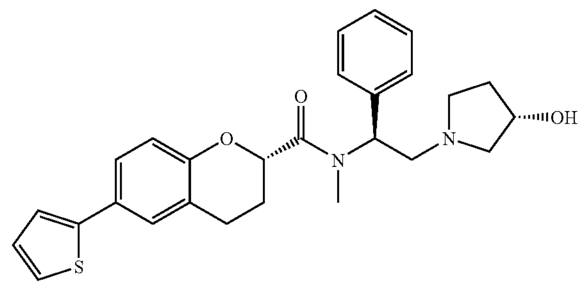 | 463 |
| 20 | (R,S)-6-Nitro-chroman-2-carboxylic acid {2-[(S)-3-hydroxy-pyrrolidin-1-yl]-(S)-1-phenyl-ethyl}-methyl-amide | 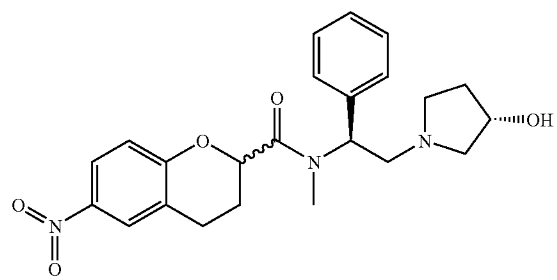 | 426 |
| 21 | (R,S)-6-Amino-chroman-2-carboxylic acid {2-[(S)-3-hydroxy-pyrrolidin-1-yl]-(S)-1-phenyl-ethyl}-methyl-amide | 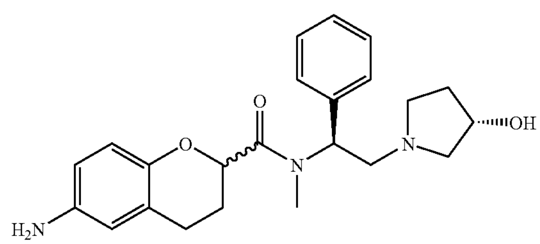 | 396 |
| 23 | (R,S)-6-Acetylamino-chroman-2-carboxylic acid {2-[(S)-3-hydroxy-pyrrolidin-1-yl]-(S)-1-phenyl-ethyl}-methyl-amide | 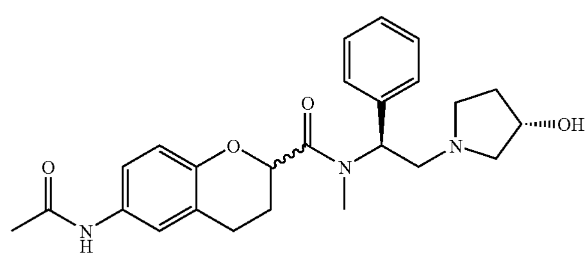 | 438 |
| 22 | (R,S)-6-Methanesulfonylamino-chroman-2-carboxylic acid {2-[(S)-3-hydroxy-pyrrolidin-1-yl]-(S)-1-phenyl-ethyl}-methyl-amide | 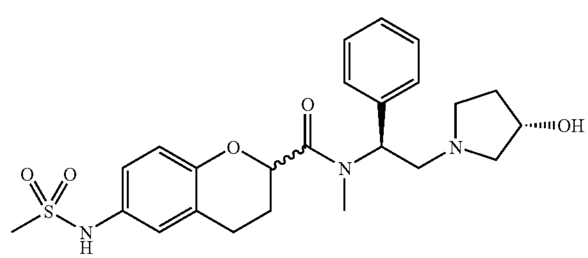 | 474 |

TABLE 4-continued

Derivatives of Chroman-2-carboxylic acid

| Example | Name | Structure | [M + 1]+ |
|---|---|---|---|
| 24 | (R,S)-6-(Cyclopropanecarbonyl-amino)-chroman-2-carboxylic acid {2-[(S)-3-hydroxy-pyrrolidin-1-yl]-(S)-1-phenyl-ethyl}-methyl-amide | 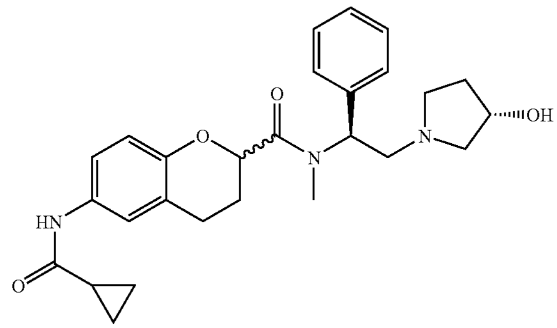 | 464 |
| 25 | (2-{[2-({S}-3-Hydroxy-pyrrolidin-1-yl]-{S}-1-phenyl-ethyl]-(R,S)-methyl-carbamoyl}-chroman-6-yl)-carbamic acid methyl ester | 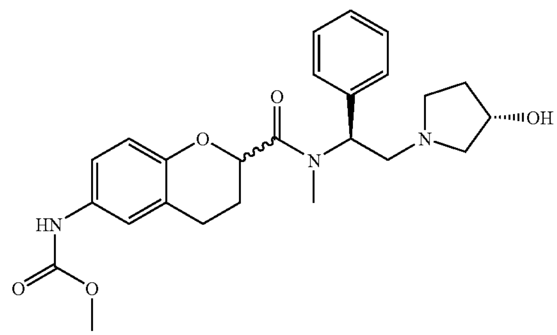 | 454 |
| 26 | (R,S)-6-(Propane-1-sulfonylamino)-chroman-2-carboxylic acid {2-[(S)-3-hydroxy-pyrrolidin-1-yl]-(S)-1-phenyl-ethyl}-methyl-amide | 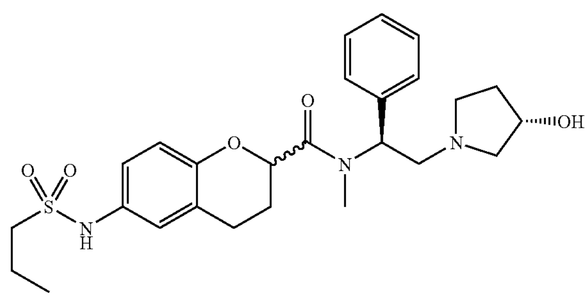 | 502 |
| 27 | (R)-6-(Propane-1-sulfonylamino)-chroman-2-carboxylic acid {2-[(S)-3-hydroxy-pyrrolidin-1-yl]-(S)-1-phenyl-ethyl}-methyl-amide | 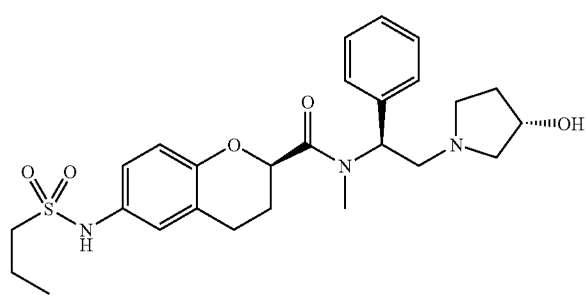 | 502 |

TABLE 4-continued

Derivatives of Chroman-2-carboxylic acid

| Example | Name | Structure | [M + 1]+ |
|---------|------|-----------|----------|
| 28 | (S)-6-(Propane-1-sulfonylamino)-chroman-2-carboxylic acid {2-[(S)-3-hydroxy-pyrrolidin-1-yl]-(S)-1-phenyl-ethyl}-methyl-amide | 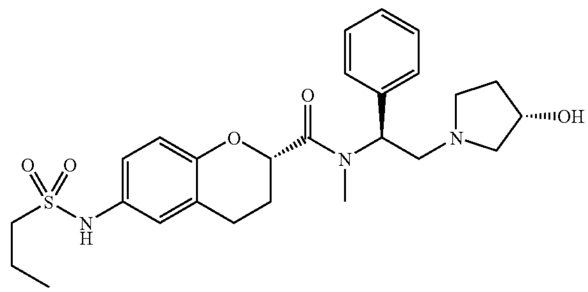 | 502 |
| 29 | (R,S)-6-(Pyrrolidine-1-sulfonyl)-chroman-2-carboxylic acid {2-[(S)-3-hydroxy-pyrrolidin-1-yl]-(S)-1-phenyl-ethyl}-methyl-amide | 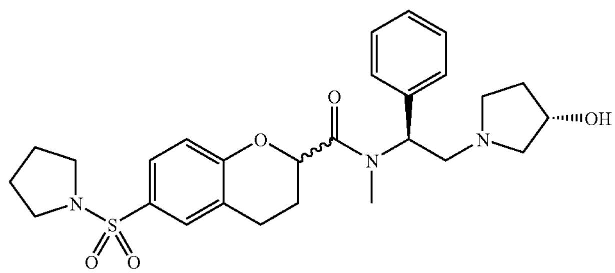 | 514 |
| 30 | (R)-6-(Pyrrolidine-1-sulfonyl)-chroman-2-carboxylic acid {2-[(S)-3-(S)-1-phenyl-ethyl}-methyl-amide | 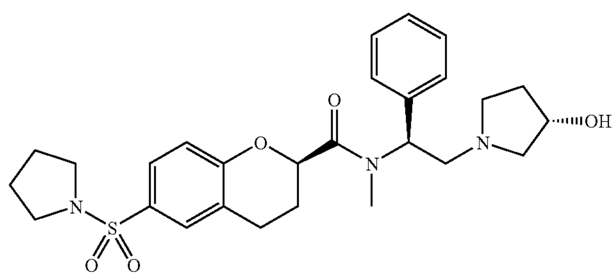 | 514 |
| 31 | (S)-6-(Pyrrolidine-1-sulfonyl)-chroman-2-carboxylic acid {2-[(S)-3-hydroxy-pyrrolidin-1-yl]-(S)-1-phenyl-ethyl}-methyl-amide | 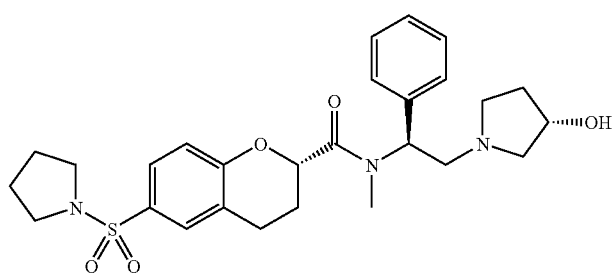 | 514 |
| 32 | (R,S)-6-Diethylsulfamoyl-chroman-2-carboxylic acid {2-[(S)-3-hydroxy-pyrrolidin-1-yl]-(S)-1-phenyl-ethyl}-methyl-amide | 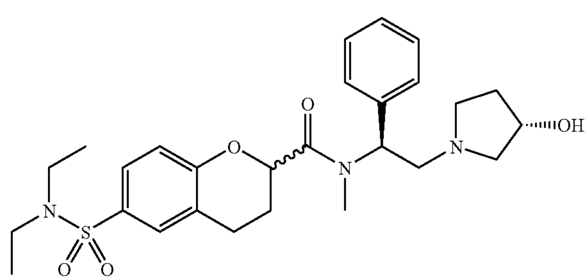 | 516 |

TABLE 4-continued

Derivatives of Chroman-2-carboxylic acid

| Example | Name | Structure | [M + 1]+ |
|---------|------|-----------|----------|
| 33 | (R)-6-Diethylsulfamoyl)-chroman-2-carboxylic acid {2-[(S)-3-hydroxy-pyrrolidin-1-yl]-(S)-1-phenyl-ethyl}-methyl-amide | 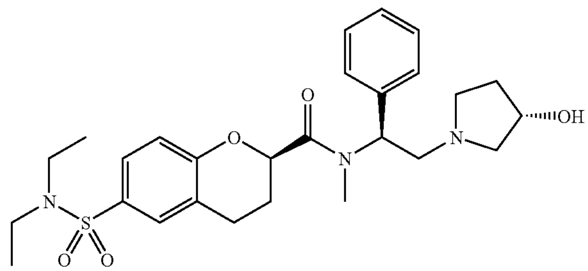 | 516 |
| 34 | (S)-6-Diethylsulfamoyl)-chroman-2-carboxylic acid {2-[(S)-3-hydroxy-pyrrolidin-1-yl]-(S)-1-phenyl-ethyl}-methyl-amide | 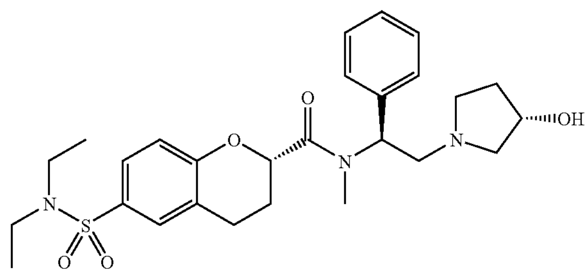 | 516 |
| 35 | (R,S)-6-Ethylsulfamoyl)-chroman-2-carboxylic acid {2-[(S)-3-hydroxy-pyrrolidin-1-yl]-(S)-1-phenyl-ethyl}-methyl-amide | 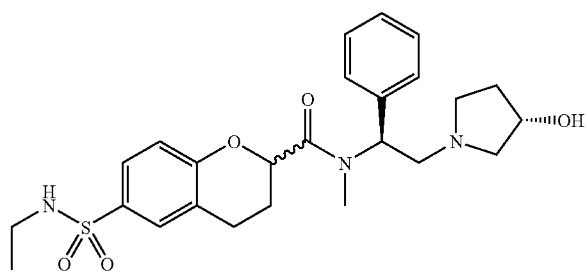 | 488 |
| 36 | (R)-6-Ethylsulfamoyl)-chroman-2-carboxylic acid {2-[(S)-3-hydroxy-pyrrolidin-1-yl]-(S)-1-phenyl-ethyl}-methyl-amide | 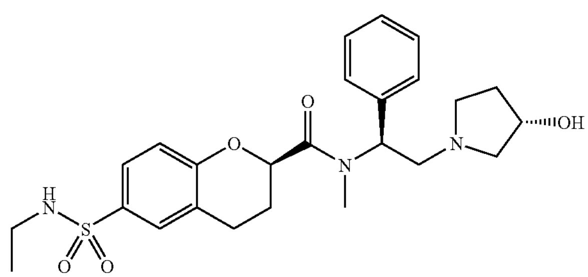 | 488 |
| 37 | (S)-6-Ethylsulfamoyl)-chroman-2-carboxylic acid {2-[(S)-3-hydroxy-pyrrolidin-1-yl]-(S)-1-phenyl-ethyl}-methyl-amide | 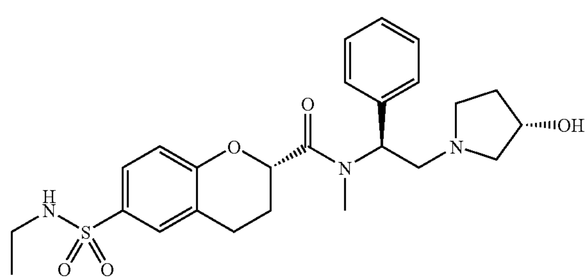 | 488 |

TABLE 4-continued

Derivatives of Chroman-2-carboxylic acid

| Example | Name | Structure | [M + 1]+ |
|---|---|---|---|
| 38 | (R,S)-6-Dimethylsulfamoyl)-chroman-2-carboxylic acid {2-[(S)-3-hydroxy-pyrrolidin-1-yl]-(S)-1-phenyl-ethyl}-methyl-amide | 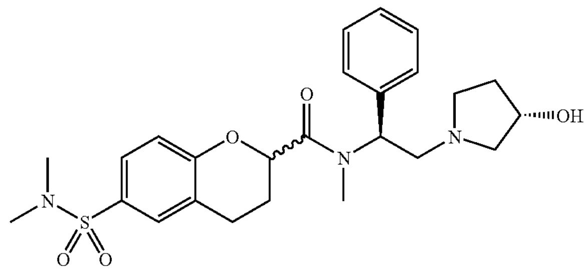 | 488 |
| 39 | (R)-6-Dimethylsulfamoyl)-chroman-2-carboxylic acid {2-[(S)-3-hydroxy-pyrrolidin-1-yl]-(S)-1-phenyl-ethyl}-methyl-amide | 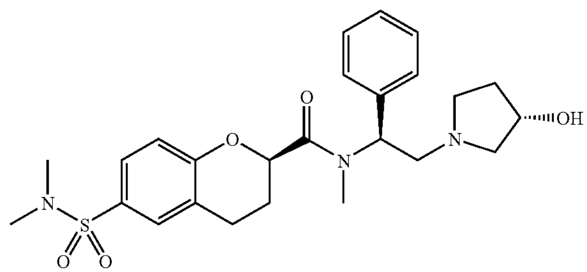 | 488 |
| 40 | (S)-6-Dimethylsulfamoyl)-chroman-2-carboxylic acid {2-[(S)-3-hydroxy-pyrrolidin-1-yl]-(S)-1-phenyl-ethyl}-methyl-amide | 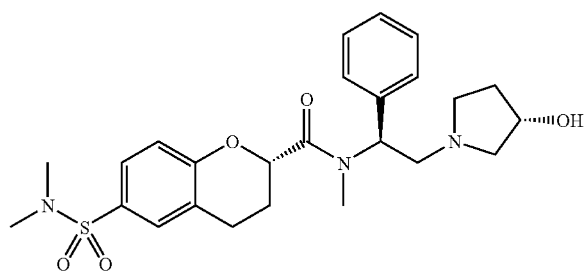 | 488 |
| 41 | (R,S)-6-Methylsulfamoyl)-chroman-2-carboxylic acid {2-[(S)-3-hydroxy-pyrrolidin-1-yl]-(S)-1-phenyl-ethyl}-methyl-amide | 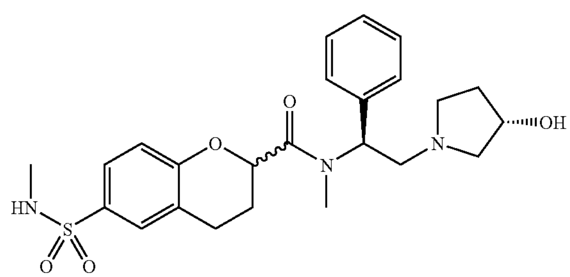 | 474 |
| 42 | (R)-6-Methylsulfamoyl)-chroman-2-carboxylic acid {2-[(S)-3-hydroxy-pyrrolidin-1-yl]-(S)-1-phenyl-ethyl}-methyl-amide | 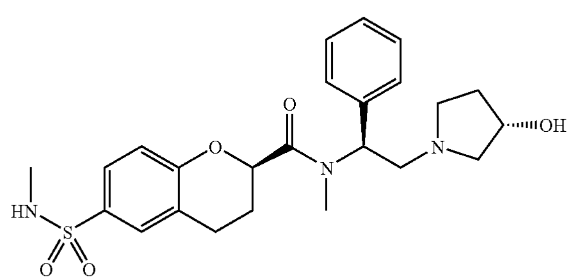 | 474 |

TABLE 4-continued

Derivatives of Chroman-2-carboxylic acid

| Example | Name | Structure | [M + 1]+ |
|---|---|---|---|
| 43 | (S)-6-Methylsulfamoyl)-chroman-2-carboxylic acid {2-[(S)-3-hydroxy-pyrrolidin-1-yl]-(S)-1-phenyl-ethyl}-methyl-amide | 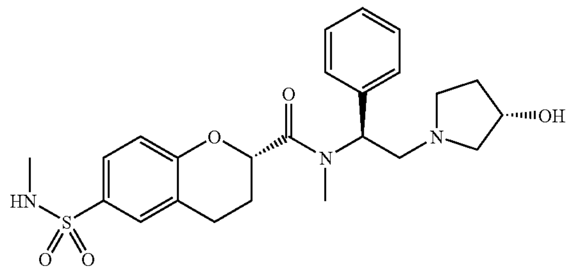 | 474 |
| 44 | (R,S)-6-(Cyclopropylmethyl-sulfamoyl)-chroman-2-carboxylic acid {2-[(S)-3-hydroxy-pyrrolidin-1-yl]-(S)-1-phenyl-ethyl}-methyl-amide | 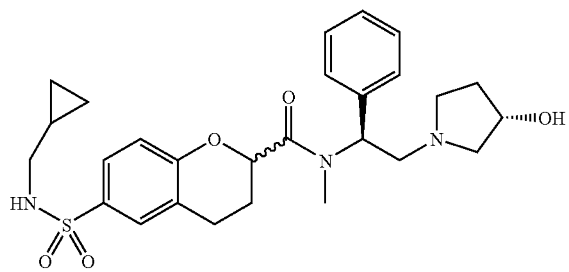 | 514 |
| 45 | (R)-6-(Cyclopropylmethyl-sulfamoyl)-chroman-2-carboxylic acid {2-[(S)-3-hydroxy-pyrrolidin-1-yl]-(S)-1-phenyl-ethyl}-methyl-amide | 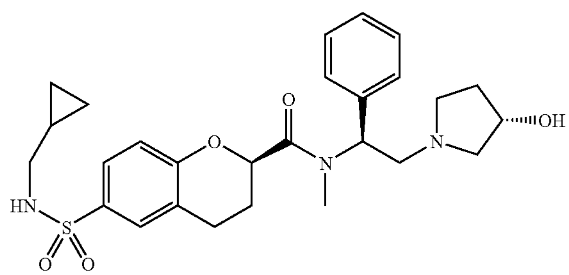 | 514 |
| 46 | (S)-6-(Cyclopropylmethyl-sulfamoyl)-chroman-2-carboxylic acid {2-[(S)-3-hydroxy-pyrrolidin-1-yl]-(S)-1-phenyl-ethyl}-methyl-amide | 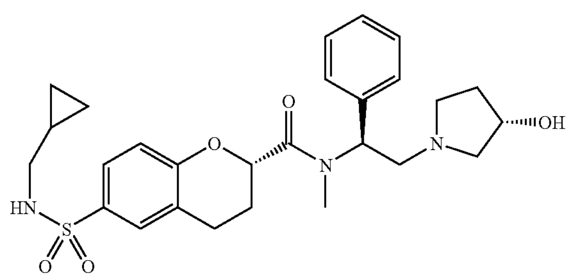 | 514 |
| 47 | (R,S)-6-Sulfamoyl-chroman-2-carboxylic acid {2-[(S)-3-hydroxy-pyrrolidin-1-yl]-(S)-1-phenyl-ethyl}-methyl-amide | 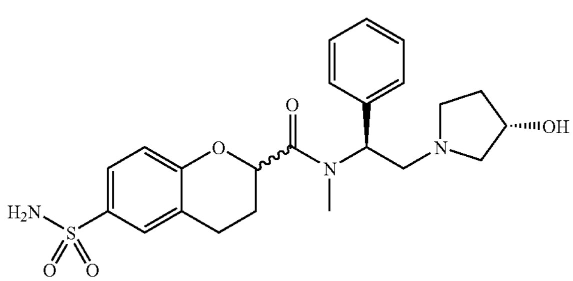 | 460 |

TABLE 4-continued

Derivatives of Chroman-2-carboxylic acid

| Example | Name | Structure | [M + 1]+ |
|---|---|---|---|
| 48 | (R,S)-6-(Methane sulfonylamino-methyl)-chroman-2-carboxylic acid {2-[(S)-3-hydroxy-pyrrolidin-1-yl]-(S)-1-phenyl-ethyl}-methyl-amide | 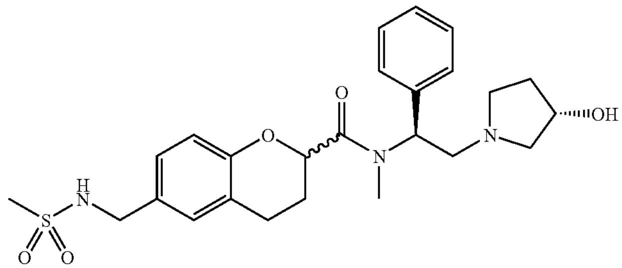 | 488 |
| 49 | (R)-6-(Methane sulfonylamino-methyl)-chroman-2-carboxylic acid {2-[(S)-3-hydroxy-pyrrolidin-1-yl]-(S)-1-phenyl-ethyl}-methyl-amide | 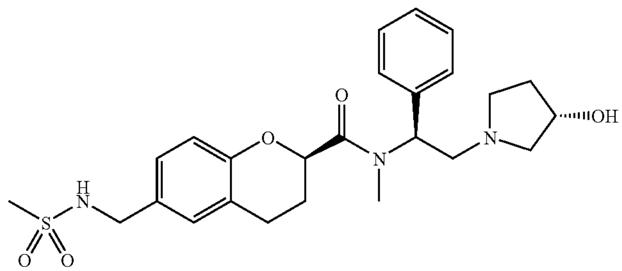 | 488 |
| 50 | (S)-6-(Methane sulfonylamino-methyl)-chroman-2-carboxylic acid {2-[(S)-3-hydroxy-pyrrolidin-1-yl]-(S)-1-phenyl-ethyl}-methyl-amide | 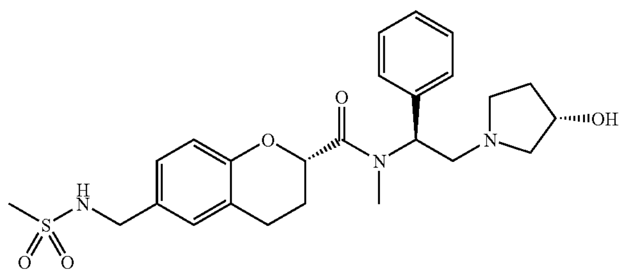 | 488 |
| 51 | (2-{[2-({S}-3-Hydroxy-pyrrolidin-1-yl)-{S}-1-phenyl-ethyl]-(R,S)-methyl-carbamoyl}-chroman-6-ylmethyl)-carbamic acid methyl ester | 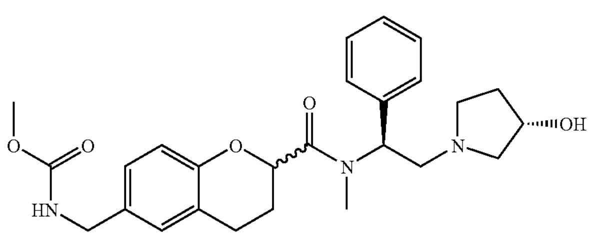 | 468 |
| 52 | (2-{[2-({S}-3-Hydroxy-pyrrolidin-1-yl)-{S}-1-phenyl-ethyl]-(R)-methyl-carbamoyl}-chroman-6-ylmethyl)-carbamic acid methyl ester | 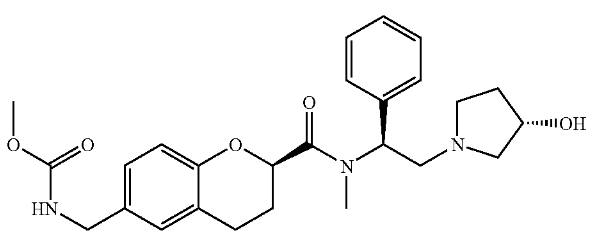 | 468 |

TABLE 4-continued

Derivatives of Chroman-2-carboxylic acid

| Example | Name | Structure | [M + 1]+ |
|---|---|---|---|
| 53 | (2-{[2-({S}-3-Hydroxy-pyrrolidin-1-yl)-{S}-1-phenyl-ethyl]-(S)-methyl-carbamoyl}-chroman-6-ylmethyl)-carbamic acid methyl ester | 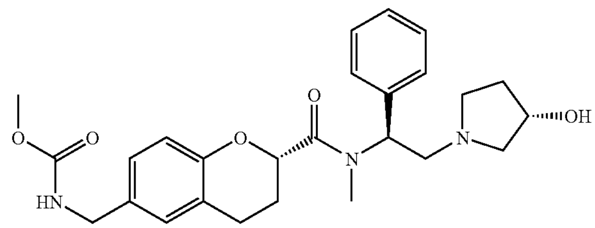 | 468 |

TABLE 5

Derivatives of 2,3-Dihydro-benzofuran-2-carboxyhc acid

| Example | Name | Structure | [M + 1]+ |
|---|---|---|---|
| 54 | (R)-2,3-Dihydro-benzofuran-2-carboxylic acid-{2-[(S)-3-hydroxy-pyrrolidin-1-yl]-(S)-1-phenyl-ethyl}-methyl-amide | 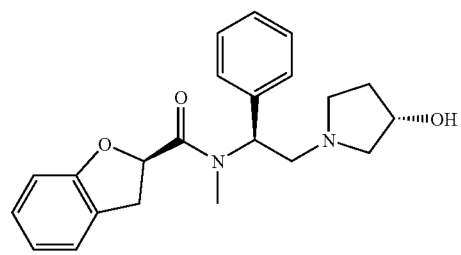 | 367 |
| 55 | (S)-2,3-Dihydro-benzofuran-2-carboxylic acid-{2-[(S)-3-hydroxy-pyrrolidin-1-yl]-(S)-1-phenyl-ethyl}-methyl-amide | 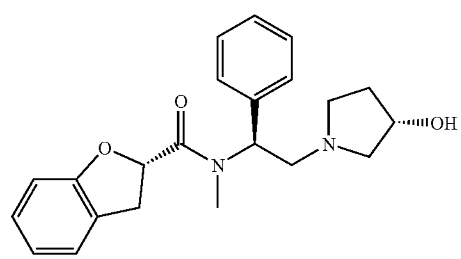 | 367 |
| 56 | (R,S)-5-Methanesulfonylamino-2,3-dihydro-benzofuran-2-carboxylic-acid-{2-[(S)-3-hydroxy-pyrrolidin-1-yl]-(S)-1-phenyl-ethyl}-methyl-amide | 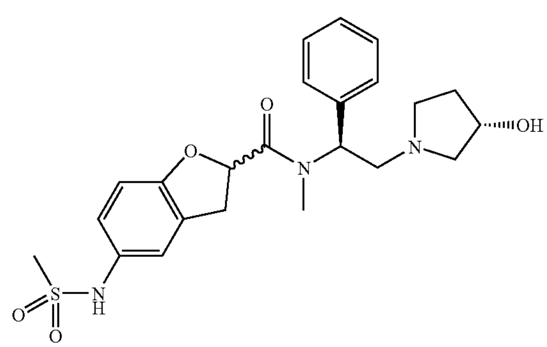 | 460 |

TABLE 5-continued

Derivatives of 2,3-Dihydro-benzofuran-2-carboxylic acid

| Example | Name | Structure | [M + 1]+ |
|---------|------|-----------|----------|
| 57 | (R)-5-Methanesulfonylamino-2,3-dihydro-benzofuran-2-carboxylic-acid-{2-[(S)-3-hydroxy-pyrrolidin-1-yl]-(S)-1-phenyl-ethyl}-methyl-amide | 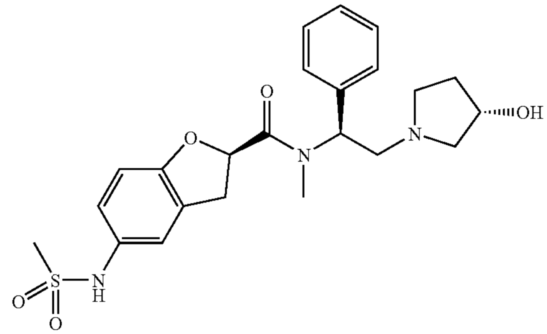 | 460 |
| 58 | (S)-5-Methanesulfonylamino-2,3-dihydro-benzofuran-2-carboxylic-acid-{2-[(S)-3-hydroxy-pyrrolidin-1-yl]-(S)-1-phenyl-ethyl}-methyl-amide | 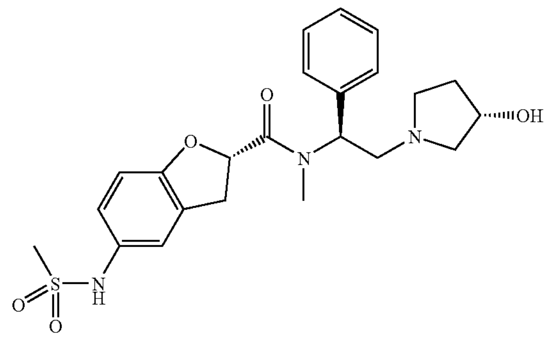 | 460 |
| 59 | (R,S)-5-Acetylamino-2,3-dihydro-benzofuran-2-carboxylic acid-{2-[(S)-3-hydroxy-pyrrolidin-1-yl]-(S)-1-phenyl-ethyl}-methyl-amide | 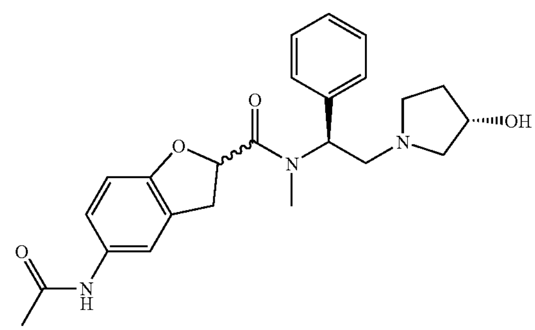 | 424 |
| 60 | (R)-5-(Cyclopropanecarbonyl-amino)-2,3-dihydro-benzofuran-2-carboxylic acid-{2-[(S)-3-hydroxy-pyrrolidin-1-yl]-(S)-1-phenyl-ethyl}-methyl-amide | 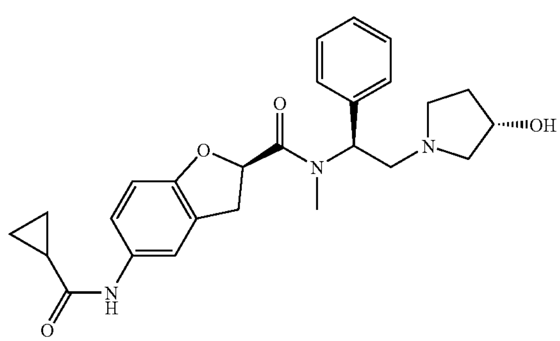 | 450 |

TABLE 5-continued

Derivatives of 2,3-Dihydro-benzofuran-2-carboxylic acid

| Example | Name | Structure | [M + 1]+ |
|---|---|---|---|
| 61 | (S)-5-(Cyclopropanecarbonyl-amino)-2,3-dihydro-benzofuran-2-carboxylic acid-{2-[(S)-3-hydroxy-pyrrolidin-1-yl]-(S)-1-phenyl-ethyl}-methyl-amide | 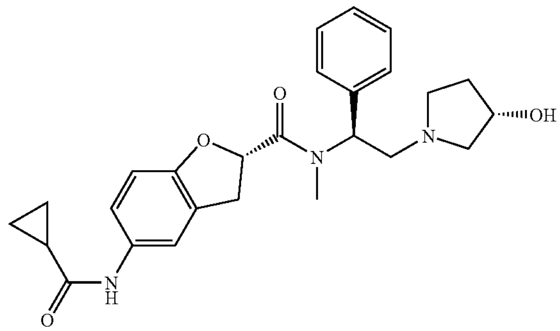 | 450 |
| 62 | (2-{[2-({S}-3-Hydroxy-pyrrolidin-1-yl)-{S}-1-phenyl-ethyl]-(R)-methyl-carbamoyl}-2,3-dihydro-benzofuran-5-yl)-carbamic acid methyl ester | 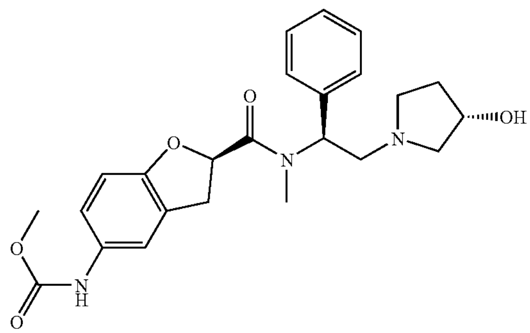 | 440 |
| 63 | (2-{[2-({S}-3-Hydroxy-pyrrolidin-1-yl)-{S}-1-phenyl-ethyl]-(S)-methyl-carbamoyl}-2,3-dihydro-benzofuran-5-yl)-carbamic acid methyl ester | 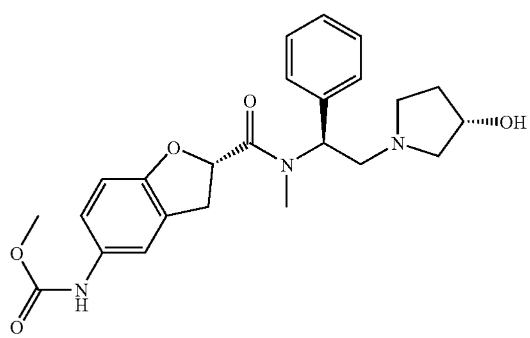 | 440 |
| 64 | (R)-7-Methanesulfonylamino-2,3-dihydro-benzofuran-2-carboxylic acid-{2-[(S)-3-hydroxy-pyrrolidin-1-yl]-(S)-1-phenyl-ethyl}-methyl-amide | 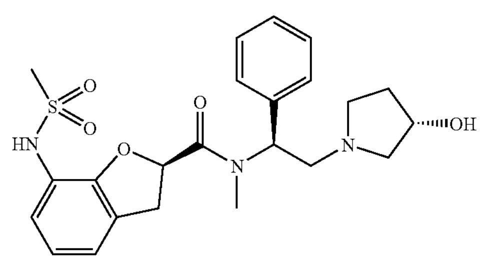 | 460 |
| 65 | (S)-7-Methanesulfonylamino-2,3-dihydro-benzofuran-2-carboxylic acid-{2-[(S)-3-hydroxy-pyrrolidin-1-yl]-(S)-1-phenyl-ethyl}-methyl-amide | 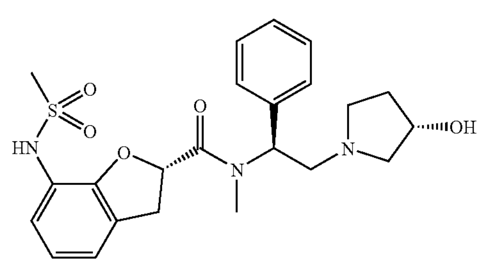 | 460 |

TABLE 5-continued

Derivatives of 2,3-Dihydro-benzofuran-2-carboxylic acid

| Example | Name | Structure | [M + 1]⁺ |
|---|---|---|---|
| 66 | (R)-7-Acetylamino-2,3-dihydro-benzofuran-2-carboxylic-{2-[(S)-3-hydroxy-pyrrolidin-1-yl]-(S)-1-phenyl-ethyl}-methyl-amide | 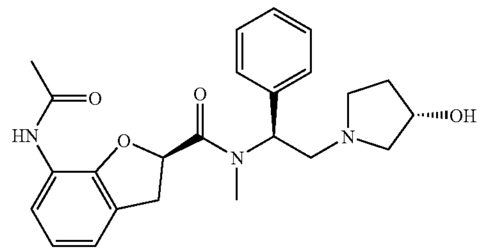 | 424 |
| 67 | (S)-7-Acetylamino-2,3-dihydro-benzofuran-2-carboxylic-{2-[(S)-3-hydroxy-pyrrolidin-1-yl]-(S)-1-phenyl-ethyl}-methyl-amide | 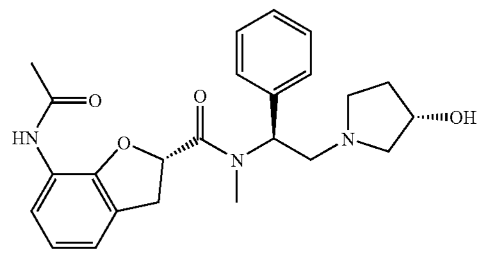 | 424 |
| 68 | (R)-5-(Pyrrolidine-1-sulfonyl)-2,3-dihydro-benzofuran-2-carboxylic acid-{2-[(S)-3-hydroxy-pyrrolidin-1-yl]-(S)-1-phenyl-ethyl}-methyl-amide | 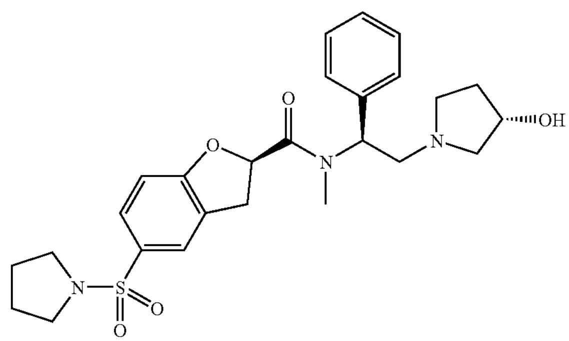 | 500 |
| 69 | (S)-5-(Pyrrolidine-1-sulfonyl)-2,3-dihydro-benzofuran-2-carboxylic acid-{2-[(S)-3-hydroxy-pyrrolidin-1-yl]-(S)-1-phenyl-ethyl}-methyl-amide | 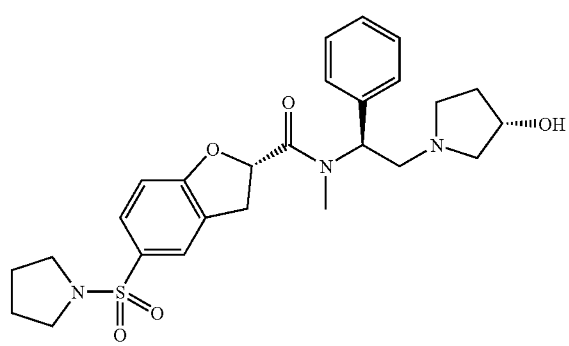 | 500 |
| 70 | (R)-5-Dimethylsulfamoyl-2,3-dihydro-benzofuran-2-carboxylic acid-{2-[(S)-3-hydroxy-pyrrolidin-1-yl]-(S)-1-phenyl-ethyl}-methyl-amide | 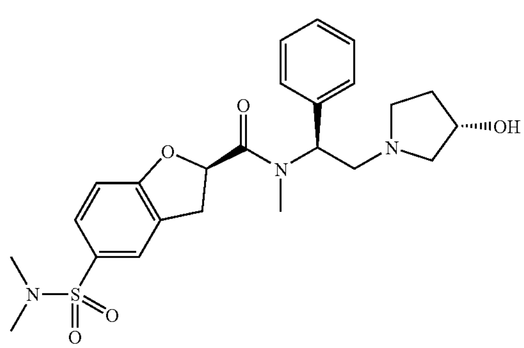 | 474 |

TABLE 5-continued

Derivatives of 2,3-Dihydro-benzofuran-2-carboxylic acid

| Example | Name | Structure | [M + 1]+ |
|---|---|---|---|
| 71 | (S)-5-Dimethylsulfamoyl-2,3-dihydro-benzofuran-2-carboxylic acid-{2-[(S)-3-hydroxy-pyrrolidin-1-yl]-(S)-1-phenyl-ethyl}-methyl-amide | 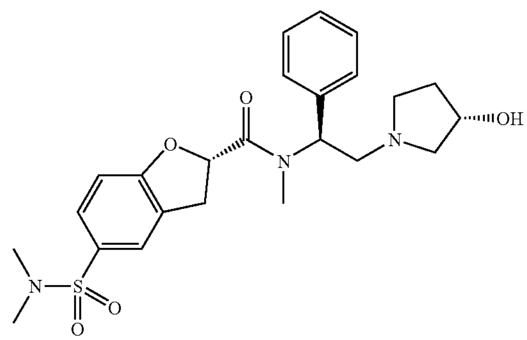 | 474 |
| 72 | (R,S)-5-Methylsulfamoyl-2,3-dihydro-benzofuran-2-carboxylic acid-{2-[(S)-3-hydroxy-pyrrolidin-1-yl]-(S) 1-phenyl-ethyl}-methyl-amide | 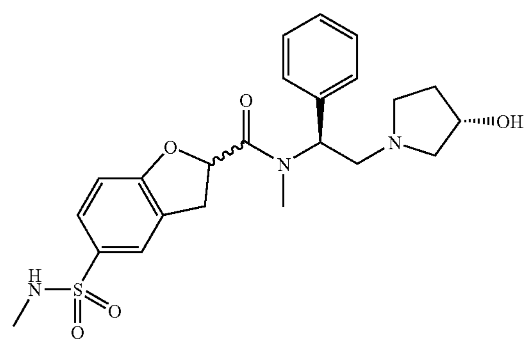 | 560 |
| 73 | (R,S)-5-(Methanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide | 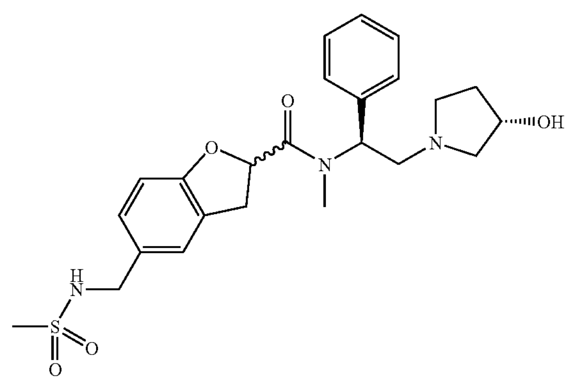 | 474 |
| 74 | (R)-5-(Methanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide | 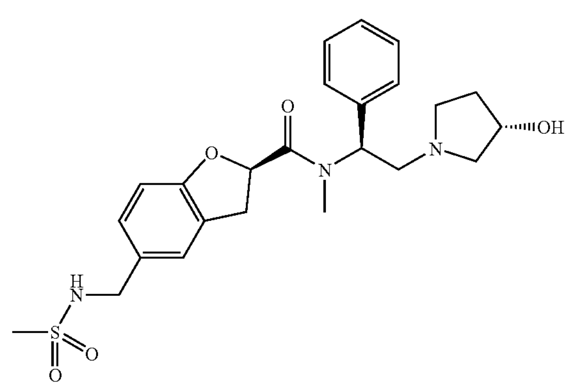 | 474 |

TABLE 5-continued

Derivatives of 2,3-Dihydro-benzofuran-2-carboxylic acid

| Example | Name | Structure | [M + 1]+ |
|---------|------|-----------|----------|
| 75 | (S)-5-(Methanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide | 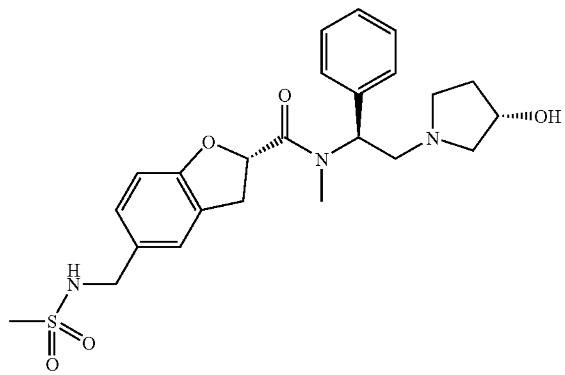 | 474 |
| 76 | (R,S)-5-(Propanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide | 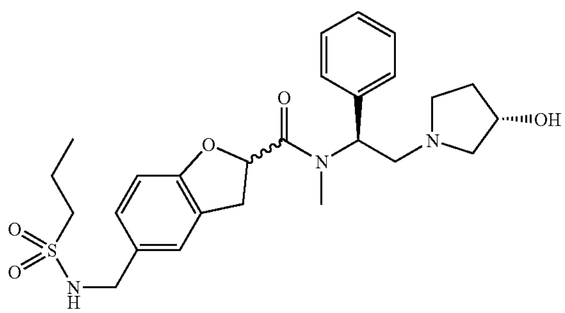 | 502 |
| 77 | (R)-5-(Propanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide | 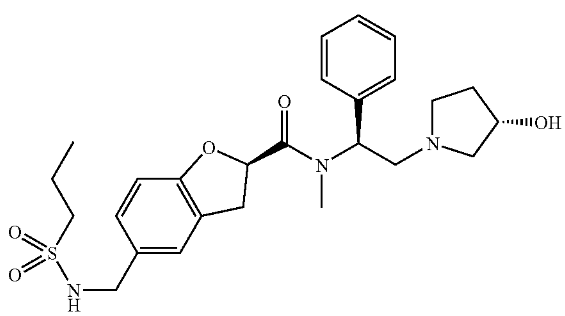 | 502 |
| 78 | (S)-5-(Propanesulfonylamino-methyl)-2,3-dihydro-benzofuran-2-carboxylic acid-{2-[(S)-3-hydroxy-pyrrolidin-1-yl]-(S)-1-phenyl-ethyl}-methyl-amide | 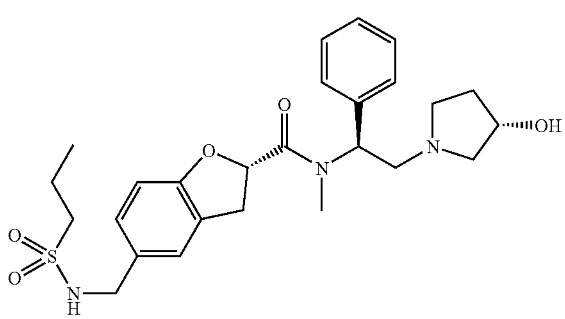 | 502 |

TABLE 5-continued

Derivatives of 2,3-Dihydro-benzofuran-2-carboxylic acid

| Example | Name | Structure | [M + 1]+ |
|---------|------|-----------|----------|
| 79 | (2-{[2-({S}-3-Hydroxy-pyrrolidin-1-yl)-{S}-1-phenyl-ethyl]-methyl-carbamoyl}-(R,S)-2,3-dihydro-benzofuran-5-ylmethyl)-carbamic acid methyl ester | 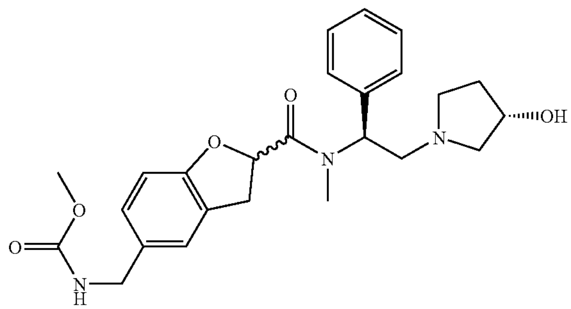 | 454 |

TABLE 6

Derivatives of Chroman-4-carboxylic acid

| Example | Name | Structure | [M + H]+ |
|---------|------|-----------|----------|
| 80e$_1$* | Chroman-4-carboxylic acid-{2-[(S)-3-hydroxy-pyrrolidin-1-yl]-(S)-1-phenyl-ethyl}-methyl-amide | 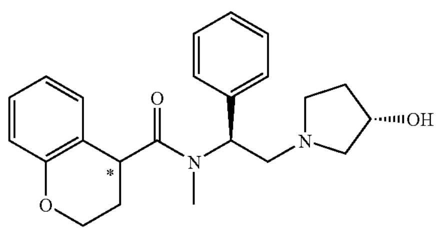 | 382 |
| 80e$_2$* | Chroman-4-carboxylic acid-{2-[(S)-3-hydroxy-pyrrolidin-1-yl]-(S)-1-phenyl-ethyl}-methyl-amide | 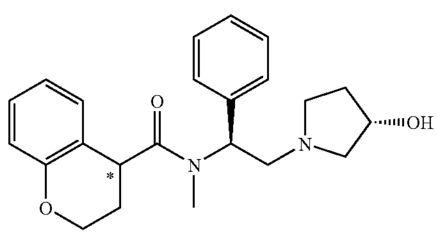 | 382 |
| 81d$_1$* | 6-(Pyrrolidine-1-sulfonyl)-chroman-4-carboxylic acid-{2-[(S)-3-hydroxy-pyrrolidin-1-yl]-(S)-1-phenyl-ethyl}-methyl-amide | 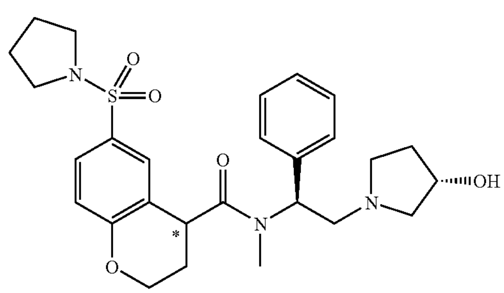 | 514 |
| 81d$_2$* | 6-(Pyrrolidine-1-sulfonyl)-chroman-4-carboxylic acid-{2-[(S)-3-hydroxy-pyrrolidin-1-yl]-(S)-1-phenyl-ethyl}-methyl-amide | 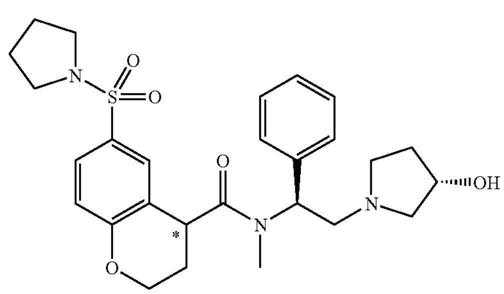 | 514 |

TABLE 6-continued

Derivatives of Chroman-4-carboxylic acid

| Example | Name | Structure | [M + H]+ |
|---|---|---|---|
| 82a* | 6-(Isopropyl-methyl-sulfamoyl)-chroman-4-carboxylic acid-{2-[(S)-3-hydroxy-pyrrolidin-1-yl]-(S)-1-phenyl-ethyl}-methyl-amide | 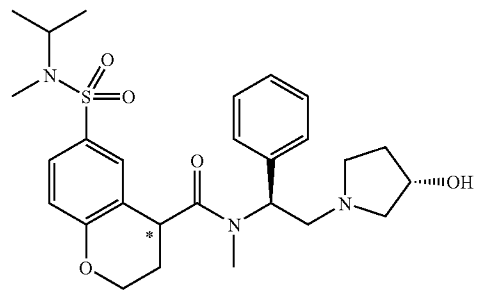 | 516 |
| 82b* | 6-(Isopropyl-methyl-sulfamoyl)-chroman-4-carboxylic acid-{2-[(S)-3-hydroxy-pyrrolidin-1-yl]-(S)-1-phenyl-ethyl}-methyl-amide | 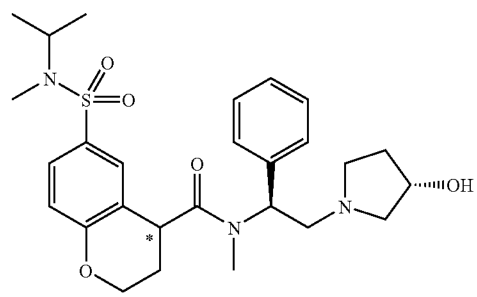 | 516 |
| 83a* | 6-(Morpholine-4-sulfonyl)-chroman-4-carboxylic acid-{2-[(S)-3-hydroxy-pyrrolidin-1-yl]-(S)-1-phenyl-ethyl}-methyl-amide | 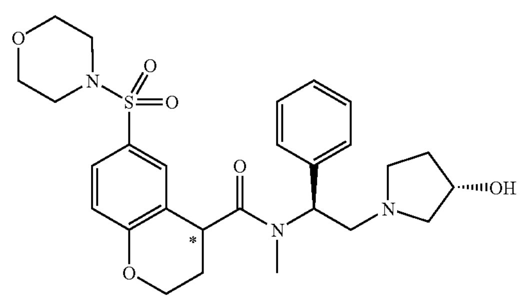 | 530 |
| 83b* | 6-(Morpholine-4-sulfonyl)-chroman-4-carboxylic acid-{2-[(S)-3-hydroxy-pyrrolidin-1-yl]-(S)-1-phenyl-ethyl}-methyl-amide | 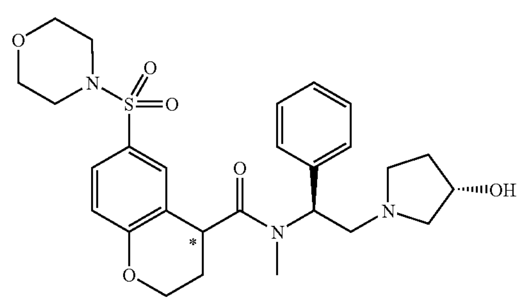 | 530 |
| 84a* | 6-(Methyl-sulfamoyl)-chroman-4-carboxylic acid-{2-[(S)-3-hydroxy-pyrrolidin-1-yl]-(S)-1-phenyl-ethyl}-methyl-amide | 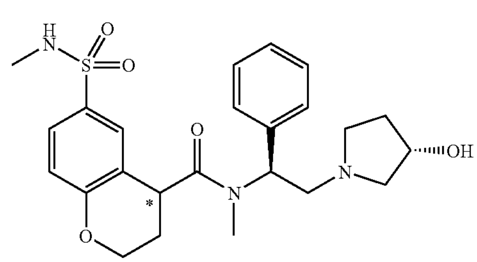 | 474 |

TABLE 6-continued

Derivatives of Chroman-4-carboxylic acid

| Example | Name | Structure | [M + H]+ |
|---------|------|-----------|----------|
| 84b* | 6-(Methyl-sulfamoyl)-chroman-4-carboxylic acid-{2-[(S)-3-hydroxy-pyrrolidin-1-yl]-(S)-1-phenyl-ethyl}-methyl-amide | 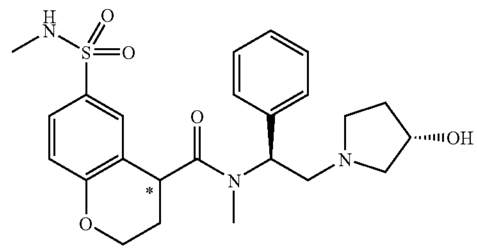 | 474 |
| 85a* | 6-(Dimethyl-sulfamoyl)-chroman-4-carboxylic acid-{2-[(S)-3-hydroxy-phenyl-ethyl}-methyl-amide | 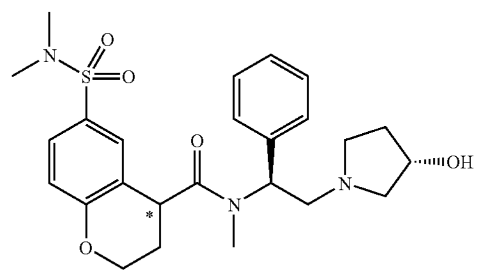 | 488 |
| 85b* | 6-(Dimethyl-sulfamoyl)-chroman-4-carboxylic acid-{2-[(S)-3-hydroxy-phenyl-ethyl}-methyl-amide | 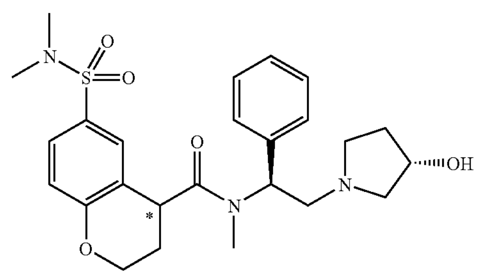 | 488 |
| 86 | (R,S)-6-[(2-Hydroxy-ethyl)-methyl-sulfamoyl]-chroman-4-carboxylic acid-{2-[(S)-3-hydroxy-pyrrolidin-1-yl]-(S)-1-phenyl-ethyl}-methyl-amide | 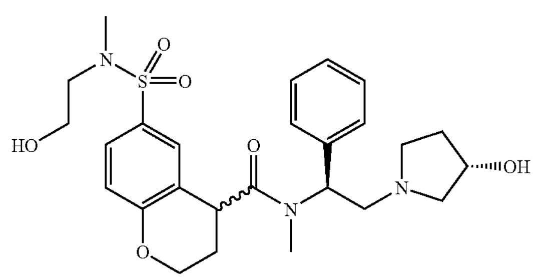 | 518 |
| 87 | (RS)-6-(Methanesulfonylamino-methyl)-chroman-4-carboxylic acid-{2-[(S)-3-hydroxy-pyrrolidin-1-yl]-(S)-1-phenyl-ethyl}-methyl-amide | 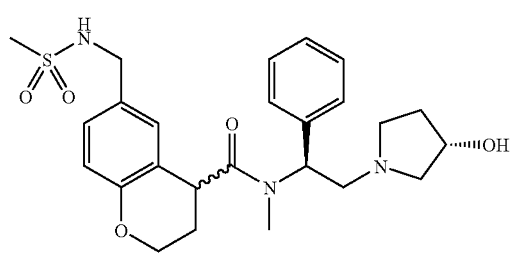 | 488 |

TABLE 6-continued

Derivatives of Chroman-4-carboxylic acid

| Example | Name | Structure | [M + H]+ |
|---|---|---|---|
| 88 | (4-{[2-({S}-3-Hydroxy-pyrrolidin-1-yl)-{S}-1-phenyl-ethyl]-(R,S)-methyl-carbamoyl}-chroman-6-ylmethyl)-carbamic acid methyl ester | 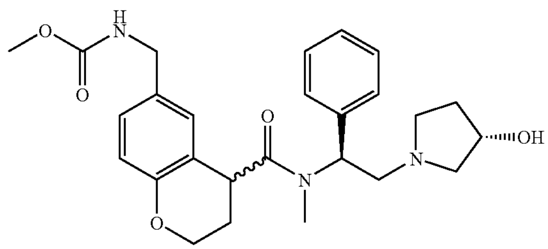 | 468 |

TABLE 7

Derivatives of 2,3-Dihydro-indole-2-carboxylic acid

| Example | Name | Structure | [M + 1]+ |
|---|---|---|---|
| 89d₁* | 1-Methyl-(R)-2,3-dihydro-1H-indole-2-carboxylic acid {2-[(S)-3-hydroxy-pyrrolidin-1-yl]-(S)-1-phenyl-ethyl}-methyl-amide | | 380 |
| 89d₂* | 1-Methyl-(S)-2,3-dihydro-1H-indole-2-carboxylic acid {2-[(S)-3-hydroxy-pyrrolidin-1-yl]-(S)-1-phenyl-ethyl}-methyl-amide | | 380 |
| 90c₁* | 1-Acetyl-(R)-2,3-dihydro-1H-indole-2-carboxylic acid {2-[(S)-3-hydroxy-pyrrolidin-1-yl]-(S)-1-phenyl-ethyl}-methyl-amide | | 408 |
| 90c₂* | 1-Acetyl-(S)-2,3-dihydro-1H-indole-2-carboxylic acid {2-[(S)-3-hydroxy-pyrrolidin-1-yl]-(S)-1-phenyl-ethyl}-methyl-amide | | 408 |

TABLE 7-continued

Derivatives of 2,3-Dihydro-indole-2-carboxylic acid

| Example | Name | Structure | [M + 1]$^+$ |
|---|---|---|---|
| 91c$_1$* | 1-Methanesulfonyl-(R)-2,3-dihydro-1H-indole-2-carboxylic acid {2-[(S)-3-hydroxy-pyrrolidin-1-yl]-(S)-1-phenyl-ethyl}-methyl-amide | 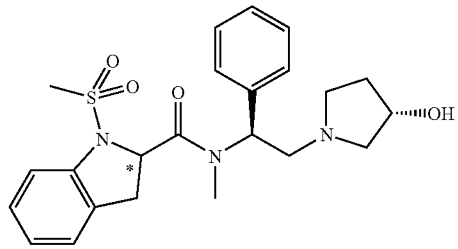 | 444 |
| 91c$_2$* | 1-Methanesulfonyl-(S)-2,3-dihydro-1H-indole-2-carboxylic acid {2-[(S)-3-hydroxy-pyrrolidin-1-yl]-(S)-1-phenyl-ethyl}-methyl-amide | 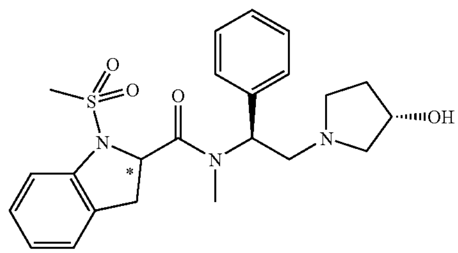 | 444 |

TABLE 8

Derivatives of 1,2,3,4-Tetrahydro-quinoline-2-carboxylic Acid

| Example | Name | Structure | [M + 1]$^+$ |
|---|---|---|---|
| 92b$_1$* | 1,2,3,4-Tetrahydro-quinoline-2-carboxylic acid {2-[(S)-3-hydroxy-pyrrolidin-1-yl]-(S)-1-phenyl-ethyl}-methyl-amide | 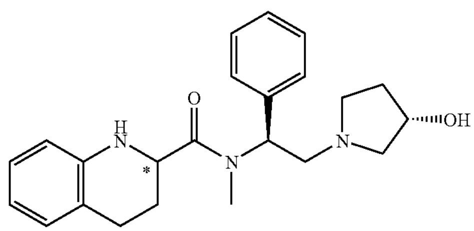 | 380 |
| 92b$_2$* | 1,2,3,4-Tetrahydro-quinoline-2-carboxylic acid {2-[(S)-3-hydroxy-pyrrolidin-1-yl]-(S)-1-phenyl-ethyl}-methyl-amide | 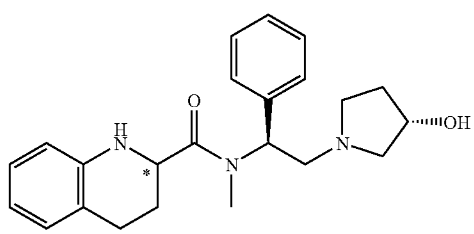 | 380 |

BIOLOGICAL ASSAYS

Assessment of Analgesic Activity

The pharmacological activity of the compounds of the present invention may be assessed by several art-recognized in vitro and in vivo models. Some of the typical models are described herein.

(a) In vitro Binding Assay (Primary Screen)

The potencies of the compounds of the invention were determined by testing the ability of a range of concentrations of each compound to inhibit the binding of the non-selective opioid antagonist, [$^3$H]diprenorphine, to the cloned human μ, κ, and δ opioid receptors, expressed in separate cell lines.

IC$_{50}$ values were obtained by nonlinear analysis of the data using GraphPad Prism version 3.00 for Windows (GraphPad Software, San Diego). K$_i$ values were obtained by Cheng-Prusoff corrections of IC$_{50}$ values.

The receptor binding method was a modification of the method of K. Raynor et al. (Mol. Pharmacol. 1994, 45, 330–334). After dilution in buffer A and homogenization as before, membrane proteins (10–80 μg) in 250 μL were added to mixtures containing test compound and [$^3$H]diprenorphine (0.5 to 1.0 nM, 40,000 to 50,000 dpm) in 250 μL of buffer A in 96-well deep-well polystyrene titer plates (Beckman). After incubation at room temperature for one hour, the samples were filtered through GF/B filters that had been presoaked in a solution of 0.5% (w/v) polyethylenimine and 0.1% (w/v) bovine serum albumin in water. The filters were rinsed 4 times with 1 mL of cold 50 mM Tris HCl, pH 7.8 and radioactivity remaining on the filters determined by scintillation spectroscopy. Nonspecific binding was determined by the minimum values of the titration curves and was confirmed by separate assay wells containing 10 µM naloxone. $K_i$ values were determined by Cheng-Prusoff corrections of $IC_{50}$ values derived from nonlinear regression fits of 12 point titration curves using GraphPad Prism® version 3.00 for Windows (GraphPad Software, San Diego, Calif.).

To determine the equilibrium dissociation constant for the inhibitors ($K_i$), radioligand bound (cpm) in the presence of various concentrations of test compounds was measured. The concentration to give half-maximal inhibition ($EC_{50}$) of radioligand binding was determined from a best nonlinear regression fit to the following equation, $$Y = \text{Bottom} + \frac{(\text{Top} - \text{Bottom})}{1 + 10^{X - LogEC50}}$$

where Y is the amount of radioligand bound at each concentration of test compound, Bottom is the calculated amount of radioligand bound in the presence of an infinite concentration of test compound, Top is the calculated amount of radioligand bound in the absence of test compound, X is the logarithm of the concentration of test compound, and LogEC50 is the log of the concentration of test compound where the amount of radioligand bound is half-way between Top and Bottom. The nonlinear regression fit was performed using the program Prism® (GraphPad Software, San Diego, Calif.). The $K_i$ values were then determined from the $EC_{50}$ values by the following equation, $$K_i = \frac{EC_{50}}{1 + \frac{[\text{ligand}]}{K_d}}$$

where [ligand] is the concentration of radioligand and $K_d$ is the equilibrium dissociation constant for the radioligand.

The potencies of the agonists were assessed by their abilities to stimulate [$^{35}$S]GTPγS binding to membranes containing the cloned human κ receptors.

To determine the $EC_{50}$ value, which was the concentration to give half-maximal stimulation of [$^{35}$S]GTPγS binding, the amount of [$^{35}$S]GTPγS bound in the presence of various concentrations of agonists was measured. The $EC_{50}$ value was then determined.

(b) Inflamed knee joint hyperalgesia model and blood pressure response to compression of the inflamed knee joint Inflammation in a joint is often associated with hyperalgesia (pain during normal flexion and extension and during the application of gentle innocuous pressure) and/or persistent pain (resting pain; Schaible et al., Pain 55: 5–54, 1993). During the course of knee joint inflammation, a cascade of events occurs, which includes: (i) synthesis and release of inflammatory mediators in the joint, (ii) release of neuropeptides from afferent fibers in the joint cavity, and (iii) increased primary afferent outflow from group II, III, IV sensory fibers (Schaible et al., Pain 55: 5–54, 1993). An important result of this cascade is that there is an augmentation in the response of small, lightly myelinated and unmyelinated afferents to low intensity stimuli. In this manner, the peripheral nerve innervating inflamed tissue can evoke an exaggerated behavioral response to otherwise innocuous stimuli, i.e., a state of hyperalgesia. Thus, inflammation of the knee joint will result in increased spontaneous afferent activity, the appearance of an exaggerated discharge with joint flexion and extension (Schaible et al, J. Neurophysiol. 54: 1109–1122, 1993) and signs of a pain-associated autonomic reaction (Sata et al., Neurosci. Lett. 52: 55–60, 1984).

Injection of a mixture of kaolin and carrageenan into the knee joint induces an experimental arthritis. As exemplified below, this treatment was characterized by a reliable increase in joint volume and circumference. In the unanesthetized rat, these joint changes were accompanied by a tendency to avoid weight bearing, suggesting an ongoing pain state. According to electrophysiological studies, in the course of the development of this acute arthritis, C and Aδ units normally responding only to extreme joint distortion become activated by slight movement (Schaible et al., J. Neurophysiol. 54: 1109–1122, 1985). Spinal neurons with knee joint receptive fields in the deep dorsal horn of the spinal cord show clear development of hyperexcitability with the acute inflammation in the joint (Neugebauer et al., J. Neurosci. 70: 1365–1377, 1993). This sensitization of group III and IV fibers was observed within 2–3 hours after injection of kaolin and carrageenan into the knee joint, a time course that closely matches the time course of the development of hyperalgesia in the rat knee joint compression model. These observations indicate that spinal cord neurons and joint primary afferent fibers become sensitized and may underlie hyperalgesia observed in this arthritic state. Such afferent input may drive autonomic responses that are typically associated with the processing of input from afferents typically activated by stimuli generated by the local inflammatory state. In addition to the above-mentioned inflamed knee joint mechanism, the blood pressure (BP) changes might also be evoked reflexively by afferent neural activity from receptors located in the skeletal muscle (Williamson et al., J Physiol. 475: 351–357, 1994). This response is dependent on the changes in intramuscular pressure and the quality of muscle mass compressed. This particular mechanical reflex, however, appears to operate independently of the pain response and appears to play a minor role in the exemplified experiments, as inflation of the cuff on the left normal knee joint had no effect upon BP. In any case, it is possible that overflow of the carrageenan from the joint capsule may serve to render surrounding tissue inflamed as well. Sensitization of C and A units was observed in the rat gastrocnemius muscle by infiltration with carrageenan (Handwerker et al., Pain and Inflammation, Proceeding of the VI$^{th}$ World Congress on Pain, Bond et al. eds., Elsevier Science Publishers BV, pp. 59–70, 1991). Based on these considerations, it appears that compression of the inflamed knee joint yields a noxious stimulus and this in turn activates a sympathetic response resulting in an increase in BP.

Local inflammation of the knee results in a state where otherwise innocuous stimuli results in a prominent autonomic response, including increased blood pressure (BP) and heart rate (see, e.g., Sata et al., Neurosci. Lett. 52: 55–60, 1984). Alternatively, neural outflow from the inflamed knee is recorded (see, e.g. Neugebauer et al., J. Neurosci. 70: 1365–1377, 1993).

An in vitro test that measures spontaneous discharge in injured skin by topical application may also be used. (see, e.g., Andreev et al., Neurosci. 58: 793–798, 1994).

(c) In vivo Evaluation of Formalin-Induced Nociception

Administration of formalin into the paw results in a localized inflammation and a pain response that is moderate in intensity and continuous in duration. Unlike many other assays of nociception, the formalin assay measures tonic pain that is a result of tissue injury, and therefore is a model which is more relevant to clinical pain states in humans (see Tjolsen et al., *Pain* 51: 5–17, 1992). In the rat the response to formalin-induced pain consists of spontaneous flinching behavior, characterized by paw lifting and paw shaking, and a rapid vibration of the paw after drawing it under the body. The flinching response can be reliably quantitated and exhibits two peaks of activity which are indicative of acute and tonic pain (Wheeler-Aceto and Cowan, *Psychophannacology* 104: 35–44, 1991). The early or acute phase lasts from 0–5 minutes post-formalin and is followed by a quiescent period lasting approximately 15 minutes. The tonic phase occurs from 20–35 minutes following formalin injection and is the interval where the number of flinching responses is maximal. This model has been characterized in several species (Tjolsen et al., *Pain* 51: 5–17, 1992) and is sensitive to the analgesic effects of opiates administered by a variety of routes, including local administration directly into the paw. In addition, the test is particularly sensitive to the effects of .kappa. agonists (Wheeler-Aceto and Cowan, *Psychopharmacology* 104: 35–44, 1991).

Inflammation is induced by subcutaneous injection of 50 ml of a 5% formalin solution into the dorsal surface of the right hind paw of male Sprague-Dawley rats weighing 70–90 g. Injections of drug are given into the dorsal surface of the paw prior to formalin injection, and flinching behavior is quantitated by counting the number of responses that occur during the tonic phase of pain, lasting from 20–35 min after formalin injection. Results are expressed as the mean percent antagonism of formalin-induced flinching calculated for individual drug-treated, formalin-injected rats using the following formula:

(mean formalin response−mean saline response)−
individual response×100(mean formalin
response−mean saline response)

The mean formalin response is the mean behavioral score of vehicle-treated and formalin-injected rats. The mean saline response is the pooled behavioral score from rats injected with 50 ml of saline into the paw.

(d) Randall-Selitto Test

Numerous variations and exemplifications of this assay are known to those of skill in this art (see, Randall et al., Arch. Int. *Pharmacodyn.* 111: 409–419, 1957; see, also, e.g., U.S. Pat. Nos. 5,434,292, 5,369,131, 5,345,943, 5,242,944 and 5,109,135.

The pain threshold is measured in this method as the amount of pressure in grams required to induce a flight reaction (struggle) when applied to the foot of an experimental animal exhibiting hyperalgesia, typically an inflamed paw, compared to a control, such as the same or equivalent animal in the absence of the inflammation, and/or in the absence of a test compound. Incremental pressure is applied to the paw with a wedge-shaped blunt piston onto the dorsal surface of the hind paw by means of a paw pressure analgesia meter. The pressure required to elicit paw withdrawal, the paw pressure threshold (PPT), is determined.

Stein and coworkers (Stein et al., *Phannacol. Biochem. Behav.* 31:445–451, 1988; Stein et al., *J. Pharmacol. Exp. Ther.* 248: 1269–1275, 1989) have developed a model of peripheral inflammation and hyperalgesia in rats, which supports the role of opiates in mediating peripheral analgesia. In this protocol, modified Freund's adjuvant is used as the inflammatory stimulus, and the paw pressure test is used to assess the response of the rat to a painful pressure stimulus. The model is sensitive to opiate agonists of the μ, δ and κ subtypes, which produce analgesia upon administration (Antonijevic et al., *J. Neurosci.* 15: 165–172, 1995; Stein et al., *Neurosci. Lett.* 84: 225–228, 1988; Stein et al., *J. Pharmacol. Exp. Ther.* 248: 1269–1275, 1989). Histological verification of opiate receptor localization and density have confirmed that peripheral opiate receptors are accessible on primary afferent nerve fibers and are upregulated following inflammation (Hassan et al., *Neuroscience* 55: 185–193, 1993; Przewlocki et al., *Neuroscience* 48: 491–500, 1992).

Experiments are conducted in rats weighing 150–250 g at the time of inoculation. Modified Freund's complete adjuvant (FCA) is used as the inflammatory stimulus. Rats are administered an i.pl. injection of the FCA suspension into the right hind foot. Hyperalgesia and antinociception are evaluated using the paw pressure test. The rat is gently restrained and incremental pressure is applied to the paw with a wedge-shaped blunt piston onto the dorsal surface of the hind paw by means of a paw pressure analgesia meter. The pressure required to elicit paw withdrawal, the paw pressure threshold (PPT), is determined. A cutoff pressure of 250 g is used to avoid undue stress and pain to the animal. Baseline responding is established by determining the average of three consecutive trials separated by 10 seconds. The same procedure is conducted on the contralateral side and the sequence of sides is alternated between animals to control for order effects. Typically injections are not made in the contralateral (noninflamed) paw; however, in selected cases drugs may be administered to the contralateral paw to evaluate the potential for drug effects in the absence of inflammation.

Analgesic activity is determined by expressing the increase in PPT resulting from the effect of the drug as a percentage of basal pre-injection thresholds.

Hyperalgesia can also be produced by inflammatory stimuli such as yeast or carrageenan, endogenous inflammatory mediators such as bradykinin or prostaglandins, or other types of chemical irritants (see Hargreaves and Joris, APS *Journal* 2: 51–59, 1993).

(e) Acetic Acid-Induced Writhing

This test identifies novel agents that exhibit peripheral analgesic activity against visceral or chemical pain (see Barber and Gottschlich, *Med. Res. Rev.* 12: 525–562, 1986; Ramabadran and Bansinath, *Pharm. Res.* 3: 263–270,1986). Injection of acetic acid into the peritoneal cavity is used as the noxious stimulus, and the number of writhing responses that occur in response to acetic acid are counted in order to quantify the response to pain. Compounds which possess analgesic activity reduce the number of writhing responses that occur. Opiate agonists of the μ and κ subtype exhibit analgesic activity in this model (Barber and Gottschlich, *Med. Res. Rev.* 12: 525–562, 1986; Millan, *Trends Pharmacol. Sci.* 11: 70–76, 1990). Novel compounds that demonstrate potency and efficacy in this assay are potential drugs for the treatment of various pathological conditions involving peripheral pain.

The writhing assay is adapted from the procedure originally described by Taber et al. (*J. Pharmacol. Exp. Ther.* 169: 29–38, 1986), using male CF-1 mice weighing 20–25 g. Animals are treated with various doses of drugs prior to the administration of an i.p. injection of 0.6% acetic acid solution. Mice are then placed into observation chambers and the number of writhing responses, as defined by a full hind limb extension and retraction, are recorded.

The mean number of writhing responses is calculated for vehicle-treated control mice, and the percent inhibition (%I) of writhing is calculated for each mouse that is treated with drug using the following formula:

%I=100×(mean control writhing responses−individual test responses)(mean control writhing responses)

(f) Hyperalgesia Induced by Tape stripping

The objective of this assay is to identify novel agents which exhibit peripherally-mediated analgesia in circumstances, such as burns and abrasions, which lead to hyperalgesia. In such injuries, the loss of the stratum corneum is followed by an inflammatory response (erythema) and a painful response to otherwise innocuous stimuli. Removal of the stratum corneum by repeated application and removal of cellophane tape, termed tape stripping, has been shown to be a simplified model of these injuries, which share characteristics of first degree burns (see Flynn, *Percutaneous Absorption*, R. L. Bronaugh and H. I. Maibach, eds., Marcel Dekker Inc., pp. 18–42, 1985). This method of barrier disruption avoids the application of potentially toxic chemicals and permits evaluation of peripheral analgesics following topical administration because tape stripping removes the barrier to effective topical therapy (the stratum corneum) while simultaneously resulting in inflammation and hyperalgesia. Tape stripping has been validated in humans as a model for the testing of topical agents (Pershing et al., *Antimicrob. Agents Chemother.* 38: 90–95, 1994; Roy and Flynn, *Pharm. Res.* 7: 842–847, 1990).

Experiments are conducted in male Sprague-Dawley rats weighing 250–500 g at the time of treatment. After anesthesia of the rat with ketarine-xylamine, a 1–3 cm² patch of rat skin is treated by repeated application and removal of tape. This procedure results in removal of the stratum corneum as determined by a glistening appearance of the skin. The tape stripped skin is evaluated for a visible erythema and for sensitivity to contact by heat or pressure stimuli using a focused beam of light, by testing in the paw pressure apparatus or by touch with von Frey hairs. The diameter of the von Frey hairs will be selected based on a diameter which causes no response in control rats but has a readily detectable response in treated rats.

Typically analgesics will be formulated in a suitable topical medium and applied to the treated skin. Some rats will receive only the topical medium without analgesic to control for an effect of the topical medium alone. The presence of analgesia is determined by the latency to respond to the heat stimulus or by response to touch or pressure.

The compound in Example 52 showed kappa receptor affinity ($K_i$)<10 nM. For example, the compound of Example 52 had a $K_i$=2.6 nM against the human kappa receptor with >100× selectivity versus the human μ ($K_i$>3000 nM) and δ ($K_i$=1600 nM) receptors and was an agonist with an $EC_{50}$=7.1 nM. The compound of Example 52 exhibited a % A=95% at a dose of 300 μg, i.paw in the in vivo formalin-induced nociception assay. This compound also blocked the action of acetic acid-induced writhing with a s.c. $ED_{50}$=0.53 mg/kg, p.o. $ED_{50}$=1 mg/kg.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula I,

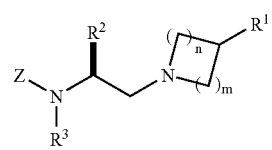

wherein:
$R^1$ is H or OH;
$R^2$ is alkyl, aralkyl, or aryl;
$R^3$ is alkyl or aralkyl;
n and m are each independently the integer 1 or 2;
Z is:

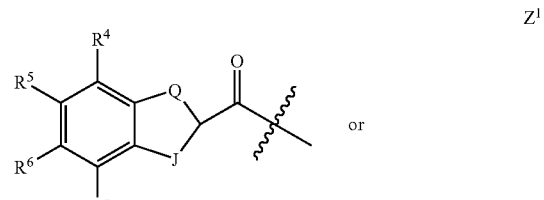

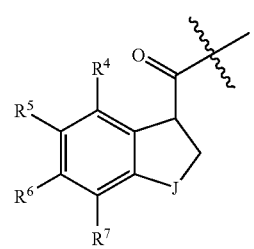

Q is —O—, —CH$_2$—, or —N(R$^8$)—;
J is —(CH$_2$)$_k$—, —O—(CH$_2$)$_{k-1}$—, —(CH═CH—CH$_2$)—, or —C(A)(B)CH$_2$—, provided that when Z is $Z^1$, k is the integer 1, and J is —O—(CH$_2$)$_{k-1}$—, then Q is —CH$_2$—;
k is the integer 1, 2, or 3;
A is H and B is alkyl or H, or when taken together, A and B are ═O or ═CH$_2$;
$R^4$, $R^5$, $R^6$, and $R^7$ are each independently H, alkyl, halo, aryl, heteroaryl, —OH, —OR$^9$, —SO$_2$NR$^{10}$R$^{11}$, —(CH$_2$)$_r$NR$^{12}$R$^{13}$, nitro, —CN, —CF$_3$, —CF$_2$CF$_3$, —OCF$_3$, —SR$^9$, —SO$_2$R$^9$, —(CH$_2$)$_r$C(═O)OR$^9$, —(CH$_2$)$_r$C(═O)NR$^{12}$R$^{12a}$, or —(CH$_2$)$_r$NHC(═O)NR$^{12}$R$^{12a}$, provided that at least two of $R^4$, $R^5$, $R^6$, and $R^7$ are other than —SO$_2$NR$^{10}$R$^{11}$, —(CH$_2$)$_r$NR$^{12}$R$^{13}$, —(CH$_2$)$_r$C(═O)NR$^{12}$R$^{12a}$, or —(CH$_2$)$_r$NHC(═O) NR$^{12}$R$^{12a}$;

$R^8$ is H, alkyl, —C(=O)$R^9$, or —S(=O)$_2R^9$;
$R^9$ is alkyl or aralkyl;
$R^{10}$ and $R^{11}$ are each independently H, alkyl, —(CH$_2$)$_p$—OH, —(CH$_2$)$_p$—O$R^9$, cycloalkyl, cycloalkylalkyl, aryl, or taken together with the nitrogen atom to which they are attached, $R^{10}$ and $R^{11}$ form a 4–7 member heterocycle, optionally interrupted by one or more O, S or N$R^8$ groups;
$R^{12}$ and $R^{12a}$ are each independently H, alkyl, or aryl;
$R^{13}$ is H, alkyl, —C(=O)$R^{14}$, —S(=O)$_2R^{14}$, or —C(=O)O$R^{15}$;
$R^{14}$ is alkyl, cycloalkyl, cycloalkylalkyl, alkylcycloalkyl, heteroaryl, heteroalkyl, heteroaralkyl, aryl, or aralkyl;
$R^{15}$ is alkyl, cycloalkyl, alkylcycloalkyl, or aralkyl;
r is the integer 0, 1, 2, 3, or 4; and
p is the integer 2, 3, 4, 5, or 6;
or a stereoisomer, prodrug, pharmaceutically acceptable salt, hydrate, solvate, acid salt hydrate, N-oxide or isomorphic crystalline form thereof.

2. A compound according to claim 1, wherein at least two of $R^4$, $R^5$, $R^6$, and $R^7$ are H.

3. A compound according to claim 1, wherein when Z is $Z^1$ then Q is —O—.

4. A compound according to claim 1, wherein J is —OCH$_2$—, —C(A)(B)CH$_2$—, or —CH$_2$CH$_2$—.

5. A compound according to claim 4, wherein J is —C(A)(B)CH$_2$—.

6. A compound according to claim 1, of formula II:

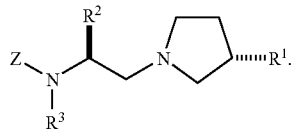

II

7. A compound according to claim 6, wherein $R^1$ is —OH.

8. A compound according to claim 6, wherein $R^2$ is aryl.

9. A compound according to claim 8, wherein $R^2$ is phenyl.

10. A compound according to claim 6, wherein $R^3$ is alkyl.

11. A compound according to claim 10, wherein $R^3$ is methyl.

12. A compound according to claim 6, wherein Z is:

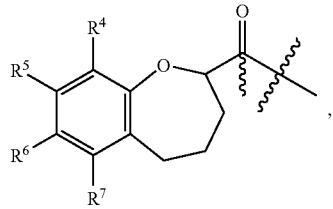

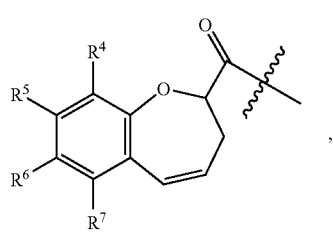

-continued

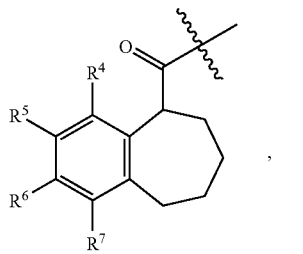

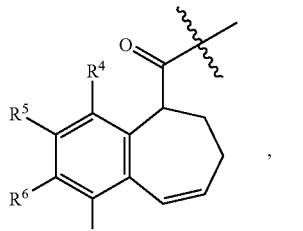

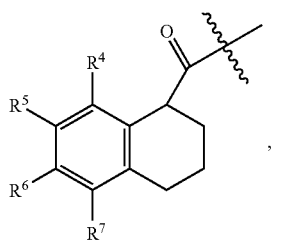

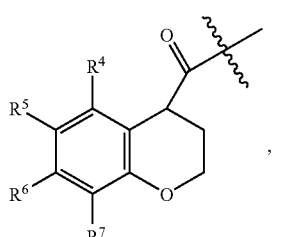

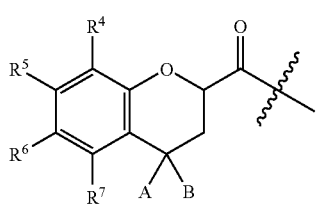

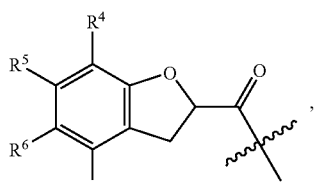

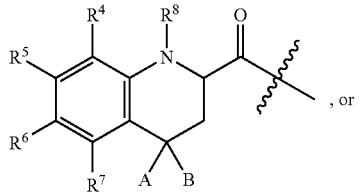, or

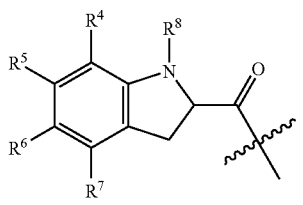

13. A compound according to claim 12, wherein Z is:

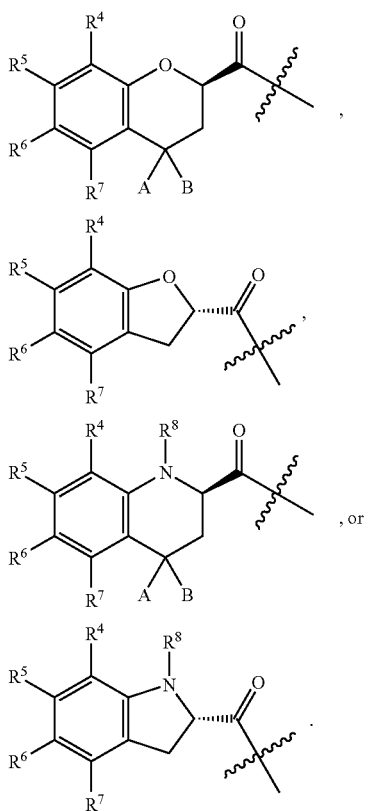

14. A compound according to claim 13, wherein Z is:

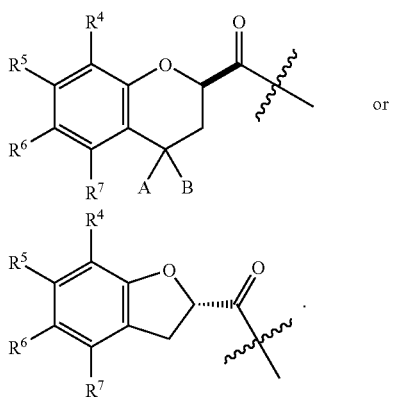

15. A compound according to claim 14, wherein Z is:

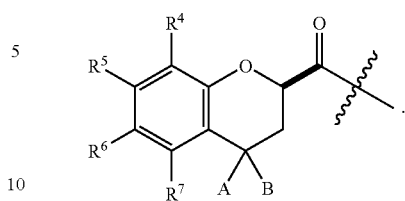

16. A compound according to claim 14, wherein Z is:

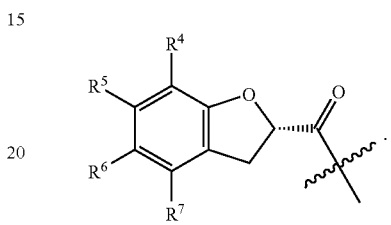

17. A compound according to claim 15, wherein A and B are H.

18. A compound according to claim 14, wherein $R^4$ and $R^7$ are H.

19. A compound according to claim 18, wherein one of $R^5$ and $R^6$ is H and the other is H, $-(CH_2)_rNR^{12}S(=O)_2R^{14}$, or $-(CH_2)_rNR^{12}C(=O)OR^{15}$.

20. A compound according to claim 1, wherein $R^4$, $R^5$, $R^6$, and $R^7$ are each independently H, halo, heteroaryl, $-OR^9$, $-S(=O)_2NR^{10}R^{11}$, $-(CH_2)_rNR^{12}R^{13}$, nitro, $-(CH_2)_rC(=O)NR^{12}R^{12a}$, or $-(CH_2)_rNHC(=O)NR^{12}R^{12a}$, provided that at least two of $R^4$, $R^5$, $R^6$, and $R^7$ are other than $-S(=O)_2NR^{10}R^{11}$, $-(CH_2)_rNR^{12}R^{13}$, $-(CH_2)_rC(=O)NR^{12}R^{12a}$, or $-(CH_2)_rNHC(=O)NR^{12}R^{12a}$.

21. A compound according to claim 20, wherein $R^4$, $R^5$, $R^6$, and $R^7$ are each independently H, halo, $-S(=O)_2NR^{10}R^{11}$, $-(CH_2)_rNR^{12}R^{13}$, $-(CH_2)_rC(=O)NR^{12}R^{12a}$, or $-(CH_2)_rNHC(=O)NR^{12}R^{12a}$.

22. A compound according to claim 21, wherein $R^4$, $R^5$, $R^6$, and $R^7$ are each independently H, halo, $-S(=O)_2NR^{10}R^{11}$, or $-(CH_2)_rNR^{12}R^{13}$.

23. A compound according to claim 22, wherein $R^4$ and $R^7$ are H.

24. A compound according to claim 23, wherein at least one of $R^5$ and $R^6$ is H.

25. A compound according to claim 1, wherein halo is $-Cl$ or $-I$.

26. A compound according to claim 25, wherein halo is $-Cl$.

27. A compound according to claim 15, wherein Z is:

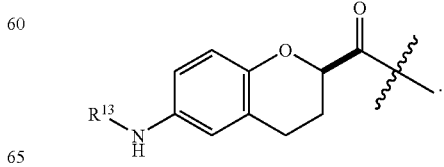

28. A compound according to claim 15, wherein Z is:

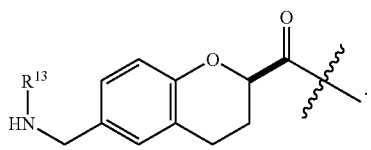

29. A compound according to claim 16, wherein Z is:

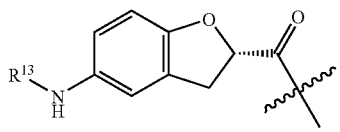

30. A compound according to claim 16, wherein Z is:

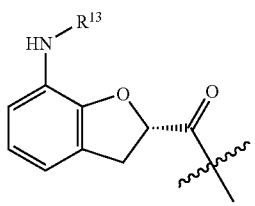

31. A compound according to claim 16, wherein Z is:

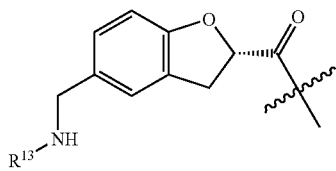

32. A pharmaceutical composition, comprising:
a pharmaceutically acceptable carrier; and an effective amount of a compound according to claim 1.

33. A pharmaceutical composition according to claim 32, further comprising an effective amount of at least one opioid.

34. A pharmaceutical composition according to claim 33, wherein said opioid is selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol and mixtures thereof.

35. A pharmaceutical composition according to claim 32, further comprising an effective amount of a compound selected from the group consisting of antibiotics, antivirals, antifungals, anti-inflammatories, anesthetics and mixtures thereof.

36. A method of binding opioid receptors in a patient in need thereof, comprising the step of:
administering to said patient an effective amount of a compound according to claim 1.

37. A method according to claim 36, wherein said compound binds κ opioid receptors.

38. A method according to claim 37, wherein said κ opioid receptors are located in the central nervous system.

39. A method according to claim 37, wherein said κ opioid receptors are located peripherally to the central nervous system.

40. A method according to claim 36, wherein said binding agonizes the activity of said opioid receptors.

41. A method according to claim 36, wherein said compound does not substantially cross the blood-brain barrier.

42. A method according to claim 36, wherein said patient is in need of an analgesic.

43. A method for or treating gastrointestinal dysfunction, comprising the step of:
administering to a patient in need of such treatment, a composition comprising an effective amount of a compound according to claim 1.

44. A method for or treating ileus, comprising the step of:
administering to a patient in need of such treatment, a composition comprising an effective amount of a compound according to claim 1.

45. A method of or treating pain, comprising the step of:
administering to a patient in need thereof, a composition, comprising:
an effective amount of an opioid; and an effective amount of a compound according to claim 1.

46. A method according to claim 45, wherein said opioid is selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol and mixtures thereof.

47. A method for or treating pruritic dermatoses and conditions characterized by pruritic dermatosis as a symptom, comprising the step of:
administering to a patient in need of such treatment, a composition comprising an effective amount of a compound according to claim 1.

48. A method according to claim 47, wherein said pruritic dermatosis is selected from allergic dermatitis, atopy, contact dermatitis, psoriasis, eczema, opioid-induced pruritus, and insect bites.

49. A method for or treating cerebral edema, comprising the step of:
administering to a patient in need of such treatment, a composition comprising an effective amount of a compound according to claim 1.

50. A method for or treating oxygen supply deficiency of the central nervous system, comprising the step of:
administering to a patient in need of such treatment, a composition comprising an effective amount of a compound according to claim 1.

51. A method for inducing diuresis, comprising the step of:
administering to a patient in need thereof, a composition comprising an effective amount of a compound according to claim 1.

52. A method for or treating tussis, comprising the step of:
administering to a patient in need thereof, a composition comprising an effective amount of a compound according to claim 1.

53. A compound according to claim 1 wherein:

Z is:

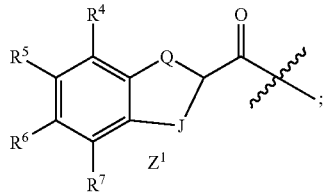

Q is —O—;

J is —(CH$_2$)$_k$— or —(CH=CH—CH$_2$)—;

R$^4$, R$^5$, R$^6$, and R$^7$ are each independently H, alkyl, halo, aryl, —OH, —OR$^9$, —SO$_2$NR$^{10}$R$^{11}$, —(CH$_2$)$_r$NR$^{12}$R$^{13}$, nitro, —CN, —CF$_3$, —CF$_2$CF$_3$, —OCF$_3$, —SR$^9$, —SO$_2$R$^9$, —(CH$_2$)$_r$C(=O)OR$^9$, —(CH$_2$)$_r$C(=O)NR$^{12}$R$^{12a}$, or —(CH$_2$)$_r$NHC(=O)NR$^{12}$R$^{12a}$;

R$^{10}$ and R$^{11}$ are each independently H, alkyl, —(CH$_2$)$_p$—OH, —(CH$_2$)$_p$—OR$^9$, cycloalkyl, cycloalkylalkyl or aryl;

R$^{14}$ is alkyl, cycloalkyl, cycloalkylalkyl, alkylcycloalkyl, a straight or branched chain heteroalkyl, aryl, or aralkyl; and R$^{15}$ is alkyl, cycloalkyl, alkylcycloalkyl, or aralkyl.

54. A compound according to claim 53 which is:

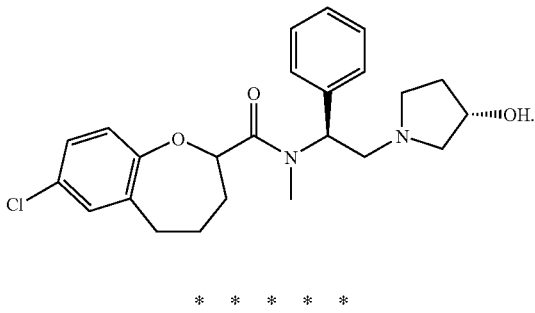

\* \* \* \* \*